(12) United States Patent
Nussenzweig et al.

(10) Patent No.: US 12,239,698 B2
(45) Date of Patent: Mar. 4, 2025

(54) HIV VACCINE IMMUNOGENS

(71) Applicants: The Rockefeller University, New York, NY (US); California Institute of Technology, Pasadena, CA (US)

(72) Inventors: Michel Nussenzweig, New York, NY (US); Pamela J. Bjorkman, Altadena, CA (US); Amelia Escolano, New York, NY (US); Harry Gristick, Pasadena, CA (US)

(73) Assignees: The Rockefeller University, New York, NY (US); California Institute of Technology, Pasadena, CA (US)

( * ) Notice: Subject to any disclaimer, the term of this patent is extended or adjusted under 35 U.S.C. 154(b) by 923 days.

(21) Appl. No.: 17/299,852

(22) PCT Filed: Nov. 27, 2019

(86) PCT No.: PCT/US2019/063619
§ 371 (c)(1),
(2) Date: Jun. 4, 2021

(87) PCT Pub. No.: WO2020/117590
PCT Pub. Date: Jun. 11, 2020

(65) Prior Publication Data
US 2022/0031830 A1 Feb. 3, 2022

Related U.S. Application Data

(60) Provisional application No. 62/775,192, filed on Dec. 4, 2018.

(51) Int. Cl.
*A61K 39/12* (2006.01)
*A61P 31/18* (2006.01)
(Continued)

(52) U.S. Cl.
CPC .............. *A61K 39/12* (2013.01); *A61P 31/18* (2018.01); *C07K 14/005* (2013.01);
(Continued)

(58) Field of Classification Search
None
See application file for complete search history.

(56) References Cited

U.S. PATENT DOCUMENTS 8,673,307 B1  3/2014 Nussenzweig et al.
2014/0212458 A1 * 7/2014 Caulfield ............... A61K 39/39
424/188.1

FOREIGN PATENT DOCUMENTS

WO  2010107939 A2  9/2010
WO  2015/134982 A1  9/2015
(Continued)

OTHER PUBLICATIONS

Greenspan et al.(Nature Biotechnology. 1999; 7: 936-937).*
(Continued)

*Primary Examiner* — Shanon A. Foley
(74) *Attorney, Agent, or Firm* — Fox Rothschild LLP

(57) ABSTRACT

This disclosure provides HIV immunogens and use thereof for generating an immune response in a subject. Also disclosed is a method of isolating anti-HIV antibodies and use thereof. This disclosure further provides a method for treating or preventing a human immunodeficiency type 1 (HIV-1) infection in a subject using the disclosed HIV immunogens and/or antibodies.

14 Claims, 21 Drawing Sheets

Specification includes a Sequence Listing.

(51) Int. Cl.
   *C07K 14/005*   (2006.01)
   *A61K 39/00*    (2006.01)
(52) U.S. Cl.
   CPC .............. *A61K 2039/55577* (2013.01); *C12N 2740/16023* (2013.01); *C12N 2740/16134* (2013.01)

(56) References Cited

FOREIGN PATENT DOCUMENTS

| WO | 2016154003 | A1 | 9/2016 |
| WO | 2016196975 | A1 | 12/2016 |
| WO | 2017/055522 | A1 | 4/2017 |
| WO | 2017/165674 | A1 | 9/2017 |
| WO | 2018/161049 | A1 | 9/2018 |

OTHER PUBLICATIONS

Escolano et al. (Science Translational Medicine; Nov. 24, 2021; 13: eabk1533).*
Haynes et al. (Nature Reviews Immunology. Mar. 2023 ;23 (3) : 142-58).*
Steichen et al. (Science. May 17, 2024; 384: 754).*
Sequence alignment of instant SEQ ID No. 2 with Geneseq database access No. BBL04845 in US2014212458 Sep. 2014.*
International Search Report and Written Opinion issued Apr. 24, 2020, for related Application No. PCT/US19/63619, 21 pages.
Walker, L. M. et al., "Broad Neutralization Coverage of HIV by Multiple Highly Potent Antibodies", Nature (2011), vol. 477, pp. 466-470.
Steichen, J. M. et al., "HIV Vaccine Design to Target Germline Precursors of Glycan-Dependent Broadly Neutralizing Antibodies", Immunity (2016), vol. 45, pp. 483-496.
Search Report issued Jan. 17, 2025 is related EP Application No. 24191310.2, 15 pgs.

* cited by examiner

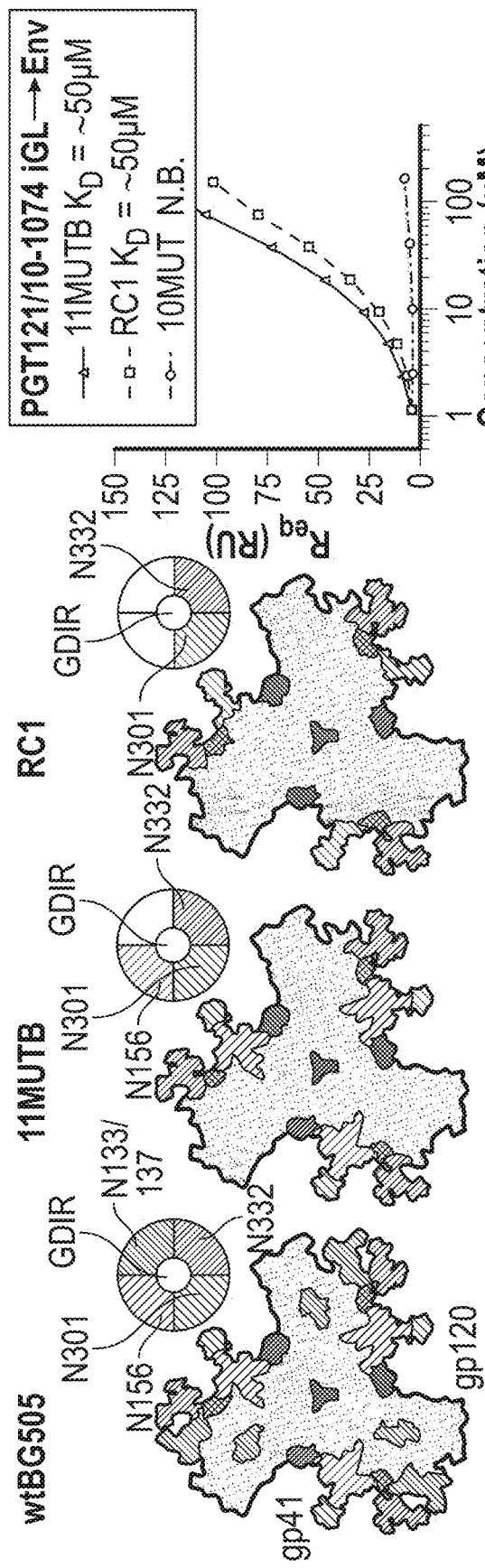
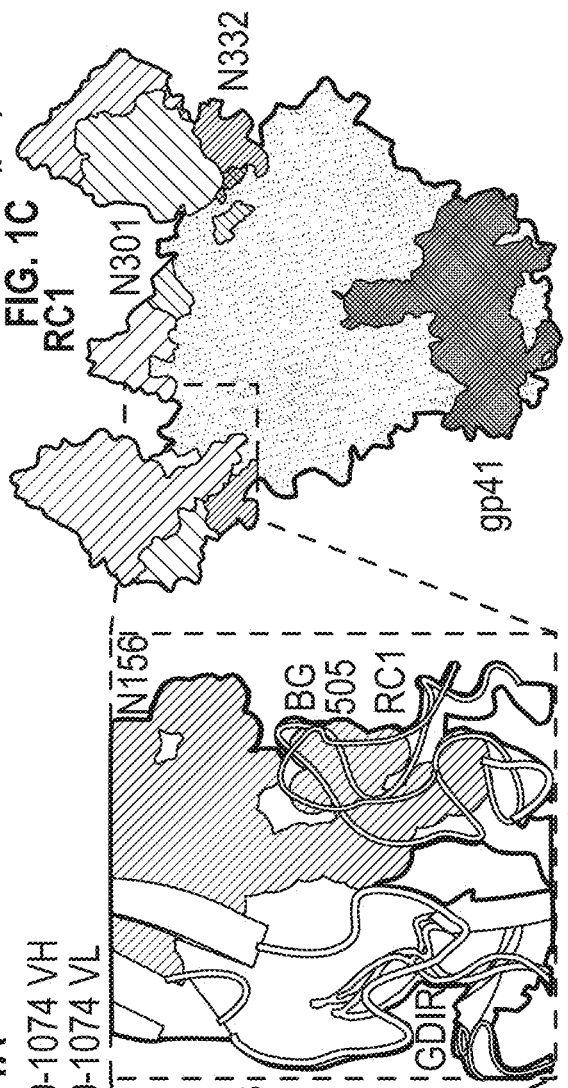
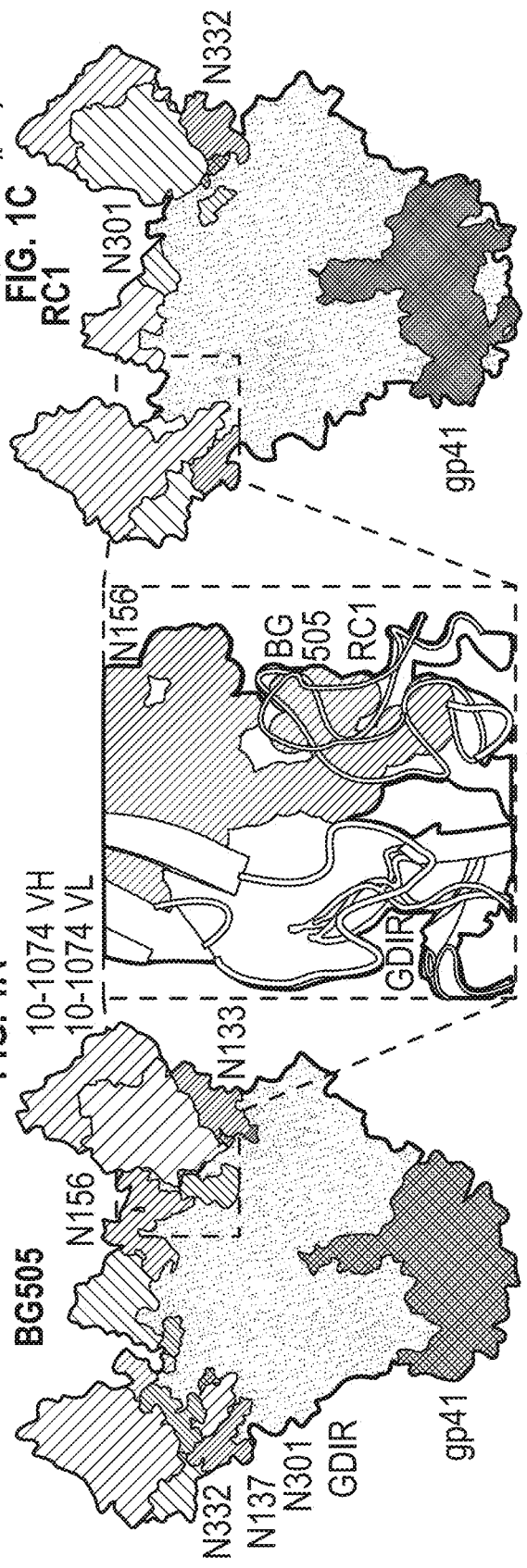

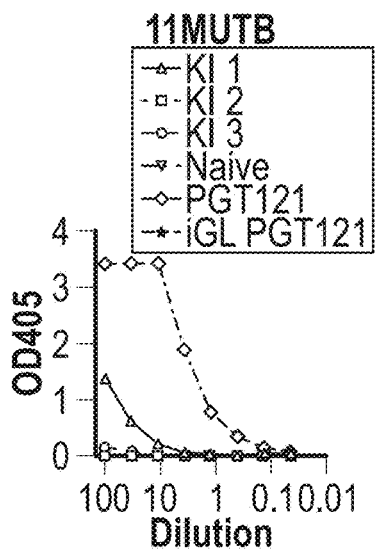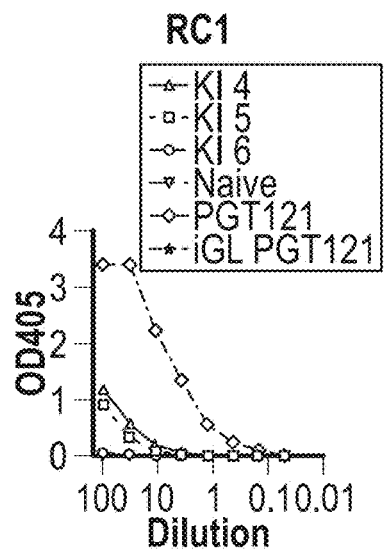
FIG. 2A  FIG. 2B
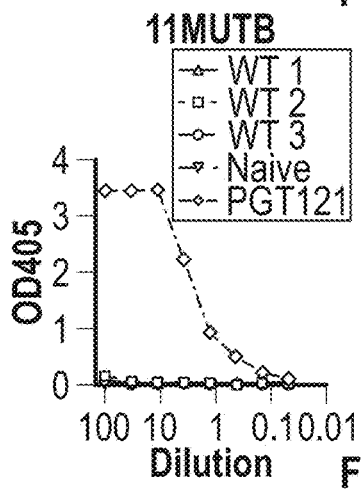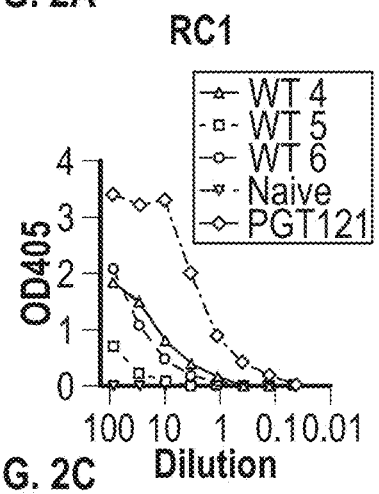
FIG. 2C  FIG. 2D
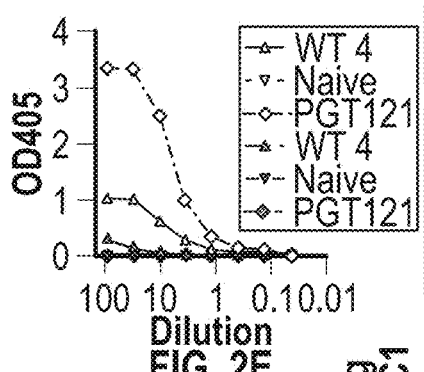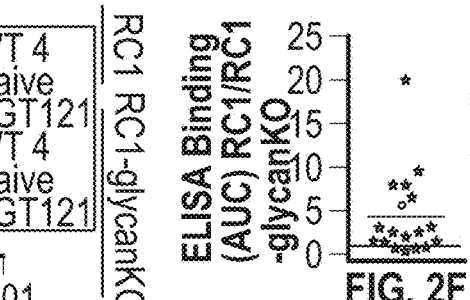
FIG. 2E  FIG. 2F  FIG. 2G
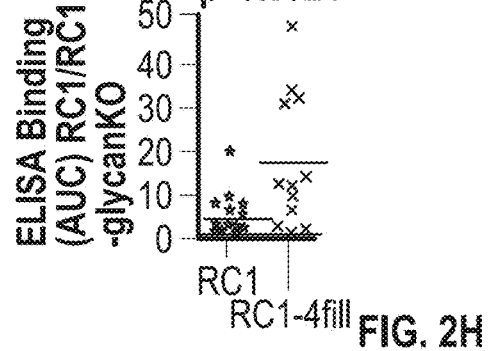
FIG. 2H

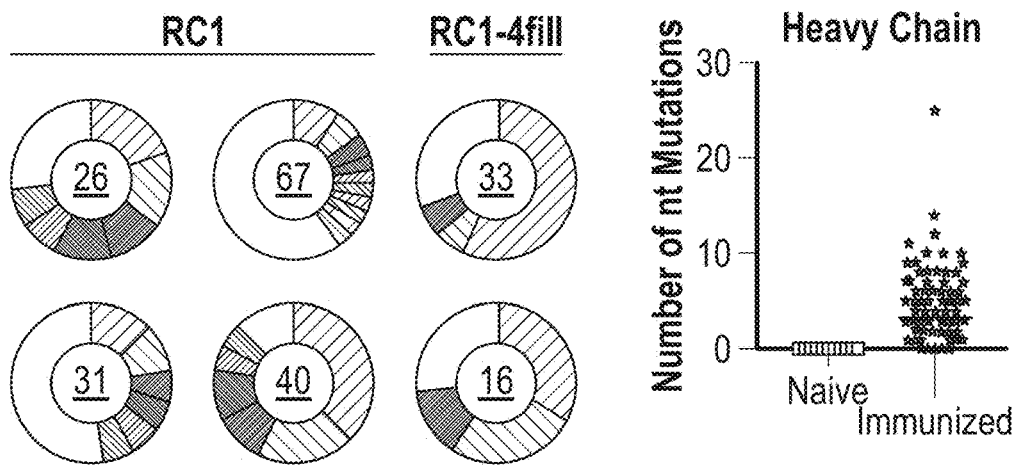
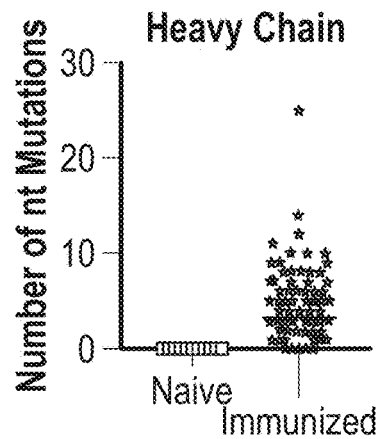
FIG. 2I
FIG. 2J
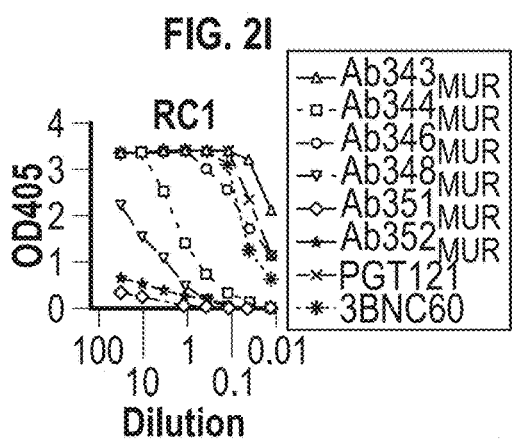
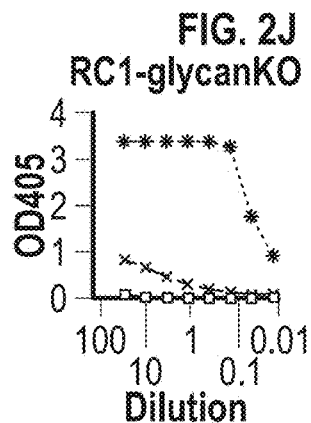
FIG. 2K
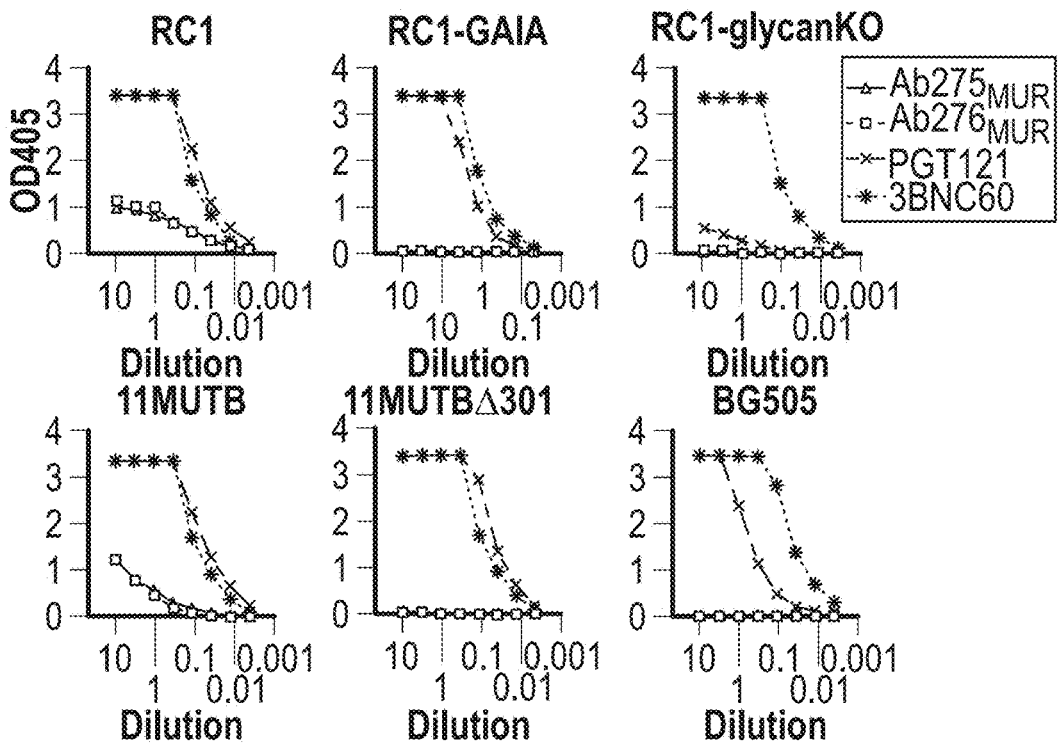
FIG. 2L

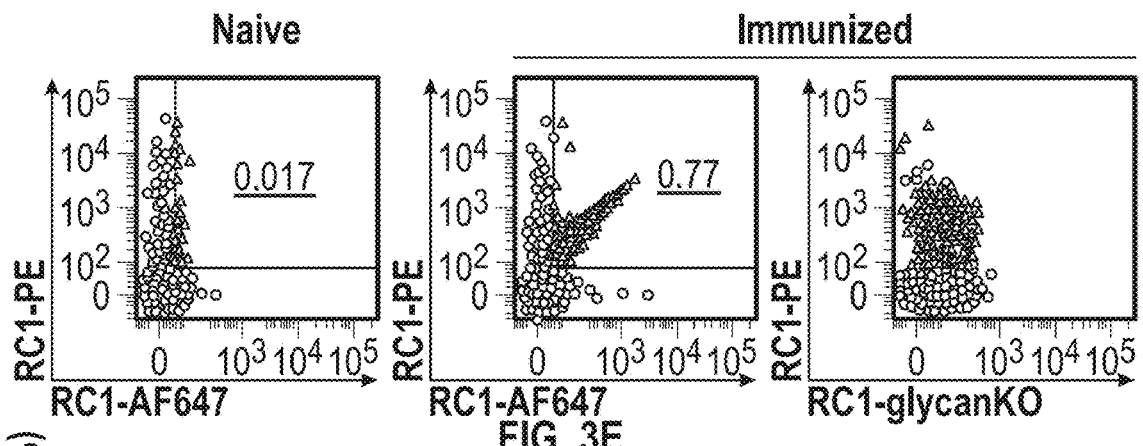
FIG. 3E
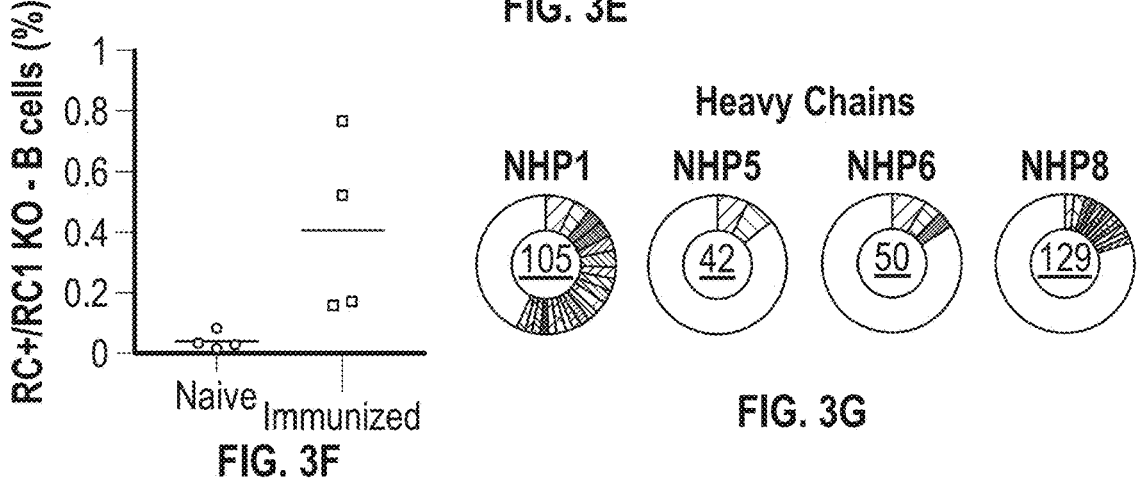
FIG. 3F
FIG. 3G
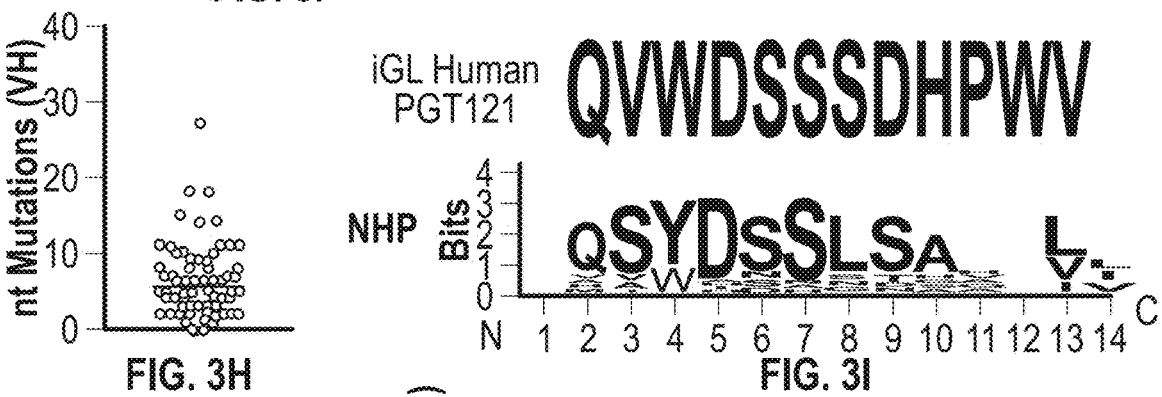
FIG. 3H
FIG. 3I
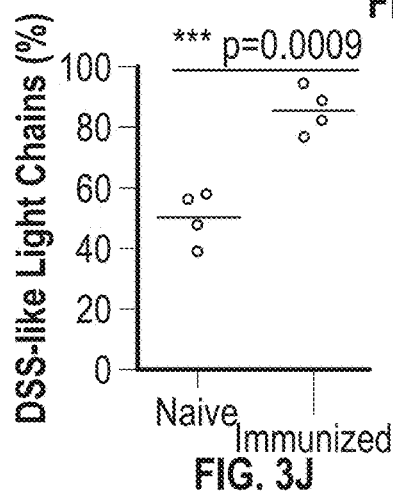
FIG. 3J

| | 10-1074 | PGT121 | BG1 |
|---|---|---|---|
| | +N332 | +N332 | +N160 |
| +N156 | 0.20 (n=75) | 0.14 (n=170) | 5.80 (n=102) |
| -N156 | 0.05 (n=8) | 0.03 (n=9) | 30.0 (n=8) |
| +N301 | 0.16 (n=81) | 0.11 (n=173) | - |
| -N301 | 1.05 (n=2) | 15.91 (n=6) | - |
| +N137 | 0.04 (n=11) | 0.10 (n=34) | - |
| -N137 | 0.21 (n=72) | 0.14 (n=145) | - |

IC50 Values (μg/ml)

FIG. 6A

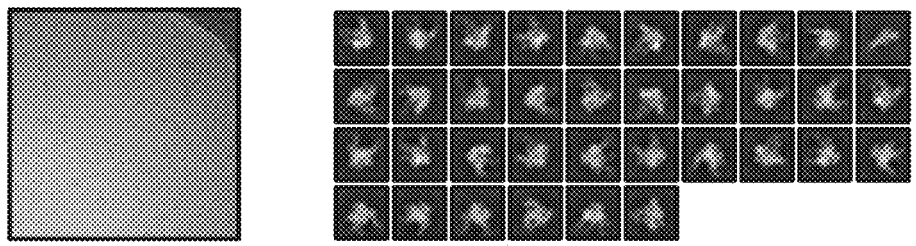
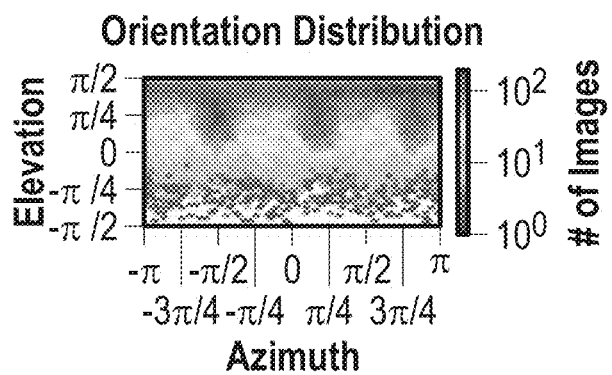
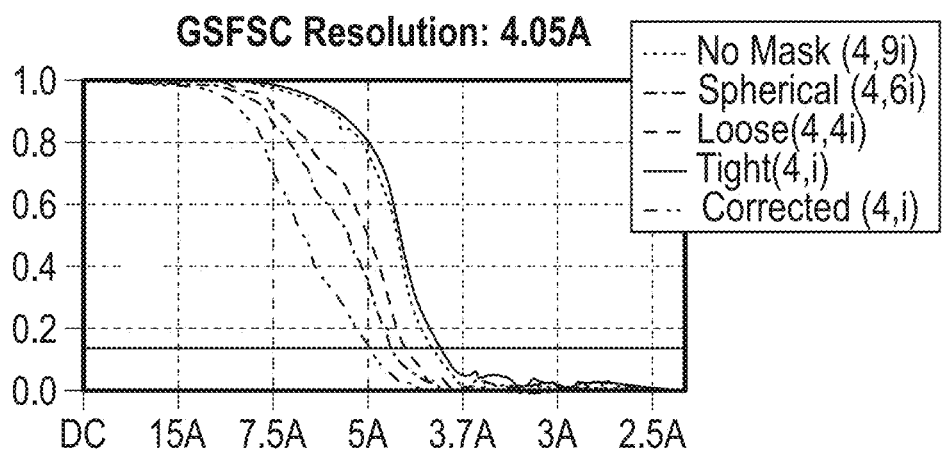
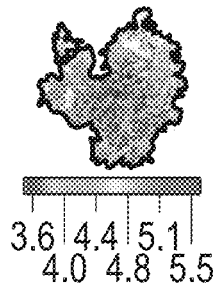
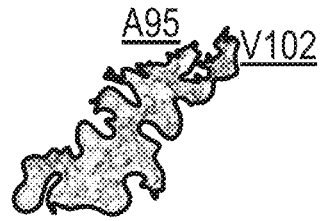
FIG. 7A

Ab275$_{MUR}$-RC1 Micrograph
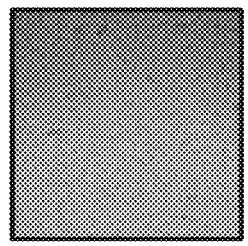
2D Class Averages
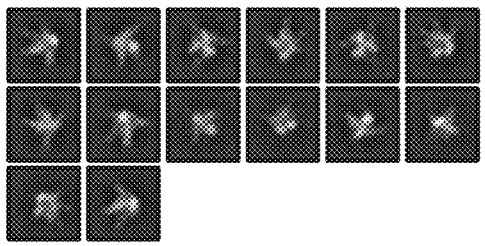
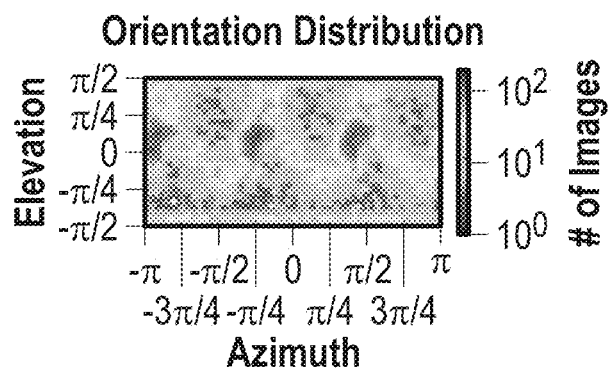
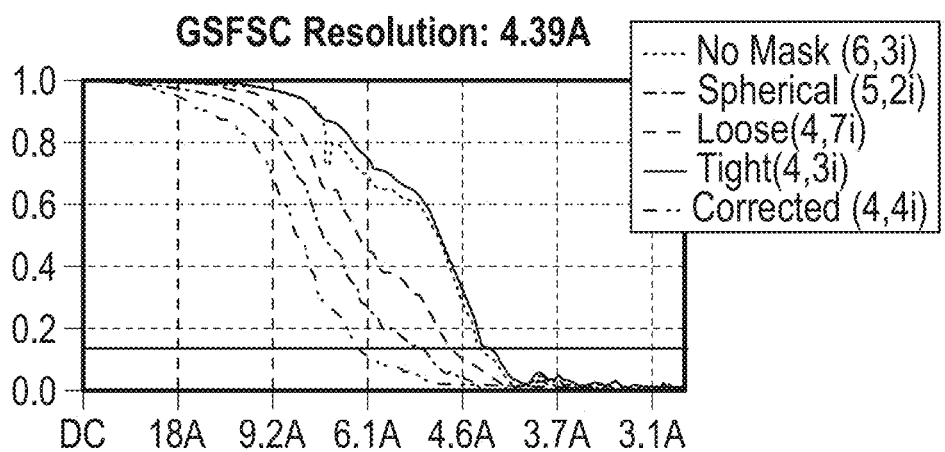
Local Resolution
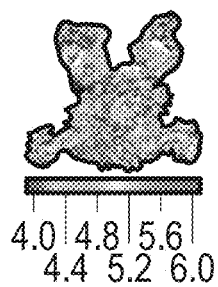
4.0 4.8 5.6
 4.4 5.2 6.0
Density: gp41
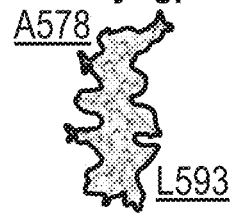
Density: CDRH3
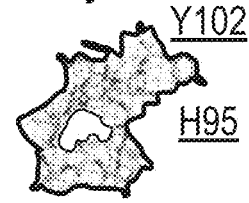
FIG. 7B

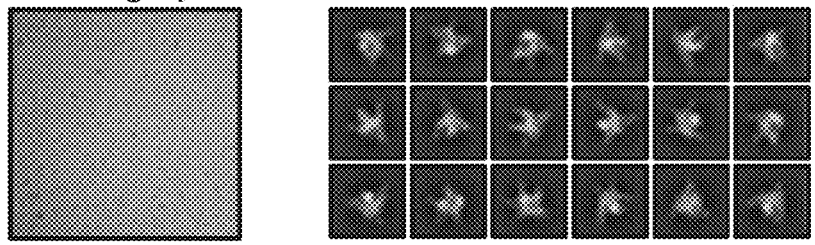
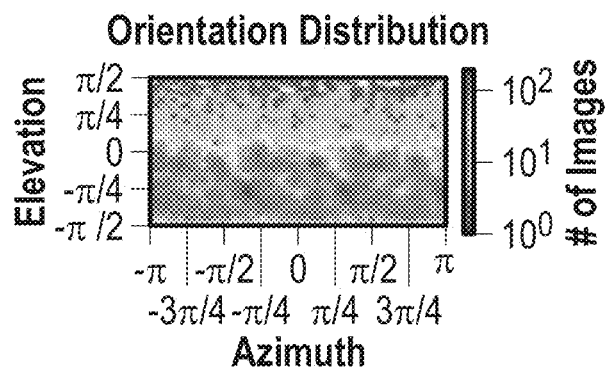
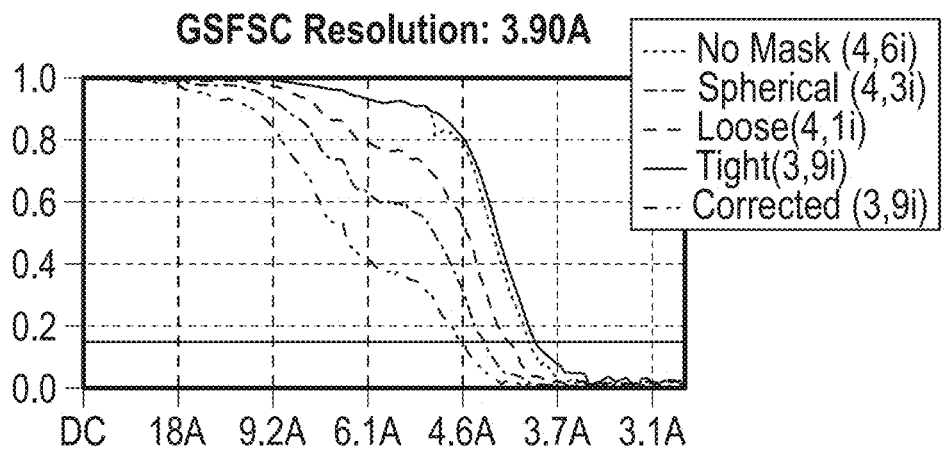
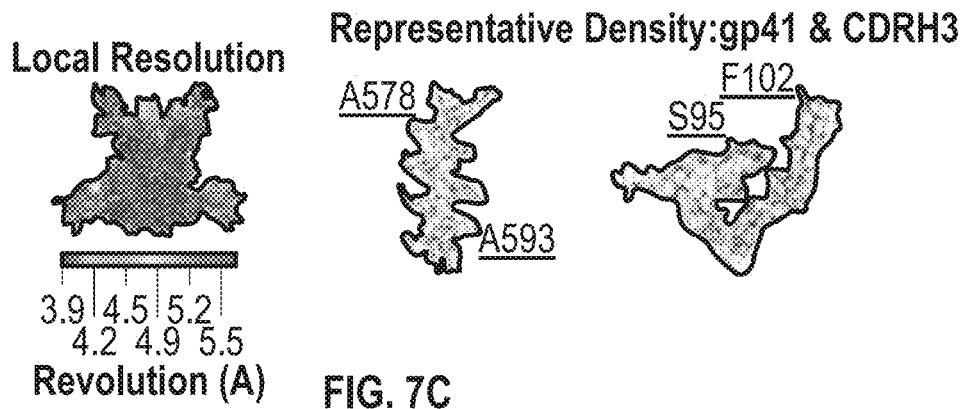
FIG. 7C

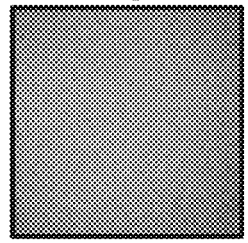 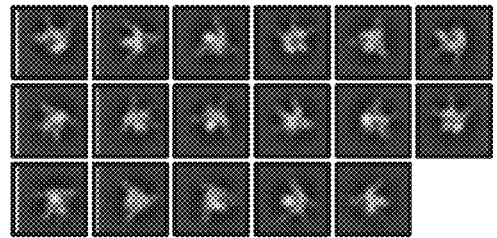
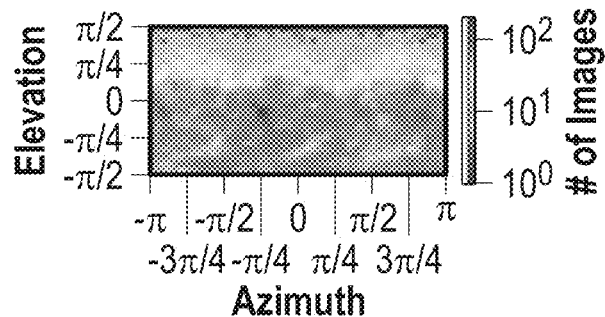
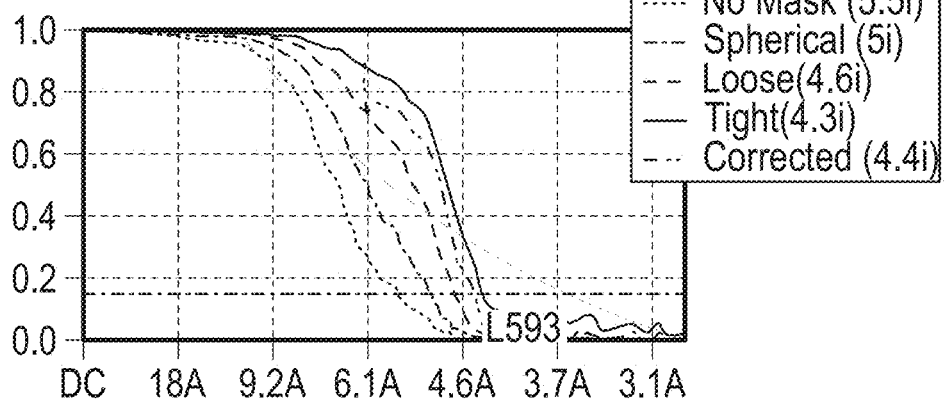
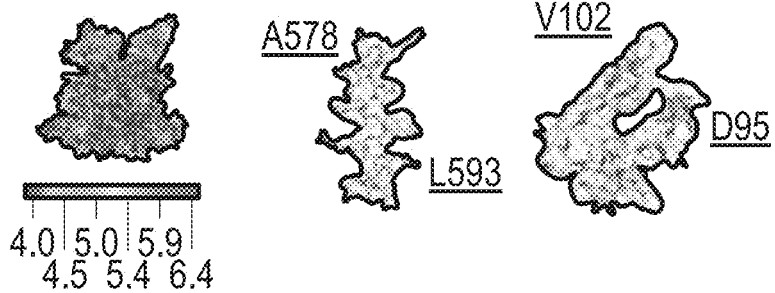
FIG. 7D

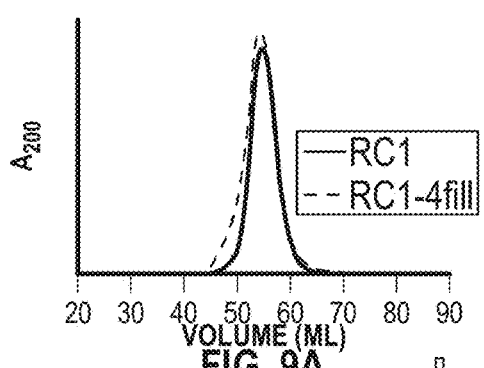
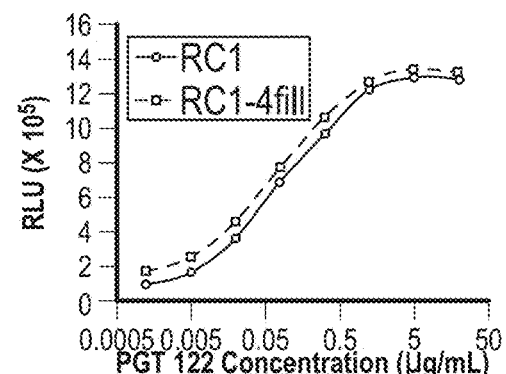
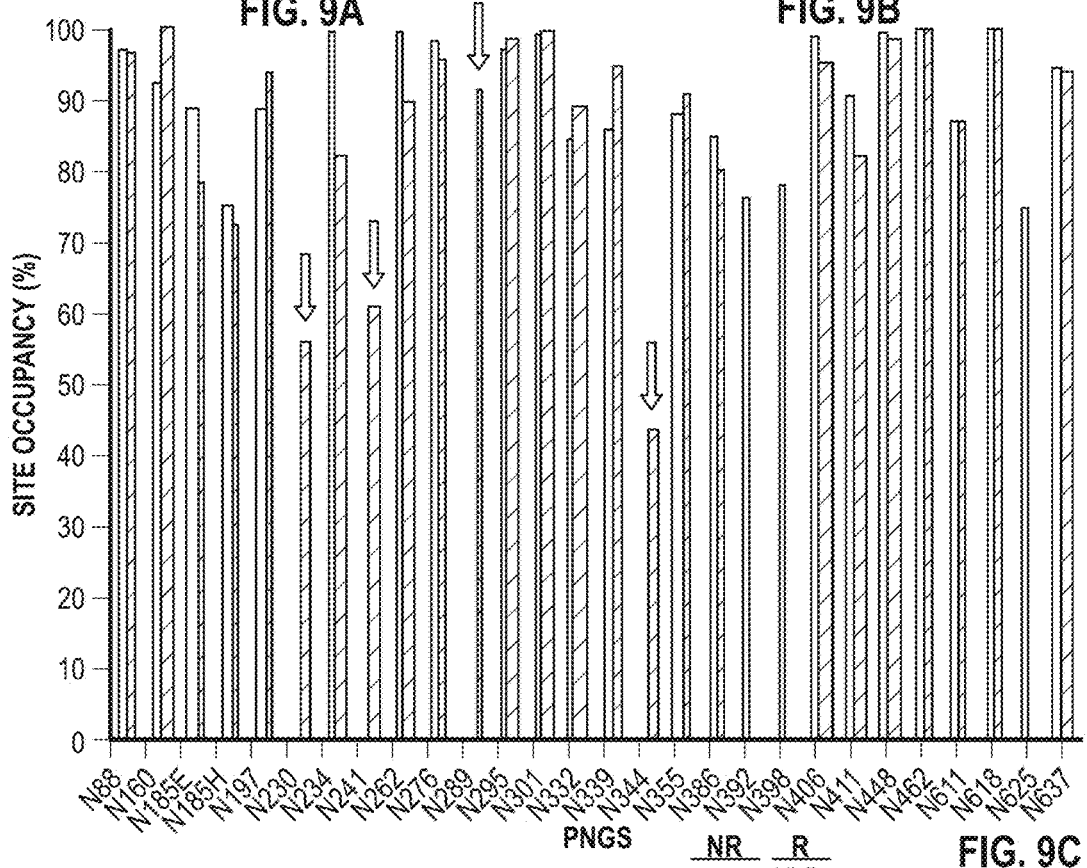
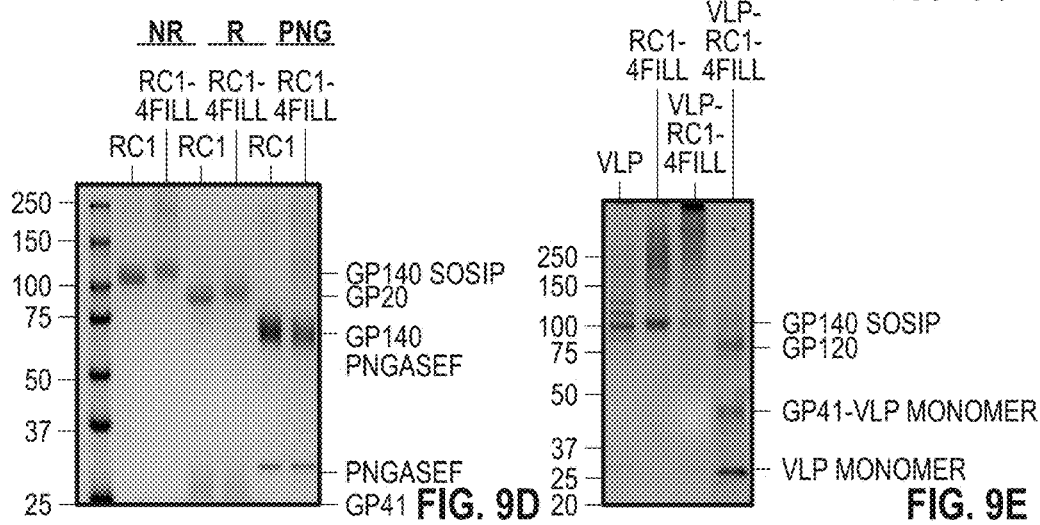
FIG. 9A
FIG. 9B
FIG. 9C
FIG. 9D
FIG. 9E

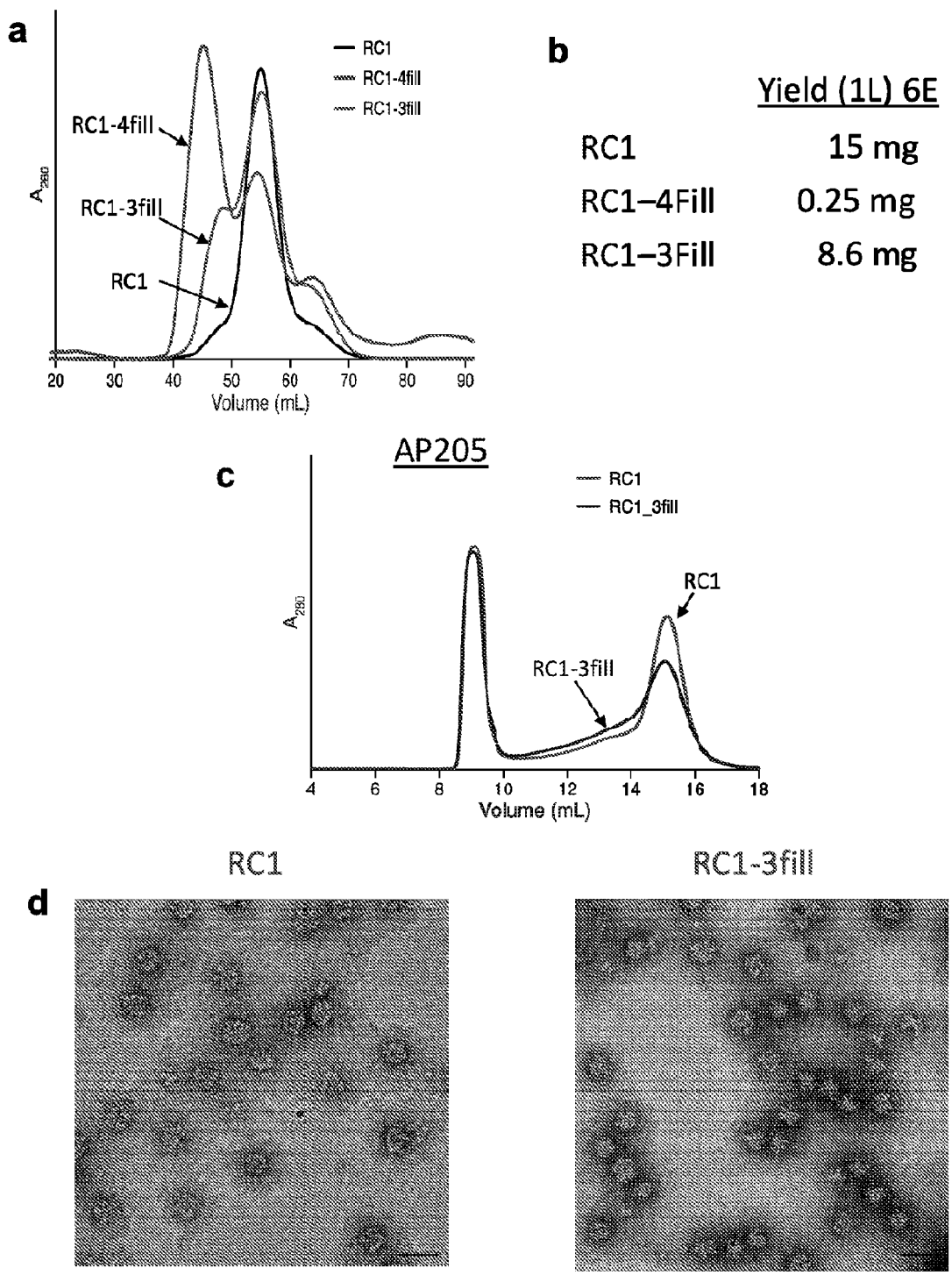
FIGs. 13a, 13b, 13c, and 13d

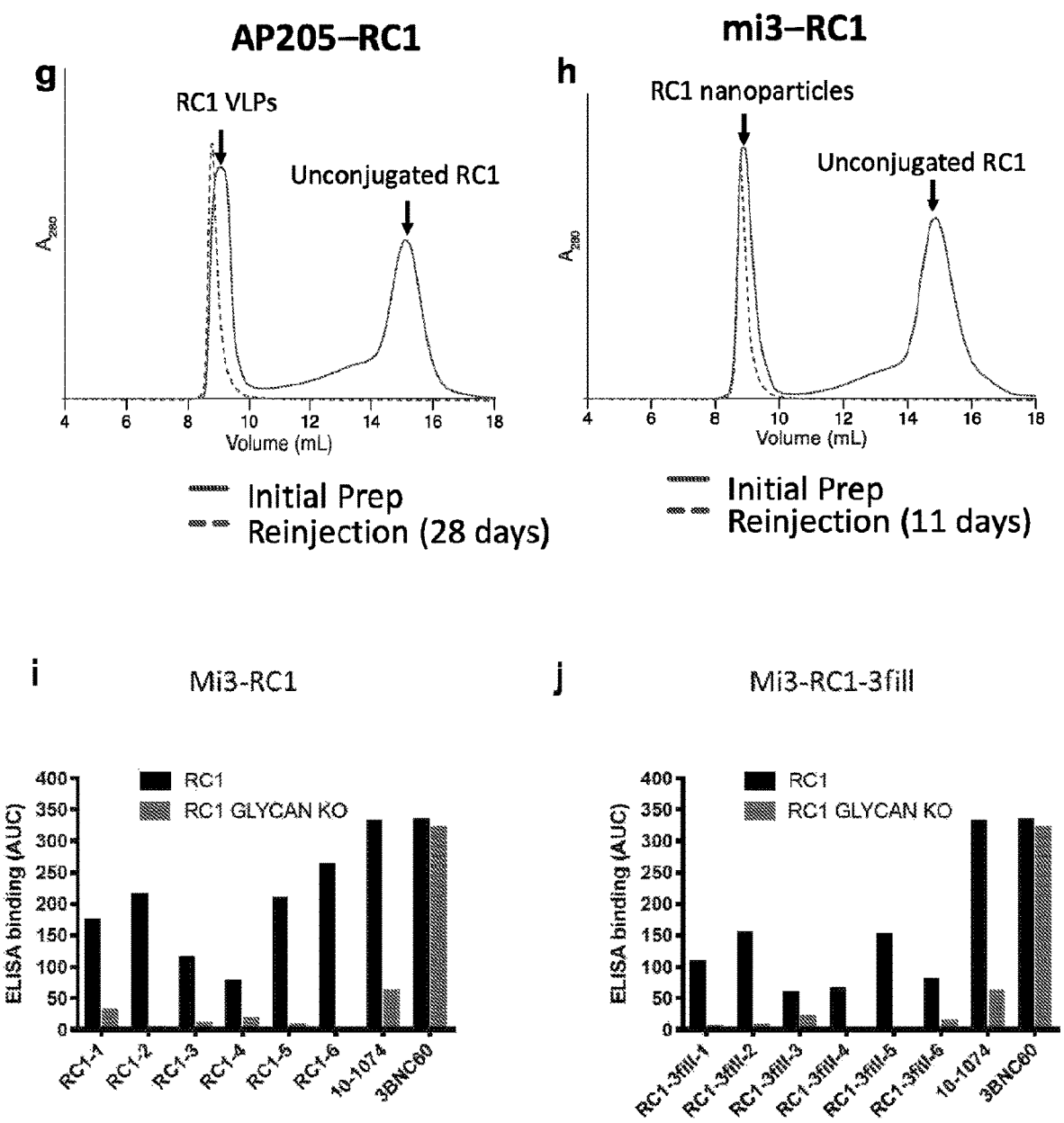
FIGs. 13g, 13h, 13i, and 13j

SEQUENCE LISTING

<160> NUMBER OF SEQ ID NOS: 495

<210> SEQ ID NO 1
<211> LENGTH: 666
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg
            20                  25                  30

Gly Ala Arg Ala Glu Asn Leu Trp Val Thr Val Tyr Tyr Gly Val Pro
        35                  40                  45

Val Trp Lys Asp Ala Glu Thr Thr Leu Phe Cys Ala Ser Asp Ala Lys
50                  55                  60

Ala Tyr Glu Thr Glu Lys His Asn Val Trp Ala Thr His Ala Cys Val
65                  70                  75                  80

Pro Thr Asp Pro Asn Pro Gln Glu Ile His Leu Glu Asn Val Thr Glu
                85                  90                  95

Glu Phe Asn Met Trp Lys Asn Asn Met Val Glu Gln Met His Thr Asp
            100                 105                 110

Ile Ile Ser Leu Trp Asp Gln Ser Leu Lys Pro Cys Val Lys Leu Thr
            115                 120                 125

Pro Leu Cys Val Thr Leu Gln Cys Thr Asn Val Thr Asn Asn Ile Thr
        130                 135                 140

Asp Asp Met Arg Gly Glu Leu Lys Asn Cys Ser Phe Asn Met Thr Thr
145                 150                 155                 160

Glu Leu Arg Asp Lys Lys Gln Lys Val Tyr Ser Leu Phe Tyr Arg Leu
                165                 170                 175

Asp Val Val Gln Ile Asn Glu Asn Gln Gly Asn Arg Ser Asn Asn Ser
            180                 185                 190

Asn Lys Glu Tyr Arg Leu Ile Asn Cys Asn Thr Ser Ala Ile Thr Gln
        195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Lys Asp Lys Lys Phe Asn Gly
225                 230                 235                 240

Thr Gly Pro Cys Pro Ser Val Ser Thr Val Gln Cys Thr His Gly Ile
            245                 250                 255

Lys Pro Trp Ser Thr Gln Leu Leu Leu Asn Gly Ser Leu Ala Glu Glu
            260                 265                 270

Glu Val Met Ile Arg Ser Glu Asn Ile Thr Asn Asn Ala Lys Asn Ile
        275                 280                 285

Leu Val Gln Phe Asn Thr Pro Val Gln Ile Asn Cys Thr Arg Pro Asn
290                 295                 300

Asn Asn Thr Arg Lys Ser Ile Arg Ile Gly Pro Gly Gln Ala Phe Tyr
305                 310                 315                 320

Ala Thr Gly Asp Ile Ile Gly Asp Ile Arg Gln Ala His Cys Asn Val
            325                 330                 335

Ser Lys Ala Thr Trp Asn Glu Thr Leu Gly Lys Trp Lys Gln Leu Arg
            340                 345                 350

Lys His Phe Gly Asn Asn Thr Ile Ile Arg Phe Ala Asn Ser Ser Gly
        355                 360                 365

Gly Asp Leu Glu Val Thr Thr His Ser Phe Asn Cys Gly Gly Glu Phe
370                 375                 380

Phe Tyr Cys Asn Thr Ser Gly Leu Phe Asn Ser Thr Trp Ile Ser Asn
385                 390                 395                 400

Thr Ser Val Gln Gly Ser Asn Ser Thr Gly Ser Asn Asp Ser Ile Thr
            405                 410                 415
```

```
Leu Pro Cys Arg Ile Lys Gln Ile Ile Asn Met Trp Gln Arg Ile Gly
                420                 425                 430

Gln Ala Met Tyr Ala Pro Pro Ile Gln Gly Val Ile Arg Cys Val Ser
            435                 440                 445

Asn Ile Thr Gly Leu Ile Leu Thr Arg Asp Gly Gly Ser Thr Asn Ser
        450                 455                 460

Thr Thr Glu Thr Phe Arg Pro Gly Gly Gly Asp Met Arg Asp Asn Trp
465                 470                 475                 480

Arg Ser Glu Leu Tyr Lys Tyr Lys Trp Lys Ile Glu Pro Leu Gly Val
                485                 490                 495

Ala Pro Thr Arg Cys Lys Arg Arg Val Val Gly Arg Arg Arg Arg
            500                 505                 510

Arg Ala Val Gly Ile Gly Ala Val Phe Leu Gly Phe Leu Gly Ala Ala
        515                 520                 525

Gly Ser Thr Met Gly Ala Ala Ser Met Thr Leu Thr Val Gln Ala Arg
530                 535                 540

Asn Leu Leu Ser Gly Ile Val Gln Gln Ser Asn Leu Leu Arg Ala
545                 550                 555                 560

Pro Glu Ala Gln Gln His Leu Leu Lys Leu Thr Val Trp Gly Ile Lys
                565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Cys Thr
        595                 600                 605

Asn Val Pro Trp Asn Ser Ser Trp Ser Asn Arg Asn Leu Ser Glu Ile
610                 615                 620

Trp Asp Asn Met Thr Trp Leu Gln Trp Asp Lys Glu Ile Ser Asn Tyr
625                 630                 635                 640

Thr Gln Ile Ile Tyr Gly Leu Leu Glu Glu Ser Gln Asn Gln Gln Glu
                645                 650                 655

Lys Asn Glu Gln Asp Leu Leu Ala Leu Asp
            660                 665

<210> SEQ ID NO 2
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Ala Met Lys Arg Gly Leu Cys Cys Val Leu Leu Leu Cys Gly
1               5                   10                  15

Ala Val Phe Val Ser Pro Ala Gly Ala Gly Ser Asn Leu Trp Val Thr
                20                  25                  30

Val Tyr Tyr Gly Val Pro Val Trp Lys Asp Ala Glu Thr Thr Leu Phe
            35                  40                  45

Cys Ala Ser Asp Ala Lys Ala Tyr Glu Thr Glu Lys His Asn Val Trp
        50                  55                  60

Ala Thr His Ala Cys Val Pro Thr Asp Pro Asn Pro Gln Glu Ile His
65                  70                  75                  80

Leu Glu Asn Val Thr Glu Glu Phe Asn Met Trp Lys Asn Asn Met Val
                85                  90                  95

Glu Gln Met His Glu Asp Ile Ile Ser Leu Trp Asp Gln Ser Leu Lys
            100                 105                 110
```

```
Pro Cys Val Lys Leu Thr Pro Leu Cys Val Thr Leu Gln Cys Thr Asn
        115                 120                 125

Tyr Ala Pro Asn Leu Leu Ser Asn Met Arg Gly Glu Leu Lys Gln Cys
        130                 135                 140

Ser Phe Asn Met Thr Thr Glu Leu Arg Asp Lys Lys Gln Lys Val Tyr
145                 150                 155                 160

Ser Leu Phe Tyr Arg Leu Asp Val Val Gln Ile Asn Glu Asn Gln Gly
                165                 170                 175

Asn Arg Ser Asn Asn Ser Asn Lys Glu Tyr Arg Leu Ile Asn Cys Asn
                180                 185                 190

Thr Ser Ala Ile Thr Gln Ala Cys Pro Lys Val Ser Phe Glu Pro Ile
        195                 200                 205

Pro Ile His Tyr Cys Ala Pro Ala Gly Phe Ala Ile Leu Lys Cys Lys
        210                 215                 220

Asp Lys Lys Phe Asn Gly Thr Gly Pro Cys Pro Ser Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Val Ile Ile Arg Ser Glu Asn Ile
                260                 265                 270

Thr Asn Asn Ala Lys Asn Ile Leu Val Gln Leu Asn Thr Pro Val Gln
        275                 280                 285

Ile Asn Cys Thr Arg Pro Asn Asn Asn Thr Val Lys Ser Ile Arg Ile
        290                 295                 300

Gly Pro Gly Gln Ala Phe Tyr Tyr Phe Gly Asp Ile Ile Gly Asp Ile
305                 310                 315                 320

Arg Met Ala His Cys Asn Val Ser Lys Ala Thr Trp Asn Glu Thr Leu
                325                 330                 335

Gly Lys Val Val Lys Gln Leu Arg Lys His Phe Gly Asn Asn Thr Ile
                340                 345                 350

Ile Arg Phe Ala Gln Ser Ser Gly Gly Asp Leu Glu Val Thr Thr His
        355                 360                 365

Ser Phe Asn Cys Gly Gly Glu Phe Phe Tyr Cys Asn Thr Ser Gly Leu
        370                 375                 380

Phe Asn Ser Thr Trp Ile Ser Asn Thr Ser Val Gln Gly Ser Asn Ser
385                 390                 395                 400

Thr Gly Ser Asn Asp Ser Ile Val Leu Pro Cys Arg Ile Lys Gln Ile
                405                 410                 415

Ile Asn Met Trp Gln Arg Ile Gly Gln Ala Met Tyr Ala Pro Pro Ile
                420                 425                 430

Gln Gly Val Ile Arg Cys Val Ser Asn Ile Thr Gly Leu Ile Leu Thr
        435                 440                 445

Arg Asp Gly Gly Ser Thr Asn Ser Thr Thr Glu Thr Phe Arg Pro Gly
        450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Arg Cys Lys Arg
                485                 490                 495

Arg Val Val Gly Arg Arg Arg Arg Ala Val Gly Ile Gly Ala
                500                 505                 510

Val Ser Leu Gly Phe Leu Gly Ala Ala Gly Ser Thr Met Gly Ala Ala
        515                 520                 525
```

```
Ser Met Thr Leu Thr Val Gln Ala Arg Asn Leu Leu Ser Gly Ile Val
    530                 535                 540

Gln Gln Gln Ser Asn Leu Leu Arg Ala Pro Glu Pro Gln Gln His Leu
545                 550                 555                 560

Leu Lys Asp Thr His Trp Gly Ile Lys Gln Leu Gln Ala Arg Val Leu
                565                 570                 575

Ala Val Glu His Tyr Leu Arg Asp Gln Gln Leu Leu Gly Ile Trp Gly
                580                 585                 590

Cys Ser Gly Lys Leu Ile Cys Cys Thr Asn Val Pro Trp Asn Ser Ser
                595                 600                 605

Trp Ser Asn Arg Asn Leu Ser Glu Ile Trp Asp Asn Met Thr Trp Leu
    610                 615                 620

Gln Trp Asp Lys Glu Ile Ser Asn Tyr Thr Gln Ile Ile Tyr Gly Leu
625                 630                 635                 640

Leu Glu Glu Ser Gln Asn Gln Gln Glu Lys Asn Glu Gln Asp Leu Leu
                645                 650                 655

Ala Leu Asp

<210> SEQ ID NO 3
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggacgcca tgaagagggg actttgctgt gttcttctgc tgtgtggcgc cgtgtttgtt     60
agccccgctg gggccggatc caacctgtgg gtcactgtgt attatggtgt gccagtgtgg    120
aaggatgcag agacaacact cttttgcgcc tccgacgcta agcatacga acggagaag      180 cacaacgtgt gggcgaccca tgcctgtgtc cctacagacc ctaaccctca ggaaattcat    240
cttgaaaatg tcacagaaga gtttaacatg tggaaaaaca catggtgga acagatgcac    300 gaggatatca tttcccctgtg ggaccagagt ctgaaaccat gtgtcaaact tactcctctg    360
tgcgtgactc tccagtgtac aaactacgca cccaaccttt tgagtaatat gcggggcgag    420
ctcaagcagt gcagtttcaa tatgacaacc gaattgagag acaaaaaaca gaaagtatac    480
tccctcttct accggctgga cgtggtgcag atcaatgaga accaaggaaa tagaagcaac    540
aacagtaaca aggaataccg gctcataaat tgcaatacca gcgctattac gcaggcttgc    600
cctaaggtga gctttgagcc aatcccgata cattattgtg ccccggcagg cttcgctata    660
ctgaaatgca aggataagaa gtttaatggg acaggccctt gccctagcgt ttcaacggtc    720
caatgtaccc acgggatcaa gcccgtagtg tctacacagc tcctgctgaa cggcagcctg    780
gccgaagagg aggtcataat taggagcgag aacataacta caacgctaa aaacattctc    840 gtccagctca atacctgt gcagatcaac tgcacccggc caacaacaa caccgtgaag    900 tccattagaa ttggtccggg acaggcattt tactacttcg agatataat aggcgatatc    960 agaatggcgc actgtaacgt gagcaaggcc acctggaacg agaccctggg caaggtggtc   1020
aaacagttgc gcaagcactt tggaacaac accattattc ggtttgccca gtcttccggc   1080
ggcgaccttg aagtgaccac tcatagcttc aactgtggag gggagttttt ctattgcaat   1140
acatcaggcc tgttcaactc tacatggatc tcaaatacca gtgtccaggg gtcaaattcc   1200
accggtagca acgacagcat cgtcttgcct tgtcgaatca agcagatcat taatatgtgg   1260
```

-continued

```
cagaggattg gtcaggccat gtacgcacct ccaatacagg gagtcattcg gtgcgtcagc    1320
aatattactg gattgatcct caccagagat ggcgggagta ccaatagcac taccgaaact    1380
ttccgcccag gaggaggcga catgcgggat aattggagat cagagctgta taagtataag    1440
gtggtgaaaa ttgaacccct gggagtggcg ccaactagta gtaaacgcg agtggttggc     1500 cggagacggc ggcggagagc agtggggatt ggcgctgtct cactcggttt cctgggtgct    1560
gccggcagta caatgggcgc cgccagcatg acgctcacag tgcaggcccg gaatcttctt    1620
agcggaattg tgcaacaaca aagcaatctg ttgagagccc cggaaccgca gcaacatctg    1680
ttgaaggaca cacattgggg catcaagcag ctgcaagctc gggttctggc tgttgagcat    1740
tacctgagag accaacagct gctgggcata tggggatgct caggaaaact gatctgctgc    1800
accaatgtcc catggaacag ctcatggtca acaggaacc tgagcgagat ctgggataac     1860
atgacctggt tgcagtggga caaagaaatt agcaattaca cacagatcat ctacggcctc    1920
ctggaggaaa gccagaatca gcaggagaaa aatgagcagg atctgcttgc ccttgactga    1980
```

```
<210> SEQ ID NO 4
<211> LENGTH: 688
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Ala Met Lys Arg Gly Leu Cys Cys Val Leu Leu Cys Gly
1               5                   10                  15

Ala Val Phe Val Ser Pro Ala Gly Ser Asn Leu Trp Val Thr
                20                  25                  30

Val Tyr Tyr Gly Val Pro Val Trp Lys Asp Ala Glu Thr Thr Leu Phe
            35                  40                  45

Cys Ala Ser Asp Ala Lys Ala Tyr Glu Thr Glu Lys His Asn Val Trp
        50                  55                  60

Ala Thr His Ala Cys Val Pro Thr Asp Pro Asn Pro Gln Glu Ile His
65                  70                  75                  80

Leu Glu Asn Val Thr Glu Glu Phe Asn Met Trp Lys Asn Asn Met Val
                85                  90                  95

Glu Gln Met His Glu Asp Ile Ile Ser Leu Trp Asp Gln Ser Leu Lys
            100                 105                 110

Pro Cys Val Lys Leu Thr Pro Leu Cys Val Thr Leu Gln Cys Thr Asn
        115                 120                 125

Tyr Ala Pro Asn Leu Leu Ser Asn Met Arg Gly Glu Leu Lys Gln Cys
    130                 135                 140

Ser Phe Asn Met Thr Thr Glu Leu Arg Asp Lys Lys Gln Lys Val Tyr
145                 150                 155                 160

Ser Leu Phe Tyr Arg Leu Asp Val Val Gln Ile Asn Glu Asn Gln Gly
                165                 170                 175

Asn Arg Ser Asn Asn Ser Asn Lys Glu Tyr Arg Leu Ile Asn Cys Asn
            180                 185                 190

Thr Ser Ala Ile Thr Gln Ala Cys Pro Lys Val Ser Phe Glu Pro Ile
        195                 200                 205

Pro Ile His Tyr Cys Ala Pro Ala Gly Phe Ala Ile Leu Lys Cys Lys
    210                 215                 220

Asp Lys Lys Phe Asn Gly Thr Gly Pro Cys Pro Ser Val Ser Thr Val
225                 230                 235                 240
```

```
Gln Cys Thr His Gly Ile Lys Pro Val Val Ser Thr Gln Leu Leu Leu
                245                 250                 255

Asn Gly Ser Leu Ala Glu Glu Val Ile Ile Arg Ser Glu Asn Ile
            260                 265                 270

Thr Asn Asn Ala Lys Asn Ile Leu Val Gln Leu Asn Thr Pro Val Gln
                275                 280                 285

Ile Asn Cys Thr Arg Pro Asn Asn Asn Thr Val Lys Ser Ile Arg Ile
290                 295                 300

Gly Pro Gly Gln Ala Phe Tyr Tyr Phe Gly Asp Ile Ile Gly Asp Ile
305                 310                 315                 320

Arg Met Ala His Cys Asn Val Ser Lys Ala Thr Trp Asn Glu Thr Leu
                325                 330                 335

Gly Lys Val Val Lys Gln Leu Arg Lys His Phe Gly Asn Asn Thr Ile
            340                 345                 350

Ile Arg Phe Ala Gln Ser Ser Gly Gly Asp Leu Glu Val Thr Thr His
            355                 360                 365

Ser Phe Asn Cys Gly Gly Glu Phe Phe Tyr Cys Asn Thr Ser Gly Leu
    370                 375                 380

Phe Asn Ser Thr Trp Ile Ser Asn Thr Ser Val Gln Gly Ser Asn Ser
385                 390                 395                 400

Thr Gly Ser Asn Asp Ser Ile Val Leu Pro Cys Arg Ile Lys Gln Ile
                405                 410                 415

Ile Asn Met Trp Gln Arg Ile Gly Gln Ala Met Tyr Ala Pro Pro Ile
                420                 425                 430

Gln Gly Val Ile Arg Cys Val Ser Asn Ile Thr Gly Leu Ile Leu Thr
            435                 440                 445

Arg Asp Gly Gly Ser Thr Asn Ser Thr Thr Glu Thr Phe Arg Pro Gly
    450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Arg Cys Lys Arg
                485                 490                 495

Arg Val Val Gly Arg Arg Arg Arg Arg Ala Val Gly Ile Gly Ala
            500                 505                 510

Val Ser Leu Gly Phe Leu Gly Ala Ala Gly Ser Thr Met Gly Ala Ala
            515                 520                 525

Ser Met Thr Leu Thr Val Gln Ala Arg Asn Leu Leu Ser Gly Ile Val
    530                 535                 540

Gln Gln Gln Ser Asn Leu Leu Arg Ala Pro Glu Pro Gln His Leu
545                 550                 555                 560

Leu Lys Asp Thr His Trp Gly Ile Lys Gln Leu Gln Ala Arg Val Leu
                565                 570                 575

Ala Val Glu His Tyr Leu Arg Asp Gln Gln Leu Leu Gly Ile Trp Gly
            580                 585                 590

Cys Ser Gly Lys Leu Ile Cys Cys Thr Asn Val Pro Trp Asn Ser Ser
    595                 600                 605

Trp Ser Asn Arg Asn Leu Ser Glu Ile Trp Asp Asn Met Thr Trp Leu
610                 615                 620

Gln Trp Asp Lys Glu Ile Ser Asn Tyr Thr Gln Ile Ile Tyr Gly Leu
625                 630                 635                 640

Leu Glu Glu Ser Gln Asn Gln Gln Glu Lys Asn Glu Gln Asp Leu Leu
                645                 650                 655
```

Ala Leu Asp Gly Gly Gly Ser Gly Gly Ser Gly Gly Ser
        660             665             670

Gly Ser Gly Ala His Ile Val Met Val Asp Ala Tyr Lys Pro Thr Lys
        675             680             685

<210> SEQ ID NO 5
<211> LENGTH: 2067
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---:|
| atggacgcca tgaagagggg actttgctgt gttcttctgc tgtgtggcgc cgtgtttgtt | 60 |
| agccccgctg gggccggatc caacctgtgg gtcactgtgt attatggtgt gccagtgtgg | 120 |
| aaggatgcag agacaacact cttttgcgcc tccgacgcta agcatacga acggagaag | 180 |
| cacaacgtgt gggcgaccca tgcctgtgtc cctacagacc ctaaccctca ggaaattcat | 240 |
| cttgaaaatg tcacagaaga gtttaacatg tggaaaaaca acatggtgga acagatgcac | 300 |
| gaggatatca tttccctgtg ggaccagagt ctgaaaccat gtgtcaaact tactcctctg | 360 |
| tgcgtgactc tccagtgtac aaactacgca cccaaccttt tgagtaatat gcggggcgag | 420 |
| ctcaagcagt gcagtttcaa tatgacaacc gaattgagag acaaaaaaca gaaagtatac | 480 |
| tccctcttct accggctgga cgtggtgcag atcaatgaga accaaggaaa tagaagcaac | 540 |
| aacagtaaca aggaataccg gctcataaat tgcaatacca cgctattac gcaggcttgc | 600 |
| cctaaggtga gctttgagcc aatcccgata cattattgtg ccccggcagg cttcgctata | 660 |
| ctgaaatgca ggataagaa gtttaatggg acaggccctt gccctagcgt ttcaacggtc | 720 |
| caatgtaccc acgggatcaa gcccgtagtg tctacacagc tcctgctgaa cggcagcctg | 780 |
| gccgaagagg aggtcataat taggagcgag aacataacta acaacgctaa aacattctc | 840 |
| gtccagctca atacacctgt gcagatcaac tgcacccggc ccaacaacaa caccgtgaag | 900 |
| tccattagaa ttggtccggg acaggcattt tactacttcg agatataat aggcgatatc | 960 |
| agaatggcgc actgtaacgt gagcaaggcc acctggaacg agaccctggg caaggtggtc | 1020 |
| aaacagttgc gcaagcactt tgggaacaac accattattc ggtttgccca gtcttccggc | 1080 |
| ggcgaccttg aagtgaccac tcatagcttc aactgtggag gggagttttt ctattgcaat | 1140 |
| acatcaggcc tgttcaactc tacatggatc tcaaatacca gtgtccaggg gtcaaattcc | 1200 |
| accggtagca acgacagcat cgtcttgcct tgtcgaatca agcagatcat taatatgtgg | 1260 |
| cagaggattg gtcaggccat gtacgcacct ccaatacagg gagtcattcg gtgcgtcagc | 1320 |
| aatattactg gattgatcct caccagagat ggcgggagta ccaatagcac taccgaaact | 1380 |
| ttccgcccag gaggaggcga catgcgggat aattggagat cagagctgta aagtataag | 1440 |
| gtggtgaaaa ttgaacccct gggagtggcg ccaactagta gtaaacgcg agtggttggc | 1500 |
| cggagacggc ggcggagagc agtggggatt ggcgctgtct cactcggttt cctgggtgct | 1560 |
| gccggcagta caatgggcgc cgccagcatg acgctcacag tgcaggcccg gaatcttctt | 1620 |
| agcggaattg tgcaacaaca aagcaatctg ttgagagccc cggaaccgca gcaacatctg | 1680 |
| ttgaaggaca cacattgggg catcaagcag ctgcaagctc gggttctggc tgttgagcat | 1740 |
| tacctgagag accaacagct gctgggcata tgggatgct caggaaaact gatctgctgc | 1800 |
| accaatgtcc catggaacag ctcatggtca aacaggaacc tgagcgagat ctgggataac | 1860 |

-continued

```
atgacctggt tgcagtggga caaagaaatt agcaattaca cacagatcat ctacggcctc    1920
ctggaggaaa gccagaatca gcaggagaaa aatgagcagg atctgcttgc ccttgacggt    1980
ggaggcggtt caggcggcgg atctggcggt gggagcggtt cgggagccca tatagtgatg    2040
gttgatgcct ataaaccgac caagtga                                        2067
```

<210> SEQ ID NO 6
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Ala Met Lys Arg Gly Leu Cys Cys Val Leu Leu Cys Gly
1               5                   10                  15

Ala Val Phe Val Ser Pro Ala Gly Ser Asn Leu Trp Val Thr
                20                  25                  30

Val Tyr Tyr Gly Val Pro Val Trp Lys Asp Ala Glu Thr Thr Leu Phe
                35                  40                  45

Cys Ala Ser Asp Ala Lys Ala Tyr Glu Thr Glu Lys His Asn Val Trp
    50                  55                  60

Ala Thr His Ala Cys Val Pro Thr Asp Pro Asn Pro Gln Glu Ile His
65                  70                  75                  80

Leu Glu Asn Val Thr Glu Glu Phe Asn Met Trp Lys Asn Asn Met Val
                85                  90                  95

Glu Gln Met His Glu Asp Ile Ile Ser Leu Trp Asp Gln Ser Leu Lys
                100                 105                 110

Pro Cys Val Lys Leu Thr Pro Leu Cys Val Thr Leu Gln Cys Thr Asn
            115                 120                 125

Tyr Ala Pro Asn Leu Leu Ser Asn Met Arg Gly Glu Leu Lys Gln Cys
    130                 135                 140

Ser Phe Asn Met Thr Thr Glu Leu Arg Asp Lys Lys Gln Lys Val Tyr
145                 150                 155                 160

Ser Leu Phe Tyr Arg Leu Asp Val Val Gln Ile Asn Glu Asn Gln Gly
                165                 170                 175

Asn Arg Ser Asn Asn Ser Asn Lys Glu Tyr Arg Leu Ile Asn Cys Asn
            180                 185                 190

Thr Ser Ala Ile Thr Gln Ala Cys Pro Lys Val Ser Phe Glu Pro Ile
        195                 200                 205

Pro Ile His Tyr Cys Ala Pro Ala Gly Phe Ala Ile Leu Lys Cys Lys
    210                 215                 220

Asn Lys Thr Phe Asn Gly Thr Gly Pro Cys Pro Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Glu Val Ile Ile Arg Ser Glu Asn Ile
            260                 265                 270

Thr Asn Asn Ala Lys Asn Ile Leu Val Gln Leu Asn Thr Ser Val Gln
        275                 280                 285

Ile Asn Cys Thr Arg Pro Asn Asn Asn Thr Val Lys Ser Ile Arg Ile
    290                 295                 300

Gly Pro Gly Gln Ala Phe Tyr Tyr Phe Gly Asp Ile Ile Gly Asp Ile
305                 310                 315                 320

```
Arg Met Ala His Cys Asn Val Ser Lys Ala Thr Trp Asn Glu Thr Leu
            325                 330                 335

Gly Asn Val Ser Lys Gln Leu Arg Lys His Phe Gly Asn Asn Thr Ile
            340                 345                 350

Ile Arg Phe Ala Gln Ser Ser Gly Gly Asp Leu Glu Val Thr Thr His
            355                 360                 365

Ser Phe Asn Cys Gly Gly Glu Phe Phe Tyr Cys Asn Thr Ser Gly Leu
    370                 375                 380

Phe Asn Ser Thr Trp Ile Ser Asn Thr Ser Val Gln Gly Ser Asn Ser
385                 390                 395                 400

Thr Gly Ser Asn Asp Ser Ile Val Leu Pro Cys Arg Ile Lys Gln Ile
                405                 410                 415

Ile Asn Met Trp Gln Arg Ile Gly Gln Ala Met Tyr Ala Pro Pro Ile
            420                 425                 430

Gln Gly Val Ile Arg Cys Val Ser Asn Ile Thr Gly Leu Ile Leu Thr
            435                 440                 445

Arg Asp Gly Gly Ser Thr Asn Ser Thr Thr Glu Thr Phe Arg Pro Gly
    450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Arg Cys Lys Arg
                485                 490                 495

Arg Val Val Gly Arg Arg Arg Arg Arg Ala Val Gly Ile Gly Ala
            500                 505                 510

Val Ser Leu Gly Phe Leu Gly Ala Ala Gly Ser Thr Met Gly Ala Ala
            515                 520                 525

Ser Met Thr Leu Thr Val Gln Ala Arg Asn Leu Leu Ser Gly Ile Val
    530                 535                 540

Gln Gln Gln Ser Asn Leu Leu Arg Ala Pro Glu Pro Gln His Leu
545                 550                 555                 560

Leu Lys Asp Thr His Trp Gly Ile Lys Gln Leu Gln Ala Arg Val Leu
                565                 570                 575

Ala Val Glu His Tyr Leu Arg Asp Gln Gln Leu Leu Gly Ile Trp Gly
            580                 585                 590

Cys Ser Gly Lys Leu Ile Cys Cys Thr Asn Val Pro Trp Asn Ser Ser
            595                 600                 605

Trp Ser Asn Arg Asn Leu Ser Glu Ile Trp Asp Asn Met Thr Trp Leu
    610                 615                 620

Gln Trp Asp Lys Glu Ile Ser Asn Tyr Thr Gln Ile Ile Tyr Gly Leu
625                 630                 635                 640

Leu Glu Glu Ser Gln Asn Gln Gln Glu Lys Asn Glu Gln Asp Leu Leu
                645                 650                 655

Ala Leu Asp

<210> SEQ ID NO 7
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggacgcca tgaagagggg actttgctgt gttcttctgc tgtgtggcgc cgtgtttgtt      60
agccccgctg gggccggatc caacctgtgg gtcactgtgt attatggtgt gccagtgtgg     120
```

```
aaggatgcag agacaacact cttttgcgcc tccgacgcta agcatacga aacggagaag    180 cacaacgtgt gggcgaccca tgcctgtgtc cctacagacc ctaaccctca ggaaattcat    240
cttgaaaatg tcacagaaga gtttaacatg tggaaaaaca acatggtgga acagatgcac    300
gaggatatca tttccctgtg ggaccagagt ctgaaaccat gtgtcaaact tactcctctg    360
tgcgtgactc tccagtgtac aaactacgca cccaaccttt tgagtaatat gcggggcgag    420
ctcaagcagt gcagtttcaa tatgacaacc gaattgagag acaaaaaaca gaaagtatac    480
tccctcttct accggctgga cgtggtgcag atcaatgaga accaaggaaa tagaagcaac    540
aacagtaaca aggaataccg gctcataaat tgcaatacca cgctattac gcaggcttgc    600 cctaaggtga gctttgagcc aatcccgata cattattgtg ccccggcagg cttcgctata    660
ctgaaatgca agaataagac gtttaatggg acaggccctt gccctaacgt ttcaacggtc    720
caatgtaccc acgggatcaa gcccgtagtg tctacacagc tcctgctgaa cggcagcctg    780
gccgaagagg aggtcataat taggagcgag aacataacta acaacgctaa aaacattctc    840
gtccagctca atacaagtgt gcagatcaac tgcaccgcc caacaacaa caccgtgaag    900 tccattagaa ttggtccggg acaggcattt tactacttcg agatataat aggcgatatc    960 agaatggcgc actgtaacgt gagcaaggcc acctggaacg agaccctggg caatgtgagc   1020
aaacagttgc gcaagcactt tgggaacaac accattattc ggtttgccca gtcttccggc   1080
ggcgaccttg aagtgaccac tcatagcttc aactgtggag gggagttttt ctattgcaat   1140
acatcaggcc tgttcaactc tacatggatc tcaaatacca gtgtccaggg gtcaaattcc   1200
accggtagca acgacagcat cgtcttgcct tgtcgaatca agcagatcat taatatgtgg   1260
cagaggattg tcaggccat gtacgcacct ccaatacagg gagtcattcg gtgcgtcagc   1320
aatattactg gattgatcct caccagagat ggcgggagta ccaatagcac taccgaaact   1380
ttccgcccag gaggaggcga catgcgggat aattggagat cagagctgta taagtataag   1440
gtggtgaaaa ttgaacccct gggagtggcg ccaactagat gtaaacggcg agtggttggc   1500
cggagacggc ggcggagagc agtggggatt ggcgctgtct cactcggttt cctgggtgct   1560
gccggcagta caatgggcgc cgccagcatg acgctcacag tgcaggcccg gaatcttctt   1620
agcggaattg tgcaacaaca aagcaatctg ttgagagccc cggaaccgca gcaacatctg   1680
ttgaaggaca cacattgggg catcaagcag ctgcaagctc gggttctggc tgttgagcat   1740
tacctgagag accaacagct gctgggcata tggggatgct caggaaaact gatctgctgc   1800
accaatgtcc catggaacag ctcatggtca aacaggaacc tgagcgagat ctgggataac   1860
atgacctggt tgcagtggga caaagaaatt agcaattaca cacagatcat ctacggcctc   1920
ctggaggaaa gccagaatca gcaggagaaa aatgagcagg atctgcttgc ccttgactga   1980
```

<210> SEQ ID NO 8
<211> LENGTH: 688
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Ala Met Lys Arg Gly Leu Cys Cys Val Leu Leu Leu Cys Gly
1               5                   10                  15

Ala Val Phe Val Ser Pro Ala Gly Ala Gly Ser Asn Leu Trp Val Thr
            20                  25                  30

```
Val Tyr Tyr Gly Val Pro Val Trp Lys Asp Ala Glu Thr Thr Leu Phe
             35                  40                  45

Cys Ala Ser Asp Ala Lys Ala Tyr Glu Thr Glu Lys His Asn Val Trp
 50                  55                  60

Ala Thr His Ala Cys Val Pro Thr Asp Pro Asn Pro Gln Glu Ile His
 65                  70                  75                  80

Leu Glu Asn Val Thr Glu Glu Phe Asn Met Trp Lys Asn Asn Met Val
                 85                  90                  95

Glu Gln Met His Glu Asp Ile Ile Ser Leu Trp Asp Gln Ser Leu Lys
                100                 105                 110

Pro Cys Val Lys Leu Thr Pro Leu Cys Val Thr Leu Gln Cys Thr Asn
            115                 120                 125

Tyr Ala Pro Asn Leu Leu Ser Asn Met Arg Gly Glu Leu Lys Gln Cys
        130                 135                 140

Ser Phe Asn Met Thr Thr Glu Leu Arg Asp Lys Lys Gln Lys Val Tyr
145                 150                 155                 160

Ser Leu Phe Tyr Arg Leu Asp Val Val Gln Ile Asn Glu Asn Gln Gly
                165                 170                 175

Asn Arg Ser Asn Asn Ser Asn Lys Glu Tyr Arg Leu Ile Asn Cys Asn
            180                 185                 190

Thr Ser Ala Ile Thr Gln Ala Cys Pro Lys Val Ser Phe Glu Pro Ile
        195                 200                 205

Pro Ile His Tyr Cys Ala Pro Ala Gly Phe Ala Ile Leu Lys Cys Lys
    210                 215                 220

Asn Lys Thr Phe Asn Gly Thr Gly Pro Cys Pro Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Val Ile Ile Arg Ser Glu Asn Ile
            260                 265                 270

Thr Asn Asn Ala Lys Asn Ile Leu Val Gln Leu Asn Thr Ser Val Gln
    275                 280                 285

Ile Asn Cys Thr Arg Pro Asn Asn Asn Thr Val Lys Ser Ile Arg Ile
290                 295                 300

Gly Pro Gly Gln Ala Phe Tyr Tyr Phe Gly Asp Ile Ile Gly Asp Ile
305                 310                 315                 320

Arg Met Ala His Cys Asn Val Ser Lys Ala Thr Trp Asn Glu Thr Leu
                325                 330                 335

Gly Asn Val Ser Lys Gln Leu Arg Lys His Phe Gly Asn Asn Thr Ile
            340                 345                 350

Ile Arg Phe Ala Gln Ser Ser Gly Gly Asp Leu Glu Val Thr Thr His
        355                 360                 365

Ser Phe Asn Cys Gly Gly Glu Phe Phe Tyr Cys Asn Thr Ser Gly Leu
    370                 375                 380

Phe Asn Ser Thr Trp Ile Ser Asn Thr Ser Val Gln Gly Ser Asn Ser
385                 390                 395                 400

Thr Gly Ser Asn Asp Ser Ile Val Leu Pro Cys Arg Ile Lys Gln Ile
                405                 410                 415

Ile Asn Met Trp Gln Arg Ile Gly Gln Ala Met Tyr Ala Pro Pro Ile
            420                 425                 430

Gln Gly Val Ile Arg Cys Val Ser Asn Ile Thr Gly Leu Ile Leu Thr
        435                 440                 445
```

| | | | | | | | | | | | | |
|---|---|---|---|---|---|---|---|---|---|---|---|---|
|Arg|Asp|Gly|Gly|Ser|Thr|Asn|Ser|Thr|Thr|Glu|Thr|Phe|Arg|Pro|Gly|
| |450| | | |455| | | |460| | | | | | |

Arg Asp Gly Gly Ser Thr Asn Ser Thr Thr Glu Thr Phe Arg Pro Gly
    450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Arg Cys Lys Arg
                485                 490                 495

Arg Val Val Gly Arg Arg Arg Arg Ala Val Gly Ile Gly Ala
                500                 505                 510

Val Ser Leu Gly Phe Leu Gly Ala Ala Gly Ser Thr Met Gly Ala Ala
            515                 520                 525

Ser Met Thr Leu Thr Val Gln Ala Arg Asn Leu Leu Ser Gly Ile Val
    530                 535                 540

Gln Gln Gln Ser Asn Leu Leu Arg Ala Pro Glu Pro Gln Gln His Leu
545                 550                 555                 560

Leu Lys Asp Thr His Trp Gly Ile Lys Gln Leu Gln Ala Arg Val Leu
                565                 570                 575

Ala Val Glu His Tyr Leu Arg Asp Gln Gln Leu Leu Gly Ile Trp Gly
            580                 585                 590

Cys Ser Gly Lys Leu Ile Cys Cys Thr Asn Val Pro Trp Asn Ser Ser
    595                 600                 605

Trp Ser Asn Arg Asn Leu Ser Glu Ile Trp Asp Asn Met Thr Trp Leu
    610                 615                 620

Gln Trp Asp Lys Glu Ile Ser Asn Tyr Thr Gln Ile Ile Tyr Gly Leu
625                 630                 635                 640

Leu Glu Glu Ser Gln Asn Gln Gln Glu Lys Asn Glu Gln Asp Leu Leu
                645                 650                 655

Ala Leu Asp Gly Gly Gly Gly Ser Gly Gly Gly Ser Gly Gly Gly Ser
            660                 665                 670

Gly Ser Gly Ala His Ile Val Met Val Asp Ala Tyr Lys Pro Thr Lys
    675                 680                 685

<210> SEQ ID NO 9
<211> LENGTH: 2067
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atggacgcca tgaagagggg actttgctgt gttcttctgc tgtgtggcgc cgtgtttgtt      60
agccccgctg gggccggatc caacctgtgg gtcactgtgt attatggtgt gccagtgtgg     120
aaggatgcag agacaacact cttttgcgcc tccgacgcta aagcatacga aacggagaag     180
cacaacgtgt gggcgaccca tgcctgtgtc cctacagacc ctaaccctca ggaaattcat     240
cttgaaaatg tcacagaaga gtttaacatg tggaaaaaca acatggtgga acagatgcac     300
gaggatatca tttccctgtg ggaccagagt ctgaaaccat gtgtcaaact tactcctctg     360
tgcgtgactc tccagtgtac aaactacgca cccaaccttt tgagtaatat gcggggcgag     420
ctcaagcagt gcagtttcaa tatgacaacc gaattgagag acaaaaaaca gaaagtatac     480
tccctcttct accggctgga cgtggtgcag atcaatgaga accaaggaaa tagaagcaac     540
aacagtaaca aggaataccg gctcataaat tgcaatacca gcgctattac gcaggcttgc     600
cctaaggtga gctttgagcc aatcccgata cattattgtg ccccggcagg cttcgctata     660
ctgaaatgca gaataagac gtttaatggg acaggccctt gccctaacgt ttcaacggtc     720

-continued

```
caatgtaccc acgggatcaa gcccgtagtg tctacacagc tcctgctgaa cggcagcctg      780
gccgaagagg aggtcataat taggagcgag aacataacta acaacgctaa aaacattctc      840
gtccagctca atacaagtgt gcagatcaac tgcacccggc ccaacaacaa caccgtgaag      900
tccattagaa ttggtccggg acaggcattt tactacttcg agatataat aggcgatatc       960
agaatggcgc actgtaacgt gagcaaggcc acctggaacg agaccctggg caatgtgagc     1020
aaacagttgc gcaagcactt tgggaacaac accattattc ggtttgccca gtcttccggc     1080
ggcgaccttg aagtgaccac tcatagcttc aactgtggag gggagttttt ctattgcaat     1140
acatcaggcc tgttcaactc tacatggatc tcaaatacca gtgtccaggg gtcaaattcc     1200
accggtagca acgacagcat cgtcttgcct tgtcgaatca agcagatcat taatatgtgg     1260
cagaggattg tcaggccat gtacgcacct ccaatacagg gagtcattcg gtgcgtcagc      1320
aatattactg gattgatcct caccagagat ggcgggagta ccaatagcac taccgaaact     1380
ttccgcccag gaggaggcga catgcgggat aattggagat cagagctgta taagtataag     1440
gtggtgaaaa ttgaacccct gggagtggcg ccaactagat gtaaacggcg agtggttggc     1500
cggagacggc ggcggagagc agtggggatt ggcgctgtct cactcggttt cctgggtgct     1560
gccggcagta caatgggcgc cgccagcatg acgctcacag tgcaggcccg gaatcttctt     1620
agcggaattg tgcaacaaca aagcaatctg ttgagagccc cggaaccgca gcaacatctg     1680
ttgaaggaca cacattgggg catcaagcag ctgcaagctc gggttctggc tgttgagcat     1740
tacctgagag accaacagct gctgggcata tggggatgct caggaaaact gatctgctgc     1800
accaatgtcc catggaacag ctcatggtca acaggaacc tgagcgagat ctgggataac       1860
atgacctggt tgcagtggga caaagaaatt agcaattaca cacagatcat ctacggcctc     1920
ctggaggaaa gccagaatca gcaggagaaa atgagcagg atctgcttgc ccttgacggt       1980
ggaggcggtt caggcggcgg atctggcggt gggagcggtt cgggagccca tatagtgatg     2040
gttgatgcct ataaaccgac caagtga                                         2067
```

<210> SEQ ID NO 10
<211> LENGTH: 45
<212> TYPE: PRT
<213> ORGANISM: Human immunodeficiency virus

<400> SEQUENCE: 10

```
Lys Gly Lys Gly Lys Gly Lys Gly Lys Gly Cys Thr Arg Pro Asn Asn
1               5                   10                  15

Asn Thr Arg Lys Ser Ile Arg Ile Gly Pro Gly Gln Thr Phe Tyr Ala
            20                  25                  30

Thr Gly Asp Ile Ile Gly Asp Ile Arg Gln Ala His Cys
        35                  40                  45
```

<210> SEQ ID NO 11
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Asp Ala Met Lys Arg Gly Leu Cys Cys Val Leu Leu Leu Cys Gly
1               5                   10                  15

Ala Val Phe Val Ser Pro Ala Gly Ala Gly Ser Asn Leu Trp Val Thr
```

```
            20                  25                  30
Val Tyr Tyr Gly Val Pro Val Trp Lys Asp Ala Glu Thr Thr Leu Phe
            35                  40                  45

Cys Ala Ser Asp Ala Lys Ala Tyr Glu Thr Glu Lys His Asn Val Trp
 50                  55                  60

Ala Thr His Ala Cys Val Pro Thr Asp Pro Asn Pro Gln Glu Ile His
 65                  70                  75                  80

Leu Glu Asn Val Thr Glu Glu Phe Asn Met Trp Lys Asn Asn Met Val
                    85                  90                  95

Glu Gln Met His Glu Asp Ile Ile Ser Leu Trp Asp Gln Ser Leu Lys
                100                 105                 110

Pro Cys Val Lys Leu Thr Pro Leu Cys Val Thr Leu Gln Cys Thr Asn
                115                 120                 125

Tyr Ala Pro Asn Leu Leu Ser Asn Met Arg Gly Glu Leu Lys Gln Cys
                130                 135                 140

Ser Phe Asn Met Thr Thr Glu Leu Arg Asp Lys Lys Gln Lys Val Tyr
145                 150                 155                 160

Ser Leu Phe Tyr Arg Leu Asp Val Val Gln Ile Asn Glu Asn Gln Gly
                165                 170                 175

Asn Arg Ser Asn Asn Ser Asn Lys Glu Tyr Arg Leu Ile Asn Cys Asn
                180                 185                 190

Thr Ser Ala Ile Thr Gln Ala Cys Pro Lys Val Ser Phe Glu Pro Ile
                195                 200                 205

Pro Ile His Tyr Cys Ala Pro Ala Gly Phe Ala Ile Leu Lys Cys Lys
                210                 215                 220

Asn Lys Thr Phe Asn Gly Thr Gly Pro Cys Pro Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Val Ile Ile Arg Ser Glu Asn Ile
                260                 265                 270

Thr Asn Asn Ala Lys Asn Ile Leu Val Gln Leu Asn Thr Pro Val Gln
                275                 280                 285

Ile Asn Cys Thr Arg Pro Asn Asn Asn Thr Val Lys Ser Ile Arg Ile
                290                 295                 300

Gly Pro Gly Gln Ala Phe Tyr Tyr Phe Gly Asp Ile Ile Gly Asp Ile
305                 310                 315                 320

Arg Met Ala His Cys Asn Val Ser Lys Ala Thr Trp Asn Glu Thr Leu
                325                 330                 335

Gly Asn Val Ser Lys Gln Leu Arg Lys His Phe Gly Asn Asn Thr Ile
                340                 345                 350

Ile Arg Phe Ala Gln Ser Ser Gly Gly Asp Leu Glu Val Thr Thr His
                355                 360                 365

Ser Phe Asn Cys Gly Gly Glu Phe Phe Tyr Cys Asn Thr Ser Gly Leu
                370                 375                 380

Phe Asn Ser Thr Trp Ile Ser Asn Thr Ser Val Gln Gly Ser Asn Ser
385                 390                 395                 400

Thr Gly Ser Asn Asp Ser Ile Val Leu Pro Cys Arg Ile Lys Gln Ile
                405                 410                 415

Ile Asn Met Trp Gln Arg Ile Gly Gln Ala Met Tyr Ala Pro Pro Ile
                420                 425                 430

Gln Gly Val Ile Arg Cys Val Ser Asn Ile Thr Gly Leu Ile Leu Thr
                435                 440                 445
```

```
Arg Asp Gly Gly Ser Thr Asn Ser Thr Thr Glu Thr Phe Arg Pro Gly
        450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Arg Cys Lys Arg
                485                 490                 495

Arg Val Val Gly Arg Arg Arg Arg Ala Val Gly Ile Gly Ala
                500                 505                 510

Val Ser Leu Gly Phe Leu Gly Ala Ala Gly Ser Thr Met Gly Ala Ala
            515                 520                 525

Ser Met Thr Leu Thr Val Gln Ala Arg Asn Leu Leu Ser Gly Ile Val
        530                 535                 540

Gln Gln Gln Ser Asn Leu Leu Arg Ala Pro Glu Pro Gln Gln His Leu
545                 550                 555                 560

Leu Lys Asp Thr His Trp Gly Ile Lys Gln Leu Gln Ala Arg Val Leu
                565                 570                 575

Ala Val Glu His Tyr Leu Arg Asp Gln Gln Leu Leu Gly Ile Trp Gly
                580                 585                 590

Cys Ser Gly Lys Leu Ile Cys Cys Thr Asn Val Pro Trp Asn Ser Ser
            595                 600                 605

Trp Ser Asn Arg Asn Leu Ser Glu Ile Trp Asp Asn Met Thr Trp Leu
        610                 615                 620

Gln Trp Asp Lys Glu Ile Ser Asn Tyr Thr Gln Ile Ile Tyr Gly Leu
625                 630                 635                 640

Leu Glu Glu Ser Gln Asn Gln Gln Glu Lys Asn Glu Gln Asp Leu Leu
                645                 650                 655

Ala Leu Asp

<210> SEQ ID NO 12
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggacgcca tgaagagggg actttgctgt gttcttctgc tgtgtggcgc cgtgtttgtt      60
agccccgctg ggccggatc aacctgtgg gtcactgtgt attatggtgt gccagtgtgg       120
aaggatgcag agacaacact cttttgcgcc tccgacgcta agcatacga acggagaag       180 cacaacgtgt gggcgaccca tgcctgtgtc cctacagacc ctaaccctca ggaaattcat     240
cttgaaaatg tcacagaaga gtttaacatg tggaaaaaca acatggtgga acagatgcac    300
gaggatatca tttccctgtg ggaccagagt ctgaaaccat gtgtcaaact tactcctctg    360
tgcgtgactc tccagtgtac aaactacgca cccaaccttt tgagtaatat gcggggcgag    420
ctcaagcagt gcagtttcaa tatgacaacc gaattgagag acaaaaaaca gaaagtatac    480
tccctcttct accggctgga cgtggtgcag atcaatgaga accaaggaaa tagaagcaac    540
aacagtaaca aggaatcccg gctcataaat tgcaatacca gcgctattac gcaggcttgc    600
cctaaggtga gctttgagcc aatcccgata cattattgtg ccccggcagg cttcgctata    660
ctgaaatgca gaataagac gtttaatggg acaggccctt gcctaacgt ttcaacggtc     720 caatgtaccc acgggatcaa gcccgtagtg tctacacagc tcctgctgaa cggcagcctg    780
```

```
gccgaagagg aggtcataat taggagcgag aacataacta acaacgctaa aaacattctc    840
gtccagctca atacacctgt gcagatcaac tgcacccggc ccaacaacaa caccgtgaag    900
tccattagaa ttggtccggg acaggcattt tactacttcg agatataat aggcgatatc    960 agaatggcgc actgtaacgt gagcaaggcc acctggaacg agaccctggg caatgtgagc   1020
aaacagttgc gcaagcactt tgggaacaac accattattc ggtttgccca gtcttccggc   1080
ggcgaccttg aagtgaccac tcatagcttc aactgtggag gggagttttt ctattgcaat   1140
acatcaggcc tgttcaactc tacatggatc tcaaatacca gtgtccaggg gtcaaattcc   1200
accggtagca acgacagcat cgtcttgcct tgtcgaatca agcagatcat taatatgtgg   1260
cagaggattg gtcaggccat gtacgcacct ccaatacagg gagtcattcg gtgcgtcagc   1320
aatattactg gattgatcct caccagagat ggcgggagta ccaatagcac taccgaaact   1380
ttccgcccag gaggaggcga catgcgggat aattggagat cagagctgta taagtataag   1440
gtggtgaaaa ttgaacccct gggagtggcg ccaactagta gtaaacgcg agtggttggc   1500 cggagacggc ggcggagagc agtggggatt ggcgctgtct cactcggttt cctgggtgct   1560
gccggcagta caatgggcgc cgccagcatg acgctcacag tgcaggcccg gaatcttctt   1620
agcggaattg tgcaacaaca aagcaatctg ttgagagccc cggaaccgca gcaacatctg   1680
ttgaaggaca cacattgggg catcaagcag ctgcaagctc gggttctggc tgttgagcat   1740
tacctgagag accaacagct gctgggcata tggggatgct caggaaaact gatctgctgc   1800
accaatgtcc catggaacag ctcatggtca acaggaacc tgagcgagat ctgggataac   1860
atgacctggt tgcagtggga caaagaaatt agcaattaca cacagatcat ctacggcctc   1920
ctggaggaaa gccagaatca gcaggagaaa aatgagcagg atctgcttgc ccttgactga   1980
```

<210> SEQ ID NO 13
<211> LENGTH: 688
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 13

Met Asp Ala Met Lys Arg Gly Leu Cys Cys Val Leu Leu Cys Gly
1               5                   10                  15

Ala Val Phe Val Ser Pro Ala Gly Ala Gly Ser Asn Leu Trp Val Thr
            20                  25                  30

Val Tyr Tyr Gly Val Pro Val Trp Lys Asp Ala Glu Thr Thr Leu Phe
        35                  40                  45

Cys Ala Ser Asp Ala Lys Ala Tyr Glu Thr Glu Lys His Asn Val Trp
    50                  55                  60

Ala Thr His Ala Cys Val Pro Thr Asp Pro Asn Pro Gln Glu Ile His
65                  70                  75                  80

Leu Glu Asn Val Thr Glu Glu Phe Asn Met Trp Lys Asn Asn Met Val
                85                  90                  95

Glu Gln Met His Glu Asp Ile Ile Ser Leu Trp Asp Gln Ser Leu Lys
            100                 105                 110

Pro Cys Val Lys Leu Thr Pro Leu Cys Val Thr Leu Gln Cys Thr Asn
        115                 120                 125

Tyr Ala Pro Asn Leu Leu Ser Asn Met Arg Gly Glu Leu Lys Gln Cys
    130                 135                 140

Ser Phe Asn Met Thr Thr Glu Leu Arg Asp Lys Lys Gln Lys Val Tyr

```
            145                 150                 155                 160
        Ser Leu Phe Tyr Arg Leu Asp Val Val Gln Ile Asn Glu Asn Gln Gly
                        165                 170                 175

Asn Arg Ser Asn Asn Ser Asn Lys Glu Tyr Arg Leu Ile Asn Cys Asn
                        180                 185                 190

Thr Ser Ala Ile Thr Gln Ala Cys Pro Lys Val Ser Phe Glu Pro Ile
                        195                 200                 205

Pro Ile His Tyr Cys Ala Pro Ala Gly Phe Ala Ile Leu Lys Cys Lys
                        210                 215                 220

Asn Lys Thr Phe Asn Gly Thr Gly Pro Cys Pro Asn Val Ser Thr Val
        225                 230                 235                 240

Gln Cys Thr His Gly Ile Lys Pro Val Val Ser Thr Gln Leu Leu Leu
                        245                 250                 255

Asn Gly Ser Leu Ala Glu Glu Val Ile Ile Arg Ser Glu Asn Ile
                        260                 265                 270

Thr Asn Asn Ala Lys Asn Ile Leu Val Gln Leu Asn Thr Pro Val Gln
                        275                 280                 285

Ile Asn Cys Thr Arg Pro Asn Asn Thr Val Lys Ser Ile Arg Ile
                        290                 295                 300

Gly Pro Gly Gln Ala Phe Tyr Tyr Phe Gly Asp Ile Ile Gly Asp Ile
        305                 310                 315                 320

Arg Met Ala His Cys Asn Val Ser Lys Ala Thr Trp Asn Glu Thr Leu
                        325                 330                 335

Gly Asn Val Ser Lys Gln Leu Arg Lys His Phe Gly Asn Asn Thr Ile
                        340                 345                 350

Ile Arg Phe Ala Gln Ser Ser Gly Gly Asp Leu Glu Val Thr Thr His
                        355                 360                 365

Ser Phe Asn Cys Gly Gly Glu Phe Phe Tyr Cys Asn Thr Ser Gly Leu
                        370                 375                 380

Phe Asn Ser Thr Trp Ile Ser Asn Thr Ser Val Gln Gly Ser Asn Ser
        385                 390                 395                 400

Thr Gly Ser Asn Asp Ser Ile Val Leu Pro Cys Arg Ile Lys Gln Ile
                        405                 410                 415

Ile Asn Met Trp Gln Arg Ile Gly Gln Ala Met Tyr Ala Pro Pro Ile
                        420                 425                 430

Gln Gly Val Ile Arg Cys Val Ser Asn Ile Thr Gly Leu Ile Leu Thr
                        435                 440                 445

Arg Asp Gly Gly Ser Thr Asn Ser Thr Thr Glu Thr Phe Arg Pro Gly
        450                 455                 460

Gly Gly Asp Met Arg Asp Asn Trp Arg Ser Glu Leu Tyr Lys Tyr Lys
        465                 470                 475                 480

Val Val Lys Ile Glu Pro Leu Gly Val Ala Pro Thr Arg Cys Lys Arg
                        485                 490                 495

Arg Val Val Gly Arg Arg Arg Arg Ala Val Gly Ile Gly Ala
                        500                 505                 510

Val Ser Leu Gly Phe Leu Gly Ala Ala Gly Ser Thr Met Gly Ala Ala
                        515                 520                 525

Ser Met Thr Leu Thr Val Gln Ala Arg Asn Leu Leu Ser Gly Ile Val
                        530                 535                 540

Gln Gln Gln Ser Asn Leu Leu Arg Ala Pro Glu Pro Gln Gln His Leu
        545                 550                 555                 560

Leu Lys Asp Thr His Trp Gly Ile Lys Gln Leu Gln Ala Arg Val Leu
                        565                 570                 575
```

```
Ala Val Glu His Tyr Leu Arg Asp Gln Gln Leu Leu Gly Ile Trp Gly
            580                 585                 590

Cys Ser Gly Lys Leu Ile Cys Cys Thr Asn Val Pro Trp Asn Ser Ser
        595                 600                 605

Trp Ser Asn Arg Asn Leu Ser Glu Ile Trp Asp Asn Met Thr Trp Leu
610                 615                 620

Gln Trp Asp Lys Glu Ile Ser Asn Tyr Thr Gln Ile Ile Tyr Gly Leu
625                 630                 635                 640

Leu Glu Glu Ser Gln Asn Gln Gln Lys Asn Glu Gln Asp Leu Leu
                645                 650                 655

Ala Leu Asp Gly Gly Gly Ser Gly Gly Ser Gly Gly Ser
            660                 665                 670

Gly Ser Gly Ala His Ile Val Met Val Asp Ala Tyr Lys Pro Thr Lys
        675                 680                 685
```

<210> SEQ ID NO 14
<211> LENGTH: 2067
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 14

```
atggacgcca tgaagagggg actttgctgt gttcttctgc tgtgtggcgc cgtgtttgtt      60
agccccgctg gggccggatc caacctgtgg gtcactgtgt attatggtgt gccagtgtgg     120
aaggatgcag agacaacact cttttgcgcc tccgacgcta agcatacga acggagaag      180 cacaacgtgt gggcgaccca tgcctgtgtc cctacagacc ctaaccctca ggaaattcat     240
cttgaaaatg tcacagaaga gtttaacatg tggaaaaaca catggtgga acagatgcac     300 gaggatatca tttccctgtg gaccagagt ctgaaaccat gtgtcaaact tactcctctg     360
tgcgtgactc tccagtgtac aaactacgca cccaaccttt tgagtaatat gcggggcgag     420
ctcaagcagt gcagtttcaa tatgacaacc gaattgagag acaaaaaaca gaaagtatac     480
tccctcttct accggctgga cgtggtgcag atcaatgaga ccaaggaaa tagaagcaac     540 aacagtaaca aggaatacccg gctcataaat tgcaatacca gcgctattac gcaggcttgc     600
cctaaggtga gctttgagcc aatcccgata cattattgtg ccccggcagg cttcgctata     660
ctgaaatgca gaataagac gtttaatggg acaggccctt gccctaacgt ttcaacggtc     720
caatgtaccc acgggatcaa gcccgtagtg tctacacagc tcctgctgaa cggcagcctg     780
gccgaagagg aggtcataat taggagcgag aacataacta acaacgctaa aaacattctc     840
gtccagctca atacccctgt gcagatcaac tgcaccccgg ccaacaacaa caccgtgaag     900
tccattagaa ttggtccggg acaggcattt tactacttcg agatataat aggcgatatc     960 agaatggcgc actgtaacgt gagcaaggcc acctggaacg agaccctggg caatgtgagc    1020
aaacagttgc gcaagcactt tgggaacaac accattattc ggtttgccca gtcttccggc    1080
ggcgaccttg aagtgaccac tcatagcttc aactgtggag gggagttttt ctattgcaat    1140
acatcaggcc tgttcaactc tacatggatc tcaaatacca gtgtccaggg gtcaaattcc    1200
accggtagca acgacagcat cgtcttgcct tgtcgaatca agcagatcat taatatgtgg    1260
cagaggattg gtcaggccat gtacgcacct ccaatacagg gagtcattcg gtgcgtcagc    1320
aatattactg gattgatcct caccagagat ggcgggagta ccaatagcac taccgaaact    1380
```

-continued

```
ttccgcccag gaggaggcga catgcgggat aattggagat cagagctgta taagtataag    1440
gtggtgaaaa ttgaacccct gggagtggcg ccaactagat gtaaacggcg agtggttggc    1500
cggagacggc ggcggagagc agtggggatt ggcgctgtct cactcggttt cctgggtgct    1560
gccggcagta caatgggcgc cgccagcatg acgctcacag tgcaggcccg gaatcttctt    1620
agcggaattg tgcaacaaca aagcaatctg ttgagagccc cggaaccgca gcaacatctg    1680
ttgaaggaca cacattgggg catcaagcag ctgcaagctc gggttctggc tgttgagcat    1740
tacctgagag accaacagct gctgggcata tggggatgct caggaaaact gatctgctgc    1800
accaatgtcc catggaacag ctcatggtca acaggaacc tgagcgagat ctgggataac     1860
atgacctggt tgcagtggga caaagaaatt agcaattaca cacagatcat ctacggcctc    1920
ctggaggaaa gccagaatca gcaggagaaa aatgagcagg atctgcttgc ccttgacggt    1980
ggaggcggtt caggcggcgg atctggcggt gggagcggtt cgggagccca tatagtgatg    2040
gttgatgcct ataaaccgac caagtga                                        2067
```

<210> SEQ ID NO 15
<211> LENGTH: 4
<212> TYPE: PRT
<213> ORGANISM: Human immunodeficiency virus

<400> SEQUENCE: 15

Gly Asp Ile Arg
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Ile Ala
1

<210> SEQ ID NO 17
<211> LENGTH: 4
<212> TYPE: PRT
<213> ORGANISM: Human immunodeficiency virus

<400> SEQUENCE: 17

Arg Glu Lys Arg
1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Arg Arg Arg Arg
1               5

<210> SEQ ID NO 19
<211> LENGTH: 6
<212> TYPE: PRT
<213> ORGANISM: Artificial Sequence

```
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 20

Gln Xaa Xaa Asp Ser Ser
1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Tyr Ala Gly
1

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ser Gly Asp Glu Leu Ala Trp Phe Ala Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ser Gly Asp Glu Leu Ala Cys Phe Ala Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Ala Asn Gly Asp Ala Leu Ala Trp Phe Ala Tyr
1               5                   10
```

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ala Cys Gly Asp Glu Leu Ala Trp Phe Ala Tyr
1               5                   10
```

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Ala Gly Gly Asp Glu Leu Ala Trp Phe Ala Tyr
1               5                   10
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Val Arg Gly Glu Val Tyr Tyr Asp Tyr Asp Gly Phe Ala Tyr
1               5                   10
```

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Ala Arg Gly Glu Val Tyr Tyr Asp Tyr Asp Gly Phe Ala Tyr
1               5                   10
```

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Ala Arg Ile Arg Ser Asp Tyr Asp Val Gly Trp Trp Tyr Phe Asp Val
1               5                   10                  15
```

<210> SEQ ID NO 30
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 30

Ala Arg Tyr Tyr Tyr Gly His Tyr Phe Asp Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Arg Ser Gly Ile Tyr Tyr Phe Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Arg Tyr Leu Leu Leu Arg Pro Phe Asp Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Ala Gly Thr Thr Gly Tyr Val Met Asp Tyr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ile Ala Ser Tyr Tyr Tyr Thr Leu Asp Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Arg Gly Ala Ala Gln Ala Pro Phe Ala Tyr
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Arg Ser Glu Leu Gly Pro Ala Phe Ala Tyr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Arg Arg Gly Tyr Gly Tyr Gly Ala Met Asp Tyr
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Arg Ala Tyr Ser Asn Tyr Val Pro Trp Phe Ala Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Arg Arg Glu Tyr Gly Phe Phe Asp Tyr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg His Gly Arg Leu Thr Gly Thr Gly Ala Met Asp Tyr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 41

Ala Arg His Gly Ala Gly Asn Ala Leu Asp Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Arg His Gly Ala Gly Asn Ala Met Asp Tyr
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Val Glu Val Thr Met Trp Thr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Ser Gly Arg Asn Tyr Val Asp Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ser Gly Pro Asn Tyr Phe Asp Tyr
1               5

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg His Gly His Tyr Tyr Gly Ser Ser Tyr Gly Met Asp Tyr
1               5                   10                  15

<210> SEQ ID NO 47
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 47

Ala Arg Asp Asp Gly Gly Tyr Trp Tyr Phe Asp Val
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Asn Ile Pro Lys Asp Arg Leu Cys Tyr Gly Pro
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Arg His Glu Glu Asp Gly Tyr Trp Phe Ala Tyr
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Gln Tyr Asp Glu Phe Pro Tyr Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu His Tyr Asp Asp Phe Pro Tyr Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gln Tyr Asp Glu Phe Pro Phe Thr
1               5
```

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Arg Tyr Asp Asp Phe Pro Tyr Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Gln Tyr Asp Glu Phe Pro Tyr Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu His Tyr Asp Glu Phe Pro Tyr Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu His Tyr Asp Asp Leu Pro Tyr Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Gln Tyr Asp Glu Phe Pro His Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 58

Leu Gln Tyr Asp Glu Ser Pro Tyr Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Gln Tyr Asp Glu Phe Pro Cys Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Gln Tyr Asp Asp Phe Pro His Thr
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Gln Ser Asn Glu Asp Pro Tyr Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gln Ser Asn Val Asp Pro Tyr Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Ser His Glu Asp Pro Tyr Thr
1               5

<210> SEQ ID NO 64
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln His Ser Asn Glu Asp Pro Tyr Thr
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Ser Asn Glu Asp Pro Pro Trp Thr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Gly Asn Glu Asp Pro Pro Trp Thr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

His Gln Ser Asn Glu Asp Pro Pro Trp Thr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Ile Asn Glu Asp Pro Pro Trp Thr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Ser Tyr Glu Asp Pro Pro Trp Thr
```

```
<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Ser Asn Glu Asp Pro Trp Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Asn Asn Glu Asp Pro Trp Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Gln Tyr Asp Glu Phe Thr Phe Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln Tyr Asp Ser Tyr Pro Tyr Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Asn Asn Tyr Pro Tyr Thr
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 75

Gln Gln Tyr Asn Ser Tyr Pro Tyr Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Tyr Asn Thr Tyr Pro Tyr Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Gln Tyr Asn Ile Tyr Pro Tyr Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Gln Ser Asn Glu Asp Pro Phe Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Gln Tyr Asp Glu Tyr Met Tyr Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Gly Asn Thr Leu Pro Trp Thr
1               5

<210> SEQ ID NO 81

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Gln Gly Asn Thr Ile Pro Trp Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Gln Gly Asn Thr Leu Pro Arg Thr
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Gln Ser Thr His Val Pro Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Gln Tyr Val Gln Phe Pro Leu Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Gln Tyr Ala Gln Phe Pro Leu Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86
```

Phe Gln Gly Ser His Val Pro Trp Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Gln Tyr Ala Gln Phe Pro Phe Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Gln His Gly Glu Ser Pro Tyr Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Phe Thr Ser Ser Pro Tyr Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gln Gly Asn Thr Leu Pro Tyr Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Gln Tyr Asp Glu Phe Arg Thr Thr
1               5

<210> SEQ ID NO 92
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 92

Gln Gln Tyr Asn Ser Tyr Pro Phe Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Cys Ser Gly Tyr Pro Leu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Tyr Ser Lys Leu Pro Trp Thr
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Gln Tyr Asp Glu Phe Pro Pro Phe Thr
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Arg His Ser Arg Thr Gly Thr Gly Ala Met Asp Tyr
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Pro Tyr Tyr Tyr Gly Ser Ser Pro Tyr Phe Asp Tyr
1               5                   10
```

```
<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg Ser Ile Val Pro Asp Tyr
1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Ser Leu Tyr Gly Asn Ala Phe Asp Tyr
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ser Gly Gly Asn Tyr Phe Asp Tyr
1               5

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Arg His Val Gly Asp His Ala Met Asp Tyr
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Arg Pro Tyr Tyr Tyr Gly Ser Ser Pro Asn Phe Asp Tyr
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103
```

```
Gly Thr Gly Lys Asn Tyr Phe Asp His
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Thr Asn Tyr Gly Ala Trp Phe Pro Tyr
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Arg His Gly Ile Thr Thr Val Gly Val Ala Met Asp Tyr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Asn Ile Pro Lys Asp Arg Leu Cys Tyr Gly
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Arg His Glu Gly Asn Tyr Leu Tyr Ala Met Asp Tyr
1               5                   10

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Arg Pro Pro Phe Ile Thr Val Val Ala Asn Tyr Phe Asp Tyr
1               5                   10                  15

<210> SEQ ID NO 109
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 109

Gln Gln Arg Ser Ser Tyr Pro Pro Thr
1               5

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Arg Val Val Asn Tyr Gly Pro Leu Asp Tyr
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Arg Val Val Lys Asn Gly Pro Leu Asp Tyr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Arg Val Val Lys Tyr Gly Pro Leu Asp Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Arg Leu Val Arg Tyr Gly Pro Leu Asp Tyr
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Arg Ile Val Lys Tyr Gly Pro Leu Asp Phe
1               5                   10
```

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Arg Gly Ser Arg Ile Ala Pro Phe Asp Tyr
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Arg Gly Ser Arg Ile Ala Pro Phe Asp His
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Arg Tyr Gln Ala Arg Gly Pro Ile Asp Ser
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Arg Asp Gln Ala Arg Gly Pro Ile Asp Tyr
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Arg Asn Gln Ala Arg Gly Pro Ile Asp Tyr
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 120

Ala Arg Asp Asn Arg Ile Gly Pro Phe Asp Tyr
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Arg Asp Lys Arg Ile Gly Pro Phe Asp Tyr
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Lys Lys Arg Arg Gln Leu Glu Asn Asp Tyr
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Val Lys Lys Arg Arg Gln Leu Glu Asn Asp Tyr
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Ser Arg Ile Ala Gly Gly Pro Phe Asp Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ser Arg Ile Ala Gly Gly Pro Phe Asp Phe
1               5                   10

<210> SEQ ID NO 126
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 126

Ala Ser Leu Ile Ala Ala Gly Pro Phe Asp Tyr
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Ser Arg Ile Arg Gly Gly Pro Phe Asp Tyr
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Arg Asp Ile Val Val Gly Pro Ile Asp Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Arg Asp Ile Val Ile Gly Pro Ile Asp Tyr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Thr Val Gly Arg Leu Ala Pro Phe Asp Tyr
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Arg Val Gly Arg Val Val Pro Phe Asp Tyr
1               5                   10
```

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Arg Val Gly Arg Val Ala Pro Phe Asp Tyr
1               5                   10

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Lys Ser Pro Trp Gly Gln Ser Ser Phe Glu Tyr Phe Glu Phe
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Lys Ser Pro Trp Gly Gln Ser Thr Ser Phe Glu Tyr Phe Glu Phe
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Lys Ser Pro Trp Gly Gln Ser Ser Tyr Phe Glu Tyr Phe Glu Phe
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ser Val Leu Trp Gly Leu Pro Gln Asp Asp Asn Ser Leu Asp Val
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ser Val Leu Trp Glu Val Pro Gln Asp Asp Asn Ser Leu Asp Val
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Asn Val Leu Trp Gly Leu Pro Gln Asp Asp Asn Ser Leu Asp Val
1               5                   10                  15

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Ser Leu Gln Arg Leu Gly Pro Ile Asp Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ser Leu Gln Tyr Phe Gly Pro Phe Glu Phe
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Ser Leu Gln Tyr Phe Gly Pro Phe Asp Phe
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Arg Ala Glu Arg Ala Gly Pro Phe Asp Tyr
1               5                   10

<210> SEQ ID NO 143
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Arg His Pro His Leu Glu Ser Phe Asp Tyr
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Arg Asn Tyr Gly Asn Tyr Gly Tyr Phe Glu Phe
1               5                   10

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Thr Gly Pro Tyr Trp Gly Asp Tyr Tyr Gly Arg Tyr Phe Glu Leu
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Thr Gly Pro Tyr Trp Gly Asp Tyr Tyr Gly Arg Tyr Phe Glu Phe
1               5                   10                  15

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Thr Glu Arg Arg Ala Gly Pro Val Asp Tyr
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Thr Asp Arg Arg Ala Gly Pro Leu Asp Tyr
```

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Gly Thr Leu Ala Gly Thr Thr Ser Phe Asp Val
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Gly Gly Leu Gly Arg Thr Thr Ser Phe Asp Val
1               5                   10

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Arg Val Gly Ser Gly Trp Ser Thr Glu Gly Asn Phe Asp Tyr
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Lys Asp Trp Ile Gln Trp Leu His Leu Gly Ser Tyr Phe Asp Phe
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Lys Asp Trp Ile Gln Trp Val His Leu Gly Ser Tyr Phe Asp Tyr
1               5                   10                  15

<210> SEQ ID NO 154
<211> LENGTH: 13
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 154

Ala Arg His Ser Ser Thr Tyr Val Ala Pro Val Asp Tyr
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Ser Ala Lys Gly Arg Leu Ala Pro Leu Asp Tyr
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Asn Trp Ala Asp Tyr Phe Asp Tyr
1               5

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Arg Asp Pro Val Ile Thr Ile Thr Thr Arg Glu Arg Phe Asp Val
1               5                   10                  15

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Arg Asp Gln Arg Thr Gly Pro Phe Asp Tyr
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Arg Gln Ala Phe Ala Gly Pro Thr Asp Ser
1               5                   10

<210> SEQ ID NO 160
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Arg Arg Gly Pro Val Asn Trp Asn Gly Ser Ser Leu Asp Val
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Arg Asp Arg Ala Asp Ser Trp Asn Phe His Asp Tyr Phe Asp Tyr
1               5                   10                  15

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Lys Ile Ala Val Ala Gly Pro Val Asp Tyr
1               5                   10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Thr Thr Tyr Ser Gly Ser Asp Tyr Tyr Arg Leu Asp Val
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Arg Pro Asp Ser Leu Trp Gly Ala Ala Phe Asp Tyr
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165
```

```
Ala Arg Ile Gly Ala Ala Gly Pro Gly Asp Tyr
1               5                   10
```

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

```
Ala Lys Tyr Trp Gly Asp Tyr Gly Tyr Ser Ser Leu Asp Val
1               5                   10                  15
```

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

```
Ala Arg Val Glu Val Val Gly Pro Thr Gly Tyr
1               5                   10
```

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

```
Ala Arg Arg Tyr Ser Gly Ser Tyr Ser Pro Phe Asp Cys
1               5                   10
```

<210> SEQ ID NO 169
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
Ala Arg Glu Gly Met Gly Cys Thr Gly Ser Gly Cys Ser Ile Ser Phe
1               5                   10                  15

Asp Tyr
```

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

```
Ala Arg Gln Gly Tyr Ser Gly Tyr Ser Leu Phe Asp Tyr
1               5                   10
```

<210> SEQ ID NO 171
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 171

Ala Ser Glu Ile Ala Gly Gly Pro Val Asp Tyr
1               5                   10

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Arg Asp Ser Ser Gly Trp Pro Trp Asp Asn Arg Phe Asp Val
1               5                   10                  15

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Arg Val Thr Gly Arg Ile Ala Pro Phe Asp Tyr
1               5                   10

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Thr Asn Ile Trp Thr Gly Tyr Ser Phe Tyr Tyr Gly Leu Asp Ser
1               5                   10                  15

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Arg Glu Gly Arg Ile His Pro Leu Asp Ser
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Lys Asp His Asp Tyr Gly Gly Gly Leu Asp Ser
1               5                   10
```

```
<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Lys Lys Ser Ser Gly Ser Trp Glu Val Asp Tyr
1               5                   10

<210> SEQ ID NO 178
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Arg His Ala Tyr Tyr Asn Ile Trp Thr Gly Tyr Ser Thr Asn Arg
1               5                   10                  15

Phe Asp Val

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Glu Gly Ser Gly Ser Trp Asn Gly Arg Phe Gly Val
1               5                   10

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Thr Gly Arg Tyr Tyr Gly Gly Ser Tyr Tyr Gly Asp Arg Phe Asp
1               5                   10                  15

Val

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Lys Cys Ser Ser Ser Ser Thr Gly Leu Asp Tyr
1               5                   10

<210> SEQ ID NO 182
<211> LENGTH: 18
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 182

Ala Arg Asp Arg Ser Val Thr Pro Phe Ser Trp Val Glu Tyr Tyr Phe
1               5                   10                  15

Asp Tyr

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Val Arg Val Val Lys Tyr Gly Pro Leu Asp Tyr
1               5                   10

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Arg Asn Pro Pro Tyr Tyr Asn Leu Trp Thr Gly Tyr Tyr Thr His
1               5                   10                  15

Ser Leu Asp Val
            20

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Arg Glu Gly Tyr Cys Ser Tyr Thr Tyr Cys Ser Asn Leu Phe Glu
1               5                   10                  15

Phe

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Arg Ala Arg Ile Ala Ala Pro Phe Asp Tyr
1               5                   10

<210> SEQ ID NO 187
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 187

Ala Arg Ala Gly Arg Met Ala Ala Thr Asp Tyr
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Val Arg Asp Val Thr Leu Gly Pro Ile Asp Asn
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Arg Glu Gly Arg Ile Gln Pro Leu Asp Ser
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Lys Cys Arg Asn Trp Asn Asp Phe Ala Tyr
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Arg Val His Arg Gly Gly Pro Phe Asp Tyr
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Arg Gly Gly Arg Val His Pro Met Asp Tyr
1               5                   10

```
<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Arg Gly Gly Pro Val Ser Pro Phe Asp Tyr
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Arg Gly Gln Arg Val Ala Pro Phe Asp Val
1               5                   10

<210> SEQ ID NO 195
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ala Lys Glu Thr Tyr Glu Asp Asp Tyr Gly Tyr Tyr Ser Leu Gly Tyr
1               5                   10                  15

Asn Arg Phe Asp Val
            20

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Ser Ala Trp Arg Glu His Leu Pro Ile Asp Tyr
1               5                   10

<210> SEQ ID NO 197
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ala Arg Asp Leu Tyr Pro Gly Val Ile Asn Pro Ser Gly Leu Asp Ser
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 198

Ala Arg Asp Lys Gly Ser Ser Tyr Tyr Gln Pro Glu Tyr Phe Glu Phe
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Val Arg Asp Lys Gly Ser Ser Tyr Tyr Gln Pro Glu Tyr Phe Glu Phe
1               5                   10                  15

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Arg Thr Gly Lys Ala Ala Pro Val Asp Tyr
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Arg Thr Gly Lys Ala Ala Pro Val Asp Cys
1               5                   10

<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Lys Gly Gly Asp Asn Tyr Tyr Asp Ser Gly Tyr Tyr Asp Asp Tyr
1               5                   10                  15

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Arg Asn Arg Gly Trp Gly Asp Leu Val Phe Asp Tyr
1               5                   10

<210> SEQ ID NO 204
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Lys Val Leu Ser Gly Trp Phe Trp Asp Tyr Phe Asp Tyr
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Arg Leu Ala Val Ala Gly Pro Val Asp Tyr
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ala Arg Gly Ser Ser Gly Trp Tyr Gly Ser Gly Leu Asp Ser
1               5                   10

<210> SEQ ID NO 207
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ala Arg Asp His Ile Glu Ser Trp Asn Lys Val Asn Trp Phe Asp Val
1               5                   10                  15

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Thr Tyr Ser Gly Ser Trp Tyr Ala Glu Tyr Phe Glu Phe
1               5                   10

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209
```

```
Ala Lys Gln Glu Asp Tyr Asn Phe Trp Ser Ser Tyr Phe Leu Pro Asp
1               5                   10                  15
Tyr

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Arg Asp Ser Ser Gly Trp Tyr Glu Gly Phe Asp Tyr
1               5                   10

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ala Thr Gly Arg Tyr Tyr Gly Pro Ser Trp Ala Ile Phe Asp Tyr
1               5                   10                  15

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Arg Asp Gly Asn Phe Gly Pro Ile Asp Tyr
1               5                   10

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Ser Gly Pro Asn Trp Phe Asp Val
1               5

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Lys Ser Glu Thr Asp Phe Trp Thr Ser Tyr Tyr Phe Asn Tyr
1               5                   10                  15

<210> SEQ ID NO 215
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 215

Ala Arg Asp Ile Cys Ser Gly Ser Gly Cys Tyr Trp Tyr Arg Asp Asn
1               5                   10                  15

Trp Phe Asp Val
            20

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Ser Asn Arg Arg Ile Ala Pro Leu Asp Tyr
1               5                   10

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Ser Gly Arg Tyr Tyr Phe Asp Tyr
1               5

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Arg Asp Arg Thr Val Thr Pro Asn Arg Gly Tyr Phe Glu Phe
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Arg Asp Gly Pro Tyr Ser Gly Gly Trp Ser Glu Leu Asp Ser
1               5                   10                  15

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220
```

```
Ala Arg Trp Glu Tyr Ser Gly Asn Trp Gly Leu Asp Tyr
1               5                   10
```

<210> SEQ ID NO 221
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Ala Arg Ser Thr Ser Ser Trp Pro Arg Thr Ser Asp Ala Phe Asp Phe
1               5                   10                  15
```

<210> SEQ ID NO 222
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

```
Ala Lys Lys Arg Ser Ser Trp Ser Arg Ile Asp Tyr
1               5                   10
```

<210> SEQ ID NO 223
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

```
Ala Arg Asp Gly Ser Gly Trp Arg Arg Val Thr Phe Asp Tyr
1               5                   10
```

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

```
Ala Thr Gly Arg Asn Tyr Phe Asp Tyr
1               5
```

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

```
Ala Lys Thr Gly Ala Val Thr Thr Gly Phe Asp Tyr
1               5                   10
```

<210> SEQ ID NO 226
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 226

Ala Arg Leu Val Gly Gly Ser Gly Tyr Tyr Tyr Ile Gly Asp
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Lys Val Pro Tyr Ser Ser Trp Ser His Phe Asp Tyr
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Thr Ser Pro Arg Met Arg Tyr Ser Ser Gly Ser Phe Asp Tyr
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Arg Val Arg Gly Tyr Ser Gly Tyr Ser Phe Phe Asp Tyr
1               5                   10

<210> SEQ ID NO 230
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Arg Gly Ser Thr Trp Ser Gly Asp Trp Phe Asp Val
1               5                   10

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Thr Lys Arg Leu Ala Tyr Ser Asn Pro Tyr Asn Arg Phe Asp Val
1               5                   10                  15
```

<210> SEQ ID NO 232
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ala Arg Gly Gly Val Gly Leu Asp Asp Val Thr Tyr Tyr Tyr Ser Gly
1               5                   10                  15

Ser Tyr Tyr Tyr His Arg Thr Ser Phe Asp Tyr
            20                  25

<210> SEQ ID NO 233
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Gly Asp Arg Gly Gly Tyr Asn Tyr Gly Phe Thr Asp Asn Trp Phe
1               5                   10                  15

Asp Val

<210> SEQ ID NO 234
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Thr Arg Gly Thr Ala Tyr Tyr Asn Phe Trp Ser Asn Ser Ser Pro Gly
1               5                   10                  15

Tyr Phe Asp Tyr
            20

<210> SEQ ID NO 235
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Arg Asp Lys Gly Ser Ser Tyr Tyr Gln Pro Glu Ser Phe Glu Phe
1               5                   10                  15

<210> SEQ ID NO 236
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Arg Arg Tyr Tyr Glu Asp Asp Tyr Gly Tyr Tyr Tyr Pro Gly Pro
1               5                   10                  15

Asn Ile Ala Gly Thr Thr Arg Gly Val Glu Glu

```
            20                  25

<210> SEQ ID NO 237
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Arg Gly Ile Thr Arg Met Ile Thr Val Thr Lys Thr Asn Trp Phe
1               5                   10                  15

Asp Val

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ala Arg Leu Ala Val Ala Gly Pro Phe Asp Tyr
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Arg Leu Gly Val Ala Gly Pro Leu Asp Tyr
1               5                   10

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Thr Tyr Lys Thr Ile Asp Tyr
1               5

<210> SEQ ID NO 241
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Ser Tyr Lys Asn Ile Asp Tyr
1               5

<210> SEQ ID NO 242
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 242

Ala Arg Asp Arg His Gly Ile Pro Phe Asp Tyr
1               5                   10

<210> SEQ ID NO 243
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Arg Ser Arg Gly Tyr Trp Gly Asp Leu Phe Asp Phe
1               5                   10

<210> SEQ ID NO 244
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Arg Leu Ser Gly Trp Gly Asp Phe Arg Ile Asp Tyr
1               5                   10

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ala Thr Gly Ile Trp Phe Asp Val
1               5

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Arg Ala Asn Asn Gly Gly Tyr Phe Asp Tyr
1               5                   10

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ala Arg Met Thr Thr Val Ala Ala Phe Gly Gly Tyr Phe Asp Leu
1               5                   10                  15
```

```
<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Ser Gly Gly Asn Tyr Ala Asp Tyr
1               5

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Arg Arg Leu Ser Arg Arg Tyr Phe Asp Tyr
1               5                   10

<210> SEQ ID NO 250
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Thr Arg Glu Phe Cys Ser Gly Ile Tyr Cys Tyr Ala Pro Phe Asp Tyr
1               5                   10                  15

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala Ser Phe Lys Thr Leu Asp Val
1               5

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Lys Gly Val Gly Gly Phe Ser Tyr Ser Tyr Pro His Tyr
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 253

Ala Arg Asp Gly His Tyr Asn Phe Trp Ser Pro Pro Gly Tyr
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Arg Ala Glu Asp Glu Asp Tyr Gly Ser Phe Asp Val
1               5                   10

<210> SEQ ID NO 255
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Arg Leu Gly Ser Ser Gly Trp Tyr Arg Asp Asp Ala Phe Asp Phe
1               5                   10                  15

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Lys Pro Arg Gly Arg Trp Leu Glu Asp Tyr
1               5                   10

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Thr Arg Pro Arg Gln Tyr Ser Thr Gly Asp Tyr
1               5                   10

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Lys Met Gly Gly Arg Gly Tyr Ser Ser Tyr Gly Pro Val Phe Asp
1               5                   10                  15

Tyr

<210> SEQ ID NO 259
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ala Arg Ile Val Thr Arg Gly Pro Phe Asp Tyr
1               5                   10

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Arg Asp Val Thr Thr Arg Val Val Ile Ile Asp His Arg Phe Asp
1               5                   10                  15

Val

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ala Arg Gln Leu Gly Gly Gly Gln Thr Asp Arg Phe Asp Val
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Arg Gln Ala Tyr Ser Asn Tyr Pro Asp Tyr
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Val Lys Leu Arg Glu Lys Trp Glu Thr Arg Gly Asp
1               5                   10

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 264

Ala Lys Ser Tyr Gly Ser Met Ser Asn Arg Phe Asp Val
1               5                   10

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ala Arg Val Ile Arg Leu Gly Pro Phe Asp Tyr
1               5                   10

<210> SEQ ID NO 266
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Arg Glu Thr Phe Glu Gly Asp Asp Tyr Gly Tyr Tyr Thr Pro
1               5                   10                  15

Asp Asn Trp Phe Asp Val
            20

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Lys Ser Gly Asn Ser Gly Ser Trp Asn Tyr Phe Asp Tyr
1               5                   10

<210> SEQ ID NO 268
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ala Arg Arg Arg Gly Trp Gly Asp Pro Tyr Phe Asp Tyr
1               5                   10

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ala Thr Gly Phe Ser Met Ile Thr Val Ala Leu Phe Asp Phe
1               5                   10
```

```
<210> SEQ ID NO 270
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ala Ser Gln Gly Tyr Glu Asp Asp Tyr Ala Tyr Trp Ala Phe Lys Phe
1               5                   10                  15

Asp Tyr

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ala Arg Ser Pro Gly Ile Val Ala Pro Phe Asp Tyr
1               5                   10

<210> SEQ ID NO 272
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Arg Ser Arg Ser Gly Ser Asn Ser Glu Ser Arg Phe Asp Val
1               5                   10                  15

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ala Arg Pro Leu Tyr Ser Gly Asn Trp Asn Val Tyr Trp Tyr Phe Asp
1               5                   10                  15

Leu

<210> SEQ ID NO 274
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ala Arg Asp Gly Trp Gly Gly Trp Thr Ile Asp Tyr
1               5                   10

<210> SEQ ID NO 275
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 275

Ala Arg Ser Gly Tyr Gly Ser Gly Gly Thr Phe Asp Tyr
1               5                   10

<210> SEQ ID NO 276
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ala Thr Thr Pro Gly Tyr Cys Ser Ser Thr Tyr Cys Arg Phe Asp Tyr
1               5                   10                  15

<210> SEQ ID NO 277
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ala Thr Lys Asn Tyr Tyr Asp Ser Gly Tyr His Leu Ser Gly Glu Tyr
1               5                   10                  15

Phe Glu Phe

<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ala Gln Cys Pro Glu Tyr Ser Trp Asn Met Gly Trp Phe Asp Val
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ala Ser Pro Phe Tyr Gly Ser Gly Tyr Tyr Thr Arg Arg Phe Asp Val
1               5                   10                  15

<210> SEQ ID NO 280
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Arg Asp Gly Tyr Tyr Ser Gly Asp Tyr Tyr Arg His Asn Trp Phe
1               5                   10                  15
```

Ala Val

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ala Arg Asp Cys Val Asp Ala Phe Asp Tyr
1               5                   10

<210> SEQ ID NO 282
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ala Thr Gly Tyr Asn Trp Asn Asp Pro Phe Asp Tyr
1               5                   10

<210> SEQ ID NO 283
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Thr Lys Val Glu Gly Gly Tyr Trp Gly Asp Tyr His Arg Phe Asp Val
1               5                   10                  15

<210> SEQ ID NO 284
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gln Ser Tyr Asp Ser Ser Leu Ser Gly His Leu
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gln Ser Tyr Asp Ser Ser Leu Ser Ala Gly Leu
1               5                   10

<210> SEQ ID NO 286
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 286

Gln Ser Tyr Asp Ser Ser Leu Ser Ala His Val
1               5                   10

<210> SEQ ID NO 287
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Gln Ser Tyr Asp Asn Ser Leu Ser Ala Trp Val
1               5                   10

<210> SEQ ID NO 288
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gln Ser Tyr Asp Ser Ser Leu Ser Val Arg Val
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gln Ser Tyr Asp Asn Ser Leu Ser Ala Arg Val
1               5                   10

<210> SEQ ID NO 290
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid

<400> SEQUENCE: 290

Gln Ser Tyr Asp Asn Ser Leu Ser Xaa Gln Val
1               5                   10

<210> SEQ ID NO 291
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291
```

```
Gln Ser Tyr Asp Asn Ser Leu Ser Ala His Val
1               5                   10

<210> SEQ ID NO 292
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gln Ser Tyr Asp Ser Ser Leu Ser Ala Asp Val
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Leu Ser Tyr Asp Ser Ser Leu Ser Ala His Ile
1               5                   10

<210> SEQ ID NO 294
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gln Val Trp Asp Ser Ser Ser Asp His Pro Leu
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gly Ala Trp Asp Ser Ser Leu Ser Ala Gly Leu
1               5                   10

<210> SEQ ID NO 296
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ser Ala Trp Asp Ser Ser Leu Ser Asp Val Leu
1               5                   10

<210> SEQ ID NO 297
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 297

Ala Ala Trp Asp Asp Ser Leu Ser Gly Val Leu
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Glu Thr Trp Asp Tyr Ser Leu Asn Gly Pro Leu
1               5                   10

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Tyr Ser Gly Asp Asp Asn Asn Asp Val
1               5

<210> SEQ ID NO 300
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gln Ser Tyr Asp Ser Ser Leu Ser Gly His Ile
1               5                   10

<210> SEQ ID NO 301
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gln Thr Trp Thr Thr Asp Val
1               5

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Cys Ser Tyr Thr Thr Ser Asn Thr Leu Leu
1               5                   10

```
<210> SEQ ID NO 303
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gln Ser Tyr Asp Ser Ser Leu Ser Val His Tyr Ile
1               5                   10

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ser Ser Tyr Ala Ser Ser Ser Thr Trp Val
1               5                   10

<210> SEQ ID NO 305
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gln Ser Tyr Asp Ser Ser Leu Ser Ala Val Leu
1               5                   10

<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Ser Tyr Asp Ser Ser Leu Ser Ala Leu Leu
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gln Ser Tyr Asp Ser Ser Leu Ser Ala Val Phe
1               5                   10

<210> SEQ ID NO 308
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308
```

```
Gln Ser Tyr Asp Ser Ser Leu Ser Ala Arg Leu
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln Ser Tyr Asp Ser Ser Leu Ser Asn Val Leu
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gln Ser Tyr Asp Ser Ser Leu Ser Gly Val Leu
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gln Ser Tyr Asp Asn Ser Leu Ser Ala Val Leu
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gln Ser Tyr Asp Asn Asn Leu Ser Ala Val Leu
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gln Ser Tyr Asp Ser Ser Leu Ser Ala Gln Val
1               5                   10

<210> SEQ ID NO 314
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 314

Gln Ser Tyr Asp Ser Ser Leu Ser Ala His Leu
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Ser Tyr Asp Ser Ser Leu Ser Ala Trp Val
1               5                   10

<210> SEQ ID NO 316
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Ser Tyr Asp Ser Tyr Leu Ser Ala Gly Leu
1               5                   10

<210> SEQ ID NO 317
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Ser Tyr Asp Asn Ser Leu Ser Asp Asp Val
1               5                   10

<210> SEQ ID NO 318
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gln Ser Tyr Asp Ser Ser Leu Ser Ala Leu Val
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gln Ser Tyr Asp Ser Asn Leu Ser Ala His Val Leu
1               5                   10
```

```
<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Ser Phe Asp Ser Asn Leu Ser Ile His Leu Leu
1               5                   10

<210> SEQ ID NO 321
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Ser Tyr Asp Ser Ser Leu Ser Ala His Val Leu
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Ser Tyr Asp Ser Ser Leu Ser Ala Tyr Ile
1               5                   10

<210> SEQ ID NO 323
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Asp Ser Trp Asp Ser Gly Gly Thr His Val Leu
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ala Ala Trp Asp Asp Ser Leu Ser Gly Pro Val
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 325

Gln Val Trp Asp Ser Arg Ser Asp His Pro Leu
1               5                   10

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Met Ile Trp His Asn Asn Ala Ser Ile
1               5

<210> SEQ ID NO 327
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Trp Leu Tyr Tyr Ser Gly Gly His Gly Leu
1               5                   10

<210> SEQ ID NO 328
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Val Trp Asp Ser Ser Ser Asp His His Asp Val
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gln Ser Tyr Asp Ser Ser Leu Arg Ala Gln Val
1               5                   10

<210> SEQ ID NO 330
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gln Ser His Asp Ser Ser Leu Thr Ala Gly Leu
1               5                   10

<210> SEQ ID NO 331
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 331

Gln Ser His Asp Ser Ser Leu Ser Ala Gly Leu
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ala Ala Trp Asp Asp Ser Leu Lys Gly Trp Val
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ala Ala Trp Asp Asp Ser Leu Ser Gly Trp Val
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ala Ala Trp Asp Asp Ser Leu Asn Gly Trp Val
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ala Ala Trp Asp Asp Ser Leu Ser Gly Pro Leu
1               5                   10

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Met Ile Trp His Asn Asn Val Trp Ala
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Val Ile Trp His Asn Asn Val Trp Ala
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Met Ile Trp His Asn Asn Ala Trp Ile
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Met Ile Trp His Asn Asn Ala Trp Val
1               5

<210> SEQ ID NO 340
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ala Ala Trp Asp Asp Ser Leu Ser Gly Tyr Ile
1               5                   10

<210> SEQ ID NO 341
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gln Ser Tyr Asp Asn Ser Leu Ser Ala Tyr Ile
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 342

Gln Ser Tyr Asp Ser Ile Leu Ser Ser Tyr Ile
1               5                   10

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gln Ser Tyr Asp Ser Arg Leu Ser Ala Asp Val
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gln Val Trp Asp Gly Ser Thr Lys Tyr Ala Gly Leu
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gln Val Trp Asp Asp Ser Thr Asn Tyr Ala Gly Leu
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Gly Ala Trp Asp Ser Ser Leu Ser Ala Leu Leu
1               5                   10

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gln Ser Tyr Asp Ser Ser Leu Ser Asp Val Leu
1               5                   10

<210> SEQ ID NO 348
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gln Ser Tyr Asp Ser Ser Leu Ser Ala Gln Leu
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Met Ile Trp His Glu Asp Asp Phe Val Leu
1               5                   10

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Ala Trp Asp Ser Ser Leu Ser Ala His Trp Val
1               5                   10

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asp Ser Trp Asp Ser Ser Gly Thr His Val Leu
1               5                   10

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ser Ser Tyr Val Gly Ser Gly Thr Tyr Ile
1               5                   10

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ser Ser Tyr Ala Gly Ser Gly Thr Gly Leu
```

```
1               5                   10
```

<210> SEQ ID NO 354
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

```
Cys Ser Tyr Thr Thr Ser Asn Thr Leu Ile
1               5                   10
```

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

```
Gln Val Trp Asp Ile Ser Ser Asp His Pro Val
1               5                   10
```

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

```
Gln Val Trp Asp Ser Ser Ser Ala His Pro Val
1               5                   10
```

<210> SEQ ID NO 357
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

```
Gln Ser Tyr Asp Ser Ser Leu Ser Ala His Tyr Ile
1               5                   10
```

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

```
Gln Ser Ala Asp Ser Ser Gly Asn His Trp Val
1               5                   10
```

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Gln Thr Trp Thr Thr Gly Ile His Val
1               5

<210> SEQ ID NO 360
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Ser Tyr Arg Thr Gly Ala Thr Phe Leu
1               5                   10

<210> SEQ ID NO 361
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ser Ser Tyr Ala Gly Ser Asn Thr Phe Ile
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Gln Val Trp Asp Ser Ser Ser Asp His Trp Val
1               5                   10

<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gln Ser Tyr Asp Gly Ser Leu Ser Ala Gln Leu
1               5                   10

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Gln Val Trp Asp Ser Asp His Pro Leu
1               5

<210> SEQ ID NO 365

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Gln Ser Tyr Asp Ser Thr Leu Ser Gly Gly Leu
1               5                   10

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gln Ser Tyr Asp Ser Ser Leu Ser Gly Gly Leu
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gln Ser Tyr Asp Asn Thr Leu Ser Ala Gly Leu
1               5                   10

<210> SEQ ID NO 368
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gln Ser Tyr Asp Ser Ser Leu Ser Val Gly Leu
1               5                   10

<210> SEQ ID NO 369
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gln Ser Tyr Asp Ser Ser Leu Thr Ala Gly Leu
1               5                   10

<210> SEQ ID NO 370
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370
```

```
Gln Ser Tyr Asp Asn Asn Leu Ser Ala Gln Val
1               5                   10
```

<210> SEQ ID NO 371
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

```
Gln Ser Tyr Asp Ser Ser Leu Ser Ala Arg Val
1               5                   10
```

<210> SEQ ID NO 372
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

```
Gln Ser Tyr Asp Ile Ser Leu Ser Ala Gly Leu
1               5                   10
```

<210> SEQ ID NO 373
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

```
Gln Ser Tyr Asp Asn Ile Leu Asn Ala Gly Leu
1               5                   10
```

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

```
His Ser Tyr Asp Ser Ser Leu Ser Ala Gln Val
1               5                   10
```

<210> SEQ ID NO 375
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

```
Gln Ser Tyr Asp Asn Ser Leu Ser Ala Val Ile
1               5                   10
```

<210> SEQ ID NO 376
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid

<400> SEQUENCE: 376

Gln Ser Tyr Asp Ser Ser Leu Ser Xaa Val Leu
1               5                   10

<210> SEQ ID NO 377
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gln Ser Tyr Asp Ser Arg Leu Ser Ala Leu Leu
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gln Ser Tyr Asp Ser Ser Leu Ser Ala Val Val
1               5                   10

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gln Ser Tyr Asp Asn Ser Leu Ser Ala Leu Leu
1               5                   10

<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(9)
<223> OTHER INFORMATION: Any amino acid

<400> SEQUENCE: 380

Gln Ser Tyr Asp Ser Ser Xaa Xaa Xaa His Val
1               5                   10

<210> SEQ ID NO 381
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 381

Gln Ser Tyr Asp Ser Ser Leu Ser Thr His Val
1               5                   10

<210> SEQ ID NO 382
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gln Ser Tyr Asp Ser Ser Leu Thr Ala Asp Val
1               5                   10

<210> SEQ ID NO 383
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ser Ser Tyr Ala Gly Ser Asn Thr Tyr Ile
1               5                   10

<210> SEQ ID NO 384
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ser Ser Tyr Ala Gly Ser Gly Thr Tyr Ile
1               5                   10

<210> SEQ ID NO 385
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gln Ser Tyr Asp Ser Arg Leu Ser Ala His Val
1               5                   10

<210> SEQ ID NO 386
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gln Ser Tyr His Ser Ser Leu Arg Ala Tyr Ile
1               5                   10

<210> SEQ ID NO 387

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Arg Ser Tyr Arg Ser Gly Arg Thr Asn Ile
1               5                   10

<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Cys Ser Tyr Arg Ser Gly Asp Thr Leu Ile
1               5                   10

<210> SEQ ID NO 389
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Tyr Ser Tyr Arg Ser Gly Asn Thr Leu Val
1               5                   10

<210> SEQ ID NO 390
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Cys Ser Tyr Arg Ser Gly Ser Thr Phe Leu
1               5                   10

<210> SEQ ID NO 391
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Cys Ser Tyr Thr Thr Ser Ser Thr Phe Ile
1               5                   10

<210> SEQ ID NO 392
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392
```

Ser Ser Tyr Ala Gly Ile Asn Thr Leu Val
1               5                   10

<210> SEQ ID NO 393
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ser Ser Tyr Ala Gly Ser Asn Thr Phe Leu
1               5                   10

<210> SEQ ID NO 394
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gln Val Trp Asp Ser Ser Ser Asp His Pro Val
1               5                   10

<210> SEQ ID NO 395
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gln Val Trp Asp Ser Ser Asn Asp His Tyr Ile
1               5                   10

<210> SEQ ID NO 396
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ala Ala Trp Asp Asp Arg Leu Ser Gly Trp Val
1               5                   10

<210> SEQ ID NO 397
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Cys Ser Tyr Thr Ser Gly Ser Thr Trp Val
1               5                   10

<210> SEQ ID NO 398
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 398

Asp Ser Trp Asp Ser Ser Gly Thr Leu Val
1               5                   10

<210> SEQ ID NO 399
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Leu Ser Tyr Asp Ser Ser Leu Ser Ala Gly Leu
1               5                   10

<210> SEQ ID NO 400
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Gln Val Trp Asp Ser Ser Ser Asp His Val Leu
1               5                   10

<210> SEQ ID NO 401
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gln Val Trp Asp Asn Ser Ser Asp His Tyr Ile
1               5                   10

<210> SEQ ID NO 402
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gln Val Trp Asp Ser Ser Cys Lys
1               5

<210> SEQ ID NO 403
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Ser Ala Trp Asp Ser Ser Leu Ser Ala Tyr Ile
1               5                   10
```

-continued

```
<210> SEQ ID NO 404
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gln Ser Tyr Asp Ser Arg Leu Arg Val Asn Trp Val
1               5                   10

<210> SEQ ID NO 405
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Glu Ala Trp Asp Arg Ser Leu Ser Ala Trp Val
1               5                   10

<210> SEQ ID NO 406
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Asp Thr Trp Asp Asn Ser Leu Asn Gly Tyr Ile
1               5                   10

<210> SEQ ID NO 407
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Ala Arg Leu Gly Glu Tyr Ser Trp Asn Ser Ile Gly Tyr Phe Asp Tyr
1               5                   10                  15

<210> SEQ ID NO 408
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Ala Arg Gly Gly Tyr Tyr Ser Gly Arg Val Phe Asp Asp Tyr
1               5                   10

<210> SEQ ID NO 409
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409
```

```
Ala Arg His Ser Gly Trp Gly Asp Pro Tyr Leu Asp Val
1               5                   10
```

<210> SEQ ID NO 410
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

```
Ala Ile Asn Ser Gly Ser Trp Asn Tyr Tyr Phe Asp Tyr
1               5                   10
```

<210> SEQ ID NO 411
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

```
Thr Ser Asp Pro Ala Thr Tyr Ser Trp Asn Glu Tyr Phe Glu Phe
1               5                   10                  15
```

<210> SEQ ID NO 412
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

```
Ala Lys Glu Asp Gly Gly Trp Ser Asn Asn Arg Val Asp Val
1               5                   10
```

<210> SEQ ID NO 413
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

```
Ala Lys Gly Arg Gly Tyr Asn Arg Phe Asp Val
1               5                   10
```

<210> SEQ ID NO 414
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

```
Val Arg Gln Gly Tyr Ser Ser Trp Tyr Asn Ser Leu Asp Val
1               5                   10
```

<210> SEQ ID NO 415
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 415

Ala Arg Asp Met Arg Asp Ile Ala Ala Gly Gly Tyr Thr Tyr Gly Tyr
1               5                   10                  15

Phe Asp Tyr

<210> SEQ ID NO 416
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Val Arg Asp Pro Ser Ile Thr Pro Gly Pro Ser Tyr Asn Arg Phe Asp
1               5                   10                  15

Val

<210> SEQ ID NO 417
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Ala Lys Gly Val Tyr Gly Ser Thr Asn Arg Phe Asp Val
1               5                   10

<210> SEQ ID NO 418
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Ala Lys Gly Val Tyr Gly Leu Thr Asn Arg Phe Asp Val
1               5                   10

<210> SEQ ID NO 419
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Thr Lys Glu Gly Gly Pro Glu Tyr Tyr Asn Ile Trp Thr Gly Trp Asn
1               5                   10                  15

Arg Phe Asp Val
            20

<210> SEQ ID NO 420
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 420

Ala Gly Gly Tyr Leu Leu Phe Pro Leu Gly Tyr Asn Ser Leu Asp Val
1               5                   10                  15

<210> SEQ ID NO 421
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Ala Lys Gly Gly Gly Pro Pro Ser Trp Asn Asp Pro Phe Asp Phe
1               5                   10                  15

<210> SEQ ID NO 422
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Ala Lys Asn Gly Pro Pro Tyr Trp Gly Met Gly Asp Tyr
1               5                   10

<210> SEQ ID NO 423
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Ala Lys Asp Arg Gly Arg Gly Gly Ser Trp Ser Leu Gly Asn Asp Tyr
1               5                   10                  15

<210> SEQ ID NO 424
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Ala Lys Gly Gly Glu Asp Asp Tyr Ile Tyr Tyr Tyr Thr Gly Ala Asp
1               5                   10                  15

Tyr

<210> SEQ ID NO 425
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Ala Arg Gly Leu Phe Asn Phe Trp Ser Gly Tyr Trp Gly His Asn Ser
1               5                   10                  15

Leu Asp Val

<210> SEQ ID NO 426
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Ala Arg Asp Tyr Ser Ser Trp Pro Thr Tyr Asn Ser Leu Asp Val
1               5                   10                  15

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ala Lys Ser Thr Leu Leu Arg Arg Ser Leu Asp Tyr
1               5                   10

<210> SEQ ID NO 428
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ala Lys Asp Gly Gly Pro Ser Gly Ser Tyr Tyr Tyr Gly Gly Arg Phe
1               5                   10                  15

Asp Val

<210> SEQ ID NO 429
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Ala Lys Asp Gly Gly Pro Ser Gly Ser Tyr Tyr Tyr Arg Gly Arg Phe
1               5                   10                  15

Asp Val

<210> SEQ ID NO 430
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Ala Arg Gly Gly Gly His Ser Ser Phe Asp Phe
1               5                   10

<210> SEQ ID NO 431
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Ala Arg Asp Ser Tyr Lys Asp Ser Pro Ala Phe Asp Phe
1               5                   10

<210> SEQ ID NO 432
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Lys Asp Gln Thr Asp Leu Asp Trp Leu Leu Tyr Gly Gly Phe Asp
1               5                   10                  15

Tyr

<210> SEQ ID NO 433
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Gln Ser Tyr Asp Asn Ser Leu Ser Ala Gln Val
1               5                   10

<210> SEQ ID NO 434
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

His Ile Trp Asp Ser Arg Val Pro Thr Lys Trp Val
1               5                   10

<210> SEQ ID NO 435
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

His Ile Trp Asp Ser Arg Arg Pro Thr Asn Trp Val
1               5                   10

<210> SEQ ID NO 436
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436
```

```
His Ile Tyr Asp Ala Arg Gly Gly Thr Asn Trp Val
1               5                   10

<210> SEQ ID NO 437
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

His Met Trp Asp Ser Arg Ser Gly Phe Ser Trp Ser
1               5                   10

<210> SEQ ID NO 438
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Met Trp Asp Ser Arg Ser Gly Phe Ser Trp Ser
1               5                   10

<210> SEQ ID NO 439
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Gln Ser Ser Asp Thr Ser Asp Ser Tyr Lys Met
1               5                   10

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Gly Ser Leu Val Gly Asn Trp Asp Val Ile
1               5                   10

<210> SEQ ID NO 441
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Ser Ser Leu Val Gly Asn Trp Asp Val Ile
1               5                   10

<210> SEQ ID NO 442
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 442

Ser Ser Leu Phe Gly Arg Trp Asp Val Val
1               5                   10

<210> SEQ ID NO 443
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Ser Ser Leu Ser Gly Arg Trp Asp Ile Val
1               5                   10

<210> SEQ ID NO 444
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Ser Phe Gly Gly Ser Ala Thr Val Val
1               5

<210> SEQ ID NO 445
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Gln Val Trp Asp Ser Ser Ser Asp His Pro Trp Val
1               5                   10

<210> SEQ ID NO 446
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(10)
<223> OTHER INFORMATION: Any amino acid

<400> SEQUENCE: 446

Ser Ser Tyr Ala Gly Ser Asn Xaa Xaa Xaa
1               5                   10

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447
```

Ser Tyr Ala Gly Ser Ser Thr Val Ile
1               5

<210> SEQ ID NO 448
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
acaggtgccc actcccaggt gcag                                              24

<210> SEQ ID NO 449
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
aaggtgtcca gtgtgargtg cag                                               23

<210> SEQ ID NO 450
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
cccagatggg tcctgtccca ggtgcag                                           27

<210> SEQ ID NO 451
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
caaggagtct gttccgaggt gcag                                              24

<210> SEQ ID NO 452
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
ttctccaagg agtctgt                                                      17

<210> SEQ ID NO 453
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
taaaaggtgt ccagtgt                                                  17

<210> SEQ ID NO 454
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
taagaggtgt ccagtgt                                                  17

<210> SEQ ID NO 455
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
tagaaggtgt ccagtgt                                                  17

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
atgaaacatc tgtggttctt                                               20

<210> SEQ ID NO 457
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
tacaaggtgt ccagtgt                                                  17

<210> SEQ ID NO 458
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
ttaaagctgt ccagtgt                                                  17

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459

-continued

```
gctgaggaga cggtgaccag                                                20
```

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460

```
gctgaggaga tggtgattgg g                                              21
```

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461

```
gctgaagaga cggtgaccct g                                              21
```

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462

```
gctgaggaga cggtgacgac g                                              21
```

<210> SEQ ID NO 463
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463

```
ctagtagcaa ctgcaaccgg tgtacattcc caggtgcagc tggtgcag                 48
```

<210> SEQ ID NO 464
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464

```
ctagtagcaa ctgcaaccgg tgtacattcc gaggtgcagc tggtgcag                 48
```

<210> SEQ ID NO 465
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465

```
ctagtagcaa ctgcaaccgg tgtacattcc caggttcagc tggtgcag                 48
```

<210> SEQ ID NO 466
<211> LENGTH: 48
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 466
ctagtagcaa ctgcaaccgg tgtacattcc caggtccagc tggtacag                    48

<210> SEQ ID NO 467
<211> LENGTH: 48
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 467
ctagtagcaa ctgcaaccgg tgtacattct gaggtgcagc tggtggag                    48

<210> SEQ ID NO 468
<211> LENGTH: 48
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 468
ctagtagcaa ctgcaaccgg tgtacattct caggtgcagc tggtggag                    48

<210> SEQ ID NO 469
<211> LENGTH: 48
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 469
ctagtagcaa ctgcaaccgg tgtacattct gaggtgcagc tgttggag                    48

<210> SEQ ID NO 470
<211> LENGTH: 48
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 470
ctagtagcaa ctgcaaccgg tgtacattct gaagtgcagc tggtggag                    48

<210> SEQ ID NO 471
<211> LENGTH: 48
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 471
ctagtagcaa ctgcaaccgg tgtacattcc caggtgcagc tgcaggag                    48

<210> SEQ ID NO 472
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
ctagtagcaa ctgcaaccgg tgtacattcc caggtgcagc tacagcagtg            50

<210> SEQ ID NO 473
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
ctagtagcaa ctgcaaccgg tgtacattcc cagctgcagc tgcaggag              48

<210> SEQ ID NO 474
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
ctagtagcaa ctgcaaccgg tgtacattcc caggtacagc tgcagcag              48

<210> SEQ ID NO 475
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
ccgatgggcc cttggtcgac gctgaggaga cggtgaccag                       40

<210> SEQ ID NO 476
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
ccgatgggcc cttggtcgac gctgaagaga cggtgaccat tg                    42

<210> SEQ ID NO 477
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
ccgatgggcc cttggtcgac gctgaggaga cggtgaccgt g                     41

-continued

```
<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
gtagcaactg caaccggtgt                                                     20

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
gcttcgttag aacgcggcta c                                                   21

<210> SEQ ID NO 480
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480
ggaaggtgtg cacgccgctg gtc                                                 23

<210> SEQ ID NO 481
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 481
ggtcctgggc ccagtctgtg ctg                                                 23

<210> SEQ ID NO 482
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 482
ggtcctgggc ccagtctgcc ctg                                                 23

<210> SEQ ID NO 483
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
gctctgtgac ctcctatgag ctg                                                 23

<210> SEQ ID NO 484
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
ggtctctctc scagcytgtg ctg                                              23

<210> SEQ ID NO 485
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
gttcttgggc caattttatg ctg                                              23

<210> SEQ ID NO 486
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
ggtccaattc ycaggctgtg gtg                                              23

<210> SEQ ID NO 487
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
gagtggattc tcagactgtg gtg                                              23

<210> SEQ ID NO 488
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
caccagtgtg gccttgttgg cttg                                             24

<210> SEQ ID NO 489
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
ctagtagcaa ctgcaaccgg ttcctgggcc cagtctgtgc tgackcag                   48

<210> SEQ ID NO 490
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
ctagtagcaa ctgcaaccgg ttcctgggcc cagtctgccc tgactcag                    48

<210> SEQ ID NO 491
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
ctagtagcaa ctgcaaccgg ttctgtgacc tcctatgagc tgacwcag                    48

<210> SEQ ID NO 492
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492
ctagtagcaa ctgcaaccgg ttctctctcs cagcytgtgc tgactca                     47

<210> SEQ ID NO 493
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
ctagtagcaa ctgcaaccgg ttcttgggcc aattttatgc tgactcag                    48

<210> SEQ ID NO 494
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
ctagtagcaa ctgcaaccgg ttccaattcy cagrctgtgg tgacycag                    48

<210> SEQ ID NO 495
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
ggcttgaagc tcctcactcg agggygggaa cagagtg                                37
```

HIV VACCINE IMMUNOGENS

CROSS-REFERENCE TO RELATED APPLICATIONS

This application is the National Stage Application of PCT/US19/63619 filed on Nov. 27, 2019, which claims the benefit of U.S. Provisional Application 62/775,192 filed on Dec. 4, 2018. The entire contents of these applications are incorporated herein by reference in their entirety.

STATEMENT REGARDING FEDERALLY SPONSORED RESEARCH

This invention was made with government support under Grant No. AI100148 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 14, 2019, is named 070413_20403_SL.txt and is 178,838 bytes in size.

FIELD OF THE INVENTION

This disclosure relates to immunogenic polypeptides, and specifically to immunogenic polypeptides capable of stimulating an immune response to human immunodeficiency virus (HIV).

BACKGROUND OF THE INVENTION

Single-cell antibody cloning from HIV-1-infected human donors revealed that broadly neutralizing anti-HIV-1 antibodies (bNAbs) are unusual in that they are highly somatically mutated. Moreover, the high degree of somatic mutations is essential for binding to native HIV-1 Env and for bNAb neutralizing activity. The accumulation of large numbers of mutations suggests that bNAbs evolve in response to iterative rounds of somatic hypermutation and selection in germinal centers (GCs). As revealed by prospective studies in humans, bNAbs do so in response to viral escape variants arising from antibody pressure. Together, these observations suggest that vaccination to elicit bNAbs requires a series of sequential immunogens starting with an immunogen that induces the expansion of B lymphocytes that carry germline precursors of bNAbs.

The idea that sequential immunization can shepherd bNAb development was confirmed by experiments in genetically-modified mice that carry the inferred germline (iGL) precursors of human bNAbs. However, the priming immunogens used to initiate the response failed to activate and expand B-cells expressing inferred precursors of bNAbs in animals with polyclonal antibody repertoires. Indeed, the iGLs of nearly all bNAbs fail to bind to native-like HIV-1 immunogens or neutralize HIV-1 strains. Thus, a critical goal of HIV-1 vaccine development has been to design immunogens that recruit B-cells expressing bNAb precursors into GC reactions in animals with polyclonal repertoires including primates.

To this end, the germline targeting approach to immunogen design has focused on producing immunogens that bind to specific bNAb precursors with high affinity, the rationale being that B-cell recruitment to GCs is in part dependent on receptor affinity for the antigen. However, this methodology effectively limits the repertoire of recruited B-cells qualitatively and quantitatively. Moreover, it fails to account for the finding that each GC can accommodate multiple different founder B-cells with a wide range of affinities and that GC entry is limited by competition and not absolute affinity. An alternative is to design immunogens that enhance the availability of the targeted epitope while masking off-target sites. This approach differs from germline targeting in that it is agnostic to the affinity of a specific germline antibody for the antigen. Instead, it aims to recruit and expand a diverse group of precursors specific to the target site. Both approaches aim to produce expanded clones of B-cells that can then be boosted by sequential immunogens to shepherd bNAb production. To date, neither of these methods has been shown to expand B-cell clones specific for a desired HIV-1 target in wild-type animals.

Accordingly, there remains a pressing need for immunogens capable of stimulating an immune response to human immunodeficiency virus (HIV), for example, by way of expanding B-cell clones specific for a desired HIV-1 target.

SUMMARY OF THE INVENTION

Various embodiments described in this document address the above-mentioned unmet needs and/or other needs by providing HIV immunogens and uses thereof.

In one aspect, the disclosure relates to an immunogen for stimulating an immune response (e.g., HIV immune response) of a subject in need thereof. The immunogen comprises a polypeptide having a sequence that is at least 75% identical to a sequence selected from the group consisting of SEQ ID NOs: 2, 4, 6, 8, 11, and 13. The polypeptide includes substitutions at the positions corresponding to N133, N137, and N156 of SEQ ID NO: 1. In one example, the polypeptide includes an N156Q substitution or a conservative substitution of N156. In another example, the polypeptide includes V134Y, T135A, I138L, T139L, D140S, D141N, T320F, Q328M, T415V substitutions or conservative substitutions thereof.

The immunogen mentioned above binds to a broadly neutralizing antibody with an affinity (e.g., $K_D$ of about 50 μM or less). Examples of broadly neutralizing antibodies may include 10-1074 and PGT121 broadly neutralizing antibodies.

Also within the scope of this invention are an isolated nucleic acid encoding the polypeptide described above, a vector comprising the nucleic acid, and a host cell comprising the nucleic acid. The host cell can be used in a method of producing the polypeptide. The method includes culturing the host cell in a medium under conditions permitting expression of a polypeptide encoded by the nucleic acid, and purifying the polypeptide from the cultured cell or the medium of the cell.

In another aspect, this disclosure provides a protein complex comprising at least one above-described polypeptide and a virus particle comprising at least one above-described polypeptide.

In another aspect, this disclosure provides an immunogenic composition for stimulating an immune response in a subject in need thereof. The immunogenic composition includes (i) the polypeptide, the nucleic acid, the host cell, the protein complex, or the virus particle described above; and (ii) a pharmaceutically acceptable carrier. The method may further include administering the composition two or more times. The administration of the composition may result in increased numbers of broadly-neutralizing antibodies in the serum capable of recognizing a V3-glycan epitope.

In another aspect, this disclosure provides a method of stimulating an immune response in a subject in need thereof. The method includes administrating to the subject an effective amount of a composition comprising the polypeptide, the nucleic acid, the host cell, the protein complex, or the virus-like particle (VLP) described above, or a combination thereof.

In another aspect, this disclosure provides a method of treating or preventing HIV infection in a subject in need thereof. The method includes administering to the subject a therapeutically effective amount of the polypeptide, the nucleic acid, the host cell, the protein complex, or the virus particle described above, or a combination thereof. In some embodiments, the method may also include administering to the subject a therapeutically effective amount of an anti-viral agent.

In another aspect, this disclosure provides use of the polypeptide, the nucleic acid, the host cell, the protein complex, or the virus particle described above, or a combination thereof in the preparation of a medicament to treat or prevent HIV infection in a subject.

In another aspect, this disclosure provides a method for detecting or isolating an HIV-1 binding antibody in a subject infected with HIV-1. The method includes: (i) providing the polypeptide, the nucleic acid, the host cell, the protein complex, or the virus particle described above, or a combination thereof; (ii) contacting the immunogenic composition with an amount of bodily fluid from the subject; and (iii) detecting binding of the HIV-1 binding antibody to the polypeptide, thereby detecting or isolating the HIV-1 binding antibody in a subject.

In yet another aspect, this disclosure provides a kit for stimulating an immune response in a subject. The kit includes (i) one or more unit dosages of the polypeptide, the nucleic acid, the host cell, the protein complex, or the virus particle described above; (ii) instructions for administrating the polypeptide, the nucleic acid, the host cell, the protein complex, or the virus particle; and (iii) optionally an adjuvant.

This disclosure also provides an isolated anti-HIV antibody, or antigen-binding portion thereof, comprising a complementarity-determining region having a sequence that is at least 75% identical to a polypeptide sequence listed in Tables 4, 5, 6, 7, 9, 10, and 11.

Also within the scope of this disclosure is a pharmaceutical composition comprising the isolated anti-HIV antibody, or antigen-binding portion thereof as described, and a pharmaceutically acceptable carrier or excipient.

In another aspect, this disclosure provides a method of preventing or treating an HIV infection or an HIV-related disease comprising the steps of: (i) identifying a patient in need of such prevention or treatment, and (ii) administering to said patient a first therapeutic agent comprising a therapeutically effective amount of at least one anti-HIV antibody describe above, or antigen-binding portion thereof. This disclosure further provides a kit comprising a pharmaceutically acceptable dose unit of a pharmaceutically effective amount of at least one above-described isolated anti-HIV antibody, or antigen-binding portion thereof.

The details of one or more embodiments of the invention are set forth in the description below. Other features, objectives, and advantages of the invention will be apparent from the description and from the claims.

BRIEF DESCRIPTION OF THE DRAWINGS

FIGS. 1a, 1b, and 1c are diagrams showing the characterization of the RC1 immunogen. FIG. 1a shows positions of N-glycans (colored spheres) and GDIR motif (SEQ ID NO: 15) (red surfaces) in V3-glycan patches of wtBG505, 11MUTB, and RC1 Env trimers. Coordinates for glycans are mapped onto a surface representation of the wtBG505 Env trimer structure (PDB 5T3Z) (N137 glycan from PDB 5FYL) seen in the top-down orientation. FIG. 1b shows a comparison of the structures of wtBG505 (PDB 5T3Z) (left) and RC1 (right) (4.0 Å cryo-EM structure) complexed with 10-1074 Fab. Env trimer-Fab complexes are shown from the side as surface representations with glycan atoms as colored spheres. The middle panel shows a close-up superimposition of the boxed regions of the 10-1074 complexes with wtBG505 and RC1. Protein regions are shown in cartoon representations (10-1074 $V_H$ and $V_L$ in dark and light purple, Env GDIR regions in red (SEQ ID NO: 15), other portions of RC1 in wheat, wtBG505 in grey, and the N156 glycan coordinates from the wtBG505 structure shown as orange spheres. The locations of regions of V1 that show the largest displacement between the structures (gp120 residues 139-140) are indicated by dots with an arrow showing the displacement. V1 residues 149-151 are ordered in the RC1 structure, but not in the wtBG505 structure. FIG. 1c shows SPR binding data ($R_{eq}$, equilibrium binding response, versus the log of the concentration of injected protein) shown for experiments in which the Fab for the common iGL of PGT121 and 10-1074 was injected over the indicated immobilized Env trimers. N.B.=no binding above background.

FIGS. 2a, 2b, 2c, 2d, 2e, 2f, 2g, 2h, 2i, 2j, 2k, and 2l are diagrams showing wild-type mouse immunization with RC1 elicits anti-glycan patch antibodies. FIG. 2a is representative ELISA results showing the binding of serum from knock-in mice that carry the PGT121/10-1074 iGL antibody to 11MUTB after immunization with 11MUTB (left) and to RC1 after immunization with RC1 (right). Controls include naïve serum, purified PGT121 and iGL-PGT121. FIG. 2b shows area under the curve (AUC) for ELISAs as in FIG. 2a, but combined results from 2 independent experiments using 3 mice each. Each dot represents the serum of one mouse. FIG. 2d shows representative ELISA results for binding of serum from wild-type mice immunized with 11MUTB (left) and RC1 (right) to 11MUTB and RC1 respectively. FIG. 2d shows AUC for ELISAs as in c, but combined results from 2 experiments using 3 mice each. Each dot represents the serum of one mouse. FIG. 2e shows binding of serum from one representative wild-type mouse immunized with RC1 to RC1 and RC1-glycanKO in ELISA. FIG. 2f shows the ratio of the AUC for RC1 vs. RC1-glycan KO ELISAs as in FIG. 2e. The graph shows the combined results from 7 experiments with 2-3 mice immunized with RC1. Each dot represents one mouse. FIG. 2g shows representative ELISA results showing the binding of serum from wild-type mice immunized with 11MUTBΔ301 to 11MUTBΔ301. FIG. 2h shows ratio of the AUC for RC1 vs. RC1-glycan KO ELISAs for wild-type mice immunized with RC1 or RC1-4fill. FIG. 2i is pie charts showing clonal expansion of RC1 binding germinal center B cells as determined by IgV$_H$ gene sequencing. Colored pie slices are proportional to the number of clonal relatives. White indicates single IgV$_H$ sequences. The number in the center indicates the number of heavy chains analyzed. FIG. 2j shows IgH nucleotide mutations from naïve and RC1 immunized mice in FIG. 2i. FIG. 2k shows binding of monoclonal antibodies obtained from RC1 immunized mice to RC1 and RC1-glycanKO in ELISA. FIG. 2l shows characterization of the binding pattern of Ab275$_{MUR}$ and Ab276$_{MUR}$ isolated from RC1 and RC1-4fill immunized wild-type mice by ELISA on the indicated Env proteins. FIG. 2*l* discloses "GALA" as SEQ ID NO: 16.

FIGS. 3*a*, 3*b*, 3*c*, 3*d*, 3*e*, 3*f*, 3*g*, 3*h*, 3*i*, and 3*j* are a set of diagrams showing macaque immunization with RC1-4fill VLPs elicits anti-V3-glycan patch antibodies that resemble iGL bNAbs. FIG. 3*a* shows a representation of RC1-4fill VLPs showing RC1, spytag, spycatcher, and VLP. FIG. 3*b* shows electron micrographs of VLPs (top) and RC1-4fill-VLPs (bottom). FIG. 3*c* shows binding of the serum from 4 rabbits immunized with RC1-4fill VLP, a naïve control, and the monoclonal antibodies PGT121 and 3BNC117 to RC1 (black) and RC1-glycanKO (grey) shown as area under the ELISA curve (AUC). FIG. 3*d* shows binding of the serum from 8 Rhesus macaques immunized with RC1-4fill VLP, a naïve control and the monoclonal antibodies PGT121 and 3BNC117 to RC1 (black) and RC1-glycanKO (grey) shown as area under the ELISA curve (AUC). FIG. 3*e* is representative flow cytometry dot plots showing macaque germinal center B cell binding to RC1-PE (Y-axis) and RC1-AF647 or RC1-glycan KO (X-axis) for naïve (left) and immunized macaques (right). FIG. 3*f* shows percent of all B cells in the germinal centers from lymph node samples from 4 naïve or 4 immunized macaques that bind to RC1 but not to RC1-glycanKO by flow cytometry. FIG. 3*g* is pie charts showing clonal expansion of RC1 binding germinal center B cells as determined by IgH gene sequencing. The number in the center indicates the number of $IgV_H$ sequences analyzed. FIG. 3*h* shows $IgV_H$ mutations for all sequences in FIG. 3*g*, each dot represents one $IgV_H$. FIG. 3*i* shows iGL sequence of CDRL3 (SEQ ID NO: 446) for PGT121/10-1074 and logo plots for all IgL chains cloned from RC1 binding GC B cells from immunized macaques. FIG. 3*j* shows fraction of IgL CDR3 sequences cloned from GC B cells from 4 naïve and 4 RC1 immunized macaques that show a DSS-like motif.

FIG. 4*a* shows ELISA results for binding of monoclonal macaque antibodies to RC1 and RC1-glycanKO-GAIA ("GAIA" disclosed as SEQ ID NO: 16). Controls are 10-1074 and 3BNC117. FIG. 4*b* shows IgH CDR3 length of V3-glycan patch specific macaque antibodies. FIG. 4*c* shows a number of nucleotide mutations in $IgV_H$ and $IgV_L$ regions of V3-glycan patch specific macaque antibodies. FIG. 4*d* shows area under the curve (AUC) for ELISAs on the indicated proteins for antibodies $Ab876_{NHP}$, $Ab897_{NHP}$, $Ab933_{NHP}$, $Ab936_{NHP}$, $Ab1170_{NHP}$, 3BNC117 and 10-1074. FIG. 4*e* discloses "GAIA" as SEQ ID NO: 16.

FIG. 5*a* shows top-down views of the binding orientation of 10-1074 Fab compared with other V3-glycan patch bNAb Fabs (PGT128 and PGT135; PDB SACO and 4JM2) (left), $Ab275_{MUR}$ (second from left), $Ab874_{NHP}$ (third from left), and $Ab897_{NHP}$ (right). Env and Fab structures are shown in cartoon representations. FIG. 5*b* (top panel) shows $V_H$-$V_L$ domains of 10-1074 (left) and elicited antibody Fabs (three right panels) bound to the V3-glycan patch on one protomer of RC1 trimer (from cryo-EM structures of complexes of 10-1074 (left), $Ab275_{MUR}$ (second from left), $Ab874_{NHP}$ (third from left), and $Ab897_{NHP}$ (right) bound to RC1 Env trimer). GDIR residues (SEQ ID NO: 15) on gp120 are it) highlighted in red, and glycan coordinates are shown as colored spheres. FIG. 5*b* (bottom panel) shows 90° rotation of complexes in top panels to show top-down views of antibody combining sites with CDRs highlighted as loops and gp120 glycans (colored spheres) and GDIR (SEQ ID NO: 15) (red) regions from RC1 mapped onto antibody combining sites. FIG. 5*c* shows comparisons of interactions of GDIR motif (SEQ ID NO: 15) with 10-1074 and with elicited antibodies.

FIGS. 6*a* and 6*b* show the characterization of RC1 by evaluating its interactions with bNAbs by ELISA. FIG. 6*a* shows that a V1-V2-specific bNAb that interacts with the N156 glycan32 showed reduced binding to RC1 as compared to BG505, and the absence of the N156 PNGS enhances neutralization by PGT121 and 10-1074. FIG. 6*b* shows that bNAbs targeting the V3-glycan epitope, the CD4 binding site, or the gp120-gp41 interface bound similarly to RC1 and BG505.

FIGS. 7*a*, 7*b*, 7*c*, and 7*d* show the single-particle cryo-EM study of RC1 respectively complexed with the antigen-binding fragment (Fab) of 10-1074 (FIG. 7*a*), $Ab874_{NHP}$ (FIG. 7*b*), $Ab275_{MUR}$ (FIG. 7*c*), and $Ab897_{NHP}$ (FIG. 7*d*).

FIGS. 9*a*, 9*b*, 9*c*, 9*d*, and 9*e* show the characterization of RC1 and RC1-4fill and their response to the off-target sites.

FIGS. 13*a*, 13*b*, 13*c*, 13*d*, 13*e*, 13*f*, 13*g*, 13*h*, 13*i*, and 13*j* (collectively "FIG. 13") are a set of diagrams showing characterization of the immunogens including RC1-3fill. FIG. 13*a* is a diagram showing size-exclusion chromatography (SEC) traces for the RC1, RC1-3fill, and RC1-4fill immunogens. FIG. 13*b* provides the representative yields from a 1 L expression in HEK 293T 6E cells for each immunogen. FIGS. 13*c*, 13*d*, 13*e*, and 13*f* are a set of diagrams showing SEC traces and electron micrographs for the RC1 and RC1-3fill immunogens. FIG. 13*g* shows representative SEC traces for the purification of the AP205-RC1-VLPs and AP205-RC1-3fill-VLPs. FIG. 13*d* shows electron micrographs of the AP205-RC1-VLPs (left) and AP205-RC1-3fill-VLPs (right). FIG. 13*e* shows representative SEC traces for the purification of the mi3-RC1-NPs and mi3-RC1-3fill-NPs. FIG. 13*f* shows electron micrographs of the mi3-RC1-NPs (left) and mi3-RC1-3fill-NPs (right). FIGS. 13*f* and 13*h* show the SEC profiles for both the initial purification of the AP205-RC1-VLPs (FIG. 13*f*) and the mi3-RC1-NPs (FIG. 13*h*), and reinjection of the sample at 28 days (AP205) and 11 days (mi3). FIGS. 13*i* and 13*j* show binding of the serum from 6 WT mice immunized with either mi3-RC1-NPs (FIG. 13*i*) or mi3-RC1-3fill-NPs (FIG.

Figures 3A, 3B, 3C, 3D:
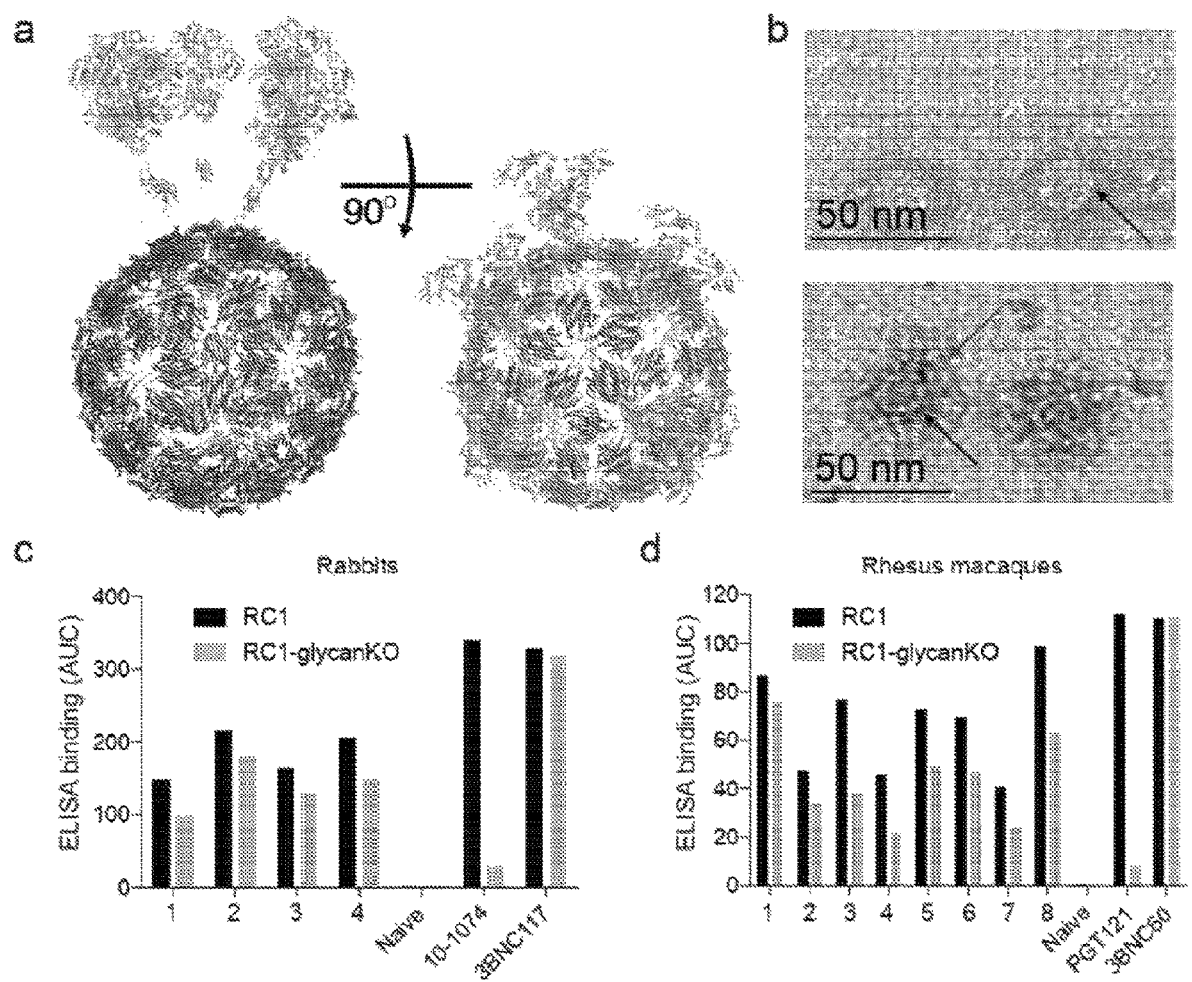

13j), a naïve control and the monoclonal antibodies 10-1074 and 3BNC117 to RC1 and RC1-glycanKO shown as area under the ELISA curve (AUC).

DETAILED DESCRIPTION OF THE INVENTION

The disclosed immunogens for stimulating an immune response in a subject are based on an unexpected discovery that a novel immunogen, RC1, and its variants, activate B-cells expressing precursors of bNAbs within polyclonal repertoires.

Broadly neutralizing antibodies (bNAbs) protect against HIV-1 infection, suggesting that a vaccine that elicits them would be effective. However, one of the major hurdles is that vaccination does not elicit bNAbs, in part, because B-cells expressing germline bNAb precursors do not respond to native-like HIV-1 envelope (Env) antigens. Accordingly, this disclosure provides immunogens that facilitate recognition of the V3-glycan patch on HIV-1 Env while concealing non-conserved immunodominant regions, for example, by addition of glycans and/or multimerization to virus-like particles. This disclosure demonstrates that mouse, rabbit, and Rhesus macaque immunizations with the disclosed immunogens (e.g., RC1, RC1-4fill, RC1-3fill) elicited serologic responses targeting the V3-glycan patch. Further, antibody cloning and cryo-EM structures of antibody-Env complexes confirmed that RC1 immunization expands clones of B-cells carrying anti-V3-glycan patch antibodies that resemble predicted precursors of human bNAbs. Thus, the disclosed immunogens, such as RC1, are a suitable priming immunogen for sequential vaccination strategies to stimulate an immune response (e.g., HIV immune response) in a subject.

I. IMMUNOGENS AND IMMUNOGENIC COMPOSITIONS

A. Polypeptide

This disclosure provides an immunogen and its variants for stimulating an immune response (e.g., HIV immune response) of a subject in need thereof. In some embodiments, the immunogen includes a portion of the HIV envelope protein, i.e., gp120, which is located on the surface of the HIV. gp120 is the N-terminal segment of the HIV envelope protein gp160, anchored in the membrane bilayer at its carboxyl-terminal region. gp120 protrudes into the aqueous environment surrounding the virion, whereas its C-terminal counterpart, gp41, spans the membrane. The gp120 molecule consists of a polypeptide core of 60,000 daltons, which is extensively modified by N-linked glycosylation to increase the apparent molecular weight of the molecule to 120,000 daltons. The amino acid sequence of gp120 contains five relatively conserved domains interspersed with five hypervariable domains. The positions of the 18 cysteine residues in the gp120 primary sequence and the positions of 13 of the approximately 24 N-linked glycosylation sites in the gp120 sequence are common to all gp120 sequences.

In some embodiments, the immunogen may include the Env V3 region of gp120. The Env V3 region of gp120 encompasses the V3-glycan patch epitope, which includes a group of high-mannose and complex-type N-glycans surrounding the Env V3 region. In the V3-glycan patch epitope, glycosylation generally occurs at gp120 residues N133, N137, N156, N295, N301, N332, N339, N385, and N392. bNAbs, such as PGT121, 10-1074, and BG18, target the V3-glycan patch epitope. They reach through the glycans using elongated CDRH3 loops and portions of CDRL1 and CDRL3 to contact the highly-conserved GDIR motif (G324-D325-I326-R327) (SEQ ID NO: 15) at the base of the V3 loop.

In some embodiments, the immunogen may include one or more modifications in the Env V3 region of gp120. The immunogen comprises a polypeptide having a sequence that is at least 75% identical to a sequence selected from the group consisting of SEQ ID NOs: 2, 4, 6, 8, 11, and 13 listed in Table 1. The polypeptide may include substitutions at one or more glycosylation sites (e.g., N133, N137, N156, N295, N301, N332, N339, N385, and N392) in the Env region. For example, the polypeptide may include a substitution at the positions corresponding to N133, N137, and N156 of SEQ ID NO: 1. In one example, the polypeptide includes an N156Q substitution or a conservative substitution of N156. In another example, the polypeptide, such as RC1 (SEQ ID NO: 2; Table 1), includes deletions at N133, N137, and N156 and additional substitutions including V134Y, T135A, I138L, T139L, D140S, D141N, T320F, Q328M, and T415V. As will be illustrated in the examples, the disclosed immunogens, such as RC1, activate and expand a diverse group of B-cells expressing antibodies that resemble human V3-glycan bNAb precursors in mice, rabbits, and Rhesus macaques.

TABLE 1

Sequences of HIV Immunogens.

| SEQ ID NO. | Sequence | Other information |
|---|---|---|
| SEQ ID NO: 1 | MDAMKRGLCCVLLLCGAVEVSPSQEIHARFRRGARAENLWVTV YYGVPVWKDAETTLFCASDAKAYETEKHNVWATHACVPTDPNPQE IHLENVTEEFNMWKNNMVEQMHTDIISLWDQSLKPCVKLTPLCVTL QCTNVTNNITDDMRGELKNCSFNMTTELRDKKQKVYSLFYRLDVV QINENQGNRSNNSNKEYRLINCNTSAITQACPKVSFEPIPIHYCAPAGF AILKCKDKKFNGTGPCPSVSTVQCTHGIKPWSTQLLLNGSLAEEEVM IRSENITNNAKNILVQFNTPVQINCTRPNNNTRKSIRIGPGQAFYATGD IIGDIRQAHCNVSKATWNETLGKWKQLRKHFGNNTIIRFANSSGGDL EVTTHSFNCG̲GEFFYCNTSGLFNSTWISNTSVQGSNSTGSNDSITLPC RIKQIINMWQRIGQAMYAPPIQGVIRCVSNITGLILTRDGGSTNSTTET FRPGGGDMRDNVVRSELYKYKWKIEPLGVAPTRCKRRVVGRRRRR RAVGIGAVFLGFLGAAGSTMGAASMTLTVQARN̲LLSGIVQ̲Q̲Q̲SNLL RAPEAQQHLLKLTVWGIKQLQARVLAVERYLRDQQLLGIVVGCSGK LIC̲C̲TNVPWNSSWSNRNLSEIWDNMTWLQWDKEISNYTQIIYGLLEE SQN̲QQEKNEQDLLALD | 11MUTB (SOSIP.664) derived from wtBG505 (changes made to wtBG505 are underlined and in bold) |

TABLE 1-continued

Sequences of HIV Immunogens.

| SEQ ID NO. | Sequence | Other information |
|---|---|---|
| SEQ ID NO: 2 | MDAMKRGLCCVLLLCGAVFVSPAGAGSNLWVTVYYGVPVWKDAE<br>TTLFCASDAKAYETEKHNVWATHACVPTDPNPQEIHLENVTEEFNM<br>WKNNMVEQMHEDIISLWDQSLKPCVKLTPLCVTLQCTNYAPNLLSN<br>MRGELKQCSFNMTTELRDKKQKVYSLFYRLDVVQINENQGNRSNNS<br>NKEYRLINCNTSAITQACPKVSFEPIPIHYCAPAGFAILKCKDKKFNGT<br>GPCPSVSTVQCTHGIKPVVSTQLLLNGSLAEEEVIIRSENITNNAKNIL<br>VQLNTPVQINCTRPNNNTVKSIRIGPGQAFYYFGDIIGDIRMAHCNVS<br>KATWNETLGKVVKQLRKHFGNNTIIRFAQSSGGDLEVTTHSFNCGG<br>EFFYCNTSGLFNSTWISNTSVQGSNSTGSNDSIVLPCRIKQIINMWQRI<br>GQAMYAPPIQGVIRCVSNITGLILTRDGGSTNSTTETFRPGGGDMRD<br>NWRSELYKYKVVKIEPLGVAPTRCKRRVVGRRRRRRAVGIGAVSLG<br>FLGAAGSTMGAASMTLTVQARNLLSGIVQQQSNLLRAPEPQQHLLK<br>DTHWGIKQLQARVLAVEHYLRDQQLLGIWGCSGKLICCTNVPWNSS<br>WSNRNLSEIWDNMTWLQWDKEISNYTQIIYGLLEESQNQQEKNEQD<br>LLALD | RC1 |
| SEQ ID NO: 3 | ATGGACGCCATGAAGAGGGGACTTTGCTGTGTTCTTCTGCTGTGT<br>GGCGCCGTGTTTGTTAGCCCCGCTGGGGCCGGATCCAACCTGTGG<br>GTCACTGTGTATTATGGTGTGCCAGTGTGGAAGGATGCAGAGACA<br>ACACTCTTTTGCGCCTCCGACGCTAAAGCATACGAAACGGAGAAG<br>CACAACGTGTGGGCGACCCATGCCTGTGTCCCTACAGACCCTAAC<br>CCTCAGGAAATTCATCTTGAAAATGTCACAGAAGAGTTTAACATG<br>TGGAAAAACAACATGGTGGAACAGATGCACGAGGATATCATTTC<br>CCTGTGGGACCAGAGTCTGAAACCATGTGTCAAACTTACTCCTCT<br>GTGCGTGACTCTCCAGTGTACAAACTACGCACCCAACCTTTTGAG<br>TAATATGCGGGGCGAGCTCAAGCAGTGCGTTTCAATATGACAAC<br>CGAATTGAGAGACAAAAAACAGAAAGTATACTCCCTCTTCTACCG<br>GCTGGACGTGGTGCAGATCAATGAGAACCAAGGAAATAGAAGCA<br>ACAACAGTAACAAGGAATACCGGCTCATAAATTGCAATACCAGC<br>GCTATTACGCAGGCTTGCCCTAAGGTGAGCTTTGAGCCAATCCCG<br>ATACATTATTGTGCCCCGGCAGGCTTCGCTATACTGAAATGCAAG<br>GATAAGAAGTTTAATGGGACAGGCCCTTGCCCTAGCGTTTCAACG<br>GTCCAATGTACCCACGGGATCAAGCCCGTAGTGTCTACACAGCTC<br>CTGCTGAACGGCAGCCTGGCCGAAGAGGAGGTCATAATTAGGAG<br>CGAGAACATAACTAACAACGCTAAAAACATTCTCGTCCAGCTCAA<br>TACACCTGTGCAGATCAACTGCACCCGGCCCAACAACAACACCGT<br>GAAGTCCATTAGAATTGGTCCGGGACAGGCATTTTACTACTTCGG<br>AGATATAATAGGCGATATCAGAATGGCGCACTGTAACGTGAGCA<br>AGGCCACCTGGAACGAGACCCTGGGCAAGGTGGTCAAACAGTTG<br>CGCAAGCACTTTGGGAACAACACCATTATTCGGTTTGCCCAGTCT<br>TCCGGCGGCGACCTTGAAGTGACCACTCATAGCTTCAACTGTGGA<br>GGGGAGTTTTTCTATTGCAATACATCAGGCCTGTTCAACTCTACAT<br>GGATCTCAAATACCAGTGTCCAGGGGTCAAATTCCACCGGTAGCA<br>ACGACAGCATCGTCTTGCCTTGTCGAATCAAGCAGATCATTAATA<br>TGTGGCAGAGGATTGGTCAGGCCATGTACGCACCTCCAATACAGG<br>GAGTCATTCGGTGCGTCAGCAATATTACTGGATTGATCCTCACCA<br>GAGATGGCGGGAGTACCAATAGCACTACCGAAACTTTCCGCCCA<br>GGAGGAGGCGACATGCGGGATAATTGGAGATCAGAGCTGTATAA<br>GTATAAGGTGGTGAAAATTGAACCCCTGGGAGTGGCGCCAACTA<br>GATGTAAACGGCGAGTGGTTGGCCGGAGACGGCGGCGGAGAGCA<br>GTGGGGATTGGCGCTGTCTCACTCGGTTTCCTGGGTGCTGCCGGC<br>AGTACAATGGGCGCCGCCAGCATGACGCTCACAGTGCAGGCCCG<br>GAATCTTCTTAGCGGAATTGTGCAACAACAAAGCAATCTGTTGAG<br>AGCCCCGGAACCGCAGCAACATCTGTTGAAGGACACACATTGGG<br>GCATCAAGCAGCTGCAAGCTCGGGTTCTGGCTGTTGAGCATTACC<br>TGAGAGACCAACAGCTGCTGGGCATATGGGGATGCTCAGGAAAA<br>CTGATCTGCTGCACCAATGTCCCATGAACAGCTCATGGTCAAAC<br>AGGAACCTGAGCGAGATCTGGGATAACATGACCTGGTTGCAGTG<br>GGACAAAGAAATTAGCAATTACACACAGATCATCTACGGCCTCCT<br>GGAGGAAAGCCAGAATCAGCAGGAGAAAAATGAGCAGGATCTG<br>CTTGCCCTTGACTGA | RC1 |
| SEQ ID NO: 4 | MDAMKRGLCCVLLLCGAVFVSPAGAGSNLWVTVYYGVPVWKDAE<br>TTLFCASDAKAYETEKHNVWATHACVPTDPNPQEIHLENVTEEFNM<br>WKNNMVEQMHEDIISLWDQSLKPCVKLTPLCVTLQCTNYAPNLLSN<br>MRGELKQCSFNMTTELRDKKQKVYSLFYRLDVVQINENQGNRSNNS<br>NKEYRLINCNTSAITQACPKVSFEPIPIHYCAPAGFAILKCKDKKFNGT<br>GPCPSVSTVQCTHGIKPVVSTQLLLNGSLAEEEVIIRSENITNNAKNIL<br>VQLNTPVQINCTRPNNNTVKSIRIGPGQAFYYFGDIIGDIRMAHCNVS<br>KATWNETLGKVVKQLRKHFGNNTIIRFAQSSGGDLEVTTHSFNCGG<br>EFFYCNTSGLFNSTWISNTSVQGSNSTGSNDSIVLPCRIKQIINMWQRI<br>GQAMYAPPIQGVIRCVSNITGLILTRDGGSTNSTTETFRPGGGDMRD<br>NVVRSELYKYKVVKIEPLGVAPTRCKRRVVGRRRRRRAVGIGAVSLG<br>FLGAAGSTMGAASMTLTVQARNLLSGIVQQQSNLLRAPEPQQHLLK<br>DTHWGIKQLQARVLAVEHYLRDQQLLGIVGCSGKLICCTNVPWNSS | RC1 spytag |

TABLE 1-continued

Sequences of HIV Immunogens.

| SEQ ID NO. | Sequence | Other information |
|---|---|---|
| | WSNRNLSEIVVDNMTWLQWDKEISNYTQIIYGLLEESQNQQEKNEQD<br>LLALDGGGGSGGGSGGGSGSGAHIVMVDAYKPTK | |
| SEQ ID NO: 5 | ATGGACGCCATGAAGAGGGGACTTTGCTGTGTTCTTCTGCTGTGT<br>GGCGCCGTGTTTGTTAGCCCCGCTGGGGCCGGATCCAACCTGTGG<br>GTCACTGTGTATTATGGTGTGCCAGTGTGGAAGGATGCAGAGACA<br>ACACTCTTTTGCGCCTCCGACGCTAAAGCATACGAAACGGAGAAG<br>CACAACGTGTGGGCGACCCATGCCTGTGTCCCTACAGACCCTAAC<br>CCTCAGGAAATTCATCTTGAAAATGTCACAGAAGAGTTTAACATG<br>TGGAAAAACAACATGGTGGAACAGATGCACGAGGATATCATTTC<br>CCTGTGGGACCAGAGTCTGAAACCATGTGTCAAACTTACTCCTCT<br>GTGCGTGACTCTCCAGTGTACAAACTACGCACCCAACCTTTTGAG<br>TAATATGCGGGGCGAGCTCAAGCAGTGCAGTTTCAATATGACAAC<br>CGAATTGAGAGACAAAAAACAGAAAGTATACTCCCTCTTCTACCG<br>GCTGGACGTGGTGCAGATCAATGAGAACCAAGGAAATAGAAGCA<br>ACAACAGTAACAAGGAATACCGGCTCATAAATTGCAATACCAGC<br>GCTATTACGCAGGCTTGCCCTAAGGTGAGCTTTGAGCCAATCCCG<br>ATACATTATTGTGCCCCGGCAGGCTTCGCTATACTGAAATGCAAG<br>GATAAGAAGTTTAATGGGACAGGCCCTTGCCCTAGCGTTTCAACG<br>GTCCAATGTACCCACGGGATCAAGCCCGTAGTGTCTACACAGCTC<br>CTGCTGAACGGCAGCCTGGCCGAAGAGGAGGTCATAATTAGGAG<br>CGAGAACATAACTAACAACGCTAAAAACATTCTCGTCCAGCTCAA<br>TACACCTGTGCAGATCAACTGCACCCGGCCCAACAACAACACCGT<br>GAAGTCCATTAGAATTGGTCCGGGACAGGCATTTTACTACTTCGG<br>AGATATAATAGGCGATATCAGAATGGCGCACTGTAACGTGAGCA<br>AGGCCACCTGGAACGAGACCCTGGGCAAGGTGGTCAAACAGTTG<br>CGCAAGCACTTTGGGAACAACACCATTATTCGGTTTGCCCAGTCT<br>TCCGGCGGCGACCTTGAAGTGACCACTCATAGCTTCAACTGTGGA<br>GGGGAGTTTTTCTATTGCAATACATCAGGCCTGTTCAACTCTACAT<br>GGATCTCAAATACCAGTGTCCAGGGGTCAAATTCCACCGGTAGCA<br>ACGACAGCATCGTCTTGCCTTGTCGAATCAAGCAGATCATTAATA<br>TGTGGCAGAGGATTGGTCAGGCCATGTACGCACCTCCAATACAGG<br>GAGTCATTCGGTGCGTCAGCAATATTACTGGATTGATCCTCACCA<br>GAGATGGCGGGAGTACCAATAGCACTACCGAAACTTTCCGCCCA<br>GGAGGAGGCGACATGCGGGATAATTGGAGATCAGAGCTGTATAA<br>GTATAAGGTGGTGAAAATTGAACCCCTGGGAGTGGCGCCAACTA<br>GATGTAAACGGCGAGTGGTTGGCCGGAGACGGCGGCGGAGAGCA<br>GTGGGGATTGGCGCTGTCTCACTCGGTTTCCTGGGTGCTGCCGGC<br>AGTACAATGGGCGCCGCCAGCATGACGCTCACAGTGCAGGCCCG<br>GAATCTTCTTAGCGGAATTGTGCAACAACAAAGCAATCTGTTGAG<br>AGCCCCGGAACCGCAGCAACATCTGTTGAAGGACACACATTGGG<br>GCATCAAGCAGCTGCAAGCTCGGGTTCTGGCTGTTGAGCATTACC<br>TGAGAGACCAACAGCTGCTGGGCATATGGGGATGCTCAGGAAAA<br>CTGATCTGCTGCACCAATGTCCCATGGAACAGCTCATGGTCAAAC<br>AGGAACCTGAGCGAGATCTGGGATAACATGACCTGGTTGCAGTG<br>GGACAAAGAAATTAGCAATTACACACAGATCATCTACGGCCTCCT<br>GGAGGAAAGCCAGAATCAGCAGGAGAAAAATGAGCAGGATCTG<br>CTTGCCCTTGACGGTGGAGGCGGTTCAGGCGGCGGATCTGGCGGT<br>GGGAGCGGTTCGGGAGCCCATAGTGATGGTTGATGCCTATAAA<br>CCGACCAAGTGA | RC1 spytag |
| SEQ ID NO: 6 | MDAMKRGLCCVLLLCGAVFVSPAGAGSNLWVTVYYGVPVWKDAE<br>TTLFCASDAKAYETEKHNVWATHACVPTDPNPQEIHLENVTEEFNM<br>WKNNMVEQMHEDIISLWDQSLKPCVKLTPLCVTLQCTNYAPNLLSN<br>MRGELKQCSFNMTTELRDKKQKVYSLFYRLDVVQINENQGNRSNNS<br>NKEYRLINCNTSAITQACPKVSFEPIPIHYCAPAGFAILKCKNKTFNGT<br>GPCPNVSTVQCTHGIKPVVSTQLLLNGSLAEEEVIIRSENITNNAKNIL<br>VQLNTSVQINCTRPNNNTVKSIRIGPGQAFYYFGDIIGDIRMAHCNVS<br>KATWNETLGNVSKQLRKHFGNNTIIRFAQSSGGDLEVTTHSFNCGGE<br>FFYCNTSGLFNSTWISNTSVQGSNSTGSNDSIVLPCRIKQIINMWQRIG<br>QAMYAPPIQGVIRCVSNITGLILTRDGGSTNSTTETFRPGGGDMRDN<br>WRSELYKYKVVKIEPLGVAPTRCKRRVVGRRRRRRAVGIGAVSLGF<br>LGAAGSTMGAASMTLTVQARNLLSGIVQQQSNLLRAPEPQQHLLKD<br>THWGIKQLQARVLAVEHYLRDQQLLGIVVGCSGKLICCTNVPWNSS<br>WSNRNLSEIVVDNMTWLQWDKEISNYTQIIYGLLEESQNQQEKNEQD<br>LLALD | RC1-4fill |
| SEQ ID NO: 7 | ATGGACGCCATGAAGAGGGGACTTTGCTGTGTTCTTCTGCTGTGT<br>GGCGCCGTGTTTGTTAGCCCCGCTGGGGCCGGATCCAACCTGTGG<br>GTCACTGTGTATTATGGTGTGCCAGTGTGGAAGGATGCAGAGACA<br>ACACTCTTTTGCGCCTCCGACGCTAAAGCATACGAAACGGAGAAG<br>CACAACGTGTGGGCGACCCATGCCTGTGTCCCTACAGACCCTAAC<br>CCTCAGGAAATTCATCTTGAAAATGTCACAGAAGAGTTTAACATG<br>TGGAAAAACAACATGGTGGAACAGATGCACGAGGATATCATTTC<br>CCTGTGGGACCAGAGTCTGAAACCATGTGTCAAACTTACTCCTCT | RC1-4fill |

TABLE 1-continued

Sequences of HIV Immunogens.

| SEQ ID NO. | Sequence | Other information |
|---|---|---|
| | GTGCGTGACTCTCCAGTGTACAAACTACGCACCCAACCTTTTGAG<br>TAATATGCGGGCGAGCTCAAGCAGTGCAGTTTCAATATGACAAC<br>CGAATTGAGAGACAAAAAACAGAAAGTATACTCCCTCTTCTACCG<br>GCTGGACGTGGTGCAGATCAATGAGAACCAAGGAAATAGAAGCA<br>ACAACAGTAACAAGGAATACCGGCTCATAAATTGCAATACCAGC<br>GCTATTACGCAGGCTTGCCCTAAGGTGAGCTTTGAGCCAATCCCG<br>ATACATTATTGTGCCCCGGCAGGCTTCGCTATACTGAAATGCAAG<br>AATAAGACGTTTAATGGGACAGGCCCTTGCCCTAACGTTTCAACG<br>GTCCAATGTACCCACGGGATCAAGCCCGTAGTGTCTACACAGCTC<br>CTGCTGAACGGCAGCCTGGCCGAAGAGGAGGTCATAATTAGGAG<br>CGAGAACATAACTAACAACGCTAAAAACATTCTCGTCCAGCTCAA<br>TACAAGTGTGCAGATCAACTGCACCCGGCCCAACAACAACACCG<br>TGAAGTCCATTAGAATTGGTCCGGGACAGGCATTTTACTACTTCG<br>GAGATATAATAGGCGATATCAGAATGGCGCACTGTAACGTGAGC<br>AAGGCCACCTGGAACGAGACCCTGGGCAATGTGAGCAAACAGTT<br>GCGCAAGCACTTTGGGAACAACACCATTATTCGGTTTGCCCAGTC<br>TTCCGGCGGCGACCTTGAAGTGACCACTCATAGCTTCAACTGTGG<br>AGGGGAGTTTTTCTATTGCAATACATCAGGCCTGTTCAACTCTAC<br>ATGGATCTCAAATACCAGTGTCCAGGGGTCAAATTCCACCGGTAG<br>CAACGACAGCATCGTCTTGCCTTGTCGAATCAAGCAGATCATTAA<br>TATGTGGCAGAGGATTGGTCAGGCCATGTACGCACCTCCAATACA<br>GGGAGTCATTCGGTGCGTCAGCAATATTACTGGATTGATCCTCAC<br>CAGAGATGGCGGAGTACCAATAGCACTACCGAAACTTTCCGCC<br>CAGGAGGAGGCGACATGCGGGATAATTGGAGATCAGAGCTGTAT<br>AAGTATAAGGTGGTGAAAATTGAACCCCTGGGAGTGGCGCCAAC<br>TAGATGTAAACGGCGAGTGGTTGGCCGGAGACGGCGGCGGAGAG<br>CAGTGGGGATTGGCGCTGTCTCACTCGGTTTCCTGGGTGCTGCCG<br>GCAGTACAATGGGCGCCGCCAGCATGACGCTACAGTGCAGGCC<br>CGGAATCTTCTTAGCGGAATTGTGCAACAACAAAGCAATCTGTTG<br>AGAGCCCCGGAACCGCAGCAACATCTGTTGAAGGACACACATTG<br>GGGCATCAAGCAGCTGCAAGCTCGGGTTCTGGCTGTTGAGCATTA<br>CCTGAGAGACCAACAGCTGCTGGGCATATGGGGATGCTCAGGAA<br>AACTGATCTGCTGCACCAATGTCCCATGGAACAGCTCATGGTCAA<br>ACAGGAACCTGAGCGAGATCTGGGATAACATGACCTGGTTGCAG<br>TGGGACAAAGAAATTAGCAATTACACACAGATCATCTACGGCCTC<br>CTGGAGGAAAGCCAGAATCAGCAGGAGAAAAATGAGCAGGATCT<br>GCTTGCCCTTGACTGA | |
| SEQ ID NO: 8 | MDAMKRGLCCVLLLCGAVFVSPAGAGSNLWVTVYYGVPVWKDAE<br>TTLFCASDAKAYETEKHNVWATHACVPTDPNPQEIHLENVTEEFNM<br>WKNNMVEQMHEDIISLWDQSLKPCVKLTPLCVTLQCTNYAPNLLSN<br>MRGELKQCSFNMTTELRDKKQKVYSLFYRLDVVQINENQGNRSNNS<br>NKEYRLINCNTSAITQACPKVSFEPIPIHYCAPAGFAILKCKNKTFNGT<br>GPCPNVSTVQCTHGIKPVVSTQLLLNGSLAEEEVIIRSENITNNAKNIL<br>VQLNTSVQINCTRPNNNTVKSIRIGPGQAFYYFGDIIGDIRMAHCNVS<br>KATWNETLGNVSKQLRKHFGNNTIIRFAQSSGGDLEVTTHSFNCGGE<br>FFYCNTSGLFNSTWISNTSVQGSNSTGSNDSIVLPCRIKQIINMWQRIG<br>QAMYAPPIQGVIRCVSNITGLILTRDGGSTNSTTETFRPGGGDMRDN<br>WRSELYKYKVVKIEPLGVAPTRCKRRVVGRRRRRAVGIGAVSLGF<br>LGAAGSTMGAASMTLTVQARNLLSGIVQQQSNLLRAPEPQQHLLKD<br>THWGIKQLQARVLAVEHYLRDQQLLGIVVGCSGKLICCTNVPWNSS<br>WSNRNLSEIVVDNMTWLQWDKEISNYTQIIYGLLEESQNQQEKNEQD<br>LLALDGGGGSGGGSGGGSGSGAHIVMVDAYKPTK | RC1-4fill spytag |
| SEQ ID NO: 9 | ATGGACGCCATGAAGAGGGGACTTTGCTGTGTTCTTCTGCTGTGT<br>GGCGCCGTGTTTGTTAGCCCCGCTGGGGCCGGATCCAACCTGTGG<br>GTCACTGTGTATTATGGTGTGCCAGTGTGGAAGGATGCAGAGACA<br>ACACTCTTTTGCGCCTCCGACGCTAAAGCATACGAAACGGAGAAG<br>CACAACGTGTGGGCGACCCATGCCTGTGTCCCTACAGACCCTAAC<br>CCTCAGGAAATTCATCTTGAAAATGTCACAGAAGAGTTTAACATG<br>TGGAAAAACAACATGGTGGAACAGATGCACGAGGATATCATTTC<br>CCTGTGGGACCAGAGTCTGAAACCATGTGTCAAACTTACTCCTCT<br>GTGCGTGACTCTCCAGTGTACAAACTACGCACCCAACCTTTTGAG<br>TAATATGCGGGCGAGCTCAAGCAGTGCAGTTTCAATATGACAAC<br>CGAATTGAGAGACAAAAAACAGAAAGTATACTCCCTCTTCTACCG<br>GCTGGACGTGGTGCAGATCAATGAGAACCAAGGAAATAGAAGCA<br>ACAACAGTAACAAGGAATACCGGCTCATAAATTGCAATACCAGC<br>GCTATTACGCAGGCTTGCCCTAAGGTGAGCTTTGAGCCAATCCCG<br>ATACATTATTGTGCCCCGGCAGGCTTCGCTATACTGAAATGCAAG<br>AATAAGACGTTTAATGGGACAGGCCCTTGCCCTAACGTTTCAACG<br>GTCCAATGTACCCACGGGATCAAGCCCGTAGTGTCTACACAGCTC<br>CTGCTGAACGGCAGCCTGGCCGAAGAGGAGGTCATAATTAGGAG<br>CGAGAACATAACTAACAACGCTAAAAACATTCTCGTCCAGCTCAA<br>TACAAGTGTGCAGATCAACTGCACCCGGCCCAACAACAACACCG<br>TGAAGTCCATTAGAATTGGTCCGGGACAGGCATTTTACTACTTCG | RC1-4fill spytag |

TABLE 1-continued

Sequences of HIV Immunogens.

| SEQ ID NO. | Sequence | Other information |
|---|---|---|
| | GAGATATAATAGGCGATATCAGAATGGCGCACTGTAACGTGAGC<br>AAGGCCACCTGGAACGAGACCCTGGGCAATGTGAGCAAACAGTT<br>GCGCAAGCACTTTGGGAACAACACCATTATTCGGTTTGCCCAGTC<br>TTCCGGCGGCGACCTTGAAGTGACCACTCATAGCTTCAACTGTGG<br>AGGGGAGTTTTTCTATTGCAATACATCAGGCCTGTTCAACTCTAC<br>ATGGATCTCAAATACCAGTGTCCAGGGGTCAAATTCCACCGGTAG<br>CAACGACAGCATCGTCTTGCCTTGTCGAATCAAGCAGATCATTAA<br>TATGTGGCAGAGGATTGGTCAGGCCATGTACGCACCTCCAATACA<br>GGGAGTCATTCGGTGCGTCAGCAATATTACTGGATTGATCCTCAC<br>CAGAGATGGCGGGAGTACCAATAGCACTACCGAAACTTTCCGCC<br>CAGGAGGAGGCGACATGCGGGATAATTGGAGATCAGAGCTGTAT<br>AAGTATAAGGTGGTGAAAATTGAACCCCTGGGAGTGGCGCCAAC<br>TAGATGTAAACGGCGAGTGGTTGGCCGGAGACGGCGGCGGAGAG<br>CAGTGGGGATTGGCGCTGTCTCACTCGGTTTCCTGGGTGCTGCCG<br>GCAGTACAATGGGCGCCGCCAGCATGACGCTCACAGTGCAGGCC<br>CGGAATCTTCTTAGCGGAATTGTGCAACAACAAAGCAATCTGTTG<br>AGAGCCCCGGAACCGCAGCAACATCTGTTGAAGGACACACATTG<br>GGGCATCAAGCAGCTGCAAGCTCGGGTTCTGGCTGTTGAGCATTA<br>CCTGAGAGACCAACAGCTGCTGGGCATATGGGGATGCTCAGGAA<br>AACTGATCTGCTGCACCAATGTCCATGGAACAGCTCATGGTCAA<br>ACAGGAACCTGAGCGAGATCTGGGATAACATGACCTGGTTGCAG<br>TGGGACAAAGAAATTAGCAATTACACACAGATCATCTACGGCCTC<br>CTGGAGGAAAGCCAGAATCAGCAGGAGAAAAATGAGCAGGATCT<br>GCTTGCCCTTGACGGTGGAGGCGGTTCAGGCGGCGGATCTGGCGG<br>TGGGAGCGGTTCGGGAGCCCATATAGTGATGGTTGATGCCTATAA<br>ACCGACCAAGTGA | |
| SEQ ID NO: 10 | KGKGKGKGKGCTRPNNNTRKSIRIGPGQTFYATGDIIGDIRQAHC | V3 loop-<br>Consensus<br>C peptide |
| SEQ ID NO: 11 | MDAMKRGLCCVLLLCGAVFVSPAGAGSNLWVTVYYGVPVW<br>KDAETTLFCASDAKAYETEKHNVWATHACVPTDPNPQEIHLE<br>NVTEEFNMWKNNMVEQMHEDIISLWDQSLKPCVKLTPLCVTL<br>QCTNYAPNLLSNMRGELKQCSFNMTTELRDKKQKVYSLFYRL<br>DVVQINENQGNRSNNSNKEYRLINCNTSAITQACPKVSFEPIPIH<br>YCAPAGFAILKCKNKTFNGTGPCPNVSTVQCTHGIKPVVSTQL<br>LLNGSLAEEEVIIRSENITNNAKNILVQLNTPVQINCTRPNNNTV<br>KSIRIGPGQAFYYFGDIIGDIRMAHCNVSKATWNETLGNVSKQ<br>LRKHFGNNTIIRFAQSSGGDLEVTTHSFNCGGEFFYCNTSGLFN<br>STWISNTSVQGSNSTGSNDSIVLPCRIKQIINMWQRIGQAMYAP<br>PIQGVIRCVSNITGLILTRDGGSTNSTTETFRPGGGDMRDNWRS<br>ELYKYKVVKIEPLGVAPTRCKRRVVGRRRRRRAVGIGAVSLG<br>FLGAAGSTMGAASMTLTVQARNLLSGIVQQQSNLLRAPEPQQ<br>HLLKDTHWGIKQLQARVLAVEHYLRDQQLLGIWGCSGKLICC<br>TNVPWNSSWSNRNLSEIWDNMTWLQWDKEISNYTQIIYGLLE<br>ESQNQQEKNEQDLLALD | RC1-3fill |
| SEQ ID NO: 12 | ATGGACGCCATGAAGAGGGGACTTTGCTGTGTTCTTCTGCT<br>GTGTGGCGCCGTGTTTGTTAGCCCCGCTGGGGCCGGATCCA<br>ACCTGTGGGTCACTGTGTATTATGGTGTGCCAGTGTGGAAG<br>GATGCAGAGACAACACTCTTTTGCGCCTCCGACGCTAAAGC<br>ATACGAAACGGAGAAGCACAACGTGTGGGCGACCCATGCC<br>TGTGTCCCTACAGACCCTAACCCTCAGGAAATTCATCTTGA<br>AAATGTCACAGAAGAGTTTAACATGTGGAAAAACAACATG<br>GTGGAACAGATGCACGAGGATATCATTTCCCTGTGGGACCA<br>GAGTCTGAAACCATGTGTCAAACTTACTCCTCTGTGCGTGA<br>CTCTCCAGTGTACAAACTACGCACCCAACCTTTTGAGTAAT<br>ATGCGGGGCGAGCTCAAGCAGTGCAGTTTCAATATGACAAC<br>CGAATTGAGAGACAAAAAACAGAAAGTATACTCCCTCTTCT<br>ACCGGCTGGACGTGGTGCAGATCAATGAGAACCAAGGAAA<br>TAGAAGCAACAACAGTAACAAGGAATACCGGCTCATAAAT<br>TGCAATACCAGCGCTATTACGCAGGCTTGCCCTAAGGTGAG<br>CTTTGAGCCAATCCCGATACATTATTGTGCCCCGGCAGGCTT<br>CGCTATACTGAAATGCAAGAATAAGACGTTTAATGGGACAG<br>GCCCTTGCCCTAACGTTTCAACGGTCCAATGTACCCACGGG<br>ATCAAGCCCGTAGTGTCTACACAGCTCCTGCTGAACGGCAG<br>CCTGGCCGAAGAGGAGGTCATAATTAGGAGCGAGAACATA<br>ACTAACAACGCTAAAAACATTCTCGTCCAGCTCAATACACC<br>TGTGCAGATCAACTGCACCCGGCCCAACAACAACACCGTGA<br>AGTCCATTAGAATTGGTCCGGGACAGGCATTTTACTACTTC<br>GGAGATATAATAGGCGATATCAGAATGGCGCACTGTAACGT<br>GAGCAAGGCCACCTGGAACGAGACCCTGGGCAATGTGAGC<br>AAACAGTTGCGCAAGCACTTTGGGAACAACACCATTATTCG<br>GTTTGCCCAGTCTTCCGGCGGCGACCTTGAAGTGACCACTC | RC1-3fill |

TABLE 1-continued

Sequences of HIV Immunogens.

| SEQ ID NO. | Sequence | Other information |
|---|---|---|
|  | ATAGCTTCAACTGTGGAGGGGAGTTTTTCTATTGCAATACAT<br>CAGGCCTGTTCAACTCTACATGGATCTCAAATACCAGTGTC<br>CAGGGGTCAAATTCCACCGGTAGCAACGACAGCATCGTCTT<br>GCCTTGTCGAATCAAGCAGATCATTAATATGTGGCAGAGGA<br>TTGGTCAGGCCATGTACGCACCTCCAATACAGGGAGTCATT<br>CGGTGCGTCAGCAATATTACTGGATTGATCCTCACCAGAGA<br>TGGCGGGAGTACCAATAGCACTACCGAAACTTTCCGCCCAG<br>GAGGAGGCGACATGCGGGATAATTGGAGATCAGAGCTGTA<br>TAAGTATAAGGTGGTGAAAATTGAACCCCTGGGAGTGGCGC<br>CAACTAGATGTAAACGGCGAGTGGTTGGCCGGAGACGGCG<br>GCGGAGAGCAGTGGGGATTGGCGCTGTCTCACTCGGTTTCC<br>TGGGTGCTGCCGGCAGTACAATGGGCGCCGCCAGCATGACG<br>CTCACAGTGCAGGCCCGGAATCTTCTTAGCGGAATTGTGCA<br>ACAACAAAGCAATCTGTTGAGAGCCCCGGAACCGCAGCAA<br>CATCTGTTGAAGGACACACATTGGGGCATCAAGCAGCTGCA<br>AGCTCGGGTTCTGGCTGTTGAGCATTACCTGAGAGACCAAC<br>AGCTGCTGGGCATATGGGGATGCTCAGGAAAACTGATCTGC<br>TGCACCAATGTCCCATGGAACAGCTCATGGTCAAACAGGAA<br>CCTGAGCGAGATCTGGGATAACATGACCTGGTTGCAGTGGG<br>ACAAAGAAATTAGCAATTACACACAGATCATCTACGGCCTC<br>CTGGAGGAAAGCCAGAATCAGCAGGAGAAAAATGAGCAGG<br>ATCTGCTTGCCCTTGACTGA |  |
| SEQ ID NO: 13 | MDAMKRGLCCVLLLCGAVFVSPAGAGSNLWVTVYYGVPVW<br>KDAETTLFCASDAKAYETEKHNVWATHACVPTDPNPQEIHLE<br>NVTEEFNMWKNNMVEQMHEDIISLWDQSLKPCVKLTPLCVTL<br>QCTNYAPNLLSNMRGELKQCSFNMTTELRDKKQKVYSLFYRL<br>DVVQINENQGNRSNNSNKEYRLINCNTSAITQACPKVSFEPIPIH<br>YCAPAGFAILKCKNKTFNGTGPCPNVSTVQCTHGIKPVVSTQL<br>LLNGSLAEEEVIIRSENITNNAKNILVQLNTPVQINCTRPNNNTV<br>KSIRIGPGQAFYYFGDIIGDIRMAHCNVSKATWNETLGNVSKQ<br>LRKHFGNNTIIRFAQSSGGDLEVTTHSFNCGGEFFYCNTSGLFN<br>STWISNTSVQGSNSTGSNDSIVLPCRIKQIINMWQRIGQAMYAP<br>PIQGVIRCVSNITGLILTRDGGSTNSTTETFRPGGGDMRDNWRS<br>ELYKYKVVKIEPLGVAPTRCKRRVVGRRRRRRAVGIGAVSLG<br>FLGAAGSTMGAASMTLTVQARNLLSGIVQQQSNLLRAPEPQQ<br>HLLKDTHWGIKQLQARVLAVEHYLRDQQLLGIWGCSGKLICC<br>TNVPWNSSWSNRNLSEIWDNMTWLQWDKEISNYTQIIYGLLE<br>ESQNQQEKNEQDLLALDGGGGSGGGSGGGSGSGAHIVMVDA<br>YKPTK | RC1-3fill-Spytag |
| SEQ ID NO: 14 | ATGGACGCCATGAAGAGGGGACTTTGCTGTGTTCTTCTGCTGTGT<br>GGCGCCGTGTTTGTTAGCCCCGCTGGGGCCGGATCCAACCTGTGG<br>GTCACTGTGTATTATGGTGTGCCAGTGTGGAAGGATGCAGAGACA<br>ACACTCTTTTGCGCCTCCGACGCTAAAGCATACGAAACGGAGAAG<br>CACAACGTGTGGGCGACCCATGCCTGTGTCCCTACAGACCCTAAC<br>CCTCAGGAAATTCATCTTGAAAATGTCACAGAAGAGTTTAACATG<br>TGGAAAAACAACATGGTGGAACAGATGCACGAGGATATCATTTC<br>CCTGTGGGACCAGAGTCTGAAACCATGTGTCAAACTTACTCCTCT<br>GTGCGTGACTCTCCAGTGTACAAACTACGCACCCAACCTTTTGAG<br>TAATATGCGGGGCGAGCTCAAGCAGTGCAGTTTCAATATGACAAC<br>CGAATTGAGAGACAAAAAACAGAAAGTATACTCCCTCTTCTACCG<br>GCTGGACGTGGTGCAGATCAATGAGAACCAAGGAAATAGAAGCA<br>ACAACAGTAACAAGGAATACCGGCTCATAAATTGCAATACCAGC<br>GCTATTACGCAGGCTTGCCCTAAGGTGAGCTTTGAGCCAATCCCG<br>ATACATTATTGTGCCCCGGCAGGCTTCGCTATACTGAAATGCAAG<br>AATAAGACGTTTAATGGGACAGGCCCTTGCCCTAACGTTTCAACG<br>GTCCAATGTACCCACGGGATCAAGCCCGTAGTGTCTACACAGCTC<br>CTGCTGAACGGCAGCCTGGCCGAAGAGGAGGTCATAATTAGGAG<br>CGAGAACATAACTAACAACGCTAAAAACATTCTCGTCCAGCTCAA<br>TACACCTGTGCAGATCAACTGCACCCGGCCCAACAACAACACCGT<br>GAAGTCCATTAGAATTGGTCCGGGACAGGCATTTTACTACTTCGG<br>AGATATAATAGGCGATATCAGAATGGCGCACTGTAACGTGAGCA<br>AGGCCACCTGGAACGAGACCCTGGGCAATGTGAGCAAACAGTTG<br>CGCAAGCACTTTGGGAACAACACCATTATTCGGTTTGCCCAGTCT<br>TCCGGCGGCGACCTTGAAGTGACCACTCATAGCTTCAACTGTGGA<br>GGGGAGTTTTTCTATTGCAATACATCAGGCCTGTTCAACTCTACAT<br>GGATCTCAAATACCAGTGTCCAGGGGTCAAATTCCACCGGTAGCA<br>ACGACAGCATCGTCTTGCCTTGTCGAATCAAGCAGATCATTAATA<br>TGTGGCAGAGGATTGGTCAGGCCATGTACGCACCTCCAATACAGG<br>GAGTCATTCGGTGCGTCAGCAATATTACTGGATTGATCCTCACCA<br>GAGATGGCGGGAGTACCAATAGCACTACCGAAACTTTCCGCCCA<br>GGAGGAGGCGACATGCGGGATAATTGGAGATCAGAGCTGTATAA<br>GTATAAGGTGGTGAAAATTGAACCCCTGGGAGTGGCGCCAACTA<br>GATGTAAACGGCGAGTGGTTGGCCGGAGACGGCGGCGGAGAGCA | RC1-3fill-Spytag |

TABLE 1-continued

Sequences of HIV Immunogens.

| SEQ ID NO. | Sequence | Other information |
|---|---|---|
| | GTGGGGATTGGCGCTGTCTCACTCGGTTTCCTGGGTGCTGCCGGC AGTACAATGGGCGCCGCCAGCATGACGCTCACAGTGCAGGCCCG GAATCTTCTTAGCGGAATTGTGCAACAACAAAGCAATCTGTTGAG AGCCCCGGAACCGCAGCAACATCTGTTGAAGGACACACATTGGG GCATCAAGCAGCTGCAAGCTCGGGTTCTGGCTGTTGAGCATTACC TGAGAGACCAACAGCTGCTGGGCATATGGGGATGCTCAGGAAAA CTGATCTGCTGCACCAATGTCCCATGGAACAGCTCATGGTCAAAC AGGAACCTGAGCGAGATCTGGGATAACATGACCTGGTTGCAGTG GGACAAAGAAATTAGCAATTACACACAGATCATCTACGGCCTCCT GGAGGAAAGCCAGAATCAGCAGGAGAAAAATGAGCAGGATCTG CTTGCCCTTGACGGTGGAGGCGGTTCAGGCGGCGGATCTGGCGGT GGGAGCGGTTCGGGAGCCCATATAGTGATGGTTGATGCCTATAAA CCGACCAAGTGA | |

The above amino acid or nucleic acid sequences of HIV Immunogens include the secretion leader sequence at the N-terminal end (for amino acide sequences) or the 5' end (for nucleic acid sequences). The secretion leader sequence is a general secretion signal and is not part of the final/mature expressed protein. As will be understood by persons having ordinary skill in the art that other secretion leader sequences can also be used to generate the same final/mature HIV Immunogens.

TABLE 2

Immunogen Variants and Specific Modifications.

| | PNGS | | | |
|---|---|---|---|---|
| Protein | Deleted | Added | Other modifications | Purpose |
| RC1 | 133, 137, 156 | — | V134Y, T135A, I138L, T139L, D140S, D141N, T320F, Q328M, T415V, MD39* | Immunization/ ELISA |
| RC1-3fill | 133, 137, 156 | N230, N241, N344 | V134Y, T135A, I138L, T139L, D140S, D141N, T320F, Q328M, T415V, MD39* | Immunization/ ELISA |
| RC1-4fill | 133, 137, 156 | N230, N241, N289, N344 | V134Y, T135A, I138L, T139L, D140S, D141N, T320F, Q328M, T415V, MD39* | Immunization/ ELISA |
| RC1-glycanKO | 133, 137, 156, 301, 332 | — | V134Y, T135A, I138L, T139L, D140S, D141N, T320F, Q328M, T415V, H330A, MD39* | ELISA |
| RC1-glycanKO-GAIA ("GAIA" disclosed as SEQ ID NO: 16) | 133, 137, 156, 301, 332 | — | V134Y, T135A, I138L, T139L, D140S, D141N, T320F, Q328M, T415V, GDIR (SEQ ID NO: 15)/GAIA (SEQ ID NO: 16), H330A, MD39* | ELISA |
| RC1-GAIA ("GAIA" disclosed as SEQ ID NO: 16) | 133, 137, 156 | — | V134Y, T135A, I138L, T139L, D140S, D141N, T320F, Q328M, T415V, GDIR (SEQ ID NO: 15)/GAIA (SEQ ID NO: 16), MD39* | ELISA |

TABLE 2-continued

| Immunogen Variants and Specific Modifications. | | | | |
|---|---|---|---|---|
| | PNGS | | | |
| Protein | Deleted | Added | Other modifications | Purpose |
| 11MUTBD301 | 133, 137, 301 | — | V134Y, T135A, I138L, T139L, D140S, D141N, T320F, Q328M, T415V, MD39* | Immunization/ ELISA |
| RC1D301 | 133, 137, 156, 301 | — | V134Y, T135A, I138L, T139L, D140S, D141N, T320F, Q328M, T415V, MD39* | ELISA |
| RC1D332 | 133, 137, 156, 332 | | V134Y, T135A, I138L, T139L, D140S, D141N, T320F, Q328M, T415V, MD39* | ELISA |
| 11MUTB | 133, 137 | — | V134Y, T135A, I138L, T139L, D140S, D141N, T320F, Q328M, T415V, MD39* | Immunization/ ELISA |
| 10MUT | 133, 137 | — | V134Y, T135A, N136P, N137F, I138L, T139I, D140N, T320F, Q328M, MD39* | ELISA |
| 7MUT | 133, 137 | — | V134Y, T135A, N136P, N137F, I138L, T139I, D140N, MD39* | ELISA |
| 5MUT | — | — | V134Y, N136P, I138L, D140N, MD39* | ELISA |
| BG505 | — | — | MD39* | ELISA |
| RC1-4fill VLP | 133, 137, 156 | N230, N241, N289, N344 | V134Y, T135A, I138L, T139L, D140S, D141N, T320F, Q328M, T415V, Spytag, MD39* | Immunization |
| RC1-Avitag | 133, 137, 156 | — | V134Y, T135A, I138L, T139L, D140S, D141N, T320F, Q328M, T415V, Avitag, MD39* | Sort |
| RC1-glycanKO-Avitag | 133, 137, 156, 301, 332 | — | V134Y, T135A, I138L, T139L, D140S, D141N, T320F, Q328M, T415V, H330A, Avitag, MD39* | Sort |

"Polypeptide" is used in its conventional meaning, i.e., as a sequence of amino acids. The polypeptides are not limited to a specific length of the product. Peptides, polypeptides, and proteins are included within the definition of polypeptide, and such terms can be used interchangeably herein unless specifically indicated otherwise. This term also includes post-expression modifications of the polypeptide, for example, glycosylations, acetylations, phosphorylations and the like, as well as other modifications known in the art, both naturally occurring and non-naturally occurring. A polypeptide can be an entire protein or a subsequence thereof. A polypeptide "variant," as the term is used herein, is a polypeptide that typically differs from a polypeptide specifically disclosed herein in one or more substitutions, deletions, additions and/or insertions. Such variants can be naturally occurring or can be synthetically generated, for example, by modifying one or more of the above polypeptide sequences of the disclosure and evaluating one or more biological activities of the polypeptide as described herein and/or using any of some techniques well known in the art.

For example, certain amino acids can be substituted for other amino acids in a protein structure without appreciable loss of its ability to bind other polypeptides (for example, antigens) or cells. Since it is the binding capacity and nature of a protein that defines that protein's biological functional activity, certain amino acid sequence substitutions can be made in a protein sequence, and, accordingly, its underlying DNA coding sequence, whereby a protein with like properties is obtained. It is thus contemplated that various changes can be made in the peptide sequences of the disclosed compositions, or corresponding DNA sequences that encode said peptides without appreciable loss of their biological utility or activity.

Variant sequences include those wherein conservative substitutions have been introduced by modification of polynucleotides encoding polypeptides of this disclosure Amino acids can be classified according to physical properties and contribution to secondary and tertiary protein structure. Such conservative modifications include amino acid substitutions, additions, and deletions. Conservative amino acid substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e g, alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

"Sequence identity" or "homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least about 70%, at least about 75%, at least about 80%, at least about 90%, at least about 95%, at least about 98%, or at least about 99% polynucleotide or polypeptide homology with a polynucleotide or polypeptide described herein.

Polypeptide variant sequences may share 70% or more (i.e. 80%, 85%, 90%, 95%, 97%, 98%, 99% or more) sequence identity with the sequences recited in this disclosure. Polypeptide variants may also include polypeptide fragments comprising various lengths of contiguous stretches of amino acid sequences disclosed herein. Polypeptide variant sequences include at least about 5, 10, 15, 20, 30, 40, 50, 75, 100, 150, or more contiguous peptides of one or more of the sequences disclosed herein as well as all intermediate lengths therebetween.

The above-described immunogens may bind specifically to bNAbs. bNAbs are neutralizing antibodies that neutralize multiple HIV-1 viral strains. bNAbs are unique in that they target conserved epitopes of the virus. Examples of broadly neutralizing antibodies may include, without limitation, VRC26.25, PCT64-24E, VRC38.01, PG9, PGDM1400, CHO1, BG18, DH270.1, DH270.6, PGDM12, VRC41.01, PGDM21, PCDN-33A, BF520.1, VRC29.03, PGT121, 10-1074, N49-P7, N6, NC-Cow1, IOMA, CH235, CH235.12, b12, VRC01, 3BNC117, CH103, VRC-PG05, VRC34.01, ACS202, PGT151, 35022, 8ANC195, DH511.11P. Among these bNAbs, BG18, DH270.1, DH270.6, PGDM12, VRC41.01, PGDM21, PCDN-33A, BF520.1, VRC29.03, PGT121, 10-1074 broadly neutralizing antibodies bind specifically to V3 glycans. In some embodiments, the disclosed immunogens bind to the PGT121 or 10-1074 broadly neutralizing antibody with an affinity having dissociation constant ($K_D$) about 50 µM or less.

The terms "specific binding," "selective binding," "selectively binds," and "specifically binds," refer to antibody binding to an epitope on a predetermined antigen but not to other antigens. Typically, the antibody binds with an equilibrium dissociation constant ($K_D$) of approximately less than $10^{-6}$ M, such as approximately less than $10^{-7}$ M, $10^{-8}$ M, $10^{-9}$ M or $10^{-19}$ M or even lower when determined by, e.g., ELISA, equilibrium dialysis or surface plasmon resonance (SPR) technology in a BIACORE® 2000 surface plasmon resonance instrument using the predetermined antigen, e.g., an epitope on the viral envelope of HIV-1, e.g., gp120, as the analyte and the antibody as the ligand, or Scatchard analysis of binding of the antibody to antigen-positive cells, and (ii) binds to the predetermined antigen with an affinity that is at least two-fold greater than its affinity for binding to a non-specific antigen (e.g., BSA, casein) other than the predetermined antigen or a closely-related antigen.

In another aspect, this disclosure provides immunogen polypeptides that are multimerized on a virus-like particle (VLP) (e.g., retrovirus-like particle, HIV-like particle). Virus-like particles, or retrovirus-like particles, in the context of the present disclosure, are membrane-surrounded structures comprising viral envelope proteins embedded within the membrane of the host cell in which they are produced, and preferably, additional viral core proteins in the VLPs. These VLPs do not contain intact viral nucleic acid, and they are non-infectious. Desirably, there is sufficient envelope protein on the surface of the VLP so that when a VLP preparation is formulated into an immunogenic composition and administered to an animal or human, an immune response (cell-mediated or humoral) is raised. Desirably, the Env protein is truncated from the carboxy terminus as compared with the naturally occurring virus envelope protein. In the context of the present invention, a "truncated" envelope protein is one which contains less than a full-length cytoplasmic domain, which but retains surface antigenic determinants against which an immune response is generated, preferably a protective immune response, and it retains sufficient envelope sequence for proper precursor processing and membrane insertion. The skilled artisan can produce truncated virus envelope proteins using recombinant DNA technology and virus coding sequences, which are readily available to the public. For example, the coding sequence of a virus envelope protein can be engineered for expression in a baculovirus expression vector, for example, using a commercially available baculovirus vector, under the regulatory control of a virus promoter, with appropriate modifications of the sequence to allow functional linkage of the coding sequence to the regulatory sequence, and truncation (deletion) of the portion of the coding sequence which encodes the cytoplasmic domain of the envelope protein, again with appropriate translation stop signals and sequences which allow operable splicing of the truncated envelope and associated sequences into the vector. A specifically exemplified truncated SIV envelope protein lacks the 89 amino acids at the carboxy terminus of the naturally occurring SIV envelope protein.

In another aspect, this disclosure provides a protein complex comprising at least one above-described immunogen polypeptide multimerized via covalent or non-covalent bonding/interaction (e.g., van der Waals interactions). For example, two or more immunogen polypeptides may be cross-linked by one or more cross-linkers. Crosslinkers are reagents having reactive ends to specific functional groups (e.g., primary amines or sulfhydryls) on proteins or other molecules. Crosslinkers are capable of joining two or more molecules by a covalent bond. Crosslinkers include but are not limited to amine-to-amine crosslinkers (e.g., disuccinimidyl suberate (DSS)), amine-to-sulfhydryl crosslinkers (e.g., N-γ-maleimidobutyryl-oxysuccinimide ester (GMBS)), carboxyl-to-amine crosslinkers (e.g., dicyclohexylcarbodiimide (DCC)), sulfhydryl-to-carbohydrate crosslinkers (e.g., N-(3-maleimidopropionic acid hydrazide (BMPH)), sulfhydryl-to-sulfhydryl crosslinkers (e.g., 1,4-bismaleimidobutane (BMB)), photoreactive crosslinkers (e.g., N-5-azido-2-nitrobenzoyloxysuccinimide (ANB—NOS)), chemo selective ligation crosslinkers (e.g., NHS-PEG4-Azide).

B. Nucleic Acids

Another aspect of this disclosure features an isolated nucleic acid comprising a sequence that encodes the polypeptide or protein described above. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA.

An "isolated nucleic acid" refers to a nucleic acid the structure of which is not identical to that of any naturally occurring nucleic acid or to that of any fragment of a naturally occurring genomic nucleic acid. The term, therefore, covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide, fusion protein, or antibody of this invention. For this purpose, one can operatively link the nucleic acid to suitable regulatory sequences to generate an expression vector.

The nucleic acid and amino acid sequences disclosed herein are shown using standard letter abbreviations for nucleotide bases, and one letter code for amino acids. Only one strand of each nucleic acid sequence is shown, but the complementary strand is understood as included by any reference to the displayed strand.

This disclosure also includes vectors containing a coding sequence for the disclosed immunogen, host cells containing the vectors, and methods of making substantially pure immunogen comprising the steps of introducing the coding sequence for the immunogen into a host cell, and cultivating the host cell under appropriate conditions such that the immunogen is produced and secreted. The immunogen so produced may be harvested in conventional ways. Therefore, the present invention also relates to methods of expressing the immunogen and biological equivalents disclosed herein, assays employing these gene products, and recombinant host cells which comprise DNA constructs which express these receptor proteins.

The disclosed immunogens may be recombinantly expressed by molecular cloning the nucleic acid encoding the immunogens into an expression vector (such as pcDNA3.neo, pcDNA3.1, pCR2.1, pBlueBacHis2 or pLITMUS28) containing a suitable promoter and other appropriate transcription regulatory elements, and transferred into prokaryotic or eukaryotic host cells to produce the immunogens. Techniques for such manipulations can be found described in Sambrook et al., 1989, Molecular Cloning: A Laboratory Manual; Cold Spring Harbor Laboratory, Cold Spring Harbor, New York, are well known and readily available to the artisan of ordinary skill in the art. Therefore, another aspect of the present invention includes host cells that have been engineered to contain and/or express DNA sequences encoding the immunogens. Such recombinant host cells can be cultured under suitable conditions to produce the disclosed immunogens or a biologically equivalent form. Recombinant host cells may be prokaryotic or eukaryotic, including but not limited to, bacteria such as E. coli, fungal cells such as yeast, mammalian cells including, but not limited to, cell lines of human, bovine, porcine, monkey and rodent origin, and insect cells including but not limited to Drosophila and silkworm derived cell lines.

For instance, one insect expression system utilizes Spodoptera frugiperda (Sf21) insect cells (Invitrogen) in tandem with a baculovirus expression vector (pAcG2T, Pharmingen). Also, mammalian species which may be suitable and which are commercially available, include but are not limited to, L cells L-M(TK~) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171) and CPAE (ATCC CCL 209).

A variety of mammalian expression vectors may be used to express recombinant immunogens in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue-green algae, plant cells, insect cells, and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency.

Expression vectors may include, but are not limited to, cloning vectors, modified cloning vectors, specifically designed plasmids or viruses. Commercially available mammalian expression vectors which may be suitable for immunogen expression, include but are not limited to, pIRES-hyg (Clontech), pIRES-puro (Clontech), pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMClneo (Stratagene), pXT1 (Stratagene), pS G5 (Stratagene), EBON-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

Also, a variety of bacterial expression vectors may be used to express the disclosed immunogens in bacterial cells. Commercially available bacterial expression vectors that may be suitable for immunogen expression include, but are not limited to pCR2.1 (Invitrogen), pETl 1a (Novagen), lambda gal (Invitrogen), and pKK223-3 (Pharmacia).

In addition, a variety of fungal cell expression vectors may be used to express the immunogens in fungal cells. Commercially available fungal cell expression vectors which may be suitable for recombinant immunogen expression include but are not limited to pYES2 (Invitrogen) and Pichia expression vector (Invitrogen).

Also, a variety of insect cell expression vectors may be used to express a recombinant receptor in insect cells. Commercially available insect cell expression vectors which may be suitable for recombinant expression of the immunogens include but are not limited to pBlueBaclll and pBlueBacHts2 (Invitrogen), and pAcG2T (Pharmingen).

The expression vector may be introduced into host cells via any one of a number of techniques including but not limited to transformation, transfection, protoplast fusion, and electroporation. Transformation is meant to encompass a genetic change to the target cell resulting from incorporation of DNA. Transfection is meant to include any method known in the art for introducing the immunogens into the test cells. For example, transfection includes calcium phosphate or calcium chloride mediated transfection, lipofection, electroporation, as well as infection with, for example, a viral vector such as a recombinant retroviral vector containing the nucleotide sequence which encodes the immunogens, and combinations thereof. The expression vector-containing cells are individually analyzed to determine whether they produce the immunogens. Identification of immunogen expressing cells may be done by several means, including but not limited to immunological reactivity with specific bNAbs, labeled ligand binding and the presence of host cell-associated activity with respect to the immunogens.

Also within the scope of this invention is a host cell that contains the above-described nucleic acid. Examples include bacterial cells (e.g., *E. coli* cells, insect cells (e.g., using baculovirus expression vectors), yeast cells, or mammalian cells. See, e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, e.g., using T7 promoter regulatory sequences and T7 polymerase.

C. Compositions

In another aspect, this disclosure provides an immunogenic composition for stimulating an immune response in a subject in need thereof. The immunogenic composition includes (i) the immunogen, the nucleic acid, the host cell, the protein complex, or the virus particle described above; and (ii) a pharmaceutically acceptable carrier. The method may further include administering the composition two or more times. The administration of the composition may result in increased numbers of broadly-neutralizing antibodies in the serum capable of recognizing a V3-glycan epitope.

An immunogenic composition is a composition comprising an immunogenic peptide that induces a measurable CTL response against a virus expressing the immunogenic peptide, or induces a measurable B cell response (such as production of antibodies) against the immunogenic peptide. In one example, an "immunogenic composition" is composition includes a disclosed immunogen derived from a gp120 or an antigenic fragment thereof. It further refers to isolated nucleic acids encoding an immunogen, such as a nucleic acid that can be used to express the immunogen (and thus be used to elicit an immune response against this polypeptide).

For in vitro use, an immunogenic composition may consist of the isolated protein, peptide epitope, or nucleic acid encoding the protein or peptide epitope. For in vivo use, the immunogenic composition will typically include the protein, immunogenic peptide or nucleic acid in pharmaceutically acceptable carriers and/or other agents. Any particular peptide, such as a disclosed immunogen or a nucleic acid encoding the immunogen, can be readily tested for its ability to induce a CTL or B cell response by art-recognized assays Immunogenic compositions can include adjuvants, which are well known to one of skill in the art.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically-acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, TWEENS or SPANS or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas. The topical composition is useful for treating inflammatory disorders in the skin, including, but not limited to, eczema, acne, rosacea, psoriasis, contact dermatitis, and reactions to poison ivy.

A topical composition contains a safe and effective amount of a dermatologically acceptable carrier suitable for application to the skin. A "cosmetically acceptable" or "dermatologically-acceptable" composition or component refers to a composition or component that is suitable for use in contact with human skin without undue toxicity, incompatibility, instability, allergic response, and the like. The carrier enables an active agent and an optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular, one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition. The topical composition may be a cosmetic or dermatologic product in the form known in the art for topical or transdermal applications, including solutions, aerosols, creams, gels, patches, ointment, lotion, or foam.

Pharmaceutically acceptable carrier includes any and all solvents, dispersion media, coatings, antibacterial and antifungal agents, isotonic and absorption delaying agents, and the like that are physiologically compatible. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

Preferably, the carrier is suitable for intravenous, intramuscular, subcutaneous, parenteral, spinal or epidermal administration (e.g., by injection or infusion). The therapeutic compounds may include one or more pharmaceutically acceptable salts. A "pharmaceutically acceptable salt" refers to a salt that retains the desired biological activity of the parent compound and does not impart any undesired toxicological effects (see, e.g., Berge, S. M., et al. (1977) J. Pharm. Sci. 66:1-19).

The host cells provided in the immunogenic compositions may be inactivated or chemically/genetically attenuated bacterial vaccine that does not elicit the cytotoxic T-lymphocyte (CTL) immune response necessary for the lysis of tumor cells and cells infected with intracellular pathogens.

II. METHODS FOR STIMULATING IMMUNE RESPONSE USING THE DISCLOSED IMMUNOGENS

The immunogens, as disclosed herein, a nucleic acid molecule encoding the disclosed immunogen, the host cell, the protein complex, or the virus particle can be administered to a subject in order to generate an immune response to a pathogen, such as HIV. In another aspect, this disclosure provides a method of treating or preventing HIV infection in a subject in need thereof. The method includes administering to the subject a therapeutically effective amount of the immunogen, the nucleic acid, the host cell, the protein complex, or the virus particle described above, or a combination thereof. This disclosure also provides use of the immunogen, the nucleic acid, the host cell, the protein complex, or the virus particle described above, or a combination thereof in the preparation of a medicament to treat or prevent HIV infection in a subject.

In exemplary applications, compositions are administered to a subject suffering from HIV infection or at risk of becoming infected from HIV. In other applications, the immunogens disclosed herein can be administered prophylactically, for example, as part of an immunization regimen.

The immunogen is administered in an amount sufficient to raise an immune response against the HIV virus. Administration induces a sufficient immune response to treat the pathogenic infection, for example, to inhibit the infection and/or reduce the signs and/or symptoms of the infection. Amounts effective for this use will depend upon the severity of the disease, the general state of the subject's health, and the robustness of the subject's immune system. A therapeutically effective amount of the immunogen is that which provides either subjective relief of a symptom(s) or an objectively identifiable improvement as noted by the clinician or other qualified observers.

Therapeutically effective amount or effective amount refers to the amount of agents, such as nucleic acid vaccine or other therapeutic agents, that is sufficient to prevent, treat (including prophylaxis), reduce and/or ameliorate the symptoms and/or underlying causes of any of a disorder or disease, for example to prevent, inhibit, and/or treat HIV. In some embodiments, an "effective amount" is sufficient to reduce or eliminate a symptom of a disease, such as AIDS. For instance, this can be the amount necessary to inhibit viral replication or to measurably alter outward symptoms of the viral infection, such as an increase of T cell counts in the case of HIV-1 infection. In general, this amount will be sufficient to measurably inhibit virus (for example, HIV) replication or infectivity. When administered to a subject, a dosage will generally be used that will achieve target tissue concentrations (for example, in lymphocytes) that have been shown to achieve in vitro inhibition of viral replication.

An immunogen can be administered by any means known to one of skill in the art (see Banga, A., "Parenteral Controlled Delivery of Therapeutic Peptides and Proteins," in Therapeutic Peptides and Proteins, Technomic Publishing Co., Inc., Lancaster, PA, 1995) either locally or systemically, such as by intramuscular, subcutaneous, or intravenous injection, but even oral, nasal, or anal administration is contemplated. In one embodiment, the administration is by subcutaneous or intramuscular injection. To extend the time during which the disclosed immunogen is available to stimulate a response, the immunogen can be provided as an implant, an oily injection, or as a particulate system. The particulate system can be a microparticle, a microcapsule, a microsphere, a nanocapsule, or similar particle, (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

Optionally, one or more cytokines, such as interleukin (IL)-2, IL-6, IL-12, IL-15, RANTES, granulocyte-macrophage colony-stimulating factor (GM-CSF), tumor necrosis factor (TNF)-a, interferon (IFN)-a or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2): 122-38; Lotze et al., 2000, Cancer J Sci. Am. 6(Suppl 1):S61-6; Cao et al., 1998, Stem Cells 16(Suppl 1 J.-251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B.7-2, OX-40L, 41 BBL, and ICAM-1 are administered.

A pharmaceutical composition including an isolated immunogen is provided. In some embodiments, the immunogen is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, D☐), TW☐☐N 40™, TWEEN 20™, TWEEN60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, J. Am. Oil. Chem. Soc. 54: 110, 1977, and Hunter et al., J. Immunol 129: 1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun 133:3167, 1984. The agent can be provided in an effective amount, for example between 0.5 and 10%, or in an amount between 1.25 and 5%.

Controlled release parenteral formulations can be made as implants, oily injections, or as particulate systems. For a broad overview of protein delivery systems, see Banga, Therapeutic Peptides and Proteins: Formulation, Processing, and Delivery Systems, Technomic Publishing Company, Inc., Lancaster, PA, 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, Colloidal Drug Delivery Systems, J. Kreuter, ed., Marcel Dekker, Inc., New York, NY, pp. 219-342, 1994; Tice & Tabibi, Treatise on Controlled Drug Delivery, A. Kydonieus, ed., Marcel Dekker, Inc. New York, NY, pp. 315-339, 1992).

Polymers can be used for ion-controlled release. Various degradable and nondegradable polymeric matrices for use in controlled drug delivery are known in the art (Langer, Accounts Chem. Res. 26:53', 1993). For example, the block copolymer, poloxamer 407 exists as a viscous yet mobile liquid at low temperatures but forms a semisolid gel at body temperature. It has shown to be an effective vehicle for formulation and sustained delivery of recombinant interleukin-2 and urease (Johnston et ah, Pharm. Res. 9:425, 1992; and Pec,/. Parent. Sci. Tech. 44(2):58, 1990). Alternatively, hydroxyapatite has been used as a microcarrier for controlled release of proteins (Ijntema et ah, Int. J. Pharm. 112:215, 1994). In yet another aspect, liposomes are used for controlled release as well as drug targeting of the lipid-capsulated drug (Betageri et ah, Liposome Drug Delivery Systems, Technomic Publishing Co., Inc., Lancaster, PA, 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding a disclosed immunogen. A therapeutically effective amount of the nucleic acid can be administered to a subject in order to generate an immune response. In one specific, non-limiting example, a therapeutically effective amount of a nucleic acid encoding a disclosed gp120 immunogen or immunogenic fragment thereof is administered to a subject to treat or prevent or inhibit HIV infection.

Optionally, one or more cytokines, such as IL-2, IL-6, IL-12, RANTES, GM-CSF, TNF-a, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2): 122-38; Lotze et al., 2000, Cancer J Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into the same vector as the disclosed immunogen coding sequence, or the nucleic acid can be cloned into one or more separate vectors for co-administration. In addition, nonspecific immunomodulating factors such as *Bacillus* Cahnette-Guerin (BCG) and levamisole can be co-administered. One approach to administration of nucleic acids is direct immunization with plasmid DNA, such as with a mammalian expression plasmid. As described above, the nucleotide sequence encoding the disclosed immunogen can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired immunogen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, Immunol. Today 12:383, 1991). Doses of antigen as low as 1 µg encapsulated in ISCOMS™ have been found to produce Class I mediated CTL responses (Takahashi et ah, Nature 344:873, 1990).

In another approach to using nucleic acids for immunization, a disclosed immunogen can also be expressed by attenuated viral hosts or vectors or bacterial vectors. Recombinant vaccinia virus, adeno-associated virus (AAV), herpes virus, retrovirus, cytomegalovirus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, Nature 351:456-460, 1991).

In one embodiment, a nucleic acid encoding a disclosed immunogen is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 g/kg to about 50 mg/kg, and typically are about 0.005 mg/kg to about 5 mg/kg (see, e.g., U.S. Pat. No. 5,589,466).

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

It may be advantageous to administer the immunogenic compositions disclosed herein with other agents such as proteins, peptides, antibodies, and other antiviral agents, such as anti-HIV agents. Examples of such anti-HIV therapeutic agents include nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, fosamprenavir, ritonavir, saquinavir, tipranavir, and the like, and fusion protein inhibitors such as enfuvirtide and the like. In certain embodiments, immunogenic compositions are administered concurrently with other anti-HIV therapeutic agents. In some examples, the disclosed immunogens are administered with T-helper cells, such as exogenous T-helper cells. Exemplary methods for producing and administering T-helper cells can be found in International Patent Publication WO 03/020904, which is incorporated herein by reference. In certain embodiments, the immunogenic compositions are administered sequentially with other anti-HIV therapeutic agents, such as before or after the other agent. One of ordinary skill in the art would know that sequential administration can mean immediately following or after an appropriate period of time, such as hours, days, weeks, months, or even years later.

The disclosed gp120 immunogen or immunogenic fragments thereof and nucleic acids encoding these immunogens can be used in a multistep immunization regime. In some examples, the regime includes administering to a subject a therapeutically effective amount of a first immunogen or immunogenic fragments thereof as disclosed herein (the prime) and boosting the immunogenic response with one or more additional immunogens or immunogenic fragments thereof after an appropriate period of time. The method of eliciting such an immune reaction is what is known as "prime-boost." In this method, the antibody response to the selected immunogenic surface is focused by giving the subject's immune system a chance to "see" the antigenic surface in multiple contexts. In other words, the use of multiple immunogens or immunogenic fragments thereof with an antigenic surface in common selects for antibodies that bind the immunogen's surface in common.

In some examples, the immunogens or immunogenic fragments thereof and nucleic acids encoding these immunogens can are administered in "prime-boost" immunization regimes. For example, the immunogens or immunogenic fragments thereof and nucleic acids encoding these immunogens can are administered to a subject, before, during, after a stabilized gp140 trimer (see for example Yang et al. J Virol. 76(9):4634-42, 2002) is administered.

One can also use cocktails containing the disclosed immunogenic agents, for example, the immunogen, the nucleic acid encoding the immunogen, the host cell, the protein complex, or the virus particle described above, or a combination thereof to prime and then boost with trimers from a variety of different HIV strains or with trimers that are a mixture of multiple HIV strains. The prime can be administered as a single dose or multiple doses, for example, two doses, three doses, four doses, five doses, six doses or more can be administered to a subject over days, weeks or months. The boost can be administered as a single dose or multiple doses, for example, two to six doses or more can be administered to a subject over a day, a week or months. Multiple boosts can also be given, such as one to five, or more. Different dosages can be used in a series of sequential inoculations. For example, a relatively large dose in a primary inoculation and then a boost with relatively smaller doses. The immune response against the selected antigenic surface can be generated by one or more inoculations of a subject with an immunogenic composition disclosed herein.

III. IMMUNODIAGNOSTIC REAGENTS AND KITS

This disclosure provides a method for detecting or isolating an HIV-1 binding antibody in a subject infected with HIV-1. The method includes contacting a sample from a subject, such as, but not limited to a blood, serum, plasma, urine or sputum sample from the subject with one or more of the disclosed immunogenic agents, for example, the immunogen, the nucleic acid encoding the immunogen, the host cell, the protein complex, or the virus particle described above, or a combination thereof. The method may also include detecting binding of antibodies in the sample to the disclosed immunogenic agents. The binding can be detected by any means known to one of skill in the art, including the use of labeled secondary antibodies that specifically bind the antibodies from the sample. Labels include radiolabels, enzymatic labels, and fluorescent labels. In some embodiments, the method may further include isolating the HIV-1 binding antibody in a subject.

The disclosed immunogenic agents can be as components of a kit. Such a kit may also include additional components including packaging, instructions and various other reagents, such as buffers, substrates, antibodies or ligands, such as control antibodies or ligands, and detection reagents. The kit may optionally include an adjuvant.

An adjuvant is a vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages) Immunostimulatory oligonucleotides (such as those including a CpG motif) can also be used as adjuvants (for example see U.S. Pat. Nos. 6,194,388; 6,207,646; 6,214,806; 6,218, 371; 6,239,116; 6,339,068; 6,406,705; and 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, and 41 BBL. Adjuvants can be used in combination with the disclosed immunogens.

IV. DEFINITIONS

As used in this document, the singular forms "a," "an," and "the" include plural references unless the context clearly dictates otherwise. Unless defined otherwise, all technical and scientific terms used here.

The term "and/or" means any one of the items, any combination of the items, or all of the items with which this term is associated.

The compositions of the present invention can comprise, consist essentially of, or consist of the claimed ingredients. The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

The terms "prevent," "preventing," "prevention," "prophylactic treatment" and the like refer to reducing the probability of developing a disorder or condition in a subject, who does not have, but is at risk of or susceptible to developing a disorder or condition.

The term "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example, "about 1" may also mean from 0.5 to 1.4.

gp120 is an envelope protein from human immunodeficiency virus (HIV). The mature gp120 wild-type polypeptides have about 500 amino acids in the primary sequence. The gp120 is heavily N-glycosylated giving rise to an apparent molecular weight of 120 kD. The polypeptide is comprised of five conserved regions (C1-C5) and five regions of high variability (V1-V5). Exemplary sequences of wild-type gp160 polypeptides are shown on GENBANK®, for example, Accession Nos. AAB05604 and AAD12142, which are incorporated herein by reference in their entirety as available on Jun. 29, 2010. Exemplary sequences of gp120 polypeptides from HIV-1 DU156 are shown on GENBANK®, for example, Accession Nos. ABD83635, AAO50350, and AAT91997, which are incorporated herein by reference in their entirety as available on Sep. 27, 2010. Exemplary sequences of gp120 polypeptides from HIV-1 ZA012 are shown on GENBANK®, for example, Accession No. ACF75939, which is incorporated herein by reference in its entirety as available on Sep. 27, 2010.

"Glycosylation site" refers to an amino acid sequence on the surface of a polypeptide, such as a protein, which accommodates the attachment of a glycan. An N-linked glycosylation site is triplet sequence of NXS/T in which N is asparagine, X is any residues except proline, S/T means serine or threonine. A glycan is a polysaccharide or oligosaccharide. Glycan may also be used to refer to the carbohydrate portion of a glycoconjugate, such as a glycoprotein, glycolipid, or a proteoglycan.

"Immunogenic polypeptide" refers to a protein or a portion thereof that is capable of inducing an immune response in a mammal, such as a mammal infected or at risk of infection with a pathogen. Administration of an immunogenic polypeptide derived from a pathogen of interest that inducing an immune response. Administration of an immunogenic polypeptide can lead to protective immunity against a pathogen of interest. In some examples, an immunogenic polypeptide is an antigen that is resurfaced to focus immunogenicity to a target epitope. An "immunogenic gp120 polypeptide" is gp120 molecule, a resurfaced gp120 molecule, or a portion thereof capable of inducing an immune response in a mammal, such as a mammal with or without an HIV infection. Administration of an immunogenic gp120 polypeptide that induces an immune response can lead to protective immunity against HIV.

"Immune response" refers to a response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response and results in the production of specific antibodies.

"Isolated" refers to an "isolated" biological component (such as a protein, for example, a disclosed antigen or nucleic acid encoding such an antigen) has been substantially separated or purified away from other biological components in which the component naturally occurs, such as other chromosomal and extrachromosomal DNA, RNA, and proteins. Proteins, peptides, and nucleic acids that have been "isolated" include proteins purified by standard purification methods. The term also embraces proteins or peptides prepared by recombinant expression in a host cell as well as chemically synthesized proteins, peptides, and nucleic acid molecules. Isolated (or purified) does not require absolute purity, and can include protein, peptide, or nucleic acid molecules that are at least 50% isolated, such as at least 75%, 80%, 90%, 95%, 98%, 99%, or even 99.9% isolated.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen. "Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

Unless defined otherwise, all technical and scientific terms used herein have the same meaning as commonly understood by one of ordinary skill in the art to which this invention belongs. Although any methods and materials similar or necesarily to those described herein can also be used in the practice or testing of the present invention, the preferred methods and materials are now described. All publications mentioned herein are incorporated herein by reference in their entireties.

V. EXAMPLES

Example 1

This example describes the materials and methods used in Examples 2-6 bellow.
Envelope Proteins Env trimers were expressed as soluble native-like soluble gp140 trimers that included the SOSIP substitutions: 'SOS' substitutions (A501C$_{gp120}$, T605C$_{gp41}$), 'IP' (I559P$_{gp41}$), addition of the N-linked glycan sequence at residue 332$_{gp120}$ (T332N$_{gp120}$), an enhanced gp120-gp41 cleavage site (REKR (SEQ ID NO: 17) to RRRRRR (SEQ ID NO: 18)), and a stop codon after residue 664$_{gp41}$ (Env numbering according to HX nomenclature). The newly-engineered Env trimers RC1, RC1-4fill, RC1-Avitag, RC1-Spytag, RC1-glycanKO, RC1-glycanKO-Avitag, RC1-glycanKO-GAIA ("GAIA" disclosed as SEQ ID NO: 16) and RC1-GALA ("GAIA" disclosed as SEQ ID NO: 16), wtBG505, and the previously-reported BG505 variants 11MUTB, 10MUT, 7MUT, 5MUT were cloned in the pPPPI4 expression vector using synthetic gene fragments (Integrated DNA Technologies (IDT)). The glycan variants RC1Δ301, RC1Δ332, and 11MUTBΔ301 were produced by site-directed mutagenesis (QuikChange Lightning Multi-site directed mutagenesis kit, Catalog #210515, Agilent Technologies).

Non-tagged versions of Env proteins were used in ELISAs (see ELISA section) and for immunizations in wild-type mice (see Animals section). The Spytagged version of RC1-4fill was conjugated to virus-like particles (VLPs) and used for immunizations in rabbits and macaques (see VLP production and conjugation and Animals sections). The Avitagged versions of RC1 and RC1-glycanKO were biotinylated and used as baits in FACS (See Flow cytometry and single B-cell sorting section).

Soluble Env trimers were expressed by transient transfection in HEK293-6E cells (National Research Council of Canada) or Expi293 cells (Life Technologies) and purified from cell supernatants by 2G12 or NIH45-46 immunoaffinity chromatography and size exclusion chromatography (SEC) as previously described (Wang, H. et al. *Elife* 6 (2017). Proteins were stored at 4° C. in 20 mM Tris pH 8.0 and 150 mM sodium chloride (TBS buffer). SpyTagged immunogens were buffer exchanged into 20 mM sodium phosphate pH 7.5, 150 mM NaCl.
VLP Production and Conjugation For attachment to VLPs, a C-terminal SpyTag sequence (13 residues) was added to RC1-4fill to form an irreversible isopeptide bond to SpyCatcher protein (Zakeri, B. et al. *Proc Natl Acad Sci USA* 109, E690-697 (2012)). The gene encoding bacteriophage AP205 coat protein to which the SpyCatcher protein was attached was the kind gift of Dr. Mark Howarth, Oxford University). SpyCatcher-AP205 VLPs was purified as described (Brune, K. D. et al. *Sci Rep* 6, 19234 (2016)), incubated with 3-fold molar excess SpyTagged RC1-4fill Env trimers, and separated conjugated VLPs from free Env trimers by SEC on a Superdex 200 column equilibrated with 20 mM sodium phosphate pH 7.5, 150 mM NaCl. Conjugation of Env trimers was verified by negative-stain EM and/or SDS-PAGE, and immunogen concentrations were estimated by comparing to known amounts of free immunogen run on the same SDS-PAGE gel.
Animals Mice carrying the Ig V(D)J genes encoding the iGL IgH and IgL corresponding to the human PGT121 and 10-1074 broadly neutralizing antibodies (GL$_{HL}$121 knock-in mice) were previously described (Escolano, A. et al. *Cell* 166, 1445-1458 e1412, (2016)). 6-8 week old C57BL6 male mice from The Jackson Laboratory were used for immunizations. All animal procedures were performed in accordance with protocols approved by the Rockefeller University IACUC. Male and female GL$_{HL}$121 knock-in mice or male C57BL6 wild-type mice were equally distributed in groups and immunized intraperitoneally with 10 µg of soluble SOSIP Envelope trimer in Ribi adjuvant (Sigma) (1:1).

Six-month-old New Zealand White rabbits (Covance) were used for immunizations. Rabbits were immunized subcutaneously with ~22 µg of RC1-4fill SOSIP Env trimer conjugated to VLP (RC1-4fill VLP) in an ISCOMs-like saponin adjuvant (see Adjuvant synthesis section). Serum samples were collected from mice and rabbits on weeks 0 and 2 after immunization.

Eight rhesus macaques (*Macaca mulatta*) of Indian genetic origin, 2 to 4 years of age, were housed and cared for in accordance with Guide for Care and Use of Laboratory Animals Report no. NIH 82-53 (Department of Health and Human Services, Bethesda, Maryland, 1985) in a biosafety level 2 NIH facility. All animal procedures and experiments were performed according to protocols approved by the Institutional Animal Care and Use Committee of NIAID, NIH.

Animals were immunized subcutaneously (s.c) with approximately 200 µg of RC1-4fill SOSIP Env trimer conjugated to VLP (RC1-4fill VLP) adjuvanted in IscoMPLA into the medial inner forelegs and hind legs (total of 4 sites/animal). Blood was drawn regularly to monitor serum neutralizing activity and characterize serum antibody binding by ELISA. Lymph node biopsies were obtained from naïve macaques and from the immunized macaques 3 weeks after immunization.

Adjuvant Synthesis

ISCOM-like saponin adjuvant was prepared as previously described (K. Lovgren-Bengtsson, et al, in *Methods in Molecular Medicine, Vaccine Adjuvants: Preparation Methods and Research Protocols*, D. O'Hagan, Ed. (Humana Press, Totowa, NJ, 2000), vol. 42, pp. 239-258). Briefly, 20 mg/ml solutions of cholesterol (Avanti Polar Lipids 700000) and 1,2-dipalmitoyl-sn-glycero-3-phosphocholine (DPPC) (Avanti Polar Lipids 850355) were prepared in 20% MEGA-10 (Sigma D6277) detergent. Quil-A saponin (InvivoGen vac-quil) was dissolved in Milli-Q water at a final concentration of 100 mg/ml. All components were mixed at a ratio of 1:1:5 (chol:DPPC:Quil-A) followed by dilution with 1×PBS for a final concentration of 1 mg/ml cholesterol. For ISCOM-MPLA saponin adjuvant, a 5 mg/ml solution of MPLA (Avanti 699800) was prepared in 20% MEGA-10, and the components were mixed at a ratio of 2:1:1:10 (chol:DPPC:MPLA:Quil-A). The solutions were allowed to equilibrate overnight at RT, followed by dialysis against 1×PBS using a 10 k MWCO membrane (ThermoFisher 66456). The adjuvant solution was then sterile filtered, concentrated using 50 k MWCO Centricon spin filters (Millipore Sigma UFC905024), and further purified by Fast Protein Liquid Chromatography (FPLC) using a Sephacryl S-500 HR size exclusion column (GE Life Sciences 28-9356-06). The final adjuvant concentration was determined by cholesterol quantification (Sigma MAK043).

ELISA

ELISAs with SOSIP Env trimers 11MUTB, RC1, 11MUTBΔ301, RC1Δ301, RC1-GAIA ("GAIA" disclosed as SEQ ID NO: 16), RC1-glycan-knock-out (RC1-glycanKO), RC1-glycanKO-GAIA ("GAIA" disclosed as SEQ ID NO: 16), RC1Δ332, BG505), 10MUT, 7MUT, 5MUT or the V3 loop-Consensus C peptide (SEQ ID NO: 10: KGKGKGKGKGCTRPNNNTRKSIRIGPGQTFYATG-DIIGDIRQAHC) were performed by direct coating of high binding 96-well plates (Corning #9018) with 50 µl per well of protein solution at 2 µg/ml in 1×PBS overnight at 4° C. Plates were washed 3 times with washing buffer (1×PBS with 0.05% Tween 20 (Sigma-Aldrich)) and incubated in blocking buffer (1×PBS with 2% Milk) for 1 hour (h) at room temperature (RT) Immediately after blocking, monoclonal antibodies or serum samples were added in blocking buffer and incubated for 2 h at RT. Serum samples were assayed at a 1:100 or 1:30 starting dilution and seven additional 3-fold serial dilutions. Mouse and human monoclonal antibodies (IgGs) or human Fabs were evaluated at the concentrations specified in the Results section. Plates were washed 3 times with washing buffer and then incubated with anti-mouse IgG (Jackson ImmunoResearch #115-035-071), anti-human IgG heavy chain (Jackson ImmunoResearch #109-035-098) or anti-human Ig heavy and light chain (Jackson ImmunoResearch #109-036-088) conjugated to horseradish peroxidase (HRP) in washing buffer at a 1:5000 dilution. Plates were developed by addition of the HRP substrate, ABTS Single Solution (Life Technologies #00-2024), and absorbance was measured at 405 nm with an ELISA microplate reader (FluoStar Omega, BMG Labtech).

In other ELISAs, high binding 96-well plates were directly coated with 50 µl of a solution of Fab at 20 µg/ml in 1×PBS overnight at 4° C. Plates were washed 3 times with washing buffer and incubated in blocking buffer for 1 hour at RT Immediately after blocking, plates were incubated in 50 µl of a solution of RC1 or RC1-glycanKO-GAIA ("GAIA" disclosed as SEQ ID NO: 16) at 2 µg/ml in blocking buffer for 1 h at RT. Plates were washed 3 times with washing buffer and incubated for 1 h at RT with 50 µl of a chimeric version (human Fabs and mouse Fc) of the CD4-binding site bNAb 3BNC60 in blocking buffer at 3-fold serial dilutions starting at 5 µg/ml. Plates were washed 3 times with washing buffer and incubated for 1 h at RT with anti-mouse IgG secondary antibody conjugated to HRP (Jackson ImmunoResearch #115-035-071). Plates were washed and developed as above.

Flow Cytometry and Single B-Cell Sorting

Single-cell suspensions were obtained from the draining lymph nodes and spleens of immunized mice, and mature B-cells were isolated by negative selection using anti-CD43 magnetic beads (MACS) following the manufacturer's instructions.

Frozen PBMCs or cells from lymph node biopsies obtained from the naïve and immunized macaques were thawed and washed in RPMI medium 1640 (1×) (Gibco #11875-093). Mouse or macaque cells were incubated with 100 µl of a solution of FACS buffer (PBS 1× with 2% fetal bovine serum and 1 mM Ethylenediaminetetraacetic acid (EDTA)) with mouse (BD Biosciences #553142) or human (BD Biosciences #564219) Fc blocker respectively at a 1:500 dilution for 30 min on ice.

RC1 and RC1-glycanKO (RC1$^+$/RC1 glycanKO$^-$) tetramers were prepared by incubating 5 µg of Avitagged and biotinylated RC1 (RC1-AviBio) or Avitagged and biotinylated RC1-glycanKO (RC1-glycanKO AviBio) with fluorophored streptavidin at a 1:200 dilution in 1×PBS for 30 min on ice.

RC1$^+$/RC1-glycanKO$^-$ mouse B-cells were isolated using RC1-AviBio conjugated to streptavidin BV711 (BD Biosciences, #563262) and RC1-glycanKO AviBio conjugated to streptavidin-PE (BD Biosciences, #554061) as baits. RC1$^+$/RC1-glycan KO$^-$ macaque B-cells were isolated using three baits: RC1-AviBio conjugated with streptavidin-PE and streptavidin AF647 and RC1-glycanKO AviBio conjugated with streptavidin BV605 (BD Biosciences, #563260). Tetramers were mixed with the human or mouse antibody cocktails indicated below to a final concentration of 5 µg/ml for each of them.

Mouse cells were stained with the following fluorophored antibodies against mouse cell surface markers: anti CD4 APC-eFluor780 (Invitrogen, #47-0042-82), anti CD8 APC-eFluor780 (Invitrogen, #47-0081-82), anti F4/80 APC-eFluor780 (Invitrogen, #47-4801-82), anti NK1.1 APC-eFluor780 (Invitrogen, #47-5941-82), anti CD11b APC-eFluor780 (eBioscience #47-0112-82), anti CD11c APCeFluor780 (eBioscience #47-0114-82), anti Gr-1 APC-eFluor780 (Invitrogen, #47-5931-82), anti B220 APC (Biolegend, #103212), anti GL7 FITC (BD Biosciences #553666) and anti CD95 BV421 (BD Biosciences #562633) at 1:200 dilution and the live/dead marker Zombie NIR (Biolegend, #77184) at a 1:400 dilution in FACS buffer. Macaque cells were stained with the following anti human antibodies: anti-CD16 APC-eFluor780 (Invitrogen, #47-0168-41), anti-CD8a APC-eFluor780 (Invitrogen, #47-0086-42), anti-CD3 APC-eFluor780 (Invitrogen, #47-0037-41), anti-CD14 APC-eFluor780 (eBiosciences, #47-0149-41), anti-CD20 PeCy7 (BD, #335793), anti CD38 FITC (Stem Cell technologies, #60131FI), anti-IgG BV421 (BD Biosciences, #562581), anti-IgM PerCP-Cy5.5 (BD Biosciences, #561285) at a 1:200 dilution and the live/dead marker Zombie NIR at a 1:400 dilution in FACS buffer. Mouse or macaque cells were incubated with the corresponding antibody cocktail containing the RC1 and RC1-glycanKO baits for 30 minutes on ice, washed with FACS buffer and resuspended in 1 ml of FACS buffer. Before sorting or analysis, the cell suspensions were filtered through a 4004 cell strainer.

Zombie NIR$^-$/CD4$^-$/CD8$^-$/F4/80$^-$/NK1.1$^-$/CD11b$^-$/CD11c$^-$/B220$^+$/GL7$^+$/CD95$^+$RC1$^+$/RC1-glycanKO$^-$ single cells were isolated from the mouse cell homogenates and Zombie NIR$^-$/CD16$^-$/CD8a$^-$/CD3$^-$/CD14$^-$/CD20$^+$/CD38$^+$/IgG$^{+/-}$/double RC1$^+$/RC1-glycanKO$^-$ single cells were isolated from the macaque cell homogenates using a FACS Aria III (Becton Dickinson).

Single cells were sorted into individual wells of a 96-well plate containing 5 µl of lysis buffer (TCL buffer (Qiagen #1031576) with 1% of 2-β-mercaptoethanol). Plates were immediately frozen on dry ice and stored at −80° C.

Antibody Sequencing and Cloning 96-well plates containing single-cell lysates were thawed on ice. Single-cell RNA was purified in a designated clean area using magnetic beads (RNAClean XP, #A63987 Beckman Coulter) following the manufacturer instructions. In the final step of the purification protocol, RNA was eluted from the magnetic beads with 11 µl of a solution containing (14.5 ng/µl of random primers (Invitrogen, #48190-011), 0.5% of tergitol, (Type NP-40, 70% in H$_2$O, Sigma-Aldrich, #NP40S-100ML), 0.6 U/µl of RNase inhibitor (Promega #N2615) in nuclease-free water (Qiagen), and incubated at 65° C. for 3 min. cDNA was subsequently synthesized by reverse transcription (SuperScript® III Reverse Transcriptase, Invitrogen, #18080-044, 10'000 U) as previously described (von Boehmer, L. et al. *Nat Protoc* 11, 1908-1923 (2016)). cDNA was stored at −80° C. or used for antibody gene amplification by nested Polymerase chain reaction (PCR). To amplify the antibody genes from single B-cells, 10 µl of nuclease-free water was added to the solution containing cDNA.

Mouse and macaque antibody genes were amplified by nested PCR as previously described (von Boehmer, L. et al. *Nat Protoc* 11, 1908-1923 (2016)). PCR protocols: (annealing (° C.)/elongation (sec)/number of cycles): 1$^{st}$ PCR (IgG IgH and Igλ): 46/55/50; 2$^{nd}$ PCR (IgG IgH and Igλ): 50/55/50. Amplified heavy chain and light chain cDNAs were individually cloned into expression vectors containing the complete mouse or human IgG antibody constant regions or the human heavy chain constant region 1 (Fragment antigen-binding (Fab) vector) by using the sequence and ligation-independent cloning (SLIC) methodology (Li, M. Z. & Elledge, S. J. *Nat Methods* 4, 251-256 (2007)).

Antibody Production and Purification

Igs were purified from 200 µl of mouse or macaque serum using Ab Spin Trap Protein G Sepharose columns (GE Healthcare, #28-4083-47) following the manufacturer's instructions. Igs were eluted in 4 fractions of 200 µl. The Ig-containing fractions were buffer exchanged with PBS by overnight dialysis at 4° C. (dialysis cassettes 20000 MWCO Thermo Scientific, #66005).

For structural studies, mouse IgGs and macaque His$_6$-tagged Fabs ("His$_6$" disclosed as SEQ ID NO: 19) were expressed by transient transfection in HEK293-6E or Expi293 cells and purified from cell supernatants using protein A or G (GE Healthcare) (for IgGs) or Ni-NTA (GE Healthcare) or Ni Sepharose 6 Fast Flow (GE Healthcare) (for Fabs) chromatography and SEC as described (Scharf, L. et al. *Cell* 162, 1379-1390 (2015)). Mouse Fab was obtained by digesting IgG at 1-5 mg ml$^{-1}$ with ficin (Sigma) using a protocol modified from Thermo Scientific. Fab was purified by protein G (GE Healthcare) and SEC chromatography as described, followed by Mono Q 5/50 (GE Healthcare) ion-exchange chromatography (Diskin, R. et al., *Nat Struct Mol Biol* 17, 608-613). The common iGL of the PGT121 and 10-1074 bNAbs was expressed as a His$_6$-tagged Fab ("His$_6$" disclosed as SEQ ID NO: 19) as described above.

In Vitro Neutralization Assay

TZM-bl assays were performed as described (Montefiori, D. C. *Curr Protoc Immunol* Chapter 12, Unit 12 11 (2005)). In brief, neutralization activity was calculated as a function of the reduction in Tat-induced luciferase expression in the TZM-bl reporter cell line after a single round of virus infection.

SPR

SPR experiments were performed using a Biacore T200 (Biacore). For measuring the affinity for PGT121/10-1074 iGL Fab, Protein A was immobilized on a CM5 chip (Biacore) by primary amine chemistry (Biacore manual) and 200 nM 8ANC195$_{G52K5}$ anti-Env IgG was injected over experimental flow cells as described (Scharf, L. et al. *Cell* 162, 1379-1390 (2015)). A reference flow cell was made by injecting 200 nM mG053 IgG, which does not bind HIV Envs. Human Fc was injected at 1 µM to block the remaining protein A sites. After capturing 10 µM SOSIP protein (RC1, 11MUTB, or 10MUT), a concentration series of PGT121/10-1074 iGL Fab (4-fold dilutions from a top concentration of 160 µM for 10MUT, and 2-fold dilutions from a top concentration of 150 µM for 11MUTB and RC1) was injected, and the binding reactions were allowed to reach equilibrium. Flow cells were regenerated with 10 mM glycine pH 2.0 and 1M guanidine HCl at a flow rate of 90 µl/min as described (Scharf, L. et al. *Cell* 162, 1379-1390 (2015)). $K_D$s were derived by nonlinear regression analysis of plots of $R_{eq}$ (the equilibrium binding response) versus the log of the injected protein concentration, and the data were fit to a 1:1 binding model as described (Vaughn, et al. *Biochemistry* 36, 9374-9380 (1997)).

For measuring the relative binding of antibodies isolated from mice and monkeys, SOSIP Env trimers were immobilized on a CM5 chip by primary amine chemistry, and selected Fabs were injected at 200 nM. Flow cells were regenerated with 10 mM glycine pH 2.0.

Cryo-EM Sample Preparation

RC1 complexed with 10-1074 was prepared by incubating purified RC1 with 10-1074 Fab and a CD4-binding site (CD4bs) Fab at a 1:3:3 molar ratio (gp140 protomer:10-1074 Fab:CD4bs Fab) overnight at room temperature. The RC1-Fab complex was isolated by SEC in TBS (20 mM Tris pH 8.0, 100 mM NaCl) using a Superdex-200 Increase 10/300 column (GE Healthcare). RC1 complexes with mouse and macaque Fabs were prepared by incubating purified RC1 with a mouse or macaque Fab and with 8ANC195 Fab at a 1:1.3:1.3 molar ratio (gp140 protomer: mouse or macaque Fab:8ANC195 Fab) overnight at room temperature and used without SEC purification. RC1-Fab complexes were diluted to 0.75-1.4 mg/mL in TBS, added to glow-discharged 300 Mesh Quantifoil R1.2/1.3 copper grids, and vitrified in liquid ethane using a Mark IV Vitrobot (FBI).

Cryo-EM Data Collection

RC1-Fab complexes were imaged on a Talos Arctica cryo-electron microscope operating at 200 kV and equipped with a Falcon 3EC direct electron detector using EPU automated image acquisition software (Tan, et al. *Microscopy (Oxf)* 65, 43-56 (2016)). The RC1-10-1074 data were collected on two separate days and combined during processing. Each micrograph was collected at a magnification of 73,000, which results in a pixel size of 1.436 Å.

Cryo-EM Data Processing

Movie micrographs were motion-corrected in RELION-3 and dose weighted using MotionCor2, CTFs were estimated using Gctf, and particles were picked from micrographs using Gaussian blob auto-picking (Zivanov, J. et al. *Elife* 7 (2018); Zheng, S. Q. et al. *Nat Methods* 14, 331-332 (2017); Zhang, K. Gctf. *J Struct Biol* 193, 1-12 (2016)). Extracted particles were imported into cryoSPARC v2 and classified into 2D class averages (Punjani, A., et al. *Nat Methods* 14, 290-296 (2017)). Selected particles were sorted into two ab initio models, and the selected model was used as a reference in the homogenous refinement of those selected particles. Resolutions were estimated using the Gold Standard Fourier shell correlation of independently-refined half-maps (where FSC=0.143), and maps were auto-sharpened in cryoSPARC (Punjani, A., et al. *Nat Methods* 14, 290-296 (2017); Scheres, S. H. & Chen, S. *Nat Methods* 9, 853-854 (2012)). For interpreting N-linked glycans, a series of maps were generated with overall B-factors ranging from −150 to −400 Å$^2$ to improve local features and map connectivity at PNGSs (Terwilliger, T. C., et al. *Acta Crystallogr D Struct Biol* 74, 545-559 (2018)).

Model Building

Coordinates for the individual components of each complex were docked into the maps using UCSF Chimera. For the RC1-10-1074 complex, BG505 (PDB 5T3Z), 10-1074 Fab (PDB 5T3Z), and 8ANC131 Fab (PDB 4RWY) were docked into the density (Goddard, T. D., et al. *J Struct Biol* 157, 281-287 (2007)). For the mouse or macaque Fab complexes with RC1, BG505 Env (PDB 5CEZ), PGT121/ 10-1074 iGL Fab (PDB 4FQQ), and 8ANC195 Fab (PDB 5CJX) coordinates were docked into density maps. After replacing sequences for the Fabs in the complexes and for RC1, the models were built following iterative rounds of refinement in Coot and Phenix (Adams, P. D. et al. *Acta Crystallogr D Biol Crystallogr* 66, 213-221 (2010); Emsley, P., et al. *Acta Crystallogr D Biol Crystallogr* 66, 486-501 (2010)). Coordinates for glycans were added as Mang and then trimmed to fit the maps at σ=5. Model validation was performed using MolProbity and Privateer (Chen, V. B. et al. *Acta Crystallogr D Biol Crystallogr* 66, 12-21 (2010); Agirre, J. et al. *Nat Struct Mol Biol* 22, 833-834 (2015)).

The CD4-binding site Fab in the RC1-10-1074 complex and the 8ANC195 Fab in the RC1 complexes with mouse and macaque Fabs were not shown in structure figures, and their coordinates were not included in the RC1-Fab complex structures deposited in the EMDB and PDB.

Analysis Software

Geneious X and MacVector 15.5.3 were used for sequence analysis and graphs were created using R language. Flow cytometry data were processed using FlowJo 10.5.0. GraphPad Prism 7 was used for data analysis.

Quantification and Statistical Analysis

Statistical information including n, mean and statistical significance values are indicated in the text or the figure legends. GraphPad Prism 7 was used for statistical analysis by unpaired T-Test. Data were considered statistically significant at *$p \leq 0.05$, $p \leq 0.01$, *$p \leq 0.001$ and ****$p \leq 0.0001$.

Example 2

RC1 Facilitates Antibody Binding to the V3-Glycan Epitope

RC1 was designed using 11MUTB, a modified native-like soluble Env trimer (SOSIP.664) derived from the clade A/E BG505 Env, as a template. Compared to BG505, 11MUTB includes multiple substitutions in V1 and lacks potential N-linked glycosylation sites (PNGS) at positions N133 and N137 (FIG. 1a) (Steichen, J. M. et al. *Immunity* 45, 483-496 (2016); Sanders, R. W. et al. *PLoS Pathog* 9, e1003618 (2013)). It was hypothesized that additional removal of the PNGS at position 156 (N156Q) would facilitate recognition of the V3-glycan patch by increasing accessibility of the parts of V1 that interact with V3-glycan patch bNAbs. Consistent with this idea, absence of the N156 PNGS enhances neutralization by PGT121 and 10-1074 (FIG. 6a). In addition, it was further hypothesized that the removal of the N156 glycan, which includes negatively-charged terminal sialic acids, would produce a more electrostatically-neutral Env surface that could facilitate the binding of the largely neutral antibody precursor of the V3-glycan bNAbs PGT121 and 10-1074 (iGL PGT121/10-1074).

Figure 6B:
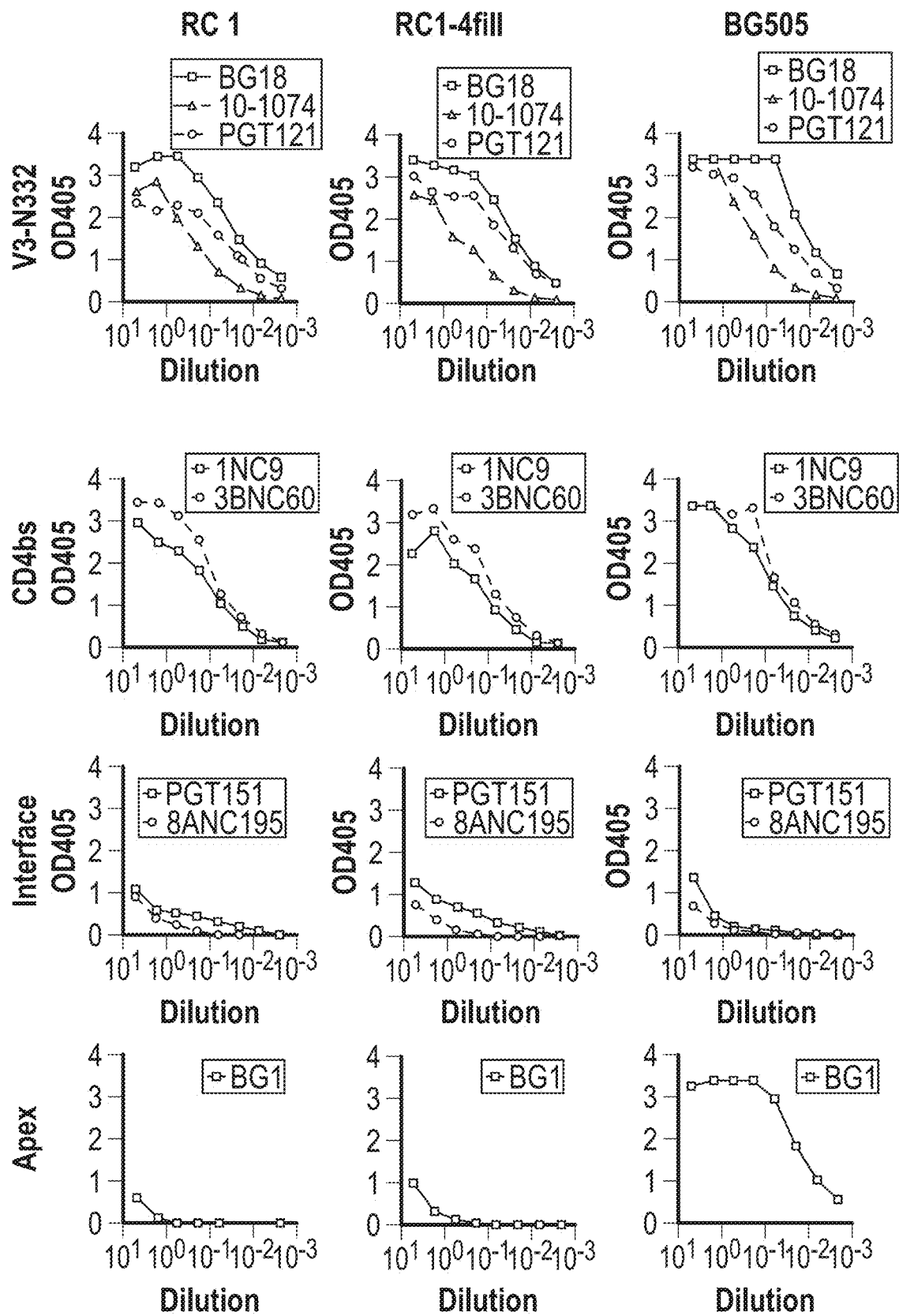

RC1 was initially characterized by evaluating its interactions with bNAbs by ELISA. As expected, a V1-V2-specific bNAb that interacts with the N156 glycan showed reduced binding to RC1 as compared to BG505 (FIGS. 6a and 6b). In contrast, bNAbs targeting the V3-glycan epitope, the CD4 binding site, or the gp120-gp41 interface bound similarly to RC1 and BG505 (FIG. 6b). Thus, RC1 retained the overall antigenic properties of BG505.

To further characterize RC1, a 4.0 Å single-particle cryo-EM structure of RC1 complexed with the antigen-binding fragment (Fab) of 10-1074 was solved and compared it to a structure of the same bNAb bound to BG505 (FIG. 1b; FIG. 7; Table 3). The RC1 structure was similar to BG505, with both showing the closed conformation of Env and containing three 10-1074 Fabs binding to the three V3-glycan patch epitopes (FIG. 1b). Compared with BG505, the V1 loop in RC1 included more ordered residues and was shifted towards the CDRH3 of 10-1074, allowing for increased interactions between the RC1 and 10-1074 (FIG. 1b).

Despite structural changes in V1 resulting from deletion of the N156 glycan (FIG. 1b), the common iGL precursor of PGT121 and 10-1074 bound RC1 and 11MUTB with similar affinities ($K_D \sim 50$ μM) (FIG. 1c). Consistent with these observations, RC1 and 11MUTB elicited comparable V3-glycan epitope-specific serologic responses in knock-in (KI) mice carrying genes encoding the iGL PGT121/10-1074 (FIGS. 2a and 2b). In conclusion, RC1 exhibited structural changes from BG505, but these did not affect its affinity for the iGL PGT121/10-1074 precursor antibody.

Example 3

RC1 Elicits V3-Glycan Patch Antibodies in Wild-Type Mice

Figure 8:
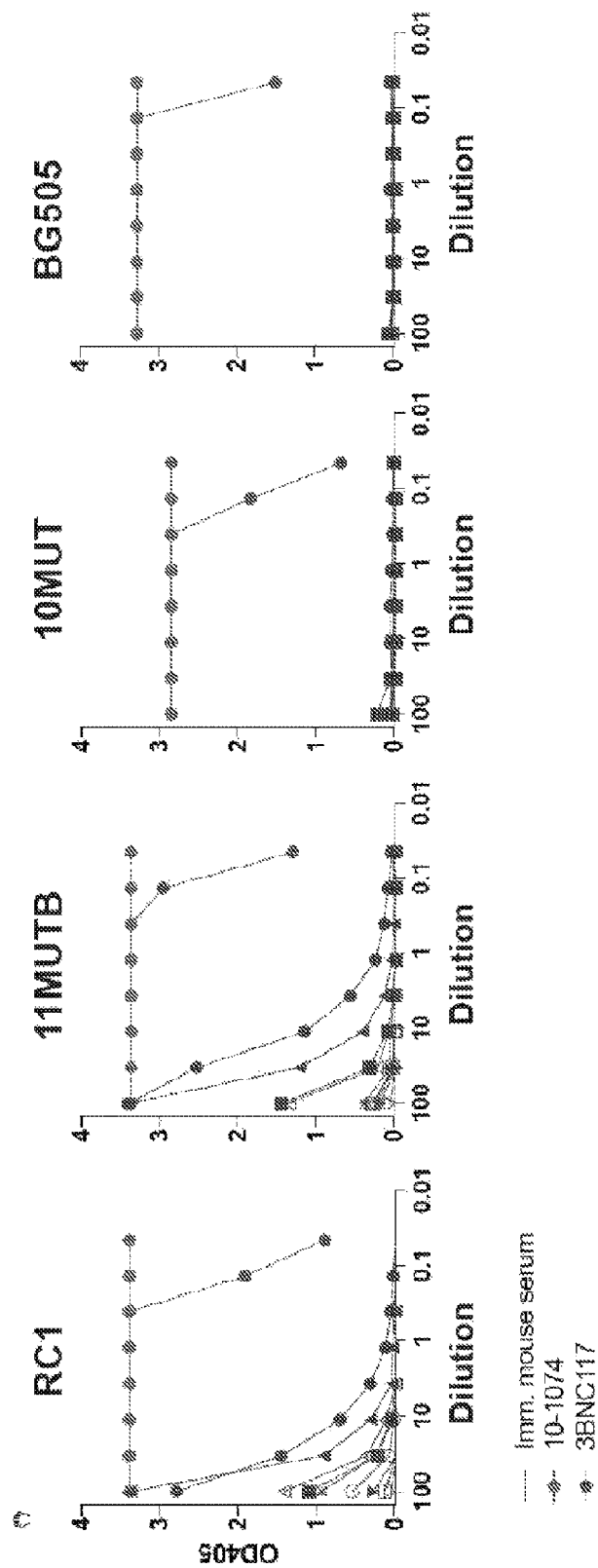
FIG. 8 shows that the serum from the RC1-immunized mice cross-reacted with 11MUTB but not to the more native 10MUT Env or to BG505.

To determine whether RC1 can activate B-cells that carry V3-glycan patch-specific antibodies in wild-type mice, C57Bl/6 mice were immunized with RC1 or 11MUTB. 11MUTB failed to produce a measurable serologic response (FIG. 2c). In contrast, RC1-immunized mice showed reproducible anti-V3-glycan patch responses as determined by ELISA comparing the binding to RC1 and to a mutant RC1 that lacks two additional V3 PNGSs at positions 301 and 332 (RC1-glycanKO) (FIGS. 2c, 2d, 2e, and 2f; Table 2). Moreover, the serum from the RC1-immunized mice cross-reacted with 11MUTB but not to the more native 10MUT Env or to BG505 (FIG. 8). The improved immunogenicity of the V3-glycan patch epitope of RC1 is the result of the specific removal of the N156 glycan from 11MUTB because removal of the N301 glycan from 11MUTB (11MUTBΔ301) (see Table 2) failed to induce detectable serologic responses in mice (FIG. 2g). It was concluded that, unlike 11MUTB and 11MUTBΔ301, RC1 elicits V3-glycan-specific serologic responses in wild-type mice.

To reduce the antibody responses to off-target epitopes and further focus the response on the V3-glycan patch, an RC1 variant, RC1-4fill, was produced by adding PNGSs to cover potential off-target sites with glycans at gp120 positions 230, 241, 289 and 344 (FIG. 9). RC1-4fill elicited serologic responses that were more specific to the V3-glycan patch in wild-type mice than those elicited by RC1, as determined by ELISAs against RC1 and RC1-glycanKO (FIG. 2h). It was concluded that RC1-4fill focuses the antibody responses to the V3-glycan patch epitope.

Example 4

Clonal Expansion of V3-Glycan Patch Specific B-Cells in Wild-Type Mice

Figure 10:
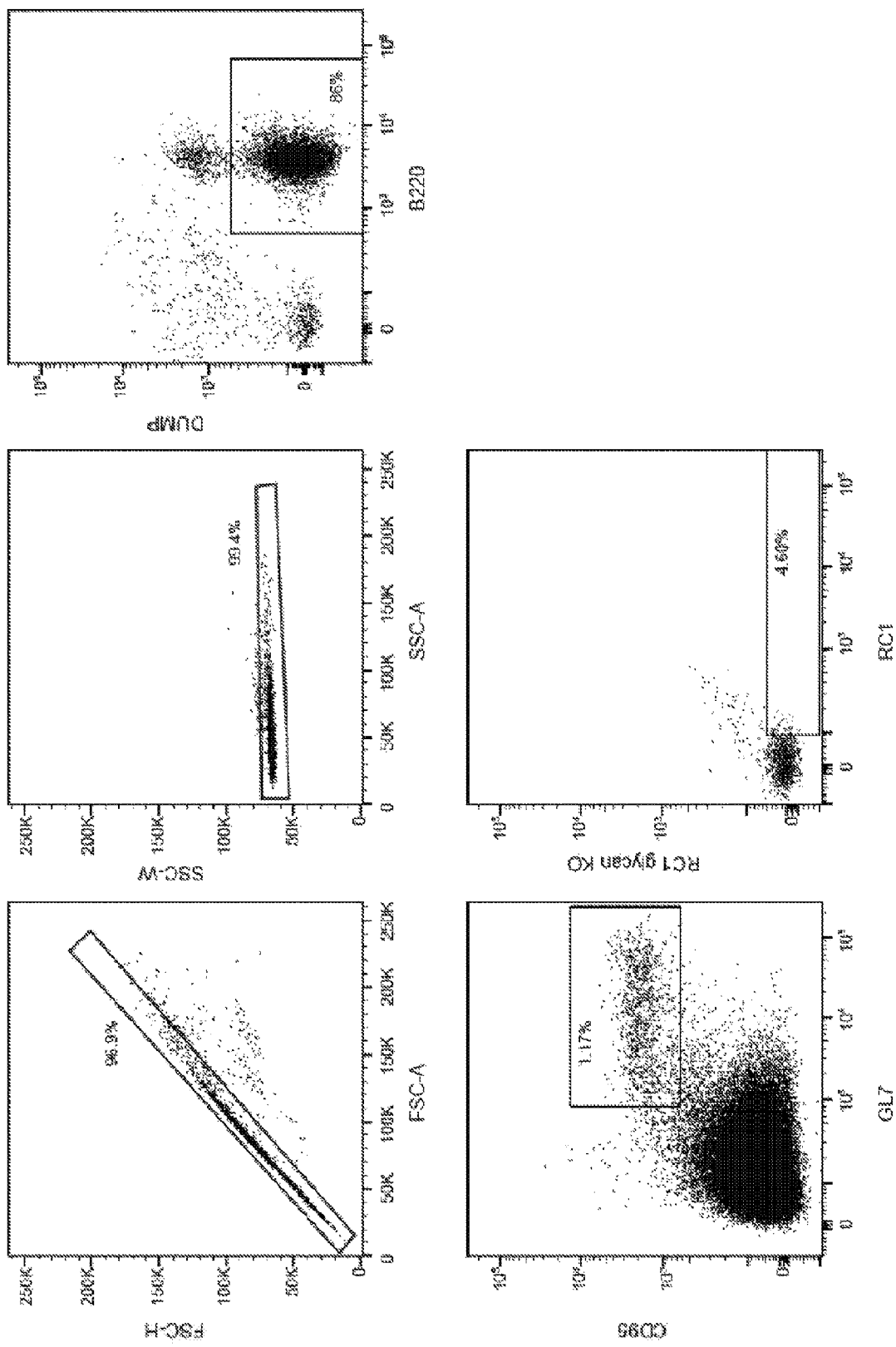
FIG. 10 shows the characterization of the humoral responses elicited by RC1 and RC1-4fill in wild-type mice. The antibody genes from single GC B-cells that bound to RC1 but not to RC1-glycanKO were sequenced.

To further characterize the humoral responses elicited by RC1 and RC1-4fill in wild-type mice, the antibody genes from single GC B-cells that bound to RC1 but not to RC1-glycanKO was sequenced (FIG. 10). All RC1- and RC1-4fill-immunized mice analyzed showed expansion of GC B-cell clones (FIG. 2i). The expanded clones predominantly expressed heavy chain V gene segments VH5-6, VH9-3 and VH2-9, and light chain segments VK3-4 and VK14-111 (FIG. 2i; Tables 4, 5, and 6). The CDRH3 sequences in expanded clones showed similarities to human V3-glycan patch bNAbs such as Tyr-rich or RxY motifs (Tables 4 and 6) and longer-than-average CDRH3s but none had insertions or deletions. The VH genes of the expanded clones had an average of 3.2 nucleotide mutations (FIG. 2j; Table 4).

Figures 11A, 11B, 11C, 11D:
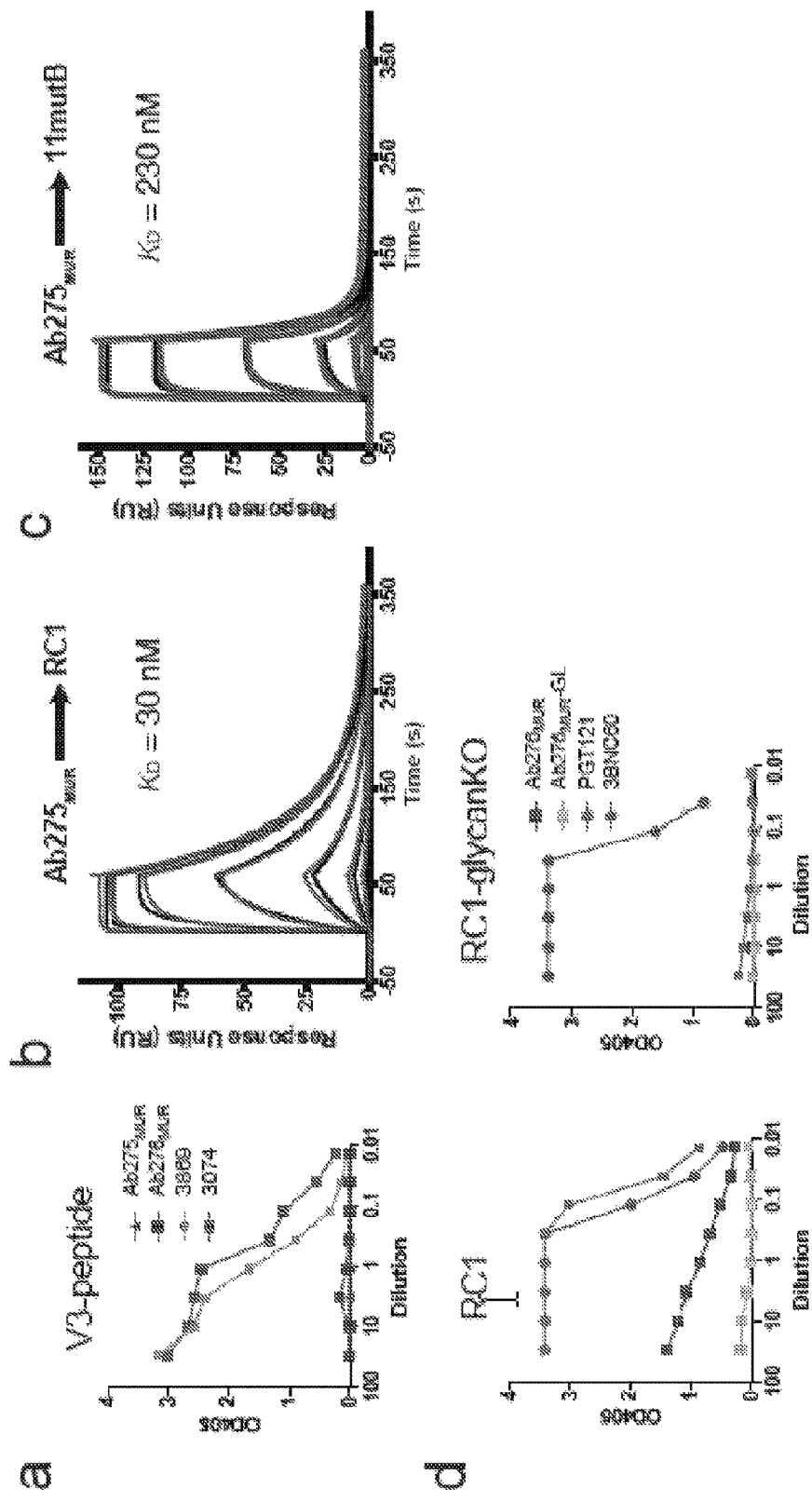
FIGS. 11*a*, 11*b*, 11*c*, and 11*d* show that RC1 and RC1-4fill expanded V3-glycan patch specific B-cells in wild-type mice. Both antibodies isolated from mice immunized with RC1 ($Ab275_{MuR}$) or RC1-4fill ($Ab276_{MUR}$) bound 11MUTB, but not BG505 or a peptide that covers the crown of the V3 loop (FIG. 11*a*). Ab275MUR bound RC1 with a $K_D$~30 nM (FIG. 11*b*). Importantly, $Ab275_{MUR}$ retained binding to 11MUTB ($K_D$~230 nM), demonstrating that it could accommodate the N156 glycan (FIG. 11*c*). The acquired mutations were essential for binding because reversion to the iGL sequence led to the loss of binding to RC1 (FIG. 11*d*).

To determine the target site of the antibodies produced by the expanded B-cell clones, selected antibodies were cloned and produced, and ELISAs were performed against RC1 and RC1 mutant proteins. A diverse group of monoclonal antibodies (mAbs) showed V3-glycan patch-specific binding in ELISA (FIG. 2k). Further characterization of the Env-binding properties of two mAbs isolated from mice immunized with RC1 (Ab275$_{MUR}$) or RC1-4fill (Ab276$_{MUR}$) showed that these antibodies bind the V3-glycan patch epitope in a GDIR (SEQ ID NO: 15)- and N301-glycan-dependent manner (FIG. 2l; Table 2). Both antibodies bound 11MUTB, but not BG505 or a peptide that covers the crown of the V3 loop (FIG. 2l; FIG. 11a). Ab275$_{MUR}$ bound RC1 with a $K_D$~30 nM (FIG. 11b). Importantly, Ab275$_{MUR}$ retained binding to 11MUTB ($K_D$~230 nM), demonstrating that it could accommodate the N156 glycan (FIG. 11c). The acquired mutations were essential for binding because reversion to the iGL sequence led to the loss of binding to RC1 (FIG. 11d). As expected, neither Ab275$_{MUR}$ nor Ab276$_{MUR}$ showed detectable neutralizing activity against a small panel of tier 1B and tier 2 HIV-1 isolates in TZMb1 assays (data not shown). Thus, it was concluded that RC1 and RC1-4fill expand mouse B-cell clones expressing antibodies that target the V3-glycan patch.

Example 5

VLP-RC1-4fill Elicits V3-Glycan Patch Antibodies in Rabbits and Rhesus Macaques

To enhance potential avidity effects and limit exposure of additional off-target epitopes at the base of the Env trimer, RC1-4fill was multimerized on virus-like particles (VLPs) using the Spytag-SpyCatcher system (FIGS. 3a and 3b). Rabbits and Rhesus macaques are thought to be better models than mice for HIV-1 vaccine studies because their antibodies have longer CDRH3s than mouse (average of 11 residues in mice, 13 in rabbits, and 15 in both Rhesus macaques and humans).

Figure 12:
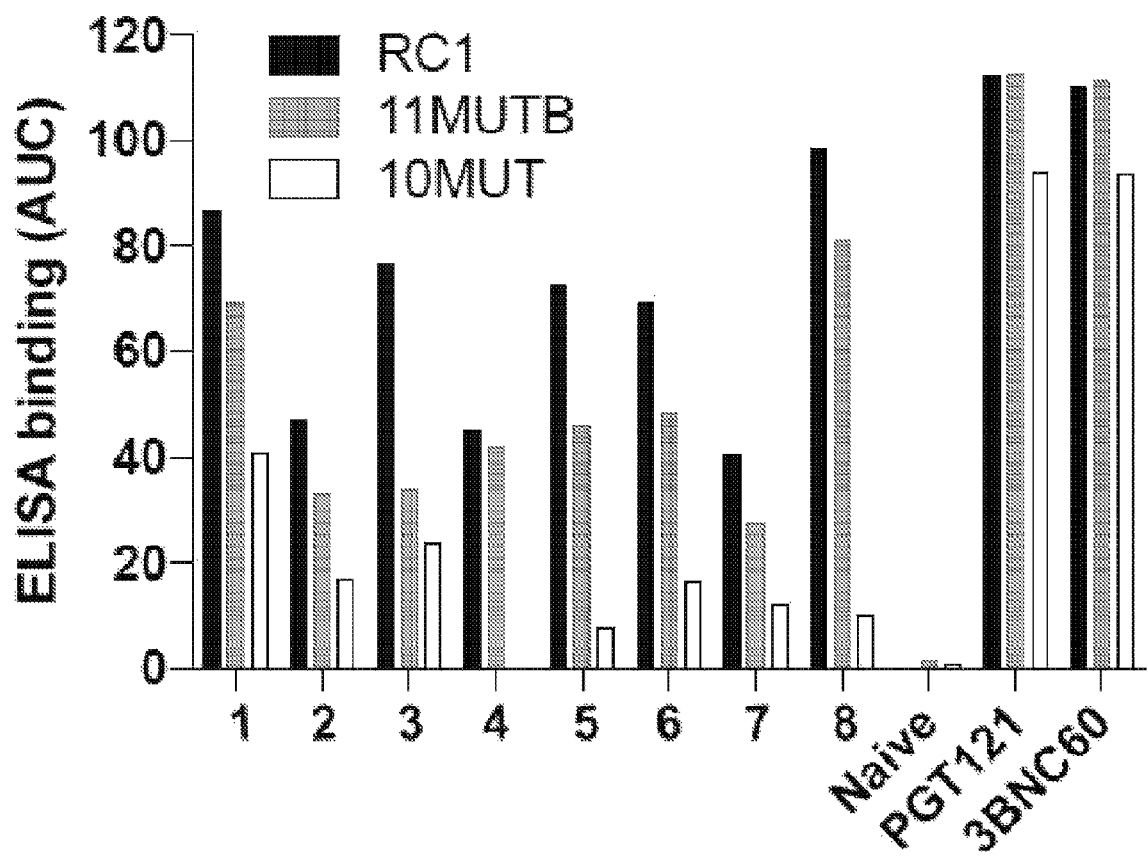
FIG. 12 shows that VLP-RC1-4fill elicits V3-glycan patch antibodies in rabbits and Rhesus macaques. The serum from the macaques primed with RC1-4fill VLPs showed sequentially reduced binding to the more native-like immunogens 11MUTB and 10MUT.

Immunization of 4 rabbits and 8 Rhesus macaques with RC1-4fill VLPs elicited serologic responses that were in part specific for the V3-glycan patch in all animals, as determined by ELISAs against RC1 and the RC1-glycanKO (FIGS. 3c and 3d). The serum from the macaques primed with RC1-4fill VLPs showed sequentially reduced binding to the more native-like immunogens 11MUTB and 10MUT (FIG. 12). Thus, RC1-4fill VLPs elicited robust serologic responses that mapped to the V3-glycan patch in rabbits and Rhesus macaques.

To further characterize responses elicited by RC1-4fill VLPs in macaques, draining lymph node GC B-cells that bound RC1 but not RC1-glycanKO was purified by flow cytometry (RC1$^+$/RC1-glycanKO$^-$). Whereas RC1$^+$ cells were absent from the GCs of naïve macaques, RC1$^+$/RC1-glycanKO$^-$ GC B-cells were found at an average frequency of 0.4% of all GC B cells in the lymph nodes in the 4 macaques analyzed (FIGS. 3e and 3f).

Antibody cloning from 4 immunized macaques revealed that all showed expanded B-cell clones that used a variety of VH genes with an average of 5.6 nucleotide somatic mutations (FIGS. 3g and 3h; Table 7). Most characterized human V3-glycan patch bNAbs contain a lambda light chain. Analysis of lambda gene usage revealed that macaque RC1 binding cells preferentially used genes VL132, which is 90.6% identical to VL2-8 in PGT125-128 and PGT130-131, and VL124, which is 93.8% identical to VL3-21 in PGT121-123/10-1074 (FIG. 3i; Table 8). Moreover, 86% of the lambda light chains had CDRL3s that included a DSS motif present in the iGLs of PGT121-123, 10-1074 and PGT124 (FIG. 3j; Table 9). This motif mutates to DSR in the mature bNAbs, and this substitution is critical for the neutralization activity of PGT121. It was concluded that macaque immunization with RC1-4fill VLPs expands B-cell clones whose antibody sequences resemble human V3-glycan patch bNAb precursors.

Figures 4A, 4B, 4C, 4D, 4E:
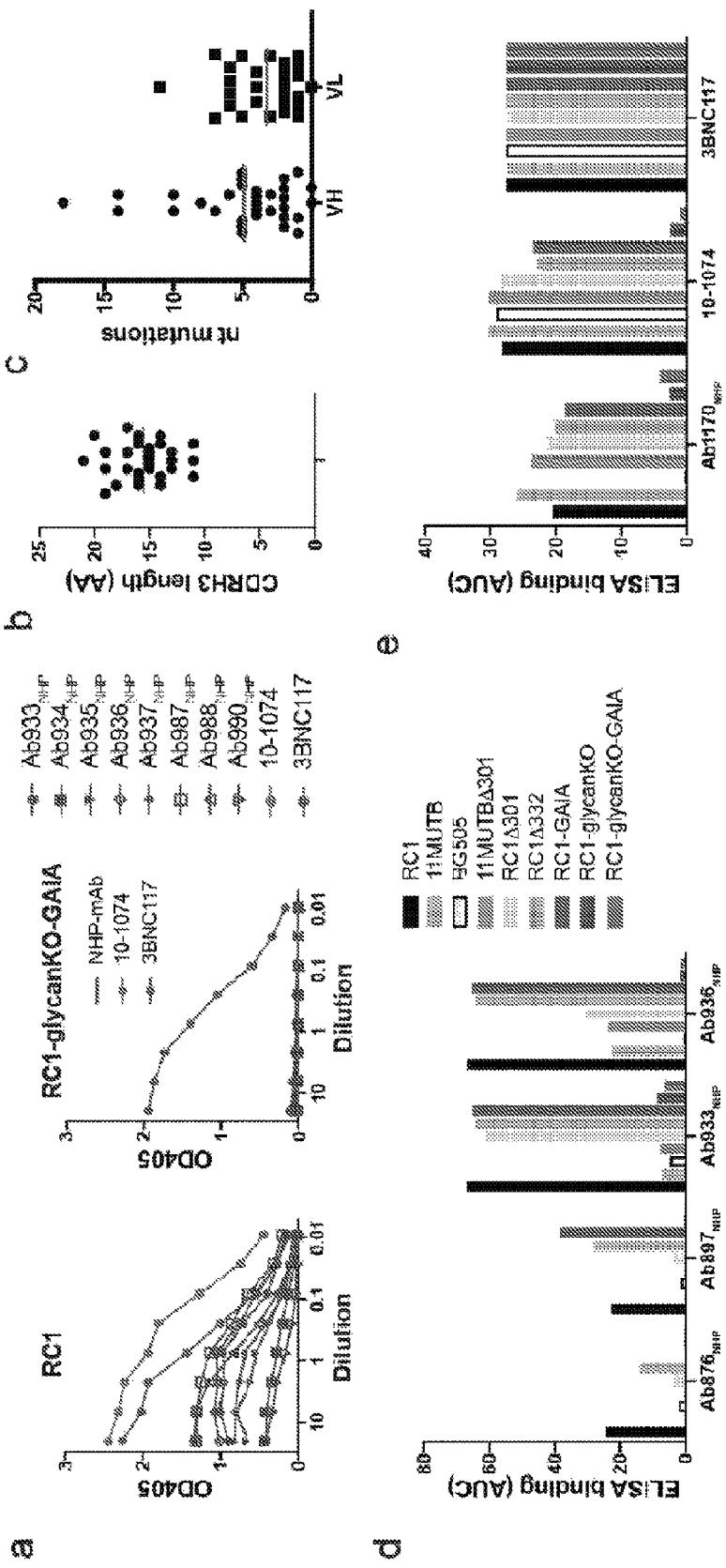
FIGS. 4*a*, 4*b*, 4*c*, 4*d*, and 4*e* show monoclonal antibodies from macaques immunized with RC1-4fill VLPs bind to the V3-glycan patch.

38 macaque GC antibodies were expressed with CDRL3s that resembled the CDRL3s of iGL V3-glycan patch bNAbs (Table 10). The CDRL3s of 33 of these antibodies contained a DSS motif and a Q at position 89 (QxxDSS motif (SEQ ID NO: 20)), also found in the CDRL3s of the PGT121-3, 10-1074, PGT124 and BG18 iGLs (Table 11). The other five antibodies contained an SYAG motif (SEQ ID NO: 21), which is present in the CDRL3s of the PGT125-7, PGT128, PGT130, and PGT131 iGLs (Table 11). Thirty of the 33 QxxDSS motif-containing antibodies ("QxxDSS" disclosed as SEQ ID NO: 20) and 2 of the 5 SYAG motif-containing antibodies ("SYAG" disclosed as SEQ ID NO: 21) bound to the V3-glycan patch epitope, as determined by ELISA using RC1 and RC1-glycanKO-GAIA ("GAIA" disclosed as SEQ ID NO: 16) (FIG. 4a; Table 10). The CDRH3 length of these 38 V3-glycan patch antibodies ranged from 11 to 21 residues (average=15.5 residues) (FIG. 4b). Longer CDRH3s included a high content of Tyr and/or Phe residues, similar to the long CDRH3s of human V3-glycan patch bNAbs (Table 10). The VH and VL genes of these antibodies had an average of 4.9 and 3.3 nucleotide mutations, respectively (FIG. 4c).

To further characterize antibody recognition of RC1, ELISAs were performed against additional mutants RC1-glycanKO, RC1-GALA ("GAIA" disclosed as SEQ ID NO: 16), RC1-glycanKO-GAIA ("GAIA" disclosed as SEQ ID NO: 16), 11MUTBΔ301, RC1Δ301, RC1Δ332, 11MUTB and BG505 (FIGS. 4d and 4e; Table 2). The ELISAs suggested four different binding patterns to RC1 among the antibodies that contained a QxxDSS motif (SEQ ID NO: 20) in the CDRL3 (FIG. 4d) and an additional pattern among the antibodies containing an SYAG motif (SEQ ID NO: 21) (FIG. 4e). Whereas all of the antibodies were glycan-dependent as determined by the absence of binding to RC1-glycanKO, they differed in their binding to 11MUTB or 10MUT, dependence on GDIR motif (SEQ ID NO: 15) and on the N301, N332, and N156 glycans (FIGS. 4a, 4d, and 4e). None of the antibodies tested bound to BG505 or had neutralizing activity against a small panel of tier 1B and tier 2 HIV-1 isolates in TZMb1 assays (FIGS. 4d and 4e; data not shown). It was concluded that macaque immunization with RC1-4fill VLPs elicits V3-glycan patch-specific antibodies that resemble the precursors of human bNAbs that target this site.

Example 6

Cryo-EM Structures of Mouse and Macaque Antibodies in Complex with RC1

Figures 5A, 5B, 5C:
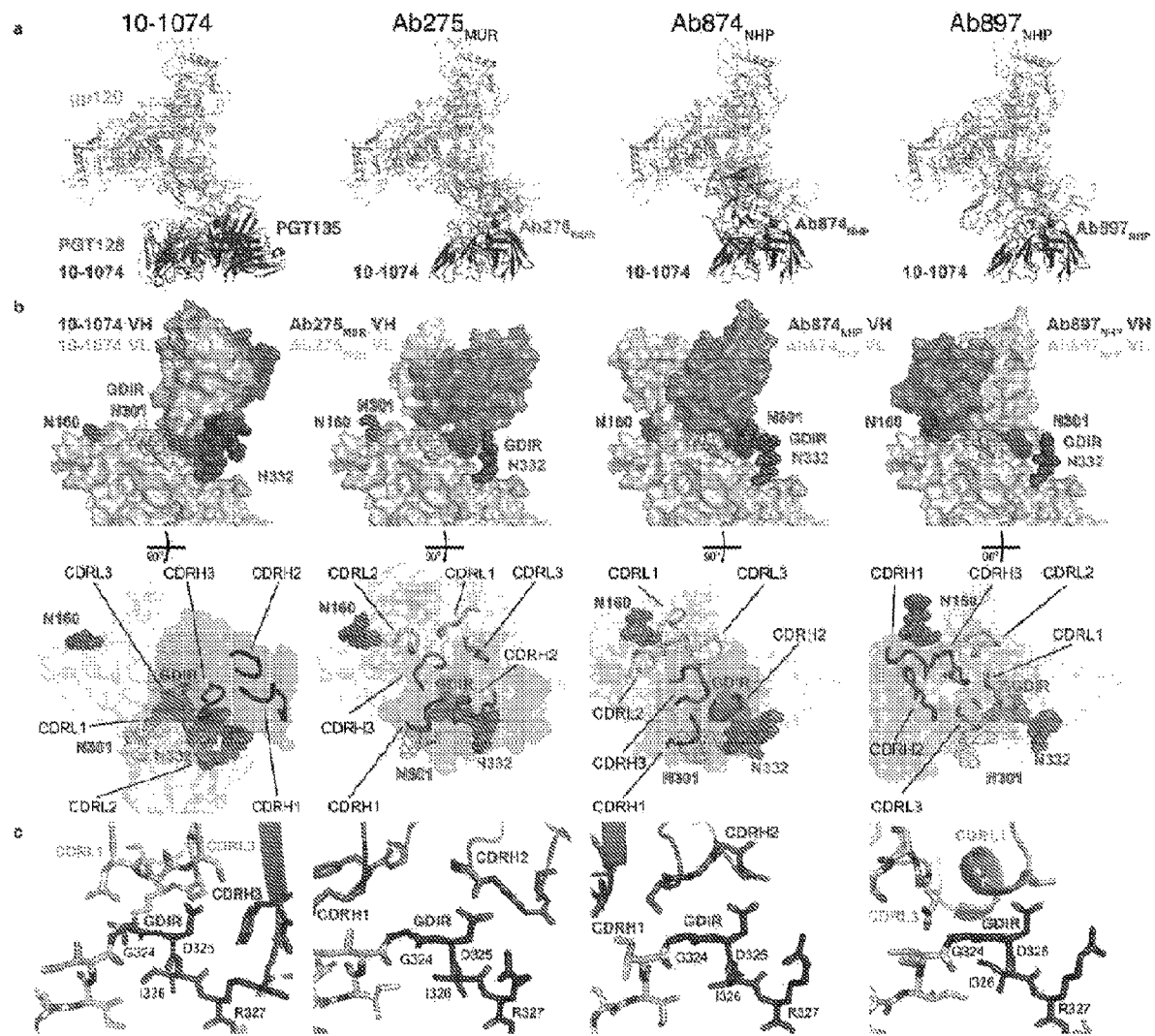
FIGS. 5*a*, 5*b*, and 5*c* show a comparison of the structures of 10-1074 and elicited antibodies bound to the RC1 immunogen.

To define the molecular mechanism of binding and compare modes of V3-glycan patch recognition, structures of one mouse and two macaque Fabs complexed with RC1 were determined using single-particle cryo-electron microscopy. All three antibodies bound to the V3-glycan patch epitope with footprints overlapping the 10-1074 footprint, but bound with different angles of approach compared to 10-1074 (FIGS. 5a and 5b). Ab275$_{MUR}$ (4.4 Å resolution) and Ab874$_{NHP}$ (3.9 Å) (derived from the same clone as Ab876$_{NHP}$) bound similarly to each other, consistent with their 69% sequence identity, whereas Ab897$_{NHP}$ (4.4 Å) (related by 48% and 54% sequence identity to Ab275$_{MUR}$ and Ab874$_{NHP}$, respectively) adopted a distinct angle of approach (FIG. 5b).

All three Fabs in the RC1 complexes contacted the GDIR motif (SEQ ID NO: 15), but with different footprints compared with each other and with 10-1074. Whereas 10-1074 contacted the conserved GDIR motif (SEQ ID NO: 15) using CDRH3, CDRL1, and CDRL3 (FIGS. 1c and 5b), Ab874$_{MUR}$, and Ab275$_{NHP}$ mainly made GDIR (SEQ ID NO: 15) contacts using their CDRH2s, and Ab897$_{NHP}$ utilized CDRL1 and CDRL3 (FIGS. 5b and 5c). In addition to GDIR (SEQ ID NO: 15) contacts, Ab275$_{MUR}$ and Ab874$_{NHP}$ interacted with the N332 glycan (FIGS. 5a and 5b). However, unlike 10-1074, which interacts extensively with the N332 glycan via its CDRL1, FRWL3, CDRH2, and CDRH3, Ab275$_{MUR}$ made minimal contacts using only its CDRH2, and Ab874$_{NHP}$ engaged the N332 glycan with its CDRH2 and FRWH3. Interactions with the N332 glycan were not observed in the Ab897$_{NHP}$-RC1 structure. Despite the reduced binding of Ab275$_{MUR}$, Ab876$_{NHP}$ (same clone as Ab874$_{NHP}$) and Ab897$_{NHP}$ to RC1Δ301 (FIG. 2l), none of the Fabs in the RC1 complexes showed interactions with the N301 glycan, suggesting either glycan heterogeneity that would obscure this interaction and/or a conformational change in a V3-glycan patch lacking this glycan that would diminish binding. It was concluded that RC1 elicits V3-glycan patch-targeting antibodies with distinct binding modes in animals with polyclonal antibody repertoires including primates.

HIV-1 bNAbs develop in infected humans by sequential rounds of somatic mutation in response to a rapidly-evolving pathogen. Vaccination with a series of related antigens can reproduce this progression of events in genetically-engineered mice that carry super-physiologic numbers of B lymphocytes expressing the iGL precursors of bNAbs. An important goal of HIV-1 vaccine design is to design immunogens that initiate this response in organisms with polyclonal immune systems with the goal of reproducing these responses in humans.

HIV-1 vaccine immunogen design has focused upon increasing the affinity of candidate immunogens for specific iGL bNAb precursors with the objective of recruiting a specific group of rare precursors into the GC. This approach typically fails to account for increases in apparent affinity produced by interactions between multimerized antigen and polyvalent antigen receptors on the surface of a B-cell. Moreover, GC entry is primarily limited by competition. Thus, the importance of affinity is relative, as evidenced by the observation that B-cells bearing low-affinity receptors are frequently found in GCs under physiologic conditions.

The principles employed to produce RC1 did not take affinity into account. Instead, RC1 was designed to increase the number of bNAb progenitors that can compete for GC entry. This was done by making the antigenic target site more available while facilitating binding to electrostatically-neutral iGL precursors. In addition, the RC1-4fill VLP incorporates the idea that masking competing for off-target epitopes minimizes competition for GC entry.

RC1 differs from other HIV-1 vaccine candidates in that it induces B-cells expressing antibodies against a targeted epitope to undergo clonal expansion in GCs in animals with a fully polyclonal B-cell repertoire. In macaques, these B-cells express antibodies that show sequence and structural similarities to iGL precursors of bNAbs targeting the V3-glycan patch. Thus, RC1-4fill VLPs are a suitable candidate immunogen for sequential vaccination strategies that aim to elicit V3-glycan bNAbs.

Example 7

RC1-3fill VLPs and NPs Behave Similarly to RC1 VLPs and NPs

Size-exclusion chromatography (SEC) traces for the RC1, RC1-3fill, and RC1-4fill immunogens (FIG. 13a) show that a smaller fraction of the RC1 and RC1-3fill immunogens elute in the void volume compared to RC1-4fill, demonstrating that RC1 and RC1-3fill are more stable and less-prone to aggregate than RC1-4fill. Representative yields from a 1 L expression in HEK 293T 6E cells for each immunogen (FIG. 13b) suggest that RC1-3fill was expressed at a higher level than RC1-4fill and at a similar level to RC1.

Figures 13E, 13F:
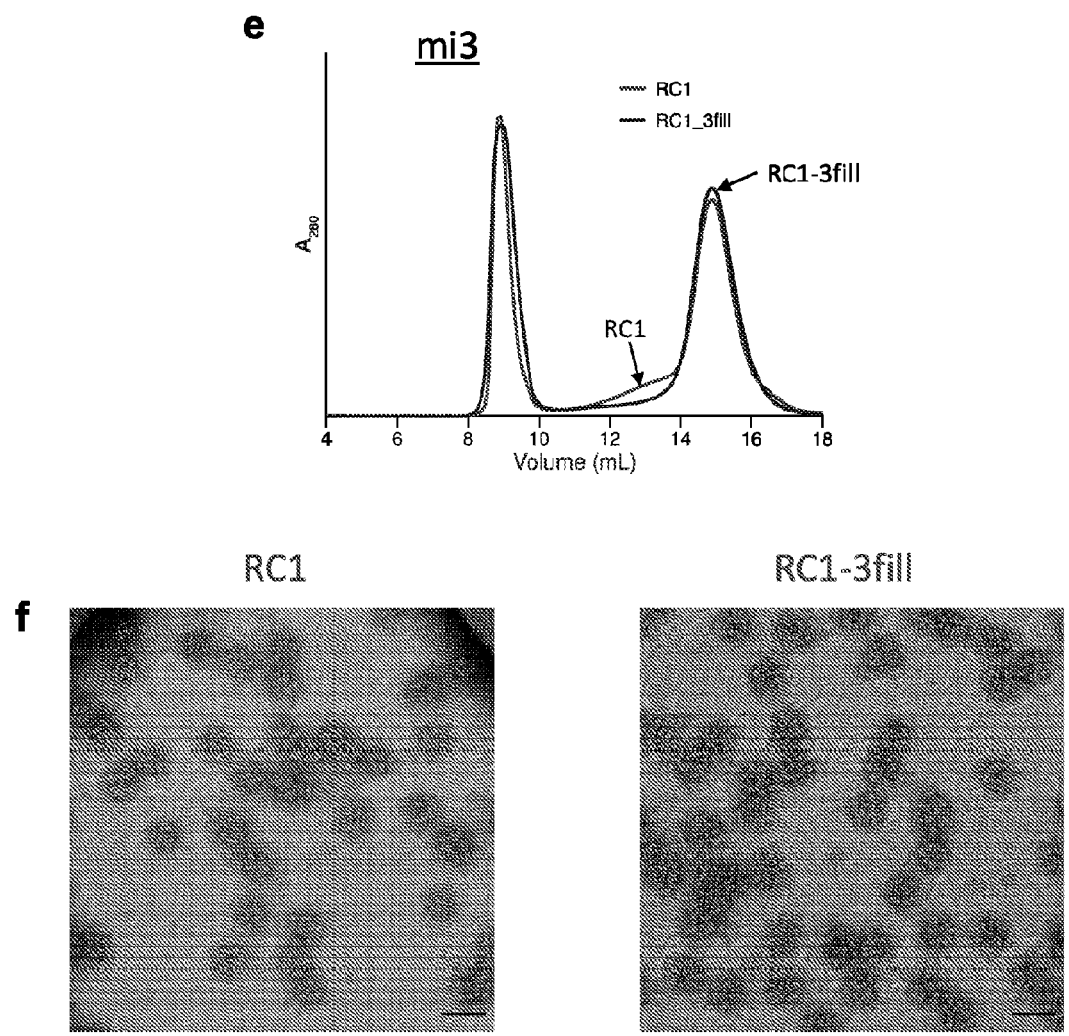

FIG. 13*c* shows representative SEC traces for the purification of the AP205-RC1-VLPs (dark gray) and AP205-RC1-3fill-VLPs (black). FIG. 13*d* shows electron micrographs of the AP205-RC1-VLPs (left) and AP205-RC1-3fill-VLPs (right), showing the AP205-RC1-3fill-VLPs look similar to AP205-RC1-VLPs and have a similar number of conjugated trimers per particle. The micrographs also show that the purification strategy was sufficient and no free trimer was present in either sample. Representative SEC traces for the purification of the mi3-RC1-NPs (dark gray) and mi3-RC1-3fill-NPs (black) (FIG. 13*e*) showing that RC1 and RC1-3fill can be conjugated to mi3 NPs. Electron micrographs of the mi3-RC1-NPs (left) and mi3-RC1-3fill-NPs (right) (FIG. 13*l*) show the mi3-RC1-3fill-NPs look similar to mi3-RC1-NPs and have a similar number of conjugated trimers per particle. The micrographs also show that the purification strategy was sufficient and no free trimer was present in either sample. SEC profiles for both the initial purification of the AP205-RC1-VLPs (FIG. 13*g*) and the mi3-RC1-NPs (FIG. 13*h*), and a reinjection of the sample at 28 days (AP205) and 11 days (mi3) show that the conjugated particles were stable over time and no unconjugated RC1 or degradation products were seen after storage for 28 or 11 days.

Serum from six WT mice immunized with either mi3-RC1-NPs (FIG. 13*i*) or mi3-RC1-3fill-NPs (FIG. 13*j*) was tested for binding to RC1 (black) and RC1 glycan KO (gray). Serum from all six mice immunized with either Mi3-RC1 or Mi3-RC1-3fill bound to RC1 in an ELISA and had reduced binding to RC1 glycan KO, suggesting a serum response specific to the V3/N332 glycan patch. Monoclonal antibodies 10-1074 and 3BNC117 were included as positive and negative controls. ELISA data are shown as area under the ELISA curve (AUC).

TABLE 3

Cryo-EM data collection and processing statistics.

| Env | RC1 | RC1 | RC1 | RC1 |
|---|---|---|---|---|
| Fabs | 10-1074; CD4bs | Ab275$_{MUR}$; 8ANC195 | Ab874$_{NHP}$; 8ANC195 | Ab897$_{NHP}$; 8ANC195 |
| Concentration (mg/mL) | 0.75 | 1.25 | 1.25 | 1.4 |
| Blot time (s) | 3.5 | 3.0 | 2.0 | 3.5 |
| Microscope | FEI Talos Arctica | FEI Talos Arctica | FEI Talos Arctica | FEI Talos Arctica |
| Voltage (kV) | 200 | 200 | 200 | 200 |
| Detector | Falcon 3EC | Falcon 3EC | Falcon 3EC | Falcon 3EC |
| Recording mode | counting | counting | counting | counting |
| Magnification | 73k | 73k | 73k | 73k |
| Pixel size (Å) | 1.436 | 1.436 | 1.436 | 1.436 |
| Dose rate (e-/px/s) | 0.73, 0.77 | 1.28 | 1.3 | 1.3 |
| frames per micrograph | 39 | 40 | 39 | 39 |
| Total dose (e-/Å$^2$) | 39.1 | 40 | 40 | 40 |
| Defocus range (μm) | 1-3.4 | 0.8-2.5 | 0.8-2.5 | 0.8-2.5 |
| number of micrographs | 684 | 328 | 465 | 510 |
| number of particles | 122,013 | 49,308 | 86,564 | 158,954 |
| symmetry | C3 | C3 | C3 | C3 |
| resolution (FSC 0.143) (Å) | 4.05 | 4.39 | 3.90 | 4.43 |
| B-factor (Å$^2$) | −281.9 | −252.4 | −230.0 | −322.1 |

TABLE 4

Sequences of Antibodies Generated from RC1- and RC1-4fill-immunized Mice.

| VH | DH | JH | CDRH3 | SEQ ID NO: | LENGTH (AA) | Nt mut. |
|---|---|---|---|---|---|---|
| Mouse 5 | | | | | | |
| IGHV1-84*01 | IGHD4-1*01 | IGHJ3*01 | ASGDELAWFAY | 22 | 11 | 5 |
| IGHV1-84*01 | IGHD4-1*01 | IGHJ3*01 | ASGDELAWFAY | 22 | 11 | 5 |
| IGHV1-84*01 | IGHD4-1*01 | IGHJ3*01 | ASGDELAWFAY | 22 | 11 | 4 |
| IGHV1-84*01 | IGHD4-1*01 | IGHJ3*01 | ASGDELAWFAY | 22 | 11 | 3 |
| IGHV1-84*01 | IGHD4-1*01 | IGHJ3*01 | ASGDELAWFAY | 22 | 11 | 6 |
| IGHV1-84*01 | IGHD4-1*01 | IGHJ3*01 | ASGDELAWFAY | 22 | 11 | 2 |
| IGHV1-84*01 | IGHD4-1*01 | IGHJ3*01 | ASGDELACFAY | 23 | 11 | 3 |
| IGHV1-84*01 | IGHD4-1*01 | IGHJ3*01 | ASGDELAWFAY | 22 | 11 | 6 |
| IGHV1-84*01 | | IGHJ3*01 | ASGDELAWFAY | 22 | 11 | 4 |
| IGHV1-84*01 | IGHD4-1*01 | IGHJ3*01 | ASGDELAWFAY | 22 | 11 | 2 |

TABLE 4-continued

Sequences of Antibodies Generated from RC1- and RC1-4fill-immunized Mice.

| VH | DH | JH | CDRH3 | SEQ ID NO: | LENGTH (AA) | Nt mut. |
|---|---|---|---|---|---|---|
| IGHV1-84*01 |  | IGHJ3*01 | ANGDALAWFAY | 24 | 11 | 5 |
| IGHV1-84*01 | IGHD4-1*01 | IGHJ3*01 | ASGDELAWFAY | 22 | 11 | 2 |
| IGHV1-84*01 | IGHD4-1*01 | IGHJ3*01 | ASGDELAWFAY | 22 | 11 | 5 |
| IGHV1-84*01 | IGHD4-1*01 | IGHJ3*01 | ASGDELAWFAY | 22 | 11 | 6 |
| IGHV1-84*01 | IGHD4-1*01 | IGHJ3*01 | ASGDELAWFAY | 22 | 11 | 5 |
| IGHV1-84*01 | IGHD4-1*01 | IGHJ3*01 | ASGDELAWFAY | 22 | 11 | 4 |
| IGHV1-84*01 | IGHD4-1*01 | IGHJ3*01 | ACGDELAWFAY | 25 | 11 | 3 |
| IGHV1-84*01 | IGHD4-1*01 | IGHJ3*01 | ASGDELAWFAY | 22 | 11 | 2 |
| IGHV1-84*01 | IGHD4-1*01 | IGHJ3*01 | AGGDELAWFAY | 26 | 11 | 7 |
| IGHV1-72*01 | IGHD2-4*01 | IGHJ3*01 | VRGEVYYDYDGFAY | 27 | 14 | 8 |
| IGHV1-72*01 | IGHD2-4*01 | IGHJ3*01 | ARGEVYYDYDGFAY | 28 | 14 | 1 |
| IGHV1-9*01 | IGHD2-4*01 | IGHJ1*03 | ARIRSDYDVGWWYFDV | 29 | 16 | 4 |
| IGHV1-9*01 | IGHD2-4*01 | IGHJ1*03 | ARIRSDYDVGWWYFDV | 29 | 16 | 4 |
| IGHV1-72*01 | IGHD1-1*01 | IGHJ2*01 | ARYYYGHYFDY | 30 | 11 | 5 |
| IGHV1-9*01 | IGHD2-14*01 | IGHJ2*01 | VRSGIYYFDY | 31 | 10 | 5 |
| IGHV1-72*01 | IGHD1-1*01 | IGHJ2*01 | ARYLLLRPFDY | 32 | 11 | 4 |
| IGHV1-22*01 | IGHD1-1*01 | IGHJ4*01 | ARAGTTGYVMDY | 33 | 12 | 3 |
| IGHV1-74*01 | IGHD6-1*01 | IGHJ4*01 | AIASYYYTLDY | 34 | 11 | 5 |
| IGHV1-19*01 | IGHD3-2*02 | IGHJ3*01 | ARRGAAQAPFAY | 35 | 12 | 3 |
| IGHV1-82*01 | IGHD4-1*01 | IGHJ3*01 | VRSELGPAFAY | 36 | 11 | 7 |
| IGHV1-22*01 | IGHD2-2*01 | IGHJ4*01 | ARRGYGYGAMDY | 37 | 12 | 1 |
| IGHV1-61*01 | IGHD2-5*01 | IGHJ3*01 | ARAYSNYVPWFAY | 38 | 13 | 0 |
| IGHV1-69*01 | IGHD2-10*02 | IGHJ2*01 | ARREYGFFDY | 39 | 10 | 6 |
| Mouse6 | | | | | | |
| IGHV5-6*01 | IGHD4-1*01 | IGHJ4*01 | ARHGRLTGTGAMDY | 40 | 14 | 3 |
| IGHV5-6*01 | IGHD4-1*01 | IGHJ4*01 | ARHGRLTGTGAMDY | 40 | 14 | 6 |
| IGHV5-6*01 | IGHD4-1*01 | IGHJ4*01 | ARHGRLTGTGAMDY | 40 | 14 | 0 |
| IGHV5-6*01 | IGHD4-1*01 | IGHJ4*01 | ARHGRLTGTGAMDY | 40 | 14 | 2 |
| IGHV5-6*01 | IGHD4-1*01 | IGHJ4*01 | ARHGRLTGTGAMDY | 40 | 14 | 2 |
| IGHV5-6*01 | IGHD3-3*01 | IGHJ4*01 | ARHGAGNALDY | 41 | 11 | 2 |
| IGHV5-6*01 |  | IGHJ4*01 | ARHGAGNAMDY | 42 | 11 | 3 |
| IGHV5-6*01 |  | IGHJ4*01 | ARHGAGNAMDY | 42 | 11 | 6 |
| IGHV5-6*01 |  | IGHJ4*01 | ARHGAGNAMDY | 42 | 11 | 2 |
| IGHV9-3*01 | IGHD2-1*01 | IGHJ2*01 | QVEVTMWTT | 43 | 9 | 0 |
| IGHV9-3*01 |  | IGHJ2*01 | ASGRNYVDY | 44 | 9 | 3 |
| IGHV9-3*01 |  | IGHJ2*01 | ASGPNYFDY | 45 | 9 | 3 |
| IGHV5-6*01 | IGHD1-1*01 | IGHJ4*01 | ARHGHYYGSSYGMDY | 46 | 15 | 2 |
| IGHV1-75*01 | IGHD1-1*02 | IGHJ1*01 | ARDDGGYWYFDV | 47 | 12 | 1 |

TABLE 4-continued

Sequences of Antibodies Generated from RC1- and RC1-4fill-immunized Mice.

| VH | DH | JH | CDRH3 | SEQ ID NO: | LENGTH (AA) | Nt mut. |
|---|---|---|---|---|---|---|
| IGHV2-9*01 | IGHD1-3*01 | IGHJ4*01 | ANIPKDRLCYGP | 48 | 12 | 2 |
| IGHV1-62-2*01 | IGHD2-3*01 | IGHJ3*01 | ARHEEDGYWFAY | 49 | 12 | 11 |

TABLE 5

Sequences of Antibodies Generated from RC1- and RC1-4fill-immunized Mice. LIGHT CHAINS

| MOUSE | VH | JH | CDRL3 | SEQ ID NO: | LENGTH (AA) | Nt mut. |
|---|---|---|---|---|---|---|
| 4 | IGKV14-111*01 | IGKJ2*01 | LQYDEFPYT | 50 | 9 | 2 |
| 4 | IGKV14-111*01 | IGKJ2*01 | LHYDDFPYT | 51 | 9 | 3 |
| 4 | IGKV14-111*01 | IGKJ2*01 | LHYDDFPYT | 51 | 9 | 4 |
| 4 | IGKV14-111*01 | IGKJ2*01 | LQYDEFPFT | 52 | 9 | 2 |
| 4 | IGKV14-111*01 | IGKJ2*01 | LQYDEFPYT | 50 | 9 | 10 |
| 4 | IGKV14-111*01 | IGKJ2*01 | LRYDDFPYT | 53 | 9 | 5 |
| 4 | IGKV14-111*01 | IGKJ2*01 | LQYDEFPYT | 50 | 9 | 5 |
| 4 | IGKV14-111*01 | IGKJ2*01 | LQYDEFPYT | 50 | 9 | 4 |
| 4 | IGKV14-111*01 | IGKJ2*01 | LQYDEFPYT | 50 | 9 | 3 |
| 4 | IGKV14-111*01 | IGKJ2*01 | LHYDDFPYT | 51 | 9 | 8 |
| 4 | IGKV14-111*01 | IGKJ2*01 | LQYDEFPYT | 50 | 9 | 0 |
| 4 | IGKV14-111*01 | IGKJ2*01 | LQYDEFPYT | 50 | 9 | 4 |
| 4 | IGKV14-111*01 | IGKJ2*01 | IQYDEFPYT | 54 | 9 | 4 |
| 4 | IGKV14-111*01 | IGKJ2*01 | LQYDEFPFT | 52 | 9 | 2 |
| 4 | IGKV14-111*01 | IGKJ2*01 | LHYDDFPYT | 51 | 9 | 5 |
| 4 | IGKV14-111*01 | IGKJ2*01 | LQYDEFPYT | 50 | 9 | 2 |
| 4 | IGKV14-111*01 | IGKJ2*01 | LQYDEFPYT | 50 | 9 | 6 |
| 4 | IGKV14-111*01 | IGKJ2*01 | LQYDEFPYT | 50 | 9 | 2 |
| 4 | IGKV14-111*01 | IGKJ2*01 | LHYDEFPYT | 55 | 9 | 2 |
| 4 | IGKV14-111*01 | IGKJ2*01 | LHYDDLPYT | 56 | 9 | 6 |
| 4 | IGKV14-111*01 | IGKJ2*01 | LQYDEFPFT | 52 | 9 | 1 |
| 4 | IGKV14-111*01 | IGKJ2*01 | LQYDEFPYT | 50 | 9 | 1 |
| 4 | IGKV14-111*01 | IGKJ2*01 | LHYDDLPYT | 56 | 9 | 5 |
| 4 | IGKV14-111*01 | IGKJ2*01 | LQYDEFPYT | 50 | 9 | 3 |
| 4 | IGKV14-111*01 | IGKJ2*01 | LQYDEFPYT | 50 | 9 | 4 |
| 4 | IGKV14-111*01 | IGKJ2*01 | LQYDEFPYT | 50 | 9 | 8 |
| 4 | IGKV14-111*01 | IGKJ2*01 | LQYDEFPYT | 50 | 9 | 5 |
| 4 | IGKV14-111*01 | IGKJ2*01 | LQYDEFPHT | 57 | 9 | 4 |
| 4 | IGKV14-111*01 | IGKJ2*01 | LQYDEFPYT | 50 | 9 | 6 |

TABLE 5-continued

Sequences of Antibodies Generated from RC1- and RC1-4fill-immunized Mice.
LIGHT CHAINS

| MOUSE | VH | JH | CDRL3 | SEQ ID NO: | LENGTH (AA) | Nt mut. |
|---|---|---|---|---|---|---|
| 4 | IGKV14-111*01 | IGKJ2*01 | LHYDDFPYT | 51 | 9 | 3 |
| 4 | IGKV14-111*01 | IGKJ2*01 | LQYDEFPYT | 50 | 9 | 0 |
| 4 | IGKV14-111*01 | IGKJ2*01 | LQYDESPYT | 58 | 9 | 9 |
| 4 | IGKV14-111*01 | IGKJ2*01 | LQYDEFPYT | 50 | 9 | 5 |
| 6 | IGKV14-111*01 | IGKJ2*01 | LQYDEFPYT | 50 | 9 | 3 |
| 6 | IGKV14-111*01 | IGKJ2*01 | LQYDEFPYT | 50 | 9 | 3 |
| 6 | IGKV14-111*01 | IGKJ2*01 | LQYDEFPCT | 59 | 9 | 1 |
| 1 | IGKV14-111*01 | IGKJ2*01 | LQYDEFPYT | 50 | 9 | 0 |
| 1 | IGKV14-111*01 | IGKJ2*01 | LQYDEFPYT | 50 | 9 | 5 |
| 1 | IGKV14-111*01 | IGKJ2*01 | LQYDEFPYT | 50 | 9 | 2 |
| 4 | IGKV14-111*01 | IGKJ2*01 | LQYDEFPYT | 50 | 9 | 3 |
| 4 | IGKV14-111*01 | IGKJ2*01 | LQYDEFPHT | 57 | 9 | 3 |
| 4 | IGKV14-111*01 | IGKJ2*01 | LQYDDFPHT | 60 | 9 | 5 |
| 4 | IGKV14-111*01 | IGKJ2*01 | LQYDEFPYT | 50 | 9 | 2 |
| 4 | IGKV14-111*01 | IGKJ2*01 | LQYDEFPYT | 50 | 9 | 3 |
| 4 | IGKV3-4*01 | IGKJ2*01 | QQSNEDPYT | 61 | 9 | 1 |
| 4 | IGKV3-4*01 | IGKJ2*01 | QQSNVDPYT | 62 | 9 | 2 |
| 4 | IGKV3-4*01 | IGKJ2*01 | QQSHEDPYT | 63 | 9 | 11 |
| 4 | IGKV3-4*01 | IGKJ2*01 | QQSNEDPYT | 61 | 9 | 8 |
| 4 | IGKV3-4*01 | IGKJ2*01 | QQSNEDPYT | 61 | 9 | 2 |
| 4 | IGKV3-4*01 | IGKJ2*01 | QQSNEDPYT | 61 | 9 | 1 |
| 4 | IGKV3-4*01 | IGKJ2*01 | QQSNEDPYT | 61 | 9 | 8 |
| 4 | IGKV3-4*01 | IGKJ2*01 | QQSNVDPYT | 62 | 9 | 27 |
| 4 | IGKV3-4*01 | IGKJ2*01 | QQSNEDPYT | 61 | 9 | 2 |
| 4 | IGKV3-4*01 | IGKJ2*01 | QQSNEDPYT | 61 | 9 | 7 |
| 4 | IGKV3-4*01 | IGKJ2*01 | QQSNEDPYT | 61 | 9 | 12 |
| 6 | IGKV3-4*01 | IGKJ2*01 | QHSNEDPYT | 64 | 9 | 2 |
| 6 | IGKV3-4*01 | IGKJ2*01 | QQSNEDPYT | 61 | 9 | 1 |
| 6 | IGKV3-4*01 | IGKJ2*01 | QQSNEDPYT | 61 | 9 | 1 |
| 6 | IGKV3-4*01 | IGKJ2*01 | QQSNEDPYT | 61 | 9 | 3 |
| 1 | IGKV3-4*01 | IGKJ2*01 | QQSNEDPYT | 61 | 9 | 0 |
| 1 | IGKV3-4*01 | IGKJ2*01 | QQSNEDPYT | 61 | 9 | 1 |
| 1 | IGKV3-4*01 | IGKJ2*01 | QQSNEDPYT | 61 | 9 | 2 |
| 1 | IGKV3-4*01 | IGKJ2*01 | QQSNEDPYT | 61 | 9 | 2 |
| 3 | IGKV3-4*01 | IGKJ2*01 | QQSNEDPYT | 61 | 9 | 0 |
| 4 | IGKV3-4*01 | IGKJ2*01 | QQSNEDPYT | 61 | 9 | 2 |
| 4 | IGKV3-4*01 | IGKJ2*01 | QQSNEDPYT | 61 | 9 | 0 |

TABLE 5-continued

Sequences of Antibodies Generated from RC1- and RC1-4fill-immunized Mice.
LIGHT CHAINS

| MOUSE | VH | JH | CDRL3 | SEQ ID NO: | LENGTH (AA) | Nt mut. |
|---|---|---|---|---|---|---|
| 6 | IGKV3-4*01 | IGKJ1*01 | QQSNEDPPWT | 65 | 10 | 1 |
| 6 | IGKV3-4*01 | IGKJ1*01 | QQSNEDPPWT | 65 | 10 | 2 |
| 6 | IGKV3-4*01 | IGKJ1*01 | QQGNEDPPWT | 66 | 10 | 1 |
| 6 | IGKV3-4*01 | IGKJ1*01 | QQSNEDPPWT | 65 | 10 | 2 |
| 6 | IGKV3-4*01 | IGKJ1*01 | QQSNEDPPWT | 65 | 10 | 2 |
| 6 | IGKV3-4*01 | IGKJ1*01 | HQSNEDPPWT | 67 | 10 | 2 |
| 6 | IGKV3-4*01 | IGKJ1*01 | QQINEDPPWT | 68 | 10 | 3 |
| 6 | IGKV3-4*01 | IGKJ1*01 | QQSNEDPPWT | 65 | 10 | 7 |
| 6 | IGKV3-4*01 | IGKJ1*01 | QQSNEDPPWT | 65 | 10 | 10 |
| 1 | IGKV3-4*01 | IGKJ1*01 | QQSNEDPPWT | 65 | 10 | 0 |
| 1 | IGKV3-4*01 | IGKJ1*01 | QQSNEDPPWT | 65 | 10 | 11 |
| 1 | IGKV3-4*01 | IGKJ1*01 | QQSYEDPPWT | 69 | 10 | 1 |
| 1 | IGKV3-4*01 | IGKJ1*01 | QQSNEDPPWT | 65 | 10 | 10 |
| 1 | IGKV3-4*01 | IGKJ1*01 | QQSYEDPPWT | 69 | 10 | 11 |
| 1 | IGKV3-4*01 | IGKJ1*01 | QQSNEDPPWT | 65 | 10 | 13 |
| 1 | IGKV3-4*01 | IGKJ1*01 | QQSNEDPPWT | 65 | 10 | 7 |
| 6 | IGKV3-4*01 | IGKJ1*01 | QQSNEDPWT | 70 | 9 | 1 |
| 6 | IGKV3-4*01 | IGKJ1*01 | QQSNEDPWT | 70 | 9 | 3 |
| 6 | IGKV3-4*01 | IGKJ1*01 | QQNNEDPWT | 71 | 9 | 3 |
| 6 | IGKV3-4*01 | IGKJ1*01 | QQSNEDPWT | 70 | 9 | 6 |
| 1 | IGKV3-4*01 | IGKJ1*01 | QQSNEDPWT | 70 | 9 | 3 |
| 1 | IGKV3-4*01 | IGKJ1*01 | QQSNEDPWT | 70 | 9 | 0 |
| 1 | IGKV3-4*01 | IGKJ1*01 | QQSNEDPWT | 70 | 9 | 8 |
| 1 | IGKV3-4*01 | IGKJ1*01 | QQSNEDPWT | 70 | 9 | 1 |
| 1 | IGKV3-4*01 | IGKJ1*01 | QQSNEDPWT | 70 | 9 | 15 |
| 1 | IGKV3-4*01 | IGKJ1*01 | QQSNEDPWT | 70 | 9 | 0 |
| 1 | IGKV3-4*01 | IGKJ1*01 | QQSNEDPWT | 70 | 9 | 4 |
| 1 | IGKV3-4*01 | IGKJ1*01 | QQSNEDPWT | 70 | 9 | 16 |
| 2 | IGKV3-4*01 | IGKJ1*01 | QQSNEDPWT | 70 | 9 | 1 |
| 2 | IGKV3-4*01 | IGKJ1*01 | QQSNEDPWT | 70 | 9 | 2 |
| 2 | IGKV3-4*01 | IGKJ1*01 | QQSNEDPWT | 70 | 9 | 5 |
| 6 | IGKV14-111*01 | IGKJ4*01 | LQYDEFPFT | 52 | 9 | 4 |
| 6 | IGKV14-111*01 | IGKJ4*01 | LQYDEFPFT | 52 | 9 | 2 |
| 6 | IGKV14-111*01 | IGKJ4*01 | LQYDEFTFT | 72 | 9 | 2 |
| 6 | IGKV14-111*01 | IGKJ4*01 | LQYDEFPFT | 52 | 9 | 8 |
| 1 | IGKV14-111*01 | IGKJ4*01 | LQYDEFPFT | 52 | 9 | 3 |
| 1 | IGKV14-111*01 | IGKJ4*01 | LQYDEFPFT | 52 | 9 | 0 |

TABLE 5-continued

Sequences of Antibodies Generated from RC1- and RC1-4fill-immunized Mice.
LIGHT CHAINS

| MOUSE | VH | JH | CDRL3 | SEQ ID NO: | LENGTH (AA) | Nt mut. |
|---|---|---|---|---|---|---|
| 1 | IGKV14-111*01 | IGKJ4*01 | LQYDEFPFT | 52 | 9 | 0 |
| 1 | IGKV14-111*01 | IGKJ4*01 | LQYDEFPFT | 52 | 9 | 0 |
| 1 | IGKV14-111*01 | IGKJ4*01 | LQYDEFPFT | 52 | 9 | 4 |
| 1 | IGKV14-111*01 | IGKJ4*01 | LQYDEFPFT | 52 | 9 | 3 |
| 6 | IGKV6-15*01 | IGKJ2*01 | QQYDSYPYT | 73 | 9 | 7 |
| 6 | IGKV6-15*01 | IGKJ2*01 | QQYNNYPYT | 74 | 9 | 2 |
| 6 | IGKV6-15*01 | IGKJ2*01 | QQYNSYPYT | 75 | 9 | 8 |
| 6 | IGKV6-15*01 | IGKJ2*01 | QQYNTYPYT | 76 | 9 | 10 |
| 6 | IGKV6-15*01 | IGKJ2*01 | QQYNSYPYT | 75 | 9 | 2 |
| 6 | IGKV6-15*01 | IGKJ2*01 | QQYNSYPYT | 75 | 9 | 8 |
| 6 | IGKV6-15*01 | IGKJ2*01 | QQYNIYPYT | 77 | 9 | 5 |
| 6 | IGKV6-15*01 | IGKJ2*01 | QQYNSYPYT | 75 | 9 | 6 |
| 6 | IGKV6-15*01 | IGKJ2*01 | QQYNSYPYT | 75 | 9 | 4 |
| 6 | IGKV6-15*01 | IGKJ2*01 | QQYNSYPYT | 75 | 9 | 2 |
| 1 | IGKV3-4*01 | IGKJ4*01 | QQSNEDPFT | 78 | 9 | 5 |
| 1 | IGKV3-4*01 | IGKJ4*01 | QQSNEDPFT | 78 | 9 | 2 |
| 1 | IGKV3-4*01 | IGKJ4*01 | QQSNEDPFT | 78 | 9 | 2 |
| 1 | IGKV3-4*01 | IGKJ4*01 | QQSNEDPFT | 78 | 9 | 5 |
| 2 | IGKV3-4*01 | IGKJ4*01 | QQSNEDPFT | 78 | 9 | 1 |
| 2 | IGKV3-4*01 | IGKJ4*01 | QQSNEDPFT | 78 | 9 | 1 |
| 2 | IGKV3-4*01 | IGKJ4*01 | QQSNEDPFT | 78 | 9 | 5 |
| 1 | IGKV14-111*01 | IGKJ2*01 | LQYDEYMYT | 79 | 9 | 2 |
| 1 | IGKV14-111*01 | IGKJ2*01 | LQYDEYMYT | 79 | 9 | 0 |
| 1 | IGKV14-111*01 | IGKJ2*01 | LQYDEYMYT | 79 | 9 | 0 |
| 1 | IGKV14-111*01 | IGKJ2*01 | LQYDEYMYT | 79 | 9 | 2 |
| 1 | IGKV10-96*01 | IGKJ1*01 | QQGNTLPWT | 80 | 9 | 1 |
| 1 | IGKV10-96*01 | IGKJ1*01 | QQGNTIPWT | 81 | 9 | 4 |
| 2 | IGKV10-96*01 | IGKJ1*01 | QQGNTLPRT | 82 | 9 | 1 |
| 2 | IGKV10-96*01 | IGKJ1*01 | QQGNTLPRT | 82 | 9 | 5 |
| 6 | IGKV1-110*01 | IGKJ1*01 | SQSTHVPT | 83 | 8 | 3 |
| 6 | IGKV1-110*01 | IGKJ1*01 | SQSTHVPT | 83 | 8 | 0 |
| 6 | IGKV1-110*01 | IGKJ1*01 | SQSTHVPT | 83 | 8 | 2 |
| 2 | IGKV14-100*01 | IGKJ5*01 | VQYVQFPLT | 84 | 9 | 2 |
| 2 | IGKV14-100*01 | IGKJ5*01 | VQYAQFPLT | 85 | 9 | 2 |
| 2 | IGKV14-100*01 | IGKJ5*01 | VQYAQFPLT | 85 | 9 | 1 |
| 3 | IGKV3-4*01 | IGKJ2*01 | QQSNEDPYT | 61 | 9 | 2 |
| 3 | IGKV3-4*01 | IGKJ2*01 | QQSNEDPYT | 61 | 9 | 1 |

TABLE 5-continued

Sequences of Antibodies Generated from RC1- and RC1-4fill-immunized Mice.
LIGHT CHAINS

| MOUSE | VH | JH | CDRL3 | SEQ ID NO: | LENGTH (AA) | Nt mut. |
|---|---|---|---|---|---|---|
| 1 | IGKV1-117*01 | IGKJ1*01 | FQGSHVPWT | 86 | 9 | 2 |
| 1 | IGKV1-117*01 | IGKJ1*01 | FQGSHVPWT | 86 | 9 | 1 |
| 3 | IGKV14-111*01 | IGKJ2*01 | LQYDEFPYT | 50 | 9 | 3 |
| 3 | IGKV14-111*01 | IGKJ2*01 | LQYDEFPYT | 50 | 9 | 2 |
| 1 | IGKV14-100*01 | IGKJ4*01 | VQYAQFPFT | 87 | 9 | 4 |
| 1 | IGKV14-126*01 | IGKJ2*01 | LQHGESPYT | 88 | 9 | 0 |
| 6 | IGKV4-50*01 | IGKJ2*01 | QQFTSSPYT | 89 | 9 | 2 |
| 2 | IGKV10-96*01 | IGKJ2*01 | QQGNTLPYT | 90 | 9 | 3 |
| 1 | IGKV14-111*01 | IGKJ2*01 | LQYDEFRTT | 91 | 9 | 5 |
| 4 | IGKV6-15*01 | IGKJ5*01 | QQYNSYPFT | 92 | 9 | 1 |
| 2 | IGKV4-62*01 | IGKJ5*01 | QQCSGYPLT | 93 | 9 | 3 |
| 6 | IGKV10-94*01 | IGKJ1*01 | QQYSKLPWT | 94 | 9 | 1 |
| 2 | IGKV14-111*01 | IGKJ2*01 | LQYDEFPYT | 50 | 9 | 4 |
| 2 | IGKV3-4*01 | IGKJ4*01 | QQSNEDPFT | 78 | 9 | 3 |
| 3 | IGKV3-4*01 | IGKJ2*01 | QQSNEDPYT | 61 | 9 | 3 |
| 2 | IGKV14-111*01 | IGKJ2*01 | LQYDEFPPFT | 95 | 10 | 2 |
| 2 | IGKV14-111*01 | IGKJ4*01 | LQYDEFPFT | 52 | 9 | 5 |

TABLE 6

Sequences of Antibodies Generated from RC1- and RC1-4fill-immunized Mice.

| ANTI-BODY | MOUSE | IMM. | VH | CDRH3 | SEQ ID NO: | LENGTH (AA). | VK | CDRL3 | SEQ ID NO: | LENGTH (AA). | RC1 BINDING |
|---|---|---|---|---|---|---|---|---|---|---|---|
| 271 | 1 | RC1 | IGHV5-6*01 | ARHSRTGTGAMDY | 96 | 13 | IGKV3-4*01 | QQSNEDPPWT | 65 | 10 | YES |
| 340 | 2 | RC1 | IGHV1- | ARPYYYGSSPYFDY | 97 | 14 | IGKV4-57*01 | QQRSSYPPT | 109 | 9 | NO |
| 341 | 2 | RC1 | IGHV5-17*01 | ARSIVPDY | 98 | 8 | IGKV14-100*01 | VQVQFPLT | 84 | 9 | YES* |
| 343 | 2 | RC1 | IGHV5-6*01 | ASLYGNAFDY | 99 | 10 | IGKV3-4*01 | QQSNEDPFT | 78 | 9 | YES |
| 344 | 2 | RC1 | IGHV9-3*01 | ASGGNYFDY | 100 | 9 | IGKV14-111*01 | LQYDEFPPFT | 95 | 10 | YES |
| 346 | 2 | RC1 | IGHV5-6*01 | ARHVGDHAMDY | 101 | 11 | IGKV3-4*01 | QQSNEDPFT | 78 | 9 | YES |
| 347 | 2 | RC1 | IGHV1-81*01 | ARPYYYGSSPNFDY | 102 | 14 | IGKV3-4*01 | QQSNEDPWT | 70 | 9 | NO |
| 351 | 3 | RC1 | IGHV9-3*01 | GTGKNYFDH | 103 | 9 | IGKV14-111*01 | LQYDEFPYT | 50 | 9 | YES |
| 352 | 3 | RC1 | IGHV5-6*01 | ATNYGAWFPY | 104 | 10 | IGKV3-4*01 | QQSNEDPYT | 61 | 9 | YES |
| 274 | 4 | RC1 | IGHV5-6*01 | ARHGITTVGVAMDY | 105 | 14 | IGKV3-4*01 | QQSNEDPWT | 70 | 9 | YES |
| 275 | 4 | RC1 | IGHV5-6*01 | ARHGITTVGVAMDY | 105 | 14 | IGKV3-4*01 | QQSNEDPYT | 61 | 9 | YES |
| 276 | 6 | RC1-4 | IGHV5-6*01 | ARHGRLTGTGAMD | 40 | 14 | IGKV3-4*01 | QQSNEDPPWT | 65 | 10 | YES |
| 278 | 6 | RC1-4 | IGHV5-6*01 | ARHGRLTGTGAMD | 40 | 14 | IGKV3-4*01 | HQSNEDPPWT | 67 | 10 | YES |
| 280 | 6 | RC1-4 | IGHV5-6*01 | ARHGHYYGSSYGM | 46 | 15 | IGKV3-4*01 | QQSNEDPPWT | 65 | 10 | YES |
| 294 | 6 | RC1-4 | IGHV2-9*01 | ANIPKDRLCYG | 106 | 11 | IGKV3-4*01 | QQSNEDPWT | 70 | 9 | YES |
| 348 | NS | RC1 | IGHV1-62- | ARHEGNYLYAMDY | 107 | 13 | IGKV4-62*01 | QQCSGYPLT | 93 | 9 | YES |
| 349 | NS | RC1 | IGHV1-7*01 | ARPPFITVVANYFDY | 108 | 15 | IGKV10-94*01 | QQYSKLPWT | 94 | 9 | YES |

TABLE 7

Sequences of Antibodies Generated from RC1-4fill VLPs-immunized macaques.
NHP 1

| VH | DH | JH | CDRH3 | SEQ ID NO: | LENGTH (AA) | Nt mut. |
|---|---|---|---|---|---|---|
| IGHV4_11*S4129 | IGHD4-1*01 | IGHJ4*01 | ARVVNYGPLDY | 110 | 11 | 3 |
| IGHV4_11*S4129 | IGHD3-2*01 | IGHJ4*01 | ARVVKNGPLDY | 111 | 11 | 6 |
| IGHV4_11*S4129 | IGHD3-1*01 | IGHJ4*01 | ARVVKYGPLDY | 112 | 11 | 3 |
| IGHV4_11*S4129 | IGHD3-1*01 | IGHJ4*01 | ARLVRYGPLDY | 113 | 11 | 7 |
| IGHV4_11*S4129 | IGHD3-1*01 | IGHJ4*01 | ARIVKYGPLDF | 114 | 11 | 6 |
| IGHV4_11*S4129 | IGHD3-1*010 | IGHJ4*01 | ARVVKYGPLDY | 112 | 11 | 4 |
| IGHV4_11*S4129 | IGHD3-1*01 | IGHJ4*01 | ARVVKYGPLDY | 112 | 11 | 2 |
| IGHV4_11*S0762 | IGHD1-2*01 | IGHJ4*01 | ARGSRIAPFDY | 115 | 11 | 7 |
| IGHV4_11*S0762 | IGHD1-2*01 | IGHJ4*01 | ARGSRIAPFDY | 115 | 11 | 5 |
| IGHV4_11*S0762 | IGHD1-2*01 | IGHJ4*01 | ARGSRIAPFDH | 116 | 11 | 7 |
| IGHV4_11*S0762 | IGHD1-2*01 | IGHJ4*01 | ARGSRIAPFDY | 115 | 11 | 9 |
| IGHV4_11*S4129 | IGHD3-3*01 | IGHJ4*01 | SRYQARGPIDS | 117 | 11 | 3 |
| IGHV4_11*S4129 | IGHD3-3*01 | IGHJ4*01 | ARDQARGPIDY | 118 | 11 | 4 |
| IGHV4_11*S4129 | IGHD3-3*01 | IGHJ4*01 | ARNQARGPIDY | 119 | 11 | 27 |
| IGHV4_11*S4129 | IGHD3-3*01 | IGHJ4*01 | ARDQARGPIDY | 118 | 11 | 9 |
| IGHV4_2C*F124 | IGHD1-3*01 | IGHJ4*01 | ARDNRIGPFDY | 120 | 11 | 6 |
| IGHV4_2C*F124 | IGHD1-3*01 | IGHJ4*01 | ARDNRIGPFDY | 120 | 11 | 6 |
| IGHV4_2C*F124 | IGHD1-3*01 | IGHJ4*01 | ARDNRIGPFDY | 120 | 11 | 4 |
| IGHV4_2C*F124 | IGHD2-1*01 | IGHJ4*01 | ARDKRIGPFDY | 121 | 11 | 6 |
| IGHV3_4I*F130 | IGHD6-3*01 | IGHJ4*01 | AKKRRQLENDY | 122 | 11 | 4 |
| IGHV3_4I*F130 | IGHD6-3*01 | IGHJ4*01 | VKKRRQLENDY | 123 | 11 | 4 |
| IGHV3_4I*F130 | IGHD6-3*01 | IGHJ4*01 | AKKRRQLENDY | 122 | 11 | 6 |
| IGHV3_4I*F130 | IGHD6-3*01 | IGHJ4*01 | VKKRRQLENDY | 123 | 11 | 4 |
| IGHV4_11*S4664 | IGHD6-2*01 | IGHJ4*01 | ASRIAGGPFDY | 124 | 11 | 4 |
| IGHV4_11*S4664 | IGHD6-2*01 | IGHJ4*01 | ASRIAGGPFDF | 125 | 11 | 8 |

TABLE 7-continued

Sequences of Antibodies Generated from RC1-4fill VLPs-immunized macaques.
NHP 1

| VH | DH | JH | CDRH3 | SEQ ID NO: | LENGTH (AA) | Nt mut. |
|---|---|---|---|---|---|---|
| IGHV4_11*S4664 | IGHD6-2*01 | IGHJ4*01 | ASLIAAGPFDY | 126 | 11 | 8 |
| IGHV4_11*S4664 | IGHD1-3*01 | IGHJ4*01 | ASRIRGGPFDY | 127 | 11 | 0 |
| IGHV4_3M*F133 | IGHD4-2*01 | IGHJ4*01 | ARDIVVGPIDY | 128 | 11 | 7 |
| IGHV4_3M*F133 | IGHD2-5*01 | IGHJ4*01 | ARDIVIGPIDY | 129 | 11 | 11 |
| IGHV4_3M*F133 | IGHD2-5*01 | IGHJ4*01 | ARDIVIGPIDY | 129 | 11 | 6 |
| IGHV4_11*S4129 | IGHD6-1*01 | IGHJ4*01 | ATVGRLAPFDY | 130 | 11 | 5 |
| IGHV4_11*S4129 | IGHD2-2*01 | IGHJ4*01 | ARVGRVVPFDY | 131 | 11 | 5 |
| IGHV4_11*S4129 | IGHD6-5*01 | IGHJ4*01 | ARVGRVAPFDY | 132 | 11 | 6 |
| IGHV3_2N*F134 | IGHD6-6*01 | IGHJ4*01 | AKSPWGQSSSFEYFEF | 133 | 16 | 4 |
| IGHV3_2N*F134 | IGHD6-6*01 | IGHJ4*01 | AKSPWGQSTSFEYFEF | 134 | 16 | 5 |
| IGHV3_2N*F134 | IGHD4-1*01 | IGHJ4*01 | AKSPWGQSSYFEYFEF | 135 | 16 | 3 |
| IGHV3_45*S5348 | IGHD1-8*01 | IGHJ5-2*02 | ASVLWGLPQDDNSLDV | 136 | 16 | 6 |
| IGHV3_45*S5348 | IGHD1-8*01 | IGHJ5-2*02 | ASVLWEVPQDDNSLDV | 137 | 16 | 3 |
| IGHV3_45*S5348 | IGHD1-8*01 | IGHJ5-2*02 | ANVLWGLPQDDNSLDV | 138 | 16 | 2 |
| IGHV4_2C*F124 | IGHD6-1*01 | IGHJ4*01 | ASLQRLGPIDY | 139 | 11 | 6 |
| IGHV4_2C*F124 | IGHD6-1*01 | IGHJ4*01 | ASLQRLGPIDY | 139 | 11 | 4 |
| IGHV4_2C*F124 | IGHD6-1*01 | IGHJ4*01 | ASLQRLGPIDY | 139 | 11 | 2 |
| IGHV4_11*S4129 | IGHD3-4*01 | IGHJ4*01 | ASLQYFGPFEF | 140 | 11 | 0 |
| IGHV4_11*S4129 | IGHD3-4*01 | IGHJ4*01 | ASLQYFGPFDF | 141 | 11 | 5 |
| IGHV4_11*S4129 | IGHD6-1*01 | IGHJ4*01 | ARAERAGPFDY | 142 | 11 | 10 |
| IGHV4_11*S4129 | IGHD6-1*01 | IGHJ4*01 | ARAERAGPFDY | 142 | 11 | 5 |
| IGHV3_45*S5348 | IGHD1-1*01 | IGHJ4*01 | ARHPHLESFDY | 143 | 11 | 4 |
| IGHV3_45*S5348 | IGHD1-1*01 | IGHJ4*01 | ARHPHLESFDY | 143 | 11 | 2 |
| IGHV4_11*S4129 | IGHD4-3*01 | IGHJ1*01 | ARNYGNYGYFEF | 144 | 12 | 5 |

TABLE 7-continued

Sequences of Antibodies Generated from RC1-4fill VLPs-immunized macaques.
NHP 1

| VH | DH | JH | CDRH3 | SEQ ID NO: | LENGTH (AA) | Nt mut. |
|---|---|---|---|---|---|---|
| IGHV4_11*S4129 | IGHD4-3*01 | IGHJ1*01 | ARNYGNYGYFEF | 144 | 12 | 2 |
| IGHV1_53*S2078 | IGHD3-3*01 | IGHJ1*01 | ATGPYWGDYYGRYFEL | 145 | 16 | 2 |
| IGHV1_53*S2078 | IGHD3-3*01 | IGHJ1*01 | ATGPYWGDYYGRYFEF | 146 | 16 | 2 |
| IGHV4_11*S4129 | IGHD6-3*01 | IGHJ4*01 | ATERRAGPVDY | 147 | 11 | 4 |
| IGHV4_11*S4129 | IGHD2-5*01 | IGHJ4*01 | ATDRRAGPLDY | 148 | 11 | 2 |
| IGHV3_1E*F130 | IGHD1-2*01 | IGHJ5-1*01 | AGTLAGTTSFDV | 149 | 12 | 11 |
| IGHV3_1E*F130 | IGHD1-7*01 | IGHJ5-1*01 | AGGLGRTTSFDV | 150 | 12 | 14 |
| IGHV4_11*S3777 | IGHD6-1*01 | IGHJ4*01 | ARVGSGWSTEGNFDY | 151 | 15 | 4 |
| IGHV4_11*S3777 | IGHD6-1*01 | IGHJ4*01 | ARVGSGWSTEGNFDY | 151 | 15 | 2 |
| IGHV3_2N*F134 | IGHD4-2*01 | IGHJ4*01 | AKDWIQWLHLGSYFDF | 152 | 16 | 6 |
| IGHV3_2N*F134 | IGHD4-2*01 | IGHJ4*01 | AKDWIQWVHLGSYFDY | 153 | 16 | 3 |
| IGHV4_11*S4664 | IGHD4-1*01 | IGHJ4*01 | ARHSSTYVAPVDY | 154 | 13 | 7 |
| IGHV4_2C*F124 | IGHD3-1*01 | IGHJ4*01 | ASAKGRLAPLDY | 155 | 12 | 8 |
| IGHV4_11*S5305 | IGHD3-3*01 | IGHJ4*01 | ANWADYFDY | 156 | 9 | 1 |
| IGHV4_2C*F124 | IGHD3-4*01 | IGHJ5-1*01 | ARDPVITITTRERFDV | 157 | 16 | 10 |
| IGHV4_11*S4129 | IGHD6-1*01 | IGHJ4*01 | ARDQRTGPFDY | 158 | 11 | 1 |
| IGHV4_11*S4129 | IGHD1-1*01 | IGHJ6*01 | ARQAFAGPTDS | 159 | 11 | 6 |
| IGHV4_11*S0762 | IGHD1-3*01 | IGHJ5-2*02 | ARRGPVNWNGSSLDV | 160 | 15 | 4 |
| IGHV3_1W*F134 | IGHD1-1*01 | IGHJ4*01 | TRDRADSWNFHDYFDY | 161 | 16 | 3 |
| IGHV4_11*S5305 | IGHD6-5*01 | IGHJ4*01 | AKIAVAGPVDY | 162 | 11 | 4 |
| IGHV4_2C*F124 | IGHD2-3*01 | IGHJ5-2*02 | ATTYSGSDYYRLDV | 163 | 14 | 6 |
| IGHV1_2B*F134 | IGHD3-3*01 | IGHJ4*01 | ARPDSLWGAAFDY | 164 | 13 | 4 |
| IGHV4_11*S4664 | IGHD6-2*01 | IGHJ4*01 | ARIGAAGPGDY | 165 | 11 | 11 |
| IGHV4_11*S9724 | IGHD3-3*01 | IGHJ5-2*02 | AKYWGDYYGYSSLDV | 166 | 15 | 6 |

TABLE 7-continued

Sequences of Antibodies Generated from RC1-4fill VLPs-immunized macaques.
NHP 1

| VH | DH | JH | CDRH3 | SEQ ID NO: | LENGTH (AA) | Nt mut. |
|---|---|---|---|---|---|---|
| IGHV4_11* S4664 | IGHD1-8*01 | IGHJ4*01 | ARVEVVGPTGY | 167 | 11 | 9 |
| IGHV4_3M* F133 | IGHD2-4*01 | IGHJ4*01 | ARRYSGSYSPFDC | 168 | 13 | 3 |
| IGHV4_11* S6427 | IGHD2-5*01 | IGHJ4*01 | AREGMGCTGSGCSISFDY | 169 | 18 | 0 |
| IGHV4_11* S9724 | IGHD5-3*01 | IGHJ4*01 | ARQGYSGYSLFDY | 170 | 13 | 7 |
| IGHV4_11* S4664 | IGHD6-2*01 | IGHJ4*01 | ASEIAGGPVDY | 171 | 11 | 3 |
| IGHV4_11* S5305 | IGHD6-1*01 | IGHJ5-1*01 | ARDSSGWPWDNRFDV | 172 | 15 | 4 |
| IGHV4_11* S4129 | IGHD2-3*01 | IGHJ4*01 | ARVTGRIAPFDY | 173 | 12 | 4 |
| IGHV5_1A* F124 | IGHD3-2*01 | IGHJ6*01 | ATNIWTGYSFYYGLDS | 174 | 16 | 18 |
| IGHV4_11* S4129 | IGHD3-1*01 | IGHJ6*01 | AREGRIHPLDS | 175 | 11 | 31 |
| IGHV3_4I* F130 | IGHD4-1*01 | IGHJ6*01 | AKDHDYGGGLDS | 176 | 12 | 3 |
| IGHV3_4I* F130 | IGHD6-3*01 | IGHJ4*01 | AKKSSGSWEVDY | 177 | 12 | 5 |
| IGHV4_11* S5891 | IGHD3-4*01 | IGHJ5-1*01 | ARHAYYNIWTGYSTNRFDV | 178 | 19 | 0 |
| IGHV5_1A* F124 | IGHD6-3*01 | IGHJ5-1*01 | AEGSGSWNGRFGV | 179 | 13 | 3 |
| IGHV1_53* S2078 | IGHD3-2*01 | IGHJ5-1*01 | ATGRYYGGSYYGDRFDV | 180 | 17 | 7 |
| IGHV3_4I* F130 | IGHD6-6*01 | IGHJ4*01 | AKCSSSSTGLDY | 181 | 12 | 3 |
| IGHV1_2B* F134 | IGHD1-7*01 | IGHJ4*01 | ARDRSVTPFSWVEYYFDY | 182 | 18 | 6 |
| IGHV4_5L* F134 | IGHD6-2*01 | IGHJ4*01 | VRVVKYGPLDY | 183 | 11 | 2 |
| IGHV4_11* S3915 | IGHD3-2*01 | IGHJ5-2*02 | ARNPPYYNLWTGYYTHSLDV | 184 | 20 | 2 |
| IGHV4_1F* F130 | IGHD3-1*01 | IGHJ4*01 | ARVVKYGPLDY | 112 | 11 | 1 |
| IGHV4_11* S3915 | IGHD2-3*01 | IGHJ4*01 | AREGYCSYTYCSNLFEF | 185 | 17 | 4 |
| IGHV4_2C* F124 | IGHD6-1*01 | IGHJ4*01 | ARARIAAPFDY | 186 | 11 | 6 |
| IGHV4_11* S4664 | IGHD1-8*01 | IGHJ4*01 | ARAGRMAATDY | 187 | 11 | 5 |
| IGHV4_11* S4129 | IGHD1-8*01 | IGHJ4*01 | VRDVTLGPIDN | 188 | 11 | 3 |
| IGHV4_11* S4129 | IGHD4-4*01 | IGHJ6*01 | AREGRIQPLDS | 189 | 11 | 4 |

TABLE 7-continued

Sequences of Antibodies Generated from RC1-4fill VLPs-immunized macaques.
NHP 1

| VH | DH | JH | CDRH3 | SEQ ID NO: | LENGTH (AA) | Nt mut. |
|---|---|---|---|---|---|---|
| IGHV3_4I*F130 | IGHD1-3*01 | IGHJ4*01 | AKCRNWNDFAY | 190 | 11 | 4 |
| IGHV4_2C*F124 | IGHD6-1*01 | IGHJ4*01 | ARVHRGGPFDY | 191 | 11 | 9 |
| IGHV4_11*S4129 | IGHD1-1*01 | IGHJ4*01 | ARGGRVHPMDY | 192 | 11 | 6 |
| IGHV4_11*S4129 | IGHD3-3*01 | IGHJ4*01 | ARGGPVSPFDY | 193 | 11 | 9 |
| IGHV4_11*S4664 | IGHD4-2*01 | IGHJ5-1*01 | ARGQRVAPFDV | 194 | 11 | 8 |
| IGHV5_1A*F124 | IGHD3-1*01 | IGHJ5-1*01 | AKETYEDDYGYYSLGYNRFDV | 195 | 21 | 2 |
| IGHV5_1F*F134 | IGHD1-7*01 | IGHJ4*01 | ASAWREHLPIDY | 196 | 12 | 7 |
| IGHV3_1Z*F134 | IGHD3-3*01 | IGHJ6*01 | ARDLYPGVINPSGLDS | 197 | 16 | 4 |

Table 7 (Continued)
Sequences of Antibodies Generated from RC1-4fill VLPs-immunized macaques.

| VH | DH | JH | CDRH3 | SEQ ID NO: | LENGTH (AA) | Nt mut. |
|---|---|---|---|---|---|---|
| NHP 5 | | | | | | |
| IGHV3_3F*F132 | IGHD3-2*01 | IGHJ1*01 | ARDKGSSYYQPEYFEF | 198 | 16 | 9 |
| IGHV3_3F*F132 | IGHD3-2*01 | IGHJ1*01 | ARDKGSSYYQPEYFEF | 198 | 16 | 10 |
| IGHV3_3F*F132 | IGHD3-2*01 | IGHJ1*01 | VRDKGSSYYQPEYFEF | 199 | 16 | 7 |
| IGHV4_1M*F130 | IGHD6-3*01 | IGHJ4*01 | ARTGKAAPVDY | 200 | 11 | 11 |
| IGHV4_1M*F130 | IGHD6-3*01 | IGHJ4*01 | ARTGKAAPVDY | 200 | 11 | 11 |
| IGHV4_1M*F130 | IGHD6-3*01 | IGHJ4*01 | ARTGKAAPVDC | 201 | 11 | 7 |
| IGHV5_1C*F130 | IGHD3-2*01 | IGHJ4*01 | AKGGDNYYDSGYYDDY | 202 | 16 | 0 |
| IGHV4_3N*F133 | IGHD3-3*01 | IGHJ4*01 | ARNRGWGDLVFDY | 203 | 13 | 3 |
| IGHV5_1H*F132 | IGHD6-1*01 | IGHJ4*01 | AKVLSGWFWDYFDY | 204 | 14 | 8 |
| IGHV4_11*S4664 | IGHD6-5*01 | IGHJ4*01 | ARLAVAGPVDY | 205 | 11 | 5 |
| IGHV3_3F*F132 | IGHD6-1*01 | IGHJ6*01 | ARGSSGWYGSGLDS | 206 | 14 | 7 |
| IGHV4_1U*F130 | IGHD1-1*01 | IGHJ5-1*01 | ARDHIESWNKVNWFDV | 207 | 16 | 7 |

Table 7 (Continued)
Sequences of Antibodies Generated from RC1-4fill VLPs-immunized macaques.

| VH | DH | JH | CDRH3 | SEQ ID NO: | LENGTH (AA) | Nt mut. |
|---|---|---|---|---|---|---|
| IGHV1_1G*F133 | IGHD6-3*01 | IGHJ1*01 | ATYSGSWYAEYFEF | 208 | 14 | 1 |
| IGHV5_1F*F134 | IGHD2-3*01 | IGHJ4*01 | AKQEDYNFWSSYFLPDY | 209 | 17 | 1 |
| IGHV1_1G*F133 | IGHD6-1*01 | IGHJ4*01 | ARDSSGWYEGFDY | 210 | 13 | 1 |
| IGHV1_53*S2078 | IGHD3-1*01 | IGHJ4*01 | ATGRYYGPSWAIFDY | 211 | 15 | 3 |
| IGHV4_11*S4290 | IGHD1-8*01 | IGHJ4*01 | ARDGNFGPIDY | 212 | 11 | 4 |
| IGHV7_1A*F124 | | IGHJ5-1*01 | ASGPNWFDV | 213 | 9 | 7 |
| IGHV5_1C*F130 | IGHD2-5*01 | IGHJ4*01 | AKSETDFWTSYYFNY | 214 | 15 | 8 |
| IGHV4_2M*F130 | IGHD2-5*01 | IGHJ5-1*01 | ARDICSGSGCYWYRDNWFDV | 215 | 20 | 1 |
| IGHV4_1T*F130 | IGHD2-1*01 | IGHJ4*01 | ASNRRIAPLDY | 216 | 11 | 6 |
| IGHV7_1A*F124 | IGHD3-1*01 | IGHJ4*01 | ASGRYYFDY | 217 | 9 | 5 |
| IGHV3_3F*F132 | IGHD4-3*01 | IGHJ1*01 | ARDRTVTPNRGYFEF | 218 | 15 | 8 |
| IGHV1_2B*F134 | IGHD6-5*01 | IGHJ6*01 | ARDGPYSGGWSELDS | 219 | 15 | 1 |
| IGHV4_5F*F132 | IGHD6-3*01 | IGHJ4*01 | ARWEYSGNWGLDY | 220 | 13 | 22 |
| IGHV4_11*S5305 | IGHD6-2*01 | IGHJ3*01 | ARSTSSWPRTSDAFDF | 221 | 16 | 1 |
| IGHV3_4I*F130 | IGHD6-2*01 | IGHJ4*01 | AKKRSSWSRIDY | 222 | 12 | 1 |
| IGHV3_3F*F132 | IGHD6-1*01 | IGHJ4*01 | ARDGSGWRRVTFDY | 223 | 14 | 10 |
| IGHV7_1A*F124 | IGHD6-1*01 | IGHJ4*01 | ATGRNYFDY | 224 | 9 | 4 |
| IGHV3_4I*F130 | IGHD4-4*01 | IGHJ4*01 | AKTGAVTTGFDY | 225 | 12 | 4 |
| IGHV4_11*S0762 | IGHD3-2*01 | IGHJ4*01 | ARLVGGSGYYYIGD | 226 | 14 | 0 |
| IGHV3_1B*F124 | IGHD6-2*01 | IGHJ4*01 | AKVPYSSWSHFDY | 227 | 13 | 6 |
| IGHV3_2M*F132 | IGHD6-1*01 | IGHJ4*01 | TSPRMRYSSGSFDY | 228 | 14 | 3 |
| IGHV1_2B*F134 | IGHD4-2*01 | IGHJ4*01 | ARVRGYSGYSFFDY | 229 | 14 | 0 |
| IGHV3_4S*F133 | IGHD6-2*01 | IGHJ5-1*01 | SRGSTWSGDWFDV | 230 | 13 | 7 |
| IGHV3_3O*F130 | IGHD4-4*01 | IGHJ5-1*01 | TKRLAYSNPYNRFDV | 231 | 15 | 2 |

Table 7 (Continued)
Sequences of Antibodies Generated from RC1-4fill VLPs-immunized macaques.

| VH | DH | JH | CDRH3 | SEQ ID NO: | LENGTH (AA) | Nt mut. |
|---|---|---|---|---|---|---|
| IGHV3_2W*F134 | IGHD3-2*01 | IGHJ4*01 | ARGGVGLDDVTYYYSGSYYYHRTSFDY | 232 | 27 | 1 |
| IGHV4_2M*F130 | IGHD5-2*01 | IGHJ5-1*01 | AGDRGGYNYGFTDNWFDV | 233 | 18 | 5 |
| IGHV3_2C*F133 | IGHD3-4*01 | IGHJ4*01 | TRGTAYYNFWSNSSPGYFDY | 234 | 20 | 3 |
| IGHV3_4V*F133 | IGHD3-2*01 | IGHJ1*01 | ARDKGSSYYQPESFEF | 235 | 16 | 8 |
| IGHV3_1N*F130 | IGHD3-1*01 | IGHJ4*01 | ARRYYEDDYGYYYPGPNIAGTTRGVEE | 236 | 27 | 6 |
| IGHV4_1I*F130 | IGHD6-2*01 | IGHJ3*01 | ARSTSSWPRTSDAFDF | 221 | 16 | 1 |
| | | | NHP 6 | | | |
| IGHV3_45*S5257 | IGHD3-1*01 | IGHJ5-1*01 | ARGITRMITVTKTNWFDV | 237 | 18 | 4 |
| IGHV3_45*S5257 | IGHD3-1*01 | IGHJ5-1*01 | ARGITRMITVTKTNWFDV | 237 | 18 | 1 |
| IGHV3_45*S5257 | IGHD3-1*01 | IGHJ5-1*01 | ARGITRMITVTKTNWFDV | 237 | 18 | 1 |
| IGHV3_45*S5257 | IGHD3-1*01 | IGHJ5-1*01 | ARGITRMITVTKTNWFDV | 237 | 18 | 6 |
| IGHV4_11*S5305 | IGHD6-5*01 | IGHJ4*01 | ARLAVAGPFDY | 238 | 11 | 5 |
| IGHV4_11*S5305 | IGHD6-5*01 | IGHJ4*01 | ARLGVAGPLDY | 239 | 11 | 2 |
| IGHV1_2B*F134 | IGHD1-8*01 | IGHJ4*01 | ATYKTIDY | 240 | 8 | 3 |
| IGHV1_2B*F134 | IGHD2-3*01 | IGHJ4*01 | ASYKNIDY | 241 | 8 | 1 |
| IGHV4_11*S9280 | IGHD4-1*01 | IGHJ4*01 | ARDRHGIPFDY | 242 | 11 | 2 |
| IGHV1_2B*F134 | IGHD3-3*01 | IGHJ4*01 | ARSRGYWGDLFDF | 243 | 13 | 0 |
| IGHV3_45*S5348 | IGHD3-3*01 | IGHJ4*01 | ARLSGWGDFRIDY | 244 | 13 | 2 |
| IGHV1_53*S2078 | IGHD2-1*01 | IGHJ5-1*01 | ATGIWFDV | 245 | 8 | 4 |
| IGHV3_45*S5257 | IGHD2-3*01 | IGHJ4*01 | ARANNGGYFDY | 246 | 11 | 6 |
| IGHV1_2B*F134 | IGHD4-1*01 | IGHJ2*01 | ARMTTVAAFGGYFDL | 247 | 15 | 5 |
| IGHV7_1A*F124 | IGHD1-8*01 | IGHJ4*01 | ASGGNYADY | 248 | 9 | 1 |
| IGHV4_11*S4664 | IGHD6-3*01 | IGHJ4*01 | ARRLSRRYFDY | 249 | 11 | 0 |
| IGHV3_2L*F132 | IGHD2-4*01 | IGHJ4*01 | TREFCSGIYCYAPFDY | 250 | 16 | 0 |
| IGHV1_2B*F134 | IGHD3-4*01 | IGHJ5-2*02 | ASFKTLDV | 251 | 8 | 3 |

Table 7 (Continued)
Sequences of Antibodies Generated from RC1-4fill VLPs-immunized macaques.

| VH | DH | JH | CDRH3 | SEQ ID NO: | LENGTH (AA) | Nt mut. |
|---|---|---|---|---|---|---|
| IGHV5_1F*F134 | IGHD5-1*01 | IGHJ4*01 | AKGVGGFSYSYPHY | 252 | 14 | 8 |
| IGHV3_45*S5257 | IGHD3-4*01 | IGHJ4*01 | ARDGHYNFWSPPGY | 253 | 14 | 5 |
| IGHV4_11*S9724 | IGHD3-1*01 | IGHJ5-1*01 | ARAEDEDDYGSFDV | 254 | 14 | 6 |
| IGHV4_11*S5305 | IGHD6-1*01 | IGHJ3*01 | ARLGSSGWYRDDAFDF | 255 | 16 | 3 |
| IGHV3_1C*F124 | IGHD6-5*01 | IGHJ4*01 | AKPRGRWLEDY | 256 | 11 | 7 |
| IGHV3_1V*F124 | IGHD4-4*01 | IGHJ4*01 | TRPRQYSTGDY | 257 | 11 | 0 |
| IGHV3_1C*F124 | IGHD4-4*01 | IGHJ4*01 | AKMGGRGYSSYGPVFDY | 258 | 17 | 2 |
| IGHV4_11*S4129 | IGHD1-8*01 | IGHJ4*01 | ARIVTRGPFDY | 259 | 11 | 3 |
| IGHV3_45*S5257 | IGHD3-3*01 | IGHJ5-1*01 | ARDVTTRVVIIDHRFDV | 260 | 17 | 1 |
| IGHV7_1A*F124 | IGHD6-1*01 | IGHJ5-1*01 | ARQLGGGQTDRFDV | 261 | 14 | 3 |
| IGHV7_1A*F124 | IGHD4-4*01 | IGHJ4*01 | ARQAYSNYPDY | 262 | 11 | 3 |
| IGHV3_4I*F130 | IGHD1-8*01 | IGHJ4*01 | VKLREKWETRGD | 263 | 12 | 4 |
| IGHV5_1F*F134 | IGHD4-1*01 | IGHJ5-1*01 | AKSYGSMSNRFDV | 264 | 13 | 3 |
| IGHV4_11*S4664 | IGHD3-2*01 | IGHJ4*01 | ARVIRLGPFDY | 265 | 11 | 2 |
| IGHV4_11*S4129 | IGHD3-1*01 | IGHJ5-1*01 | ARETFEGDDYGYYYTPDNWFDV | 266 | 22 | 3 |
| IGHV3_2P*F133 | IGHD6-3*01 | IGHJ4*01 | AKSGNSGSWNYFDY | 267 | 14 | 9 |
| IGHV3_45*S5348 | IGHD3-3*01 | IGHJ4*01 | ARRGWGDPYFDY | 268 | 13 | 1 |
| IGHV1_53*S2078 | IGHD3-1*01 | IGHJ1*01 | ATGFSMITVALFDF | 269 | 14 | 1 |
| IGHV4_11*S4359 | IGHD3-1*01 | IGHJ4*01 | ASQGYEDDYAYWAFKFDY | 270 | 18 | 1 |
| IGHV4_11*S4664 | IGHD6-1*01 | IGHJ4*01 | ARSPGIVAPFDY | 271 | 12 | 10 |
| IGHV7_A*F132 | IGHD4-1*01 | IGHJ5-1*01 | ARSRSGSNSESRFDV | 272 | 15 | 5 |
| IGHV7_1A*F124 | IGHD6-3*01 | IGHJ2*01 | ARPLYSGNWNVYWYFDL | 273 | 17 | 4 |
| IGHV4_11*S4290 | IGHD6-1*01 | IGHJ4*01 | ARDGWGGWTIDY | 274 | 12 | 3 |
| IGHV4_11*S9724 | IGHD4-1*01 | IGHJ4*01 | ARSGYGSGGTFDY | 275 | 13 | 4 |

Table 7 (Continued)
Sequences of Antibodies Generated from RC1-4fill VLPs-immunized macaques.

| VH | DH | JH | CDRH3 | SEQ ID NO: | LENGTH (AA) | Nt mut. |
|---|---|---|---|---|---|---|
| IGHV1_53* S2078 | IGHD2-3*01 | IGHJ4*01 | ATTPGYCSSTYCRFDY | 276 | 16 | 0 |
| IGHV1_53* S2078 | IGHD3-2*01 | IGHJ1*01 | ATKNYYDSGYHLSGEYFEF | 277 | 19 | 4 |
| IGHV3_4I* F130 | IGHD1-2*01 | IGHJ5-1*01 | AQCPEYSWNMGWFDV | 278 | 15 | 2 |
| IGHV4_11* S3915 | IGHD3-2*01 | IGHJ5-1*01 | ASPFYGSGYYTRRFDV | 279 | 16 | 9 |
| IGHV4_5B* F133 | IGHD3-3*01 | IGHJ5-1*01 | ARDGYYSGDYYRHNWFAV | 280 | 18 | 5 |
| IGHV4_11* S4290 | IGHD2-1*01 | IGHJ4*01 | ARDCVDAFDY | 281 | 10 | 0 |
| IGHV1_53* S2078 | IGHD1-3*01 | IGHJ4*01 | ATGYNWNDPFDY | 282 | 12 | 2 |
| IGHV5_1E* F133 | IGHD3-3*01 | IGHJ5-1*01 | TKVEGGYWGDYHRFDV | 283 | 16 | 5 |

TABLE 8

Usage of Lambda Gene.

| | IGLV124*4 | IGLV3-21*01|Homo |
|---|---|---|
| IGLV124*4 | | 93.8 |
| IGLV3-21*01|Homo | 93.8 | |

| | IGLV132*15 | IGLV2-8*01|Homo |
|---|---|---|
| IGLV132*15 | | 90.6 |
| IGLV2-8*01|Homo | 90.6 | |

TABLE 9

DSS-motif-containing Sequences of Antibodies Generated from RC1-4fill VLPs-immunized macaques.

NHP 1

| VH | JH | CDRL3 | SEQ ID NO: | LENGTH (AA) | Nt mut. |
|---|---|---|---|---|---|
| IGLV132*12 | IGLJ2*01 | QSYDSSLSGHL | 284 | 11 | 1 |
| IGLV132*12 | IGLJ2*01 | QSYDSSLSAGL | 285 | 11 | 1 |
| IGLV132*12 | IGLJ2*01 | QSYDSSLSAHV | 286 | 11 | 1 |
| IGLV132*12 | IGLJ2*01 | QSYDNSLSAWV | 287 | 11 | 2 |
| IGLV132*12 | IGLJ2*01 | QSYDSSLSVRV | 288 | 11 | 1 |
| IGLV132*12 | IGLJ2*01 | QSYDNSLSARV | 289 | 11 | 4 |
| IGLV132*12 | IGLJ2*01 | QSYDNSLSXQV | 290 | 11 | 6 |
| IGLV132*12 | IGLJ2*01 | QSYDSSLSAGL | 285 | 11 | 5 |
| IGLV132*12 | IGLJ2*01 | QSYDSSLSAGL | 285 | 11 | 7 |
| IGLV132*12 | IGLJ6*01 | QSYDSSLSAHV | 286 | 11 | 1 |
| IGLV132*12 | IGLJ6*01 | QSYDNSLSAHV | 291 | 11 | 3 |

TABLE 9-continued

DSS-motif-containing Sequences of Antibodies Generated from RC1-4fill VLPs-immunized macaques.

| | | | | | |
|---|---|---|---|---|---|
| IGLV132*12 | IGLJ6*01 | QSYDSSLSADV | 292 | 11 | 1 |
| IGLV124*30 | IGLJ1*01 | LSYDSSLSAHI | 293 | 11 | 10 |
| IGLV124*30 | IGLJ1*01 | LSYDSSLSAHI | 293 | 11 | 12 |
| IGLV124*43 | IGLJ3*01 | QVWDSSSDHPL | 294 | 11 | 2 |
| IGLV124*43 | IGLJ3*01 | QVWDSSSDHPL | 294 | 11 | 1 |
| IGLV124*30 | IGLJ2*01 | GAWDSSLSAGL | 295 | 11 | 27 |
| IGLV124*41 | IGLJ3*01 | SAWDSSLSDVL | 296 | 11 | 2 |
| IGLV132*20 | IGLJ3*01 | AAWDDSLSGVL | 297 | 11 | 4 |
| IGLV124*30 | IGLJ2*01 | ETWDYSLNGPL | 298 | 11 | 21 |
| IGLV124*24 | IGLJ6*01 | YSGDDNNDV | 299 | 9 | 2 |
| IGLV132*12 | IGLJ1*01 | QSYDSSLSGHI | 300 | 11 | 2 |
| IGLV130*2 | IGLJ6*01 | QTWTTDV | 301 | 7 | 82 |
| IGLV130*2 | IGLJ3*01 | CSYTTSNTLL | 302 | 10 | 2 |
| IGLV124*30 | IGLJ3*01 | ETWDYSLNGPL | 298 | 11 | 22 |
| IGLV132*12 | IGLJ1*01 | QSYDSSLSVHYI | 303 | 12 | 2 |
| IGLV130*31 | IGLJ2*01 | SSYASSSTWV | 304 | 10 | 1 |

NHP 5

| VH | JH | CDRL3 | SEQ ID NO: | LENGTH (AA) | Nt mut. |
|---|---|---|---|---|---|
| IGLV132*12 | IGLJ3*01 | QSYDSSLSAVL | 305 | 11 | 3 |
| IGLV132*12 | IGLJ3*01 | QSYDSSLSAVL | 305 | 11 | 3 |
| IGLV132*12 | IGLJ3*01 | QSYDSSLSALL | 306 | 11 | 3 |
| IGLV132*12 | IGLJ3*01 | QSYDSSLSAVF | 307 | 11 | 3 |
| IGLV132*12 | IGLJ3*01 | QSYDSSLSAVL | 305 | 11 | 4 |
| IGLV132*12 | IGLJ3*01 | QSYDSSLSARL | 308 | 11 | 5 |
| IGLV132*12 | IGLJ3*01 | QSYDSSLSNVL | 309 | 11 | 1 |
| IGLV132*12 | IGLJ3*01 | QSYDSSLSGVL | 310 | 11 | 4 |
| IGLV132*12 | IGLJ3*01 | QSYDNSLSAVL | 311 | 11 | 3 |
| IGLV132*12 | IGLJ3*01 | QSYDNNLSAVL | 312 | 11 | 7 |
| IGLV132*12 | IGLJ2*01 | QSYDSSLSAQV | 313 | 11 | 2 |
| IGLV132*12 | IGLJ2*01 | QSYDSSLSAHL | 314 | 11 | 3 |
| IGLV132*12 | IGLJ2*01 | QSYDSSLSAHL | 314 | 11 | 3 |
| IGLV132*12 | IGLJ2*01 | QSYDSSLSAHL | 314 | 11 | 6 |
| IGLV132*12 | IGLJ2*01 | QSYDSSLSAWV | 315 | 11 | 2 |
| IGLV132*12 | IGLJ2*01 | QSYDSSLSAGL | 285 | 11 | 1 |
| IGLV132*12 | IGLJ2*01 | QSYDSSLSGHL | 284 | 11 | 1 |
| IGLV132*12 | IGLJ2*01 | QSYDSYLSAGL | 316 | 11 | 9 |
| IGLV132*12 | IGLJ2*01 | QSYDSSLSAWV | 315 | 11 | 3 |
| IGLV132*9 | IGLJ6*01 | QSYDSSLSADV | 292 | 11 | 13 |

TABLE 9-continued

DSS-motif-containing Sequences of Antibodies Generated from RC1-4fill VLPs-immunized macaques.

| VH | JH | CDRL3 | SEQ ID NO: | LENGTH (AA) | Nt mut. |
|---|---|---|---|---|---|
| IGLV132*12 | IGLJ6*01 | QSYDSSLSAHV | 286 | 11 | 2 |
| IGLV132*12 | IGLJ6*01 | QSYDNSLSDDV | 317 | 11 | 3 |
| IGLV132*12 | IGLJ6*01 | QSYDSSLSAHV | 286 | 11 | 5 |
| IGLV132*12 | IGLJ6*01 | QSYDSSLSALV | 318 | 11 | 1 |
| IGLV132*12 | IGLJ3*01 | QSYDSNLSAHVL | 319 | 12 | 3 |
| IGLV132*12 | IGLJ3*01 | QSFDSNLSIHLL | 320 | 12 | 4 |
| IGLV132*12 | IGLJ3*01 | QSYDSSLSAHVL | 321 | 12 | 1 |
| IGLV132*12 | IGLJ3*01 | QSYDSSLSAHVL | 321 | 12 | 3 |
| IGLV132*12 | IGLJ1*01 | QSYDSSLSAYI | 322 | 11 | 1 |
| IGLV132*12 | IGLJ1*01 | QSYDSSLSAYI | 322 | 11 | 7 |
| IGLV132*39 | IGLJ3*01 | DSWDSGGTHVL | 323 | 11 | 29 |
| IGLV132*20 | IGLJ2*01 | AAWDDSLSGPV | 324 | 11 | 1 |
| IGLV132*11 | IGLJ3*01 | QVWDSRSDHPL | 325 | 11 | 8 |
| IGLV124*38 | IGLJ1*01 | MIWHNNASI | 326 | 9 | 4 |
| IGLV132*43 | IGLJ2*01 | WLYYSGGHGL | 327 | 10 | 4 |
| IGLV130*33 | IGLJ1*01 | QSYDSSLSAYI | 322 | 11 | 8 |
| IGLV130*21 | IGLJ6*01 | QVWDSSSDHHDV | 328 | 12 | 4 |

NHP 6

| VH | JH | CDRL3 | SEQ ID NO: | LENGTH (AA) | Nt mut. |
|---|---|---|---|---|---|
| IGLV132*12 | IGLJ2*01 | QSYDNSLSAWV | 287 | 11 | 4 |
| IGLV132*12 | IGLJ2*01 | QSYDSSLSAGL | 285 | 11 | 1 |
| IGLV132*12 | IGLJ2*01 | QSYDSSLSAWV | 315 | 11 | 4 |
| IGLV132*12 | IGLJ2*01 | QSYDSSLRAQV | 329 | 11 | 7 |
| IGLV132*12 | IGLJ2*01 | QSYDSSLSAWV | 315 | 11 | 10 |
| IGLV132*12 | IGLJ2*01 | QSYDSSLSAQV | 313 | 11 | 0 |
| IGLV132*12 | IGLJ2*01 | QSHDSSLTAGL | 330 | 11 | 3 |
| IGLV132*12 | IGLJ2*01 | QSYDSSLSAGL | 285 | 11 | 5 |
| IGLV132*12 | IGLJ2*01 | QSHDSSLSAGL | 331 | 11 | 2 |
| IGLV132*20 | IGLJ2*01 | AAWDDSLKGWV | 332 | 11 | 10 |
| IGLV132*20 | IGLJ2*01 | AAWDDSLSGWV | 333 | 11 | 3 |
| IGLV132*20 | IGLJ2*01 | AAWDDSLNGWV | 334 | 11 | 4 |
| IGLV132*20 | IGLJ2*01 | AAWDDSLSGPL | 335 | 11 | 3 |
| IGLV132*21 | IGLJ2*01 | MIVVHNNVWA | 336 | 9 | 5 |
| IGLV132*21 | IGLJ2*01 | VIVVHNNVWA | 337 | 9 | 6 |
| IGLV132*21 | IGLJ2*01 | MIVVHNNAWI | 338 | 9 | 3 |
| IGLV132*21 | IGLJ2*01 | MIVVHNNAWV | 339 | 9 | 5 |
| IGLV132*20 | IGLJ1*01 | AAWDDSLSGYI | 340 | 11 | 4 |
| IGLV132*20 | IGLJ1*01 | AAWDDSLSGYI | 340 | 11 | 2 |

TABLE 9-continued

DSS-motif-containing Sequences of Antibodies Generated from RC1-4fill VLPs-immunized macaques.

| VH | JH | CDRL3 | SEQ ID NO: | LENGTH (AA) | Nt mut. |
|---|---|---|---|---|---|
| IGLV132*20 | IGLJ1*01 | AAWDDSLSGYI | 340 | 11 | 3 |
| IGLV132*12 | IGLJ1*01 | QSYDNSLSAYI | 341 | 11 | 6 |
| IGLV132*12 | IGLJ1*01 | QSYDSILSSYI | 342 | 11 | 7 |
| IGLV132*12 | IGLJ1*01 | QSYDSSLSAYI | 322 | 11 | 4 |
| IGLV132*12 | IGLJ6*01 | QSYDSRLSADV | 343 | 11 | 13 |
| IGLV132*12 | IGLJ6*01 | QSYDSSLSAHV | 286 | 11 | 3 |
| IGLV132*33 | IGLJ2*01 | QVWDGSTKYAGL | 344 | 12 | 13 |
| IGLV132*33 | IGLJ2*01 | QVWDDSTNYAGL | 345 | 12 | 16 |
| IGLV124*30 | IGLJ3*01 | GAWDSSLSALL | 346 | 11 | 20 |
| IGLV124*30 | IGLJ3*01 | GAWDSSLSALL | 346 | 11 | 20 |
| IGLV132*12 | IGLJ3*01 | QSYDSSLSDVL | 347 | 11 | 4 |
| IGLV132*12 | IGLJ3*01 | QSYDSSLSAQL | 348 | 11 | 1 |
| IGLV132*21 | IGLJ3*01 | MIWHEDDFVL | 349 | 10 | 24 |
| IGLV130*33 | IGLJ2*01 | GAWDSSLSAHWV | 350 | 12 | 28 |
| IGLV132*39 | IGLJ3*01 | DSWDSSGTHVL | 351 | 11 | 24 |
| IGLV132*15 | IGLJ1*01 | SSYVGSGTYI | 352 | 10 | 6 |
| IGLV132*15 | IGLJ2*01 | SSYAGSGTGL | 353 | 10 | 2 |
| IGLV130*2 | IGLJ2*01 | CSYTTSNTLI | 354 | 10 | 4 |
| IGLV124*17 | IGLJ2*01 | QVWDISSDHPV | 355 | 11 | 2 |
| IGLV130*21 | IGLJ2*01 | QVWDSSSAHPV | 356 | 11 | 1 |
| IGLV124*17 | IGLJ3*01 | QVWDSSSDHPL | 294 | 11 | 6 |
| IGLV130*33 | IGLJ1*01 | QSYDSSLSAHYI | 357 | 12 | 9 |
| IGLV132*29 | IGLJ2*01 | QSADSSGNHWV | 358 | 11 | 23 |
| IGLV132*27 | IGLJ6*01 | QTWTTGIHV | 359 | 9 | 75 |
| IGLV124*3 | IGLJ2*01 | GSYRTGATFL | 360 | 10 | 17 |
| IGLV124*6 | IGLJ1*01 | SSYAGSNTFI | 361 | 10 | 2 |
| IGLV132*11 | IGLJ2*01 | QVWDSSSDHWV | 362 | 11 | 7 |
| IGLV130*33 | IGLJ3*01 | QSYDGSLSAQL | 363 | 11 | 11 |
| IGLV130*21 | IGLJ2*01 | QVWDSDHPL | 364 | 9 | 3 |

NHP 8

| VH | JH | CDRL3 | SEQ ID NO: | LENGTH (AA) | Nt mut. |
|---|---|---|---|---|---|
| IGLV132*12 | IGLJ2*01 | QSYDSTLSGGL | 365 | 11 | 2 |
| IGLV132*12 | IGLJ2*01 | QSYDSSLSAQV | 313 | 11 | 3 |
| IGLV132*12 | IGLJ2*01 | QSYDSSLSGGL | 366 | 11 | 1 |
| IGLV132*12 | IGLJ2*01 | QSYDNTLSAGL | 367 | 11 | 3 |
| IGLV132*12 | IGLJ2*01 | QSYDSSLSGHL | 284 | 11 | 1 |
| IGLV132*12 | IGLJ2*01 | QSYDSSLSVGL | 368 | 11 | 2 |
| IGLV132*12 | IGLJ2*01 | QSYDSSLSAGL | 285 | 11 | 1 |

TABLE 9-continued

DSS-motif-containing Sequences of Antibodies Generated from RC1-4fill VLPs-immunized macaques.

| | | | | | |
|---|---|---|---|---|---|
| IGLV132*12 | IGLJ2*01 | QSYDSSLSAWV | 315 | 11 | 3 |
| IGLV132*12 | IGLJ2*01 | QSYDSSLSAGL | 285 | 11 | 2 |
| IGLV132*12 | IGLJ2*01 | QSYDSSLTAGL | 369 | 11 | 2 |
| IGLV132*12 | IGLJ2*01 | QSYDNNLSAQV | 370 | 11 | 6 |
| IGLV132*12 | IGLJ2*01 | QSHDSSLSAGL | 331 | 11 | 2 |
| IGLV132*12 | IGLJ2*01 | QSYDSSLSAWV | 315 | 11 | 3 |
| IGLV132*12 | IGLJ2*01 | QSYDSSLSARV | 371 | 11 | 5 |
| IGLV132*12 | IGLJ2*01 | QSYDSSLSAWV | 315 | 11 | 2 |
| IGLV132*12 | IGLJ2*01 | QSYDSSLSAWV | 315 | 11 | 4 |
| IGLV132*12 | IGLJ2*01 | QSYDSSLSGHL | 284 | 11 | 0 |
| IGLV132*12 | IGLJ2*01 | QSYDSSLSGHL | 284 | 11 | 1 |
| IGLV132*12 | IGLJ2*01 | QSYDSSLSAHL | 314 | 11 | 2 |
| IGLV132*12 | IGLJ2*01 | QSYDSSLSAHL | 314 | 11 | 2 |
| IGLV132*12 | IGLJ2*01 | QSYDSSLSAWV | 315 | 11 | 2 |
| IGLV132*12 | IGLJ2*01 | QSYDISLSAGL | 372 | 11 | 3 |
| IGLV132*12 | IGLJ2*01 | QSYDSSLSAGL | 285 | 11 | 2 |
| IGLV132*12 | IGLJ2*01 | QSYDNILNAGL | 373 | 11 | 4 |
| IGLV132*12 | IGLJ2*01 | HSYDSSLSAQV | 374 | 11 | 2 |
| IGLV132*12 | IGLJ2*01 | QSYDSSLSAWV | 315 | 11 | 1 |
| IGLV132*12 | IGLJ3*01 | QSYDNSLSAVL | 311 | 11 | 2 |
| IGLV132*12 | IGLJ3*01 | QSYDSSLSAVL | 305 | 11 | 4 |
| IGLV132*12 | IGLJ3*01 | QSYDSSLSALL | 306 | 11 | 5 |
| IGLV132*12 | IGLJ3*01 | QSYDNSLSAVI | 375 | 11 | 5 |
| IGLV132*12 | IGLJ3*01 | QSYDSSLSXVL | 376 | 11 | 3 |
| IGLV132*12 | IGLJ3*01 | QSYDSSLSAVL | 305 | 11 | 0 |
| IGLV132*12 | IGLJ3*01 | QSYDSSLSAQL | 348 | 11 | 1 |
| IGLV132*12 | IGLJ3*01 | QSYDSSLSGVL | 310 | 11 | 1 |
| IGLV132*12 | IGLJ3*01 | QSYDSRLSALL | 377 | 11 | 5 |
| IGLV132*12 | IGLJ3*01 | QSYDSSLSAVV | 378 | 11 | 5 |
| IGLV132*12 | IGLJ3*01 | QSYDNSLSAVL | 311 | 11 | 2 |
| IGLV132*12 | IGLJ3*01 | QSYDNSLSALL | 379 | 11 | 3 |
| IGLV132*12 | IGLJ6*01 | QSYDSSLSADV | 292 | 11 | 4 |
| IGLV132*12 | IGLJ6*01 | QSYDSSLSADV | 292 | 11 | 4 |
| IGLV132*12 | IGLJ6*01 | QSYDSSLSALV | 318 | 11 | 1 |
| IGLV132*12 | IGLJ6*01 | QSYDSSLSAHV | 286 | 11 | 4 |
| IGLV132*12 | IGLJ6*01 | QSYDSSLSADV | 292 | 11 | 5 |
| IGLV132*12 | IGLJ6*01 | QSYDSSLSAHV | 286 | 11 | 1 |
| IGLV132*12 | IGLJ6*01 | QSYDSWQCHV | 380 | 11 | 3 |

TABLE 9-continued

DSS-motif-containing Sequences of Antibodies Generated from RC1-4fill VLPs-immunized macaques.

| | | | | | |
|---|---|---|---|---|---|
| IGLV132*12 | IGLJ6*01 | QSYDSSLSAHV | 286 | 11 | 2 |
| IGLV132*12 | IGLJ6*01 | QSYDSSLSTHV | 381 | 11 | 9 |
| IGLV132*12 | IGLJ6*01 | QSYDSSLTADV | 382 | 11 | 4 |
| IGLV132*1 | IGLJ1*01 | SSYAGSNTYI | 383 | 10 | 1 |
| IGLV132*15 | IGLJ1*01 | SSYAGSGTYI | 384 | 10 | 2 |
| IGLV132*15 | IGLJ1*01 | SSYAGSNTYI | 383 | 10 | 5 |
| IGLV132*15 | IGLJ1*01 | SSYAGSNTYI | 383 | 10 | 6 |
| IGLV132*12 | IGLJ1*01 | QSYDSRLSAHV | 385 | 11 | 6 |
| IGLV132*12 | IGLJ1*01 | QSYDSSLSAYI | 322 | 11 | 4 |
| IGLV132*12 | IGLJ1*01 | QSYHSSLRAYI | 386 | 11 | 5 |
| IGLV124*3 | IGLJ1*01 | RSYRSGRTNI | 387 | 10 | 4 |
| IGLV124*3 | IGLJ1*01 | CSYRSGDTLI | 388 | 10 | 4 |
| IGLV124*3 | IGLJ2*01 | YSYRSGNTLV | 389 | 10 | 3 |
| IGLV124*3 | IGLJ2*01 | CSYRSGSTFL | 390 | 10 | 2 |
| IGLV130*2 | IGLJ1*01 | CSYTTSSTFI | 391 | 10 | 2 |
| IGLV130*2 | IGLJ1*01 | CSYTTSSTFI | 391 | 10 | 2 |
| IGLV132*1 | IGLJ2*01 | SSYAGINTLV | 392 | 10 | 1 |
| IGLV132*15 | IGLJ2*01 | SSYAGSNTFL | 393 | 10 | 9 |
| IGLV132*17 | IGLJ3*01 | DSWDSSGTHVL | 351 | 11 | 15 |
| IGLV132*39 | IGLJ3*01 | DSWDSSGTHVL | 351 | 11 | 28 |
| IGLV124*4 | IGLJ2*01 | QVWDSSSDHWV | 362 | 11 | 1 |
| IGLV124*4 | IGLJ2*01 | QVWDISSDHPV | 355 | 11 | 5 |
| IGLV130*21 | IGLJ6*01 | QVWDSSSDHPV | 394 | 11 | 2 |
| IGLV130*21 | IGLJ2*01 | QVWDSSSDHWV | 362 | 11 | 0 |
| IGLV130*21 | IGLJ1*01 | QVWDSSNDHYI | 395 | 11 | 2 |
| IGLV132*37 | IGLJ2*01 | AAWDDRLSGWV | 396 | 11 | 1 |
| IGLV132*2 | IGLJ2*01 | CSYTSGSTWV | 397 | 10 | 4 |
| IGLV132*17 | IGLJ6*01 | DSWDSSGTLV | 398 | 10 | 29 |
| IGLV124*30 | IGLJ2*01 | LSYDSSLSAGL | 399 | 11 | 12 |
| IGLV132*33 | IGLJ3*01 | QVWDSSSDHVL | 400 | 11 | 3 |
| IGLV132*11 | IGLJ1*01 | QVWDNSSDHYI | 401 | 11 | 10 |
| IGLV130*21 | IGLJ2*01 | QVWDSSCK | 402 | 8 | 2 |
| IGLV132*29 | IGLJ2*01 | QSADSSGNHWV | 358 | 11 | 24 |
| IGLV124*30 | IGLJ1*01 | SAWDSSLSAYI | 403 | 11 | 33 |
| IGLV132*12 | IGLJ2*01 | QSYDSRLRVNWV | 404 | 12 | 2 |
| IGLV130*2 | IGLJ3*01 | CSYTTSNTLL | 302 | 10 | 3 |
| IGLV130*21 | IGLJ3*01 | QVWDSSSDHVL | 400 | 11 | 1 |
| IGLV124*30 | IGLJ2*01 | GAWDSSLSAGL | 295 | 11 | 19 |
| IGLV132*11 | IGLJ2*01 | QVWDSSSDHWV | 362 | 11 | 5 |

TABLE 9-continued

DSS-motif-containing Sequences of Antibodies Generated from RC1-4fill VLPs-immunized macaques.

| | | | | | |
|---|---|---|---|---|---|
| IGLV130*35 | IGLJ2*01 | EAWDRSLSAWV | 405 | 11 | 34 |
| IGLV124*30 | IGLJ1*01 | DTWDNSLNGYI | 406 | 11 | 20 |

TABLE 10

Macaque GC Antibodies with CDRL3s resembling the CDRL3s of iGL V3-glycan Patch bNAbs.

| ANTI-BODY | FORMAT | CELLS | NHP | VH | DH | JH | nt mut | CDRH3 | SEQ ID NO: | LENGTH (AA) | VL | JL | nt mut | CDRL3 | SEQ ID NO: | LENGTH (AA) | V3-GL SPEC. | METHOD |
|---|---|---|---|---|---|---|---|---|---|---|---|---|---|---|---|---|---|---|
| 874 | Fab | LN | 1 | IgHV3_2N*F_134_1 | IgHD6-6*0_1 | IgHJ1*0_1 | 5 | AKSPWG QSTSFEY FEF | 134 | 16 | IgLV 124*4_3 | IgLJ 3*0_1 | 1 | QV WD SSS DHP L | 294 | 11 | YES | OCTET/ SPR/ Cryo-EM |
| 876 | Ig | LN | 1 | IgHV3_2N*F_134_1 | IgHD6-6*0_1 | IgHJ 1*0_1 | 4 | AKSPWG QSSSFEY FEF | 133 | 16 | IgLV 124*4_3 | IgLJ 3*0_1 | 2 | QV WD SSS DHP L | 294 | 11 | YES | ELISA |
| 890 | Ig | LN | 1 | IgHV1_2B*F_134 | IgHD1-7*0_1 | IgHJ 4*0_1 | 6 | ARDRSVT PFSWVEY YFDY | 182 | 18 | IgLV 132*1_2 | IgLJ 2*0_1 | 7 | QSY DSS LSA GL | 285 | 11 | YES | ELISA |
| 890 | Fab | LN | 1 | IgHV1_2B*F_134 | IgHD1-7*0_1 | IgHJ 4*0_1 | 6 | ARDRSVT PFSWVEY YFDY | 182 | 18 | IgLV 132*1_2 | IgLJ 2*0_1 | 7 | QSY DSS LSA GL | 285 | 11 | YES | OCTET |
| 893 | Ig | LN | 1 | IgHV1_53*S2_078 | IgHD3-3*0_1 | IgHJ 1*0_1 | 2 | ATGPW GDYYGR YFEL | 145 | 16 | IgLV 132*1_2 | IgLJ 6*0_1 | 3 | QSY DNS LSA HV | 291 | 11 | YES | ELISA |
| 893 | Fab | LN | 1 | IgHV1_53*S2_078 | IgHD6-1*0_1 | IgHJ 1*0_1 | 2 | ATGPW GDYYGR YFEL | 145 | 16 | IgLV 132*1_2 | IgLJ 6*0_1 | 3 | QSY DNS LSA HV | 291 | 11 | YES | OCTET |
| 897 | Ig | LN | 1 | IgHV4_11*S5_305 | IgHD6-1*0_1 | IgHJ 5-1*0_1 | 4 | ARDSSG WPWDNR FDV | 172 | 15 | IgLV 132*1_2 | IgLJ 2*0_1 | 6 | QSY DNS LSA QV | 433 | 11 | YES | ELISA |
| 897 | Fab | LN | 1 | IgHV4_11*S5_305 | IgHD6-1*0_1 | IgHJ 5-1*0_1 | 4 | ARDSSG WPWDNR FDV | 172 | 15 | IgLV 132*1_2 | IgLJ 2*0_1 | 6 | QSY DNS LSA QV | 433 | 11 | YES | OCTET/ SPR/ Cryo-EM |

TABLE 10-continued

Macaque GC Antibodies with CDRL3s resembling the CDRL3s of iGL V3-glycan Patch bNAbs.

| ANTI-BODY | FORMAT | CELLS | NHP | VH | DH | JH | nt mut | CDRH3 | SEQ ID NO: | LENGTH (AA) | VL | JL | nt mut | CDRL3 | SEQ ID NO: | LENGTH (AA) | V3-GL SPEC. | METHOD |
|---|---|---|---|---|---|---|---|---|---|---|---|---|---|---|---|---|---|---|
| 901 | Fab | LN | 1 | IgHV5_1A*F124 | IgHD3-1*01 | IgHJ5-1*01 | 2 | AKETYEDDYGYYSLGYNRFDV | 195 | 21 | IgLV132*12 | IgLJ2*01 | 5 | QSYDSSLSAGL | 285 | 11 | YES | OC LET |
| 933 | Ig | LN | 8 | IgHV7_1A*F124 | IgHD1-2*01 | IgHJ4*01 | 5 | ARLGEYSWNSIGYFDY | 407 | 16 | IgLV132*12 | IgLJ2*01 | 2 | QSYDSSLSAHL | 314 | 11 | YES | ELISA |
| 934 | Ig | LN | 8 | IgHV3_3F*F132 | IgHD1-8*01 | IgHJ4*01 | 10 | ARGGYYSGRVFDDY | 408 | 14 | IgLV132*12 | IgLJ2*01 | 0 | QSYDSSLSGHL | 284 | 11 | YES | ELISA |
| 935 | Ig | LN | 8 | IgHV4_3I*F132 | IgHD3-3*01 | IgHJ5-2*02 | 2 | ARHSGWGDPYLDV | 409 | 13 | IgLV132*11 | IgLJ2*01 | 6 | QVWDSSSDHWV | 362 | 11 | YES | ELISA |
| 936 | Ig | LN | 8 | IgHV4_6G*F124 | IgHD6-3*01 | IgHJ4*01 | 14 | ANSGSWNYYFDY | 410 | 13 | IgLV130*21 | IgLJ6*01 | 2 | QVWDSSSDHPV | 394 | 11 | YES | ELISA |
| 937 | Ig | LN | 8 | IgHV3_1T*F132 | IgHD1-2*01 | IgHJ1*01 | 1 | TSDPATYSWNEYFEF | 411 | 15 | IgLV132*12 | IgLJ3*01 | 2 | QSYDNSLSAVL | 311 | 11 | YES | ELISA |
| 938 | Ig | LN | 8 | IgHV5_1H*F132 | IgHD6-5*01 | IgHJ5-1*01 | 1 | AKEDGGWSNNRVDV | 412 | 14 | IgLV132*12 | IgLJ3*01 | 1 | QSYDSSLSAQL | 348 | 11 | YES | ELISA |
| 986 | Fab | LN | 8 | IgHV5_1F*F134 | | IgHJ5-1*01 | 3 | AKGRGYNRFDVDH | 413 | 11 | IgLV130*21 | IgLJ1*01 | 3 | QVWDSSNYI | 395 | 11 | YES | ELISA |

TABLE 10-continued

Macaque GC Antibodies with CDRL3s resembling the CDRL3s of iGL V3-glycan Patch bNAbs.

| ANTI-BODY | FORMAT | CELLS | NHP | VH | DH | JH | nt mut | CDRH3 | SEQ ID NO: | LENGTH (AA) | VL | JL | nt mut | CDRL3 | SEQ ID NO: | LENGTH (AA) | V3-GL SPEC. | METHOD |
|---|---|---|---|---|---|---|---|---|---|---|---|---|---|---|---|---|---|---|
| 987 | Ig | LN | 8 | IgHV7-1A*F_124 | IgHD6-2*01 | IgHJ5-2*02 | 8 | VRQGYSS WYNSLD V | 414 | 14 | IgLV130*21 | IgLJ3*01 | 2 | QV WD SSS DH VL | 400 | 11 | YES | ELISA |
| 987 | Fab | LN | 8 | IgHV7-1A*F_124 | IgHD6-2*01 | IgHJ5-2*02 | 8 | VRQGYSS WYNSLD V | 414 | 14 | IgLV130*21 | IgLJ3*01 | 2 | QV WD SSS DH VL | 400 | 11 | YES | ELISA |
| 988 | Ig | LN | 8 | IgHV3-4J*F1_32 | IgHD5-2*01 | IgHJ4*01 | 18 | ARDMRDI AAGGYT YGYFDY | 415 | 19 | IgLV130*21 | IgLJ3*01 | 2 | QV WD SSC K | 402 | 8 | YES | ELISA |
| 988 | Fab | LN | 8 | IgHV3-4J*F1_32 | IgHD5-2*01 | IgHJ4*01 | 18 | ARDMRDI AAGGYT YGYFDY | 415 | 19 | IgLV130*21 | IgLJ3*01 | 2 | QV WD SSC K | 402 | 8 | YES | ELISA |
| 990 | Ig | LN | 8 | IgHV3-3F*F1_32 | IgHD6-2*01 | IgHJ5-1*01 | 10 | VRDPSITP GPSYNRF DV | 416 | 17 | IgLV132*12 | IgLJ6*01 | 4 | QSY DSS LSA HV | 286 | 11 | YES | ELISA |
| 990 | Fab | LN | 8 | IgHV3-3F*F1_32 | IgHD6-2*01 | IgHJ5-1*01 | 10 | VRDPSITP GPSYNRF DV | 416 | 17 | IgLV132*12 | IgLJ6*01 | 4 | QSY DSS LSA HV | 286 | 11 | YES | ELISA |
| 992 | Ig | LN | 8 | IgHV5-1F*F1_34 | IgHD4-1*01 | IgHJ5-1*01 | 2 | AKGVYG STNRPDV | 417 | 13 | IgLV132*12 | IgLJ2*01 | 1 | QSY DSS LSG HL | 284 | 11 | ND | ELISA |
| 992 | Fab | LN | 8 | IgHV5-1F*F1_34 | IgHD4-1*01 | IgHJ5-1*01 | 2 | AKGVYG LTNRFDV | 418 | 13 | IgLV132*12 | IgLJ2*01 | 1 | QSY DSS LSG HL | 284 | 11 | ND | ELISA |
| 996 | Ig | LN | 8 | IgHV3-30*F_130 | IgHD3-4*01 | IgHJ5-1*01 | 5 | TKEGGPE YYNIWT GWNRFD V | 419 | 20 | IgLV132*12 | IgLJ6*01 | 1 | QSY DSS LSA LV | 318 | 11 | YES | ELISA |

TABLE 10-continued

Macaque GC Antibodies with CDRL3s resembling the CDRL3s of iGL V3-glycan Patch bNAbs.

| ANTI-BODY | FORMAT | CELLS | NHP | VH | DH | JH | nt mut | CDRH3 | SEQ ID NO: | LENGTH (AA) | VL | JL | nt mut | CDRL3 | SEQ ID NO: | LENGTH (AA) | V3-GL SPEC. | METHOD |
|---|---|---|---|---|---|---|---|---|---|---|---|---|---|---|---|---|---|---|
| 997 | Ig | LN | 8 | IgHV4_3M*F133 | IgHD2-3*01 | IgHJ5-2*02 | 2 | AGGYLLFPLGYNSLDV | 420 | 16 | IgLV132*12 | IgLJ6*01 | 1 | QSYDSSLSAHV | 286 | 11 | YES | ELISA |
| 997 | Fab | LN | 8 | IgHV4_3M*F133 | IgHD2-3*01 | IgHJ5-2*02 | 2 | AGGYLLFPLGYNSLDV | 420 | 16 | IgLV132*12 | IgLJ6*01 | 1 | QSYDSSLSAHV | 286 | 11 | YES | OC LET |
| 998 | Fab | LN | 8 | IgHV5_1F*F134 | IgHD1-2*01 | IgHJ3*01 | 1 | AKGGGPPSWNDPFDF | 421 | 15 | IgLV132*12 | IgLJ2*01 | 3 | QSYDSSLSAWV | 315 | 11 | ND | ELISA |
| 1000 | Fab | LN | 8 | IgHV5_1F*F134 | IgHD3-3*01 | IgHJ4*01 | 4 | AKNGPPYWGMGDY | 422 | 13 | IgLV132*12 | IgLJ2*01 | 2 | QSYDSSLSAGL | 285 | 11 | YES | ELISA |
| 1000 | Ig | LN | 8 | IgHV5_1F*F134 | IgHD3-3*01 | IgHJ4*01 | 4 | AKNGPPYWGMGDY | 422 | 13 | IgLV132*12 | IgLJ2*01 | 2 | QSYDSSLSAGL | 285 | 11 | YES | ELISA |
| 1002 | Fab | LN | 8 | IgHV5_1F*F134 | IgHD6-2*01 | IgHJ4*01 | 2 | AKDRGRGGSWSLGNDY | 423 | 16 | IgLV132*12 | IgLJ2*01 | 4 | QSYDNILNAGL | 373 | 16 | YES | ELISA |
| 1003 | Ig | LN | 8 | IgHV3_1I*F130 | IgHD3-1*01 | IgHJ4*01 | 5 | AKGGEDDYIYYYTGADY | 424 | 17 | IgLV132*12 | IgLJ2*01 | 1 | QSYDSSLSAWV | 315 | 11 | YES | ELISA |
| 1004 | Ig | LN | 8 | IgHV4_3M*F133 | IgHD3-2*01 | IgHJ5-2*02 | 3 | ARGLFNFWSGWGHNSLDV | 425 | 19 | IgLV132*12 | IgLJ6*01 | 4 | QSYDSSLTADV | 382 | 11 | YES | ELISA |
| 1005 | Ig | LN | 8 | IgHV4_11*54970 | IgHD6-2*01 | IgHJ5-2*02 | 14 | ARDYSSWPTYNSLDV | 426 | 15 | IgLV132*12 | IgLJ3*01 | 2 | QSYDNSLSAVL | 311 | 11 | YES | ELISA |

TABLE 10-continued

Macaque GC Antibodies with CDRL3s resembling the CDRL3s of iGL V3-glycan Patch bNAbs.

| ANTI-BODY | FORMAT | CELLS | NHP | VH | DH | JH | nt mut | CDRH3 | SEQ ID NO: | LENGTH (AA) | VL | JL | nt mut | CDRL3 | SEQ ID NO: | LENGTH (AA) | V3-GL SPEC. | METHOD |
|---|---|---|---|---|---|---|---|---|---|---|---|---|---|---|---|---|---|---|
| 1013 | Fab | LN | 8 | IgHV5-1F*F134 | IgHD2-1*01 | IgHJ4*01 | 1 | AKSTLLRRSLDY | 427 | 12 | IgLV132*12 | IgLJ3*01 | 4 | QSYDSSLSAVL | 305 | 11 | ND | ELISA |
| 1053 | Ig | LN | 5 | IgHV5-1C*F130 | IgHD2-5*01 | IgHJ4*01 | 1 | AKSETDFWTSYYFNY | 214 | 15 | IgLV132*12 | IgLJ2*01 | 2 | QSYDSSLSAQV | 313 | 11 | YES | ELISA |
| 1054 | Ig | LN | 5 | IgHV1-2B*F134 | IgHD6-5*01 | IgHJ6*01 | 2 | ARDGPYSGGWSELDS | 219 | 15 | IgLV132*12 | IgLJ2*01 | 1 | QSYDSSLSGHL | 284 | 11 | YES | ELISA |
| 1061 | Ig | LN | 6 | IgHV1-53*52078 | IgHD2-3*01 | IgHJ4*01 | 0 | ATTPGYCSSTYCRFDY | 276 | 16 | IgLV132*12 | IgLJ1*01 | 7 | QSYDSILSSYI | 342 | 11 | YES | ELISA |
| 1062 | Ig | LN | 6 | IgHV5-1F*F134 | IgHD5-1*01 | IgHJ4*01 | 4 | AKGVGGFSYSYPHY | 252 | 14 | IgLV132*12 | IgLJ1*01 | 5 | QSYDSSLSAYI | 322 | 11 | YES | ELISA |
| 1063 | Ig | LN | 6 | IgHV1-2B*F134 | IgHD4-1*01 | IgHJ2*01 | 5 | ARMTTVAAFGYFDL | 247 | 15 | IgLV132*12 | IgLJ3*01 | 6 | QSYDSSLSDVL | 347 | 11 | YES | ELISA |
| 1064 | Ig | LN | 6 | IgHV3-1V*F124 | IgHD4-4*01 | IgHJ4*01 | 36 | TRPRQYSTGDY | 257 | 11 | IgLV124*17 | IgLJ2*01 | 2 | QVWDISSDHPV | 355 | 11 | YES | ELISA |
| 1068 | Ig | LN | 6 | IgHV1-53*52078 | IgHD3-2*01 | IgHJ1*01 | 4 | ATKNYYDSGYHLSGEYFEF | 277 | 19 | IgLV130*33 | IgLJ3*01 | 11 | QSYDGSLSAQL | 363 | 11 | YES | ELISA |
| 1169 | Ig | LN | 8 | IgHV5-1F*F134 | IgHD2-4*01 | IgHJ5-1*01 | 2 | AKDGGPSGSYYYGGRFDV | 428 | 18 | IgLV132*15 | IgLJ1*01 | 6 | SSYAGSNTYI | 383 | 10 | ND | ELISA |

TABLE 10-continued

Macaque GC Antibodies with CDRL3s resembling the CDRL3s of iGL V3-glycan Patch bNAbs.

| ANTI-BODY | FORMAT | CELLS | NHP | VH | DH | JH | nt mut | CDRH3 | SEQ ID NO: | LENGTH (AA) | VL | JL | nt mut | CDRL3 | SEQ ID NO: | LENGTH (AA) | V3-GL SPEC. | METHOD |
|---|---|---|---|---|---|---|---|---|---|---|---|---|---|---|---|---|---|---|
| 1169 | Fab | LN | 8 | IgHV5-1F*F1_34 | IgHD2-4*01 | IgHJ5-1*01 | 2 | AKDGGPSGSYYYRGRFDV | 429 | 18 | IgLV1_32*15 | IgLJ1*01 | 6 | SSYAGSNTYI | 383 | 10 | ND | OC LET |
| 1170 | Ig | LN | 8 | IgHV1_2G*F_130 | IgHD2-2*01 | IgHJ4*01 | 7 | ARGGGHSSFDF | 430 | 11 | IgLV1_32*1 | IgLJ2*01 | 2 | SSYAGINTLV | 392 | 10 | YES | ELISA |
| 1170 | Fab | LN | 8 | IgHV1_1P*F1_33 | IgHD2-2*01 | IgHJ4*01 | 7 | ARGGGHSSFDF | 430 | 11 | IgLV1_32*1 | IgLJ2*01 | 2 | SSYAGINTLV | 392 | 10 | YES | ELISA/OCTET |
| 1177 | Fab | LN | 6 | IgHV4_5N*F_133 | IgHD4-1*01 | IgHJ5-1*01 | 10 | ARSRSGSNSESREDV | 272 | 15 | IgLV1_32*15 | IgLJ1*01 | 6 | SSYVGSGTYI | 352 | 10 | ND | ELISA/OCTET |
| 1178 | Fab | LN | 6 | IgHV4_11*59_280 | IgHD1-8*01 | IgHJ3*01 | 0 | ARDSYKDSPAFDF | 431 | 13 | IgLV1_24*6 | IgLJ1*01 | 2 | SSYAGSNTFI | 361 | 10 | ND | ELISA/OCTET |
| 1180 | Fab | LN | 8 | IgHV5_1F*F1_34 | IgHD3-2*01 | IgHJ4*01 | 5 | AKDQTDLDWLLYGGFDY | 432 | 17 | IgLV1_32*15 | IgLJ1*01 | 6 | SSYAGSNTYI | 383 | 10 | YES | ELISA/OCTET |

TABLE 11

QxxDSS motif-containing bNAbs ("QxxDSS" disclosed as SEQ ID NO: 20).

| bNAb | VH | VL | CDRL3 (MT) | SEQ ID NO: | CDRL3 (iGL) | SEQ ID NO: |
|---|---|---|---|---|---|---|
| PGT121 | 4-59 | L3-21 | HIWDSRVPTKWV | 434 | QVWDSSSDHPWV | 445 |
| PGT122 | 4-59 | L3-21 | HIWDSRRPTNWV | 435 | QVWDSSSDHPWV | 445 |
| PGT123 | 4-59 | L3-21 | HIYDARGGTNWV | 436 | QVWDSSSDHPWV | 445 |
| 10-1074 | 4-59 | L3-21 | HMWDSRSGFSWS | 437 | QVWDSSSDHPWV | 445 |
| PGT124 | 4-59 | L3-21 | MWDSRSGFSWS | 438 | QVWDSSSDHPWV | 445 |
| BG18 | 4-4 | L3-25 | QSSDTSDSYKM | 439 | | |
| PGT125 | 4-39 | L2-8 | GSLVGNWDVI | 440 | SSYAGSNXXX | 446 |
| PGT126 | 4-39 | L2-8 | SSLVGNWDVI | 441 | SSYAGSNXXX | 446 |
| PGT127 | 4-39 | L2-8 | SSLVGNWDVI | 441 | SSYAGSNXXX | 446 |
| PGT128 | 4-39 | L2-8 | GSLVGNWDVI | 440 | SSYAGSNXXX | 446 |
| PGT130 | 4-39 | L2-8 | SSLFGRWDVV | 442 | SSYAGSNXXX | 446 |
| PGT131 | 4-39 | L2-8 | SSLSGRWDIV | 443 | SSYAGSNXXX | 446 |
| DH270.6 | 1-2 | L2-23 | SFGGSATVV | 444 | SYAGSSTVI | 447 |

TABLE 12

PCR Primers.

Heavy chain

| | | Primer name | Primer sequence | SEQ ID NO: |
|---|---|---|---|---|
| 1st PCR | Forward | p1350 | ACAGGTGCCCACTCCCAGGTGCAG | 448 |
| | | p1351 | AAGGTGTCCAGTGTGARGTGCAG | 449 |
| | | p1352 | CCCAGATGGGTCCTGTCCCAGGTGCAG | 450 |
| | | p1353 | CAAGGAGTCTGTTCCGAGGTGCAG | 451 |
| | | VH5 LEADER-A | TTCTCCAAGGAGTCTGT | 452 |
| | | VH3 LEADER-A | TAAAAGGTGTCCAGTGT | 453 |
| | | VH3 LEADER-AB | TAAGAGGTGTCCAGTGT | 454 |
| | | VH3 LEADER-C | TAGAAGGTGTCCAGTGT | 455 |
| | | VH4 LEADER-D | ATGAAACATCTGTGGTTCTT | 456 |
| | | VH3 LEADER-E | TACAAGGTGTCCAGTGT | 457 |
| | | VH3 LEADER-F | TTAAAGCTGTCCAGTGT | 458 |
| | Reverse | 3'SalI.JH1/4/5 | GCTGAGGAGACGGTGACCAG | 459 |
| | | 3'SalI.JH2 | GCTGAGGAGATGGTGATTGGG | 460 |
| | | 3'SalI.JH3 | GCTGAAGAGACGGTGACCCTG | 461 |
| | | 3'SalI.JH6 | GCTGAGGAGACGGTGACGACG | 462 |
| 2nd PCR | Forward | p1355 | CTAGTAGCAACTGCAACCGGTGTACATTCCCAGGTGCAGCTGGTGCAG | 463 |
| | | p1356 | CTAGTAGCAACTGCAACCGGTGTACATTCCGAGGTGCAGCTGGTGCAG | 464 |
| | | p1357 | CTAGTAGCAACTGCAACCGGTGTACATTCCCAGGTTCAGCTGGTGCAG | 465 |
| | | p1358 | CTAGTAGCAACTGCAACCGGTGTACATTCCCAGGTCCAGCTGGTACAG | 466 |
| | | p1359 | CTAGTAGCAACTGCAACCGGTGTACATTCTGAGGTGCAGCTGGTGGAG | 467 |
| | | p1360 | CTAGTAGCAACTGCAACCGGTGTACATTCTCAGGTGCAGCTGGTGGAG | 468 |
| | | p1361 | CTAGTAGCAACTGCAACCGGTGTACATTCTGAGGTGCAGCTGGTTGAG | 469 |
| | | p1362 | CTAGTAGCAACTGCAACCGGTGTACATTCTCAGGTGCAGCTGGTGGAG | 468 |
| | | p1363 | CTAGTAGCAACTGCAACCGGTGTACATTCTGAAGTGCAGCTGGTGGAG | 470 |

TABLE 12-continued

PCR Primers.

| | | | | |
|---|---|---|---|---|
| | | p1364 | CTAGTAGCAACTGCAACCGGTGTACA TTCCCAGGTGCAGCTGCAGGAG | 471 |
| | | p1365 | CTAGTAGCAACTGCAACCGGTGTACA TTCCCAGGTGCAGCTACAGCAGTG | 472 |
| | | p1366 | CTAGTAGCAACTGCAACCGGTGTACA TTCCCAGCTGCAGCTGCAGGAG | 473 |
| | | p1367 | CTAGTAGCAACTGCAACCGGTGTACA TTCCCAGGTACAGCTGCAGAG | 474 |
| | Reverse | p1370 | CCGATGGGCCCTTGGTCGACGCTGAG GAGACGGTGACCAG | 475 |
| | | p1371 | CCGATGGGCCCTTGGTCGACGCTGAA GAGACGGTGACCATTG | 476 |
| | | p1372 | CCGATGGGCCCTTGGTCGACGCTGAG GAGACGGTGACCAG | 475 |
| | | p1373 | CCGATGGGCCCTTGGTCGACGCTGAG GAGACGGTGACCGTG | 477 |
| Sequencing | | RM_FWD_T4_Seq | GTAGCAACTGCAACCGGTGT | 478 |
| Colony PCR | Forward | Ab-sense | GCTTCGTTAGAACGCGGCTAC | 479 |
| | Reverse | p1354 | GGAAGGTGTGCACGCCGCTGGTC | 480 |
| | Sequencing | Ab-sense | GCTTCGTTAGAACGCGGCTAC | 479 |

Light chain (λ)

| | | Primer name | Primer sequence | SEQ ID NO: |
|---|---|---|---|---|
| 1st PCR | Forward | p1394 | GGTCCTGGGCCCAGTCTGTGCTG | 481 |
| | | p1395 | GGTCCTGGGCCCAGTCTGCCCTG | 482 |
| | | p1396 | GCTCTGTGACCTCCTATGAGCTG | 483 |
| | | p1397 | GGTCTCTCTCSCAGCYTGTGCTG | 484 |
| | | p1398 | GTTCTTGGGCCAATTTTATGCTG | 485 |
| | | p1399 | GGTCCAATTCYCAGGCTGTGGTG | 486 |
| | | p1400 | GAGTGGATTCTCAGACTGTGGTG | 487 |
| | Reverse | p1401 | CACCAGTGTGGCCTTGTTGGCTTG | 488 |
| 2nd PCR | Forward | p1402 | CTAGTAGCAACTGCAACCGGTTCCTG GGCCCAGTCTGTGCTGACKCAG | 489 |
| | | p1403 | CTAGTAGCAACTGCAACCGGTTCCTG GGCCCAGTCTGCCCTGACTCAG | 490 |
| | | p1404 | CTAGTAGCAACTGCAACCGGTTCTGT GACCTCCTATGAGCTGACWCAG | 491 |
| | | p1405 | CTAGTAGCAACTGCAACCGGTTCTCT CTCSCAGCYTGTGCTGACTCA | 492 |
| | | p1406 | CTAGTAGCAACTGCAACCGGTTCTTG GGCCAATTTTATGCTGACTCAG | 493 |
| | | p1407 | CTAGTAGCAACTGCAACCGGTTCCAA TTCYCAGRCTGTGGTGACYCAG | 494 |
| | Reverse | p1409 | GGCTTGAAGCTCCTCACTCGAGGGYG GGAACAGAGTG | 495 |
| Sequencing | | p1409 | GGCTTGAAGCTCCTCACTCGAGGGYG GGAACAGAGTG | 495 |
| Colony PCR | Forward | Ab-sense | GCTTCGTTAGAACGCGGCTAC | 479 |
| | Reverse | p1409 | GGCTTGAAGCTCCTCACTCGAGGGYG GGAACAGAGTG | 495 |
| | Sequencing | Ab-sense | GCTTCGTTAGAACGCGGCTAC | 479 |

We claim:

1. An isolated polypeptide having an amino acid sequence selected from the group consisting of SEQ ID NOs: 2, 4, 6, 8, 11, and 13.

2. The polypeptide of claim 1 binds to a broadly neutralizing antibody with an affinity having a $K_D$ of about 50 µM or less.

3. The polypeptide of claim 2, wherein the broadly neutralizing antibody is 10-1074 or PGT121 broadly neutralizing antibody.

4. A nucleic acid molecule encoding the polypeptide of claim 1.

5. A vector comprising the nucleic acid molecule of claim 4.

6. A host cell comprising the nucleic acid molecule of claim 4.

7. A protein complex comprising at least one polypeptide of claim 1.

8. A virus-like particle comprising at least one polypeptide of claim 1.

9. An immunogenic composition for stimulating an immune response in a subject in need thereof, comprising the polypeptide of claim 1; and a pharmaceutically acceptable carrier.

10. A method of stimulating an immune response in a subject in need thereof, comprising administrating to the subject an effective amount of a composition comprising the polypeptide of claim 1.

11. The method of claim 10, wherein the composition is administered to the subject two or more times.

12. The method of claim 10, wherein administrating the composition results in increased numbers of broadly-neutralizing antibodies in the serum capable of recognizing a V3-glycan epitope.

13. A method of producing a polypeptide, comprising culturing the host claim 6 in a medium under conditions permitting expression of a polypeptide encoded by the nucleic acid molecule, and purifying the polypeptide from the cultured cell or the medium of the cell.

14. A kit, comprising (i) one or more unit dosages of the polypeptide of claim 1; (ii) instructions for administrating the polypeptide, the nucleic acid molecule, the host cell, the protein complex, or the virus particle; and (iii) optionally an adjuvant.

* * * * *